USOO5691336A

United States Patent [19]
Dorn et al.

[11] Patent Number: 5,691,336
[45] Date of Patent: Nov. 25, 1997

[54] MORPHOLINE COMPOUNDS ARE PRODRUGS USEFUL AS TACHYKININ RECEPTOR ANTAGONISTS

[75] Inventors: Conrad P. Dorn, Plainfield; Jeffrey J. Hale, Westfield; Malcolm Maccoss, Freehold; Sander G. Mills, Woodbridge, all of N.J.

[73] Assignee: Merck & Co., Inc., Rahway, N.J.

[21] Appl. No.: 525,870

[22] Filed: Sep. 8, 1995

Related U.S. Application Data

[63] Continuation-in-part of PCT/US95/02551 Feb. 28, 1995, continuation-in-part of Ser. No. 206,771, Mar. 4, 1994, abandoned.

[51] Int. Cl.$^6$ .................. C07D 265/32; C07D 279/12; C07D 413/04; C07D 413/06; C07D 413/14
[52] U.S. Cl. .................. 514/236.2; 514/233.5; 514/235.2; 514/235.5; 514/235.8; 544/132; 544/134; 544/139; 544/141; 544/143
[58] Field of Search .................. 544/132, 134, 544/139, 141, 143; 514/235.2, 235.5, 235.8, 233.5, 236.2

[56] References Cited

U.S. PATENT DOCUMENTS

| | | | |
|---|---|---|---|
| 2,943,022 | 6/1960 | Siemer et al. | 167/65 |
| 3,005,818 | 10/1961 | Siemer et al. | 260/247.2 |
| 3,458,509 | 7/1969 | Levine et al. | 260/243 |
| 3,506,673 | 4/1970 | Warawa et al. | 260/294.7 |
| 3,541,090 | 11/1970 | Herlinger et al. | 260/243 |
| 4,010,266 | 3/1977 | McLoughlin et al. | 424/248.4 |
| 4,360,519 | 11/1982 | White et al. | 424/248.55 |
| 4,476,311 | 10/1984 | Shetty et al. | 424/243 |
| 4,705,553 | 11/1987 | Buschmann et al. | 71/76 |
| 4,782,054 | 11/1988 | Regnier et al. | 514/235.2 |
| 4,943,578 | 7/1990 | Naylor et al. | 514/252 |
| 5,064,838 | 11/1991 | Carr et al. | 514/317 |
| 5,095,021 | 3/1992 | Zipplies et al. | 167/65 |

FOREIGN PATENT DOCUMENTS

| | | | |
|---|---|---|---|
| 0 360 390 | 3/1990 | European Pat. Off. | 514/235.2 |
| 0 436 334 | 7/1991 | European Pat. Off. | 544/132 |
| 0 499 313 | 8/1992 | European Pat. Off. | 514/235.2 |
| 0 528 495 | 2/1993 | European Pat. Off. | 544/132 |
| 0 533 280 A1 | 3/1993 | European Pat. Off. | 544/132 |
| 2534915 | 4/1984 | France | 544/132 |
| WO 90/05525 | 5/1990 | WIPO | 514/235.2 |
| WO 90/05729 | 5/1990 | WIPO | 514/235.2 |
| WO 91/18899 | 12/1991 | WIPO | 514/235.2 |
| WO 92/01679 | 2/1992 | WIPO | 514/252 |
| WO 92/06079 | 4/1992 | WIPO | 514/235.2 |
| WO 92/12128 | 7/1992 | WIPO | 514/317 |
| WO 92/12151 | 7/1992 | WIPO | 514/317 |
| WO 92/12152 | 7/1992 | WIPO | 514/252 |
| WO 94/00440 | 1/1994 | WIPO | 544/132 |
| WO 95/16679 | 6/1995 | WIPO | 544/132 |

OTHER PUBLICATIONS

Advenier, et al., "Neurokinin A (NK2) Receptor Revisited With SR48968 . . . ", Biochem. and Biophys., Res. Comm., 184(3), pp. 1418–1424 (1992).

Edmonds–Alt, et al., "A Potent and Selective Non–Peptide Antagonist of the Neurokinin A (NK2) Receptor", Life Sci., 50, pp. PL101–PL106 (1992).

Frossard, et al. "Tachykinin Receptors and the Airways", Life Sci., 49, pp. 1491–1953, (1991).

Guthrie, et al., "The Use of Periodate–Oxidized Glycosides in the Robinson–Schopf . . . ", J. Chem. Society, vol. C(1), pp. 62–66 (1967).

Howson, et al., "An SAR Study for the Non–Peptide Substance P Receptor . . . ", Biorg. & Med. Chem. Lett., vol. 2(6), pp. 559–564 (1992).

G. Rucker, et al., Arch. Pharm., (Weinheim, Ger.) 315(10), 839–846 (1982), "Stabilitasuntersuchungen and Phenylethylaminsubstituierten Pyrazolonein".

Chem. Abstracts, 73 (3) p. 361, No. 14777c (Jul. 20, 1970), "Diastereoisomeric Configuration of Morpholine Derivatives".

I.V. Bozhko, et al., Kinet. Katal., 31 (3), 737–738 (1990) (Russ.).

Lowe, et al., "The Discovery of (2S, 3S)–cis–2(Diphenylmethyl)–N–(2–methoxyphenyl)methyl . . . ", J. Med. Chem., vol. 35, pp. 2591–2600 (1992).

McCormick, "Properties of Periodate–Oxidised Polysaccharides", J. Chem. Society, vol. C(23), pp. 2121–2127 (1966).

Montgomery, et al., "2–Fluoropurine Ribonucleosides", J. of Med. Chem., vol. 13(3), pp. 421–427 (1970).

Payan, et al., "Substance P. Recognition by a Subset of Human T Lymphocytes", J. Clin. Invest., 74, 1532–1539 (1984).

Peyronel, et al., "Synthesis of RP–67,580, a New Potent Nonpeptide Subtance P Antagonist", Biorg. and Med. Chem. Lett., vol. 2(6), pp. 559–564 (1992).

Siemer, et al., "Analgesic 1–phenyl–2, 3–dimethyl–4–morpholinomethyl–3–pyrazolin–5–ones . . . " Chem. Abstracts, 56, No. 6, No. 5977e (1962).

(List continued on next page.)

Primary Examiner—Floyd D. Higel
Attorney, Agent, or Firm—J. Eric Thies; David L. Rose

[57] ABSTRACT

Substituted heterocycles of the general structural formula:

are tachykinin receptor antagonists useful in the treatment of inflammatory diseases, pain or migraine, asthma, and emesis.

25 Claims, No Drawings

OTHER PUBLICATIONS

*Chem. Abstracts,* 113 (20) p. 123, No. 174441m (Nov. 12, 1990), "Amine Hydrochlorides–Catalysts for Hydrochlorination".

Sinkula, et al., "Rationale for Design of Biologically Reversible Drug Derivatives: Prodrugs", *J. Pharm. Sciences,* 64 (2), pp. 181–210 (1975).

Svensson, "Prodrugs: metabolism–based drug design", *Pharmaceutisch Weekblad,* 122, pp. 245–250, (1987).

Balant, et al., "Prodrugs for the improvement of drug absorption via different routes of administration.", *Eur. J. Drug Metab. Pharmaco.,* 15(2), pp. 143–153, (1990).

Bodar, et al., "Novel Approaches in Prodrug Design", *Drugs Future,* VI(3), pp. 165–182 (1981).

Bundgaard, "The double prodrug concept and its applications", *Adv. Drug Delivey Rev.,* 3 pp. 39–65, (1989).

MORPHOLINE COMPOUNDS ARE PRODRUGS USEFUL AS TACHYKININ RECEPTOR ANTAGONISTS

CROSS REFERENCE TO RELATED APPLICATIONS

This application is a continuation-in-part of PCT application U.S. Ser. No. 95/02551, filed Feb. 28, 1995, and a continuation-in-part of application Ser. No. 08/206,771 filed Mar. 4, 1994, now abandoned.

BACKGROUND OF THE INVENTION

Analgesia has historically been achieved in the central nervous system by opiates and analogs which are addictive, and peripherally by cyclooxygenase inhibitors that have gastric side effects. Substance P antagonists may induce analgesia both centrally and peripherally. In addition, substance P antagonists are inhibitory of neurogenic inflammation.

The neuropeptide receptors for substance P (neurokinin-1; NK-1) are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (B. Pernow, Pharmacol. Rev., 1983, 35, 85–141). The NK1 and NK2 receptor subtypes are implicated in synaptic transmission (Laneuville et al., Life Sci., 42: 1295–1305 (1988)).

The receptor for substance P is a member of the superfamily of G protein-coupled receptors. This superfamily is an extremely diverse group of receptors in terms of activating ligands and biological functions. In addition to the tachykinin receptors, this receptor superfamily includes the opsins, the adrenergic receptors, the muscarinic receptors, the dopamine receptors, the serotonin receptors, a thyroid-stimulating hormone receptor, a luteinizing hormone-choriogonadotropic hormone receptor, the product of the oncogene ras, the yeast mating factor receptors, a Dictyostelium cAMP receptor, and receptors for other hormones and neurotransmitters (see A. D. Hershey, et al., J. Biol. Chem., 1991, 226, 4366–4373).

Substance P (also called "SP" herein) is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence Phe-X-Gly-Leu-Met-$NH_2$. In addition to SP the known mammalian tachykinins include neurokinin A and neurokinin B. The current nomenclature designates the receptors for SP, neurokinin A, and neurokinin B as NK-1, NK-2, and NK-3, respectively.

More specifically, substance P is a pharmacologically-active neuropeptide that is produced in mammals and possesses a characteristic amino acid sequence (Chang et al., Nature New Biol. 232, 86 (1971); D. F. Veber et al., U.S. Pat. No. 4,680,283.

Substance P is a pharmacologically-active neuropeptide that is produced in mammals and acts as a vasodilator, a depressant, stimulates salivation and produces increased capillary permeability. It is also capable of producing both analgesia and hyperalgesia in animals, depending on dose and pain responsiveness of the animal (see R. C. A. Frederickson et al., Science, 199, 1359 (1978); P. Oehme et al., Science, 208, 305 (1980)) and plays a role in sensory transmission and pain perception (T. M. Jessell, Advan. Biochem. Psychopharmacol. 28, 189 (1981)). For example, substance P is believed to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS, 8 506–510 (December 1987)], specifically in the transmission of pain in migraine (see B. E. B. Sandberg et al., Journal of Medicinal Chemistry, 25, 1009 (1982); M. A. Moskowitz, Trends Phamacol. Sci., 13, 307–311 (1992)), and in arthritis (Levine, et al. Science, 226 547–549 (1984); M. Lotz, et al., Science, 235, 893–895 (1987)). Tachykinins have also been implicated in gastrointestinal (GI) disorders and diseases of the GI tract, such as inflammatory bowel disease [see Mantyh et al., Neuroscience, 25 (3), 817–37 (1988) and D. Regoli in "Trends in Cluster Headache" Ed. F. Sicuteri et al., Elsevier Scientific Publishers, Amsterdam, pp. 85–95 (1987)], and emesis [Trends Pharmacol. Sci., 9, 334–341 (1988), F. D. Tatersall, et al., Eur. J. Pharmacol., 250, R5–R6 (1993)].

It is also hypothesized that there is a neurogenic mechanism for arthritis in which substance P may play a role [Kidd et al., "A Neurogenic Mechanism for Symmetric Arthritis" in The Lancet, 11 Nov. 1989 and Gronblad et al., "Neuropeptides in Synovium of Patients with Rheumatoid Arthritis and Osteoarthritis" in J. Rheumatol. 15(12) 1807–10 (1988)]. Therefore, substance P is believed to be involved in the inflammatory response in diseases such as rheumatoid arthritis and osteoarthritis [O'Byrne et al., Arthritis and Rheumatism, 33 1023–8 (1990)].

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Chrohn's disease, ocular injury and ocular inflammatory diseases, proliferative vitreoretinopathy, irritable bowel syndrome and disorders of bladder function including cystitis and bladder detruser hyperreflexia is reviewed in "Tachykinin Receptors and Tachykinin Receptor Antagonists," C. A. Maggi, R. Patacchini, P. Rovero and A. Giachetti, J. Auton. Pharmacol, 13, 23–93 (1993); see also R. M. Snider, et al., Chem. Ind., 11, 792–794 (1991). Neurokinin-1 receptor antagonists alone or in combination with bradykinin receptor antagonists may also be useful in the prevention and treatment of inflammatory conditions in the lower urinary tract, especially cystitis [Giuliani, et al., J. Urology, 150, 1014–1017 (1993)]. Other disease areas where tachykinin antagonists are believed to be useful are allergic conditions [Hamelet et al., Can. J. Pharmacol. Physiol., 66, 1361–7 (1988)], immunoregulation [Lotz, et al., Science, 241 1218–21 (1988), Kimball, et al., J. Immunol., 141 (10) 3564–9 (1988); A. Perianin, et al., Biochem. Biophys. Res Commun. 161, 520 (1989)], post-operative pain and nausea [C. Bountra, et al., Eur. J. Pharmacol., 249, R3–R4 (1993), F. D. Tattersall, et al., Neuropharmacology, 33, 259–260 (1994)], vasodilation, bronchospasm, reflex or neuronal control of the viscera [Mantyh et al., PNAS, 85, 3235–9 (1988)] and, possibly by arresting or slowing β-amyloid-mediated neurodegenerative changes [Yankner et al., *Science*, 250, 279–82 (1990)] in senile dementia of the Alzheimer type, Alzheimer's disease and Downs Syndrome. Substance P may also play a role in demyelinating diseases such as multiple sclerosis and amyotrophic lateral sclerosis [J. Luber-Narod, et. al., poster C.I.N.P. XVIIIth Congress, 28th Jun.–2nd Jul., 1992], and in disorders of bladder function such as bladder detrusor hyperreflexia [*Lancet*, 16th May 1992, 1239]. Antagonists selective for the neurokinin-1 (NK-1) and/or the neurokinin-2 (NK-2) receptor may be useful in the treatment of asthmatic disease (Frossard et al., *Life Sci.*, 49, 1941–1953 (1991); Advenier, et al., *Biochem. Biophys. Res. Comm.*, 184(3), 1418–1424 (1992); P. Barnes, et al., *Trends Pharmacol. Sci.*, 11, 185–189 (1993)). Tachykinin antagonists may also be useful in the treatment of small cell carcinomas, in particular small cell lung cancer (SCLC) [Langdon et al., *Cancer Research*, 52, 4554–7 (1992)].

It has furthermore been suggested that tachykinin receptor antagonists have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorder related to immune enhancement or suppression such as systemic lupus erythmatosus (EPO Publication No. 0,436,334), ophthalmic diseases such as conjunctivitis, vernal conjunctivitis, and the like, and cutaneous diseases such as contact dermatitis, atopic dermatitis, urticaria, and other eczematoid dermatitis (EPO Publication No. 0,394,989).

Substance P antagonists may be useful in mediating neurogenic mucus secretion in mammalian airways and hence provide treatment and symptomatic relief in diseases characterized by mucus secretion, in particular, cystic fibrosis [S. Ramnarine, et al., abstract presented at 1993 ALA/ATS Int'l Conference, 16–19 May, 1993, published in *Am. Rev. of Respiratory Dis.*, May 1993].

In the recent past, some attempts have been made to provide peptide-like substances that are antagonists for the receptors of substance P and other tachykinin peptides in order to more effectively treat the various disorders and diseases mentioned above. For example Lowe, *Drugs of the Future*, 17 (12) 1115–1121 (1992) and EPO Publication Nos. 0,347,802, 0,401,177 and 0,412,452 disclose various peptides as neurokinin A antagonists. Also, PCT Patent Publication WO 93/14113 discloses certain peptides as tachykinin antagonists. In addition, EPO Publication No. 0,336,230 discloses heptapeptides which are substance P antagonists useful in the treatment of asthma. Merck U.S. Pat. No. 4,680,283 also discloses peptidal analogs of substance P. Certain inhibitors of tachykinins have been described in U.S. Pat. No. 4,501,733, by replacing residues in substance P sequence by Trp residues. A further class of tachykinin receptor antagonists, comprising a monomeric or dimeric hexa- or heptapeptide unit in linear or cyclic form, is described in GB-A-2216529.

The peptide-like nature of such substances make them too labile from a metabolic point of view to serve as practical therapeutic agents in the treatment of disease. The non-peptidic antagonists of the present invention, on the other hand, do not possess this drawback, as they are expected to be more stable from a metabolic point of view than the previously-discussed agents.

It is known in the an that baclofen (β-(aminoethyl)-4-chlorobenzenepropanoic acid) in the central nervous system effectively blocks the excitatory activity of substance P, and the excitatory responses to other compounds such as acetylcholine and glutamate are inhibited as well. Pfizer WIPO patent applications (PCT publication Nos. WO 90/05525, WO 90/05729, WO 91/18899, WO 92/12151 and WO 92/12152) and publications (*Science*, 251, 435–437 (1991); *Science*, 251, 437–439 (1991); *J. Med. Chem.*, 35, 2591–2600 (1992)) disclose 2-arylmethyl-3-substituted amino-quinuclidine derivatives which are disclosed as being useful as substance P antagonists for treating gastrointestinal disorders, central nervous system disorders, inflammatory diseases and pain or migraine. A Glaxo European patent application (EPO Publication No. 0,360,390) discloses various spirolactam-substituted amino acids and peptides which are antagonists or agonists of substance P. A Pfizer WIPO patent application (PCT Publication No. WO 92/06079) discloses fused-ring analogs of nitrogen-containing nonaromatic heterocycles as useful for the treatment of diseases mediated by an excess of substance P. A Pfizer WIPO patent application (PCT Publication No. WO 92/15585 discloses 1-azabicyclo[3.2.2]nonan-3-amine derivatives as substance P antagonists. A Pfizer WIPO patent application (PCT Publication No. WO 93/10073) discloses ethylenediamine derivatives as substance P antagonists. PCT Publication No. WO 93/01169 discloses certain aromatic compounds as tachykinin receptor antagonists. A Sanofi publication (*Life Sci.*, 50, PL101–PL106 (1992)) discloses a 4-phenyl piperidine derivative as an antagonist of the neurokinin A (NK2) receptor.

Howson et al. (*Biorg. & Med. Chem. Lett.*, 2 (6), 559–564 (1992)) disclose certain 3-amino and 3-oxy quinuclidine compounds and their binding to substance P receptors. EPO Publication 0,499,313 discloses certain 3-oxy and 3-thio azabicyclic compounds as tachykinin antagonists. U.S. Pat. No. 3,506,673 discloses certain 3-hydroxy quinuclidine compounds as central nervous system stimulants. A Pfizer EPO Patent application (EPO Publication 0,436,334) discloses certain 3-aminopiperidine compounds as substance P antagonists. U.S. Pat. No. 5,064,838 discloses certain 1,4-disubstituted piperidinyl compounds as analgesics. PCT Publication No. WO 92/12128 discloses certain piperidine and pyrrolidine compounds as analgesics. Peyronel, et al. (*Biorg & Med. Chem. Lett.*, 2 (1), 37–40 (1992)) disclose a fused ring pyrrolidine compound as a substance P antagonist. EPO Publication No. 0,360,390 discloses certain spirolactam derivatives as substance P antagonists. U.S. Pat. No. 4,804,661 discloses certain piperazine compounds as analgesics. U.S. Pat. No. 4,943,578 discloses certain piperazine compounds useful in the treatment of pain. PCT Publication No. WO 92/01679 discloses certain 1,4-disubstituted piperazines useful in the treatment of mental disorders in which a dopaminergic deficit is implicated. PCT Publication No. WO 94/00440, EPO Publication No. 0,577,394 and PCT Publication No. WO 95/16679 disclose certain morpholine and thiomorpholine substance P antagonists, some of which are the parent compounds to the instant prodrugs.

Prodrugs are entities structurally related to a biologically active substance (the "parent drug") which, after administration, release the parent drug in vivo as the result of some metabolic process, such as enzymatic or chemical hydrolysis of a carboxylic, phosphoric or sulfate ester or reduction or oxidation of a susceptible functionality (see, for example, discussions by (1) A. A. Sinkula and S. H. Yalkowsky, *J. Pharm. Sci.* 64, 181 (1975); (2) L. A. Svensson, *Pharm Weekbl*, 122, 245–250 (1987); (3) L. P. Balant, E. Doelker and P. Buri *Eur. J. Drug Metab. and Pharmacokinetics*, 15, 143–153 (1990); (4) N. Bodor, *Drugs* of the Future, 6, 165–182 (1981); (5) Design of Biopharmaceutical Properties through Prodrugs and Analogs, E. B. Roche, Ed., American Pharmaceutical Association Academy of Pharmaceutical Sciences, Washington, D.C., (1977); (6) H. Bundgaard Advanced Drug Delivery Reviews, 3, 39–65 (1989)). The advantage of a prodrug may lie in its physical properties, such as enhanced water solubility for parenteral administration compared to the parent drug, or it may enhance absorption from the digestive tract, or it may enhance drug stability for long-ten storage. In general, a prodrug possesses less biological activity than its parent drug.

SUMMARY OF THE INVENTION

This invention is concerned with novel compounds represented by structural formula I:

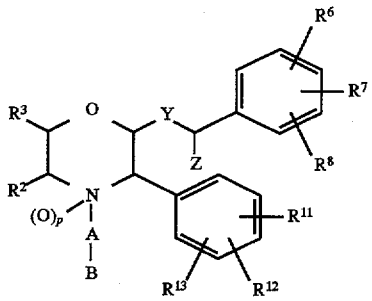

wherein $R^2$, $R^3$, $R^6$, $R^7$, $R^8$, $R^{11}$, $R^{12}$, $R^{13}$, A, B, p, Y and Z are hereinafter defined.

The invention is also concerned with pharmaceutical formulations comprising these novel compounds as active ingredients and the use of the novel compounds and their formulations in the treatment of certain disorders.

The compounds of this invention are tachykinin receptor antagonists and are useful in the treatment of inflammatory diseases, pain or migraine, asthma, and emesis.

DETAILED DESCRIPTION OF THE INVENTION

The novel compounds of this invention are represented by structural formula I:

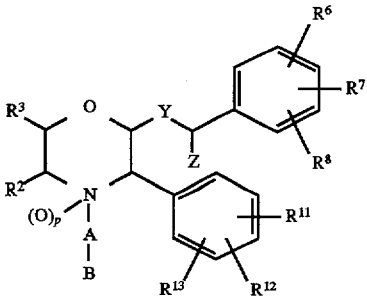

or a pharmaceutically acceptable salt thereof, wherein:
$R^2$ and $R^3$ are independently selected from the group consisting of:
(1) hydrogen,
(2) $C_{1-6}$ alkyl, unsubstituted or substituted with one or more of the substituents selected from:
  (a) hydroxy,
  (b) oxo,
  (c) $C_{1-6}$ alkoxy,
  (d) phenyl-$C_{1-3}$ alkoxy,
  (e) phenyl,
  (f) —CN,
  (g) halo,
  (h) —$NR^9R^{10}$, wherein $R^9$ and $R^{10}$ are independently selected from:
    (i) hydrogen,
    (ii) $C_{1-6}$ alkyl,
    (iii) hydroxy-$C_{1-6}$ alkyl, and
    (iv) phenyl,
  (i) —$NR^9COR^{10}$, wherein $R^9$ and $R^{10}$ are as defined above,
  (j) —$NR^9CO_2R^{10}$, wherein $R^9$ and $R^{10}$ are as defined above,
  (k) —$CONR^9R^{10}$, wherein $R^9$ and $R^{10}$ are as defined above,
  (l) —$COR^9$, wherein $R^9$ is as defined above, and
  (m) —$CO_2R^9$, wherein $R^9$ is as defined above;
(3) $C_{2-6}$ alkenyl, unsubstituted or substituted with one or more of the substituent(s) selected from:
  (a) hydroxy,
  (b) oxo,
  (c) $C_{1-6}$ alkoxy,
  (d) phenyl-$C_{1-3}$ alkoxy,
  (e) phenyl,
  (f) —CN,
  (g) halo,
  (h) —$CONR^9R^{10}$ wherein $R^9$ and $R^{10}$ are as defined above,
  (i) —$COR^9$ wherein $R^9$ is as defined above,
  (j) —$CO_2R^9$, wherein $R^9$ is as defined above;
(4) $C_{2-6}$ alkynyl;
(5) phenyl, unsubstituted or substituted with one or more of the substituent(s) selected from:
  (a) hydroxy,
  (b) $C_{1-6}$ alkoxy,
  (c) $C_{1-6}$ alkyl,
  (d) $C_{2-5}$ alkenyl,
  (e) halo,
  (f) —CN,
  (g) —$NO_2$,
  (h) —$CF_3$,
  (i) —$(CH_2)_m$—$NR^9R^{10}$, wherein m, $R^9$ and $R^{10}$ are as defined above,
  (j) —$NR^9COR^{10}$, wherein $R^9$ and $R^{10}$ are as defined above,
  (k) —$NR^9CO_2R^{10}$, wherein $R^9$ and $R^{10}$ are as defined above,
  (l) —$CONR^9R^{10}$, wherein $R^9$ and $R^{10}$ are as defined above,
  (m) —$CO_2NR^9R^{10}$, wherein $R^9$ and $R^{10}$ are as defined above,
  (n) —$COR^9$, wherein $R^9$ is as defined above;
  (o) —$CO_2R^9$, wherein $R^9$ is as defined above;
and, alternatively, the groups $R^2$ and $R^3$ are joined together to form a carbocyclic ring selected from the group consisting of:
(a) cyclopentyl,
(b) cyclohexyl,
(c) phenyl,
and wherein the carbocyclic ring is unsubstituted or substituted with one or more substituents selected from:
(i) $C_{1-6}$alkyl,
(ii) $C_{1-6}$alkoxy,
(iii) —$NR^9R^{10}$, wherein $R^9$ and $R^{10}$ are as defined above,
(iv) halo, and
(v) trifluoromethyl;

and, alternatively, the groups $R^2$ and $R^3$ are joined together to form a heterocyclic ring selected from the group consisting of:
- (a) pyrrolidinyl,
- (b) piperidinyl,
- (c) pyrrolyl,
- (d) pyridinyl,
- (e) imidazolyl,
- (f) furanyl,
- (g) oxazolyl,
- (h) thienyl, and
- (i) thiazolyl, and wherein the heterocyclic ring is unsubstituted or substituted with one or more substituent(s) selected from:
- (i) $C_{1-6}$alkyl,
- (ii) oxo,
- (iii) $C_{1-6}$alkoxy,
- (iv) —$NR^9R^{10}$, wherein $R^9$ and $R^{10}$ are as defined above,
- (v) halo, and
- (vi) trifluoromethyl;

$R^6$, $R^7$ and $R^8$ are independently selected from the group consisting of:
(1) hydrogen;
(2) $C_{1-6}$ alkyl, unsubstituted or substituted with one or more of the substituents selected from:
- (a) hydroxy,
- (b) oxo,
- (c) $C_{1-6}$ alkoxy,
- (d) phenyl-$C_{1-3}$ alkoxy,
- (e) phenyl,
- (f) —CN,
- (g) halo,
- (h) —$NR^9R^{10}$, wherein $R^9$ and $R^{10}$ are as defined above,
- (i) —$NR^9COR^{10}$, wherein $R^9$ and $R^{10}$ are as defined above,
- (j) —$NR^9CO_2R^{10}$, wherein $R^9$ and $R^{10}$ are as defined above,
- (k) —$CONR^9R^{10}$, wherein $R^9$ and $R^{10}$ are as defined above,
- (l) —$COR^9$, wherein $R^9$ is as defined above, and
- (m) —$CO_2R^9$, wherein $R^9$ is as defined above;

(3) $C_{2-6}$ alkenyl, unsubstituted or substituted with one or more of the substituent(s) selected from:
- (a) hydroxy,
- (b) oxo,
- (c) $C_{1-6}$ alkoxy,
- (d) phenyl-$C_{1-3}$ alkoxy,
- (e) phenyl,
- (f) —CN,
- (g) halo,
- (h) —$CONR^9R^{10}$ wherein $R^9$ and $R^{10}$ are as defined above,
- (i) —$COR^9$ wherein $R^9$ is as defined above,
- (j) —$CO_2R^9$, wherein $R^9$ is as defined above;

(4) $C_{2-6}$ alkynyl;
(5) phenyl, unsubstituted or substituted with one or more of the substituent(s) selected from:
- (a) hydroxy,
- (b) $C_{1-6}$ alkoxy,
- (c) $C_{1-6}$ alkyl,
- (d) $C_{2-5}$ alkenyl,
- (e) halo,
- (f) —CN,
- (g) —$NO_2$,
- (h) —$CF_3$,
- (i) —$(CH_2)_m$—$NR^9R^{10}$, wherein m, $R^9$ and $R^{10}$ are as defined above,
- (j) —$NR^9COR^{10}$, wherein $R^9$ and $R^{10}$ are as defined above,
- (k) —$NR^9CO_2R^{10}$, wherein $R^9$ and $R^{10}$ are as defined above,
- (l) —$CONR^9R^{10}$, wherein $R^9$ and $R^{10}$ are as defined above,
- (m) —$CO_2NR^9R^{10}$, wherein $R^9$ and $R^{10}$ are as defined above,
- (n) —$COR^9$, wherein $R^9$ is as defined above;
- (o) —$CO_2R^9$, wherein $R^9$ is as defined above;

(6) halo,
(7) —CN,
(8) —$CF_3$,
(9) —$NO_2$,
(10) —$SR^{14}$, wherein $R^{14}$ is hydrogen or $C_{1-5}$alkyl,
(11) —$SOR^{14}$, wherein $R^{14}$ is as defined above,
(12) —$SO_2R^{14}$, wherein $R^{14}$ is as defined above,
(13) $NR^9COR^{10}$, wherein $R^9$ and $R^{10}$ are as defined above,
(14) $CONR^9COR^{10}$, wherein $R^9$ and $R^{10}$ are as defined above,
(15) $NR^9R^{10}$, wherein $R^9$ and $R^{10}$ are as defined above,
(16) $NR^9CO_2R^{10}$, wherein $R^9$ and $R^{10}$ are as defined above,
(17) hydroxy,
(18) $C_{1-6}$alkoxy,
(19) $COR^9$, wherein $R^9$ is as defined above,
(20) $CO_2R^9$, wherein $R^9$ is as defined above,
(21) 2-pyridyl,
(22) 3-pyridyl,
(23) 4-pyridyl,
(24) 5-tetrazolyl,
(25) 2-oxazolyl, and
(26) 2-thiazolyl;

$R^{11}$, $R^{12}$ and $R^{13}$ are independently selected from the definitions of $R^6$, $R^7$ and $R^8$, or —OX;

A is selected from the group consisting of:
(1) $C_{1-6}$ alkyl, unsubstituted or substituted with one or more of the substituents selected from:
- (a) hydroxy,
- (b) oxo,
- (c) $C_{1-6}$ alkoxy,
- (d) phenyl-$C_{1-3}$ alkoxy,
- (e) phenyl,
- (f) —CN,
- (g) halo, wherein halo is fluoro, chloro, bromo or iodo,
- (h) —$NR^9R^{10}$, wherein $R^9$ and $R^{10}$ are as defined above,
- (i) —$NR^9COR^{10}$, wherein $R^9$ and $R^{10}$ are as defined above,
- (j) —$NR^9CO_2R^{10}$, wherein $R^9$ and $R^{10}$ are as defined above,
- (k) —$CONR^9R^{10}$, wherein $R^9$ and $R^{10}$ are as defined above,
- (l) —$COR^9$, wherein $R^9$ is as defined above, and
- (m) —$CO_2R^9$, wherein $R^9$ is as defined above;

(2) $C_{2-6}$ alkenyl, unsubstituted or substituted with one or more of the substituent(s) selected from:
- (a) hydroxy,
- (b) oxo,
- (c) $C_{1-6}$ alkoxy,
- (d) phenyl-$C_{1-3}$ alkoxy,
- (e) phenyl,
- (f) —CN, (g) halo, (h) —CONR⁹R¹⁰ wherein $R^9$ and $R^{10}$ are as defined above, (i) —COR⁹ wherein $R^9$ is as defined above, and (j) —CO₂R⁹, wherein $R^9$ is as defined above; and (3) $C_{2-6}$ alkynyl;

B is a heterocycle, wherein the heterocycle is selected from the group consisting of:

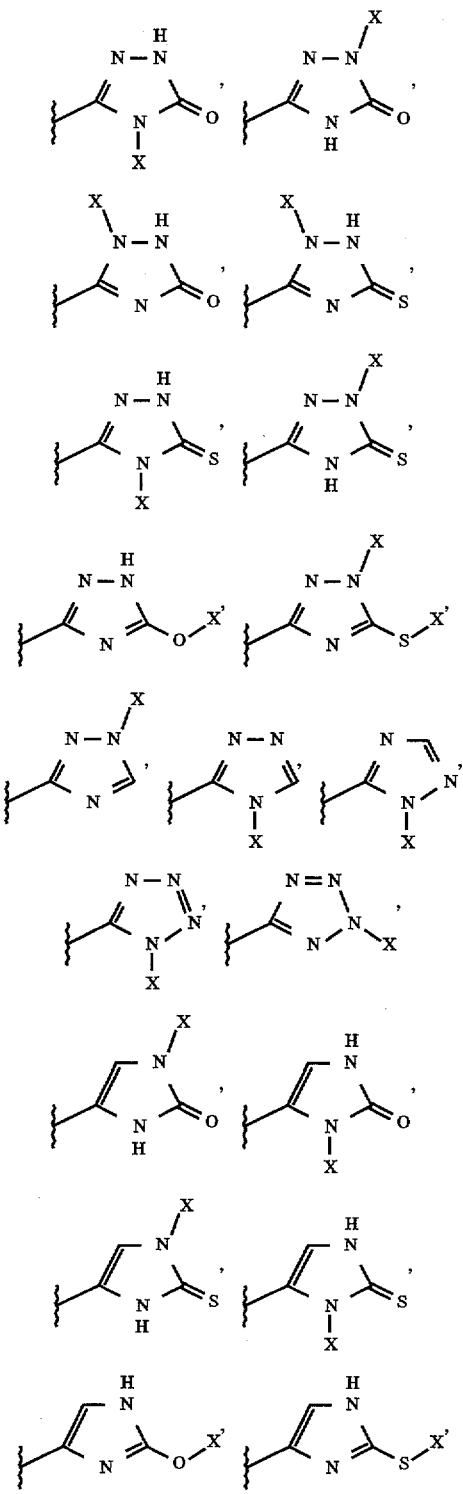
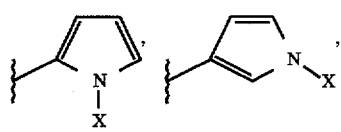
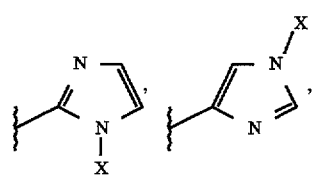
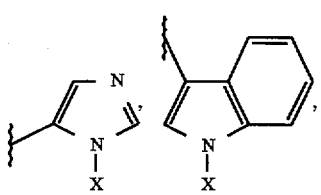
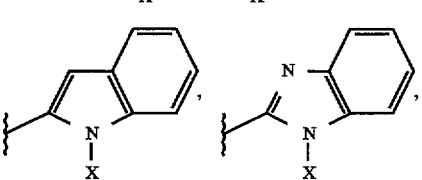

and wherein the heterocycle is substituted in addition to —X with one or more substituent(s) selected from:

(i) hydrogen (ii) $C_{1-6}$ alkyl, unsubstituted or substituted with halo, —CF₃, —OCH₃, or phenyl, (iii) $C_{1-6}$ alkoxy, (iv) oxo, (v) hydroxy, (vi) thioxo, (vii) —SR⁹, wherein $R^9$ is as defined above, (viii) halo, (ix) cyano, (x) phenyl, (xi) trifluoromethyl, (xii) —(CH₂)$_m$—NR⁹R¹⁰, wherein m is 0, 1 or 2, and $R^9$ and $R^{10}$ are as defined above, (xiii) —NR⁹COR¹⁰, wherein $R^9$ and $R^{10}$ are as defined above, (xiv) —CONR⁹R¹⁰, wherein $R^9$ and $R^{10}$ are as defined above, (xv) —CO₂R⁹, wherein $R^9$ is as defined above, and (xvi) —(CH₂)$_m$—OR⁹, wherein m and $R^9$ are as defined above;

p is 0 or 1;

X is selected from:

(a) —PO(OH)O⁻•M⁺, wherein M⁺ is a pharmaceutically acceptable monovalent counterion, (b) —PO(O⁻)₂•2M⁺, (c) —PO(O⁻)₂•D²⁺, wherein D²⁺ is a pharmaceutically acceptable divalent counterion, (d) —CH(R⁴)—PO(OH)O⁻•M⁺, wherein R⁴ is hydrogen or $C_{1-3}$ alkyl, (e) —CH(R⁴)—PO(O⁻)₂•2M⁺, (f) —CH(R⁴)—PO(O⁻)₂•D²⁺, (g) —SO₃⁻•M+, (h) —CH(R⁴)—SO₃⁻•M⁺, (i) —CO—CH₂CH₂—CO₂⁻•M⁺, (j) —CH(CH₃)—O—CO—R⁵, wherein R⁵ is selected from the group consisting of:

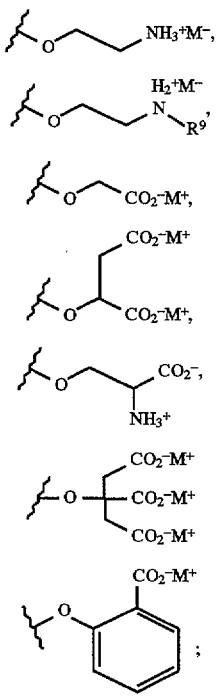

and (k) hydrogen, with the proviso that if p is 0 and none of $R^{11}$, $R^{12}$ or $R^{13}$ are —OX, then X is other than hydrogen;

Y is selected from the group consisting of:
(1) a single bond,
(2) —O—,
(3) —S—,
(4) —CO—,
(5) —CH₂—,
(6) —CHR¹⁵—, and
(7) —CR¹⁵R¹⁶—, wherein $R^{15}$ and $R^{16}$ are independently selected from the group consisting of:
(a) C₁₋₆ alkyl, unsubstituted or substituted with one or more of the substituents selected from:
(i) hydroxy,
(ii) oxo,
(iii) C₁₋₆ alkoxy,
(iv) phenyl-C₁₋₃ alkoxy,
(v) phenyl,
(vi) —CN,
(vii) halo,
(viii) —NR⁹R¹⁰, wherein $R^9$ and $R^{10}$ are as defined above,
(ix) —NR⁹COR¹⁰, wherein $R^9$ and $R^{10}$ are as defined above,
(x) —NR⁹CO₂R¹⁰, wherein $R^9$ and $R^{10}$ are as defined above,
(xi) —CONR⁹R¹⁰, wherein $R^9$ and $R^{10}$ are as defined above,
(xii) —COR⁹, wherein $R^9$ is as defined above, and
(xiii) —CO₂R⁹, wherein $R^9$ is as defined above;
(b) phenyl, unsubstituted or substituted with one or more of the substituent(s) selected from:
(i) hydroxy,
(ii) C₁₋₆ alkoxy,
(iii) C₁₋₆ alkyl,
(iv) C₂₋₅ alkenyl,
(v) halo,
(vi) —CN,
(vii) —NO₂,
(viii) —CF₃,
(ix) —(CH₂)ₘ—NR⁹R¹⁰, wherein m, $R^9$ and $R^{10}$ are as defined above,
(x) —NR⁹COR¹⁰, wherein $R^9$ and $R^{10}$ are as defined above,
(xi) —NR⁹CO₂R¹⁰, wherein $R^9$ and $R^{10}$ are as defined above,
(xii) —CONR⁹R¹⁰, wherein $R^9$ and $R^{10}$ are as defined above,
(xiii) —CO₂NR⁹R¹⁰, wherein $R^9$ and $R^{10}$ are as defined above,
(xiv) —COR⁹, wherein $R^9$ is as defined above, and
(xv) —CO₂R⁹, wherein $R^9$ is as defined above;

Z is selected from:
(1) hydrogen,
(2) C₁₋₆ alkyl, and
(3) hydroxy, with the proviso that if Y is —O—, Z is other than hydroxy, or if Y is —CHR¹⁵—, then Z and $R^{15}$ are optionally joined together to form a double bond.

The instant compounds are prodrugs of their parent compounds. A principal advantage of the instant compounds is that they possess enhanced solubility in aqueous solutions relative to their parent compounds. In addition, the prodrugs generally have diminished activity at antagonizing tachykinin receptors than their parent compounds. Thus, the activity exhibited upon administration of the prodrug is principally due to the presence of the parent compound that results from cleavage of the prodrug.

The term "prodrug" refers to compounds which are drug precursors which, following administration and absorption, release the drug in vivo via some metabolic process.

Prodrugs are entities structurally related to an biologically active substance (the "parent drug") which, after administration, release the parent drug in vivo as the result of some metabolic process, such as enzymatic or chemical hydrolysis of a carboxylic, phosphoric or sulfate ester or reduction or oxidation of a susceptible functionality (see, for example, discussions by (1) A. A. Sinkula and S. H. Yalkowsky, *J. Pharm. Sci*, 64, 181 (1975); (2) L. A. Sevensson, *Pharm Weekbl*, 122, 245–250 (1987); (3) L. P. Balant, E. Doelker and P. Buri *Eur. J. Drug Metab. and Pharmacokinetics*, 15, 143–153 (1990); (4) N. Bodor, *Drugs of the Future*, 6, 165–182 (1981); (5) *Design of Biopharmaceutical Properties through Prodrugs and Analogs.*, E. B. Roche, Ed., American Pharmaceutical Association Academy of Pharmaceutical Sciences, Washington, D.C., (1977); (6) H. Bundgaard *Advanced Drug Delivery Reviews*, 3, 39–65 (1989)). The advantage of a prodrug may lie in its physical properties, such as enhanced water solubility for parenteral administration compared to the parent drug, or it may enhance absorption from the digestive tract, or it may enhance drug stability for long-term storage. In general, a prodrug possesses less biological activity than its parent drug. A prodrug may also improve overall drug efficacy, for example, through the reduction of toxicity and unwanted effects of a drug by controlling its absorption, blood levels, metabolic distribution and cellular uptake.

The term "parent compound" or "parent drug" refers to the biologically active entity that is released via enzymatic action of a metabolic or a catabolic process, or via a chemical process following administration of the prodrug.

The parent compound may also be the starting material for the preparation of its corresponding prodrug.

While all of the usual routes of administration are useful with the present compounds, the preferred routes of administration are oral and intravenous. After gastrointestinal absorption or intravenous administration, the present compounds are hydrolyzed or otherwise cleaved in vivo to the corresponding parent compounds of formula I, wherein X is hydrogen or X is absent, or a salt thereof. Since the parent compounds may be relatively insoluble in aqueous solutions, the instant prodrugs provide a distinct advantage by virtue of their relatively enhanced aqueous solubility.

The compounds of the present invention have asymmetric centers and this invention includes all of the optical isomers and mixtures thereof.

In addition compounds with carbon-carbon double bonds may occur in Z- and E- forms with all isomeric forms of the compounds being included in the present invention.

When any variable (e.g., alkyl, aryl, $R^6$, $R^7$, $R^8$, $R^9$, $R^{10}$, $R^{11}$, $R^{12}$, $R^{13}$, etc.) occurs more than one time in any variable or in Formula I, its definition on each ocurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy. "Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethylpentyl, and the like, and includes E and Z forms, where applicable. "Halogen" or "halo", as used herein, means fluoro, chloro, bromo and iodo.

The compounds of the present invention are capable of forming salts with various inorganic and organic acids and bases and such salts are also within the scope of this invention. Examples of such acid addition salts (which are negative counterions defined herein as "$M^-$") include acetate, adipate, benzoate, benzenesulfonate, bisulfate, butyrate, camphorate, camphorsulfonate, citrate, ethanesulfonate, fumarate, hemisulfate, 2-hydroxyethylsulfonate, heptanoate, hexanoate, hydrochloride, hydrobromide, hydroiodide, lactate, malate, maleate, methanesulfonate, 2-naphthalenesulfonate, oxalate, pamoate, persulfate, picrate, pivalate, propionate, salicylate, stearate, succinate, surf ate, tartrate, tosylate (p-toluenesulfonate), and undecanoate. Base salts (which are pharmaceutically acceptable monovalent cations defined herein as "$M^+$ or $K^+$" or pharmaceutically acceptable divalent cations defined herein as "$D^{2+}$", if appropriate) include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. If $M^+$ is a monovalent cation, it is recognized that if the definition $2M^+$ is present, each of $M^+$ may be the same or different. In addition, it is similarly recognized that if the definition $2M^+$ is present, a divalent cation $D^{2+}$ may instead be present. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

In the compounds of formula I it is preferred that:

$R^2$ and $R^3$ are independently selected from the group consisting of:
(1) hydrogen,
(2) $C_{1-6}$ alkyl,
(3) $C_{2-6}$ alkenyl, and
(4) phenyl;

$R^6$, $R^7$ and $R^8$ are independently selected from the group consisting of:
(1) hydrogen,
(2) $C_{1-6}$ alkyl,
(3) fluoro,
(4) chloro,
(5) bromo,
(6) iodo, and
(7) —$CF_3$;

$R^{11}$, $R^{12}$ and $R^{13}$ are independently selected from the group consisting of:
(1) fluoro,
(2) chloro,
(3) bromo, and
(4) iodo;

A is unsubstituted $C_{1-6}$ alkyl;

B is selected from the group consisting of:

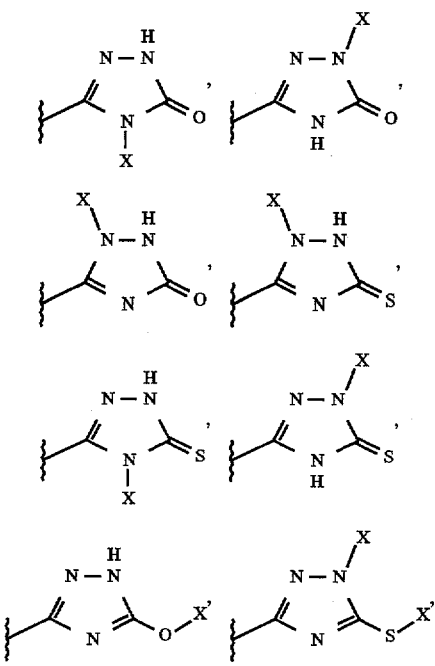

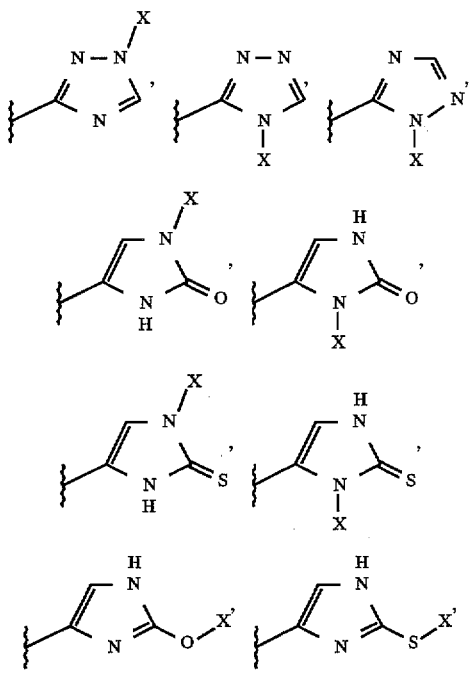

p is 0;

X is selected from:

(a) —PO(OH)O⁻•M⁺, wherein M⁺ is a pharmaceutically acceptable monovalent counterion, (b) —PO(O⁻)$_2$•2M⁺, (c) —PO(O⁻)$_2$•D²⁺, wherein D²⁺ is a pharmaceutically acceptable divalent counterion, (d) —CH(R⁴)—PO(OH)O⁻•M⁺, wherein R⁴ is hydrogen or methyl, (e) —CH(R⁴)—PO(O⁻)$_2$•2M⁺, wherein R⁴ is hydrogen or methyl, (f) —CH(R⁴)—PO(O⁻)$_2$•D²⁺, wherein R⁴ is hydrogen or methyl, (i) —CO—CH$_2$CH$_2$—CO$_2$⁻•M⁺, (j) —CH(CH$_3$)—O—CO—R⁵, wherein R⁵ is selected from the group consisting of:

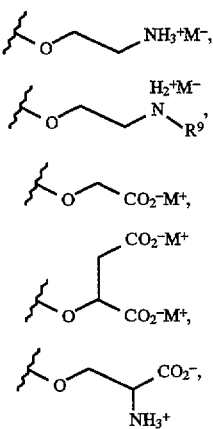

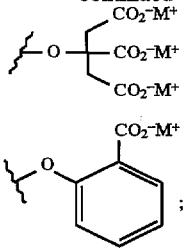
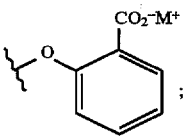

and

Y is —O—;

Z is hydrogen or C$_{1-4}$ alkyl.

In the compounds of the present invention a preferred embodiment includes those compounds wherein Z is C$_{1-4}$ alkyl. An especially preferred embodiment of the compounds of formula I includes those compounds wherein Z is —CH$_3$. These compounds bearing a substituent on the alpha-carbon atom exibit advantageous pharmacological properties, in particular, enhanced duration of action in models of extravasation, presumably due to biological stability and resistance to enzymatic degradation.

In the compounds of the present invention if p is 1, it is preferred that X is hydrogen or is absent.

In the compounds of the present invention a particularly preferred embodiment is that in which A is —CH$_2$— or —CH(CH$_3$)—.

A particularly preferred embodiment of the compounds of the present invention includes the prodrugs of compounds of formula I wherein —A—B is a (1,2,4-triazolo)methyl or a (5-oxo-1,2,4-triazolo)methyl group.

Another particularly preferred embodiment of the compounds of the present invention includes the prodrugs of compounds of formula I wherein —A—B is a (1,3-imidazolo)methyl or a (5-oxo-1,3-imidazolo)methyl group.

An additional particularly preferred embodiment of the compounds of the present invention includes those compounds of formula I wherein —A—B is a (1,2,4-triazolo) methyl or a (5-oxo-1,2,4-triazolo)methyl group beating a phosphoryl group attached to the heterocycle.

Yet another particularly preferred embodiment of the compounds of the present invention includes those compounds of formula I wherein —A—B is a (1,3-imidazolo) methyl or a (1,3-imidazolo)methyl group bearing a phosphoryl group attached to the heterocycle.

A preferred embodiment of the compounds of the present invention includes the compounds of formula I wherein X is selected from:

(a) —PO(O⁻)$_2$•2M⁺, wherein M⁺ is a pharmaceutically acceptable monovalent counterion, (b) —PO(O⁻)$_2$•D²⁺, wherein D²⁺ is a pharmaceutically acceptable divalent counterion, (c) —CH(CH$_3$)—O—CO—CH$_2$CH$_2$—NH$_3$⁺•M⁻, and (d) —CH(CH$_3$)—O—CO—CH$_2$CH$_2$—NH$_2$⁺—(CH$_2$CH$_2$—OH)•M⁻.

In the compounds of the present invention a particularly preferred embodiment is that in which —A—B is selected from the following group of substituents:

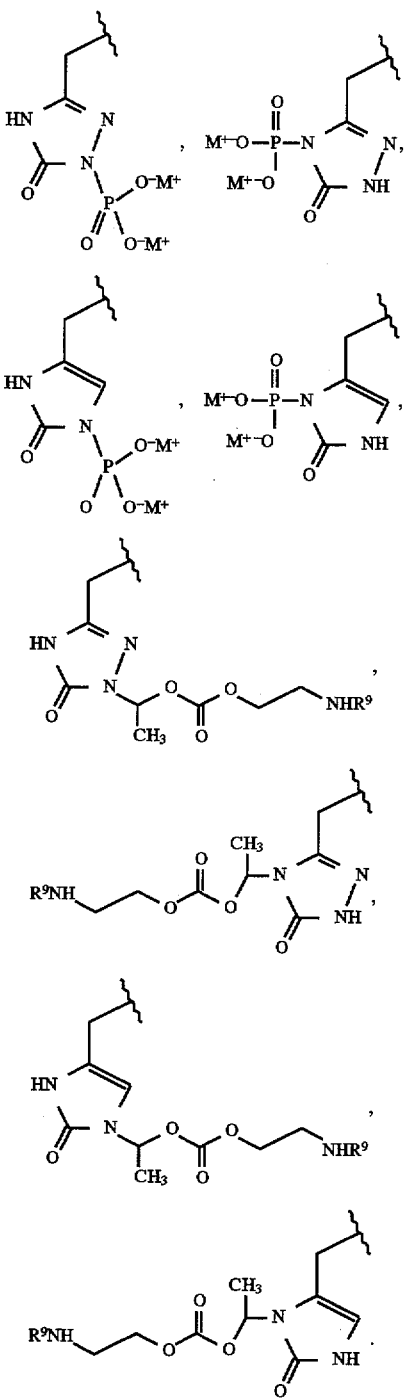

Specific compounds within the scope of the present invention include the prodrugs of the following parent compounds:
1) (±)-2-(3,5-bis(trifluoromethyl)benzyloxy)-3-phenylmorpholine;
2) (2R,S)-(3,5-bis(trifluoromethyl)benzyloxy)-(3R)-phenyl-(6R)-methyl-morpholine;
3) (2R,S)-(3,5-bis(trifluoromethyl)benzyloxy)-(3S)-phenyl-(6R)-methyl-morpholine;
4) (±)-2,(3,5-bis(trifluoromethyl)benzyloxy)-3-phenyl-4-methylcarboxamido-morpholine;
5) (±)-2-(3,5-bis(trifluoromethyl)benzyloxy)-3-phenyl-4-methoxycarbonylmethyl-morpholine;
6) 2-(2-(3,5-bis(trifluoromethyl)phenyl)ethenyl)-3-phenyl-5-oxo-morpholine;
7) 3-phenyl-2-(2-(3,5-bis(trifluoromethyl)phenyl)-ethyl) morpholine;
8) 2-(R)-(3,5-bis(trifluoromethyl)benzyloxy)-3-(R)-phenyl-6-(S)-methyl-morpholine;
9) 2-(R)-(3,5-bis(trifluoromethyl)benzyloxy)-3-(S)-phenyl-6-(S)-methyl-morpholine;
10) 2-(S)-(3,5-bis(trifluoromethyl)benzyloxy)-3-(R)-phenyl-6-(S)-methyl-morpholine;
11) 2-(S)-(3,5-bis(trifluoromethyl)benzyloxy)-3-(S)-phenyl-6-(S)-methyl-morpholine;
12) 2-(R)-(3,5-bis(trifluoromethyl)benzyloxy)-3-(R)-phenyl-5-(R)-methyl-morpholine;
13) 2-(R)-(3,5-bis(trifluoromethyl)benzyloxy)-3-(S)-phenyl-5-(R)-methyl-morpholine;
14) 2-(S)-(3,5-bis(trifluoromethyl)benzyloxy)-3-(R)-phenyl-5-(R)-methyl-morpholine;
15) 2-(S)-(3,5-bis(trifluoromethyl)benzyloxy)-3-(S)-phenyl-5-(R)-methyl-morpholine;
16) 2-(S)-(3,5-bis(trifluoromethyl)benzyloxy)-3-(S)-phenyl-morpholine;
17) 4-(3-(1,2,4-triazolo)methyl)-2-(S)-(3,5-bis(trifluoromethyl)benzyloxy)-3-(S)-phenyl-morpholine;
18) 4-(3-(5-oxo-1H,4H-1,2,4-triazolo)methyl)-2-(S)-(3,5-bis(trifluoromethyl)benzyloxy)-3-(S)-phenyl-morpholine;
19) 2-(R)-(3,5-bis(trifluoromethyl)benzyloxy)-3-(R)-phenyl-6-(R)-methyl-morpholine;
20) 2-(S)-(3,5-bis(trifluoromethyl)benzyloxy)-3-(R)-phenyl-6-(R)-methyl-morpholine;
21) 2-(R)-(3,5-bis(trifluoromethyl)benzyloxy)-3-(S)-phenyl-6-(R)-methyl-morpholine;
22) 2-(S)-(3,5-bis(trifluoromethyl)benzyloxy)-3-(S)-phenyl-6-(R)-methyl-morpholine;
23) 2-(R)-(3,5-bis(trifluoromethyl)-benzyloxy)-3-(S)-phenyl-5-(S)-methyl-morpholine;
24) 2-(S)-(3,5-bis(trifluoromethyl)benzyloxy)-3-(S)-phenyl-5-(S)-methyl-morpholine;
25) 2-(R)-(3,5-bis(trifluoromethyl)benzyloxy)-3-(R)-phenyl-5-(S)-methyl-morpholine;
26) 2-(R)-(3,5-bis(trifluoromethyl)benzyloxy)-3-(S)-phenyl-5-(R)-phenyl-morpholine;
27) 2-(S)-(3,5-bis(trifluoromethyl)benzyloxy)-3-(S)-phenyl-5-(R)-phenyl-morpholine;
28) 2-(S)-(3,5-bis(trifluoromethyl)benzyloxy)-3-(R)-phenyl-5-(S)-phenyl-morpholine;
29) 2-(R)-(3,5-bis(trifluoromethyl)benzyloxy)-3-(R)-phenyl-5-(S)-phenyl-morpholine;
30) 2-(S)-(3,5-bis(trifluoromethyl)benzyloxy)-6-(R)-methyl-3-(S)-phenyl-4-(3-(1,2,4-triazolo)methyl)-morpholine;
31) 2-(S)-(3,5-bis(trifluoromethyl)benzyloxy)-6-(R)-methyl-4-(3-(5-oxo-1H,4H-1,2,4-triazolo)methyl)-3-(S)-phenyl-morpholine;
32) 2-(S)-(3,5-bis(trifluoromethyl)benzyloxy)-3-(R)-phenylmorpholine;
33) 4-(3-(1,2,4-triazolo)methyl)-2-(S)-(3,5-bis(trifluoromethyl)benzyloxy)-3-(R)-phenyl-morpholine;
34) 4-(3-(5-oxo-1H,4H-1,2,4-triazolo)methyl)-2-(S)-(3,5-bis-(trifluoromethyl)benzyloxy)-3-(R)-phenyl-morpholine;
35) 4-(2-(imidazolo)methyl)-2-(S)-(3,5-bis(trifluoromethyl)benzyloxy)-3-(R)-phenyl-morpholine;
36) 4-(4-(imidazolo)methyl)-2-(S)-(3,5-bis(trifluoromethyl)benzyloxy)-3-(R)-phenyl-morpholine;
37) 4-(aminocarbonylmethyl)-2-(S)-(3,5-bis(trifluoromethyl)benzyloxy)-3-(R)-phenyl-morpholine;

38) 4-(2-(imidazolo)methyl)-2-(S)-(3,5-bis(trifluoromethyl)benzyloxy)-3-(S)-phenyl-morpholine;
39) 4-(4-(imidazolo)methyl)-2-(S)-(3,5-bis(trifluoromethyl)benzyloxy)-3-(S)-phenyl-morpholine;
40) 4-(2-(imidazolo)methyl)-2-(S)-(3,5-bis(trifluoromethyl)benzyloxy)-3-(S)-phenyl-6-(R)-methyl-morpholine;
41) 4-(4-(imidazolo)methyl)-2-(S)-(3,5-bis(trifluoromethyl)benzyloxy)-3-(S)-phenyl-6(R)-methyl-morpholine;
42) 2-(S)-(3,5-bis(trifluoromethyl)benzyloxy)-4-((6-hydroxy)-hexyl)-3-(R)-phenyl-morpholine;
43) 2-(S)-(3,5-bis(trifluoromethyl)benzyloxy)-4-(5-(methylaminocarbonyl)pentyl)-3-(R)-phenyl-morpholine;
44) 4-(3-(1,2,4-triazolo)methyl)-2-(3,5-dimethylbenzyloxy)-3-phenylmorpholine;
45) 4-(3-(5-oxo-1H,4H-1,2,4-triazolo)methyl)-2-(3,5-dimethyl)benzyloxy)-3-phenyl-morpholine;
46) 4-(3-(1,2,4-triazolo)methyl)-2-(3,5-di(tert-butyl)benzyloxy)-3-phenylmorpholine;
47) 4-(3-(5-oxo-1H,4H-1,2,4-triazolo)methyl)-2-(3,5-di(tert-butyl)benzyloxy)-3-phenyl-morpholine;
48) 4-(3-(1,2,4-triazolo)methyl)-2-(3-(tert-butyl)-5-methylbenzyloxy)-3-phenyl-morpholine;
49) 4-(3-(5-oxo-1H,4H-1,2,4-triazolo)methyl)-2-(3-(tert-butyl)-5-methylbenzyloxy)-3-phenyl-morpholine;
50) 4-(3-(1,2,4-triazolo)methyl)-2-(3-(trifluoro-methyl)-5-methyl-benzyloxy)-3-phenyl-morpholine;
51) 4-(3-(5-oxo-1H,4H-1,2,4-triazolo)methyl)-2-(3-(trifluoromethyl)-5-methylbenzyloxy)-3-phenyl-morpholine;
52) 4-(3-(1,2,4-triazolo)methyl)-2-(3-(tert-butyl)-5-(trifluoromethyl)benzyloxy)-3-phenyl-morpholine;
53) 4-(3-(5-oxo-1H,4H-1,2,4-triazolo)methyl)-2-(3-(tert-butyl)-5-(trifluoromethyl)benzyloxy)-3-phenyl-morpholine;
54) 4-(2-(imidazolo)methyl)-2-(3,5-dimethyl-benzyloxy)-3-phenyl-morpholine;
55) 4-(4-(imidazolo)methyl)-2-(3,5-dimethyl-benzyloxy)-3-phenyl-morpholine;
56) 4-(2-(imidazolo)methyl)-2-(3,5-di(tert-butyl)-benzyloxy)-3-phenyl-morpholine;
57) 4-(4-(imidazolo)methyl)-2-(3,5-di(tert-butyl)-benzyloxy)-3-phenyl-morpholine;
58) 4-(2-(imidazolo)methyl)-2-(3-(tert-butyl)-5-methylbenzyloxy)-3-phenyl-morpholine;
59) 4-(4-(imidazolo)methyl)-2-(3-(tert-butyl)-5-methylbenzyloxy)-3-phenyl-morpholine;
60) 4-(2-(imidazolo)methyl)-2-(3-(trifluoro-methyl)-5-methylbenzyloxy)-3-phenyl-morpholine;
61) 4-(4-(imidazolo)methyl)-2-(3-(trifluoro-methyl)-5-methylbenzyloxy)-3-phenyl-morpholine;
62) 4-(2-(imidazolo)methyl)-2-(3-(tert-butyl)-5-(trifluoromethyl)benzyloxy)-3-phenyl-morpholine;
63) 2-(S)-(3,5-dichlorobenzyloxy)-3-(S)-phenyl-morpholine;
64) 2-(S)-(3,5-dichlorobenzyloxy)-4-(3-(5-oxo-1H,4H-1,2,4-triazolo)methyl)-3-(S)-phenylmorpholine;
65) 2-(S)-(3,5-bis(trifluoromethyl)benzyloxy)-4-(methoxycarbonylmethyl)-3-(S)-phenyl-morpholine;
66) 2-(S)-(3,5-bis(trifluoromethyl)benzyloxy)-4-(carboxymethyl)-3-(S)-phenyl-morpholine;
67) 2-(S)-(3,5-bis(trifluoromethyl)benzyloxy)-4-((2-aminoethyl)aminocabonylmethyl)-3-(S)-phenyl-morpholine;
68) 2-(S)-(3,5-bis(trifluoromethyl)benzyloxy)-4-((3-aminopropyl)amino carbonylmethyl)-3-(S)-phenylmorpholine;
69) 4-benzyl-5-(S),6-(R)-dimethyl-3-(S)-phenylmorpholinone and 4-benzyl-5-(R),6-(S)-dimethyl-3-(S)-phenyl-morpholinone;
70) 2-(R)-(3,5-bis(trifluoromethyl)benzyloxy)-[5-(S),6-(R) or 5-(R),6-(S)-dimethyl]-3-(S)-phenyl-morpholinone;
71) 2-(S)-(3,5-bis(trifluoromethyl)benzyloxy)-[5-(R),6-(S) or 5-(S),6-(R)-dimethyl]-3-(S)-phenyl-morpholinone;
72) 2-(R)-(3,5-bis(trifluoromethyl)benzyloxy)-4-(3-(1,2,4-triazolo)methyl)-[5-(S),6-(R) or 5-(R),6-(S)-dimethyl]-3-(S)-phenyl-morpholinone;
73) 2-(R)-(3,5-bis(trifluoromethyl)benzyloxy)-4-(3-(5-oxo-1H,4H-1,2,4-triazolo)methyl)-[5-(S),6-(R) or 5-(R),6-(S)-dimethyl]-3-(S)-phenyl-morpholinone;
74) 2-(S)-(3,5-bis(trifluoromethyl)benzyloxy)-4-(3-(1,2,4-triazolo)methyl)-[5-(R),6-(S) or 5-(S),6-(R)-dimethyl]-3-(S)-phenyl-morpholinone;
75) 2-(S)-(3,5-bis(trifluoromethyl)benzyloxy)-4-(3-(5-oxo-1H,4H-1,2,4-triazolo)methyl)-[5-(R),6-(S) or 5-(S),6-(R)-dimethyl]-3-(S)-phenyl-morpholinone;
76) 2-(S)-(3,5-bis(trifluoromethyl)benzyloxy)-4-(2-(1-(4-benzyl)piperidino)ethyl)-3-(S)-phenyl-morpholine;
77) 3-(S)-(4-fluorophenyl)-4-benzyl-2-morpholinone;
78) 2-(S)-(3,5-bis(trifluoromethyl)benzyloxy)-3-(S)-(4-fluorophenyl)-4-benzyl-morpholine;
79) 2-(S)-(3,5-Bis(trifluoromethyl)benzyloxy)-3-(S)-(4-fluorophenyl)morpholine;
80) 2-(S)-(3,5-bis(trifluoromethyl)benzyloxy)-3-(S)-(4-fluorophenyl)-4-(3-(5-oxo-1H,4H-1,2,4-triazolo)methyl-morpholine;
81) 2-(S)-(3,5-bis(trifluoromethyl)benzyloxy)-4-((3-pyridyl)methyl carbonyl)-3-(R)-phenyl-morpholine;
82) 2-(S)-(3,5-bis(trifluoromethyl)benzyloxy)-4-(methoxycarbonylpentyl)-3-(R)-phenyl-morpholine;
83) 2-(S)-(3,5-bis(trifluoromethyl)benzyloxy)-4-(carboxypentyl)-3-(R)-phenyl-morpholine;
84) 2-(S)-(3,5-bis(trifluoromethyl)benzyloxy)-4-(methylaminocarbonylpentyl)-6-oxo-hexyl)-3-(R)-phenyl-morpholine;
85) 2-(R)-(3,5-bis(trifluoromethyl)benzoyloxy)-3-(S)-phenyl-4-benzyl-morpholine;
86) 2-(R)-(1-(3,5-bis(trifluoromethyl)phenyl)ethenyloxy)-3-(S)-phenyl-4-benzyl-morpholine;
87) 2-(R)-(1-(S)-(3,5-bis(trifluoromethyl)phenyl)ethoxy)-3-(S)-phenyl-morpholine;
88) 2-(R)-(1-(R)-(3,5-bis(trifluoromethyl)phenyl)ethoxy)-3-(S)-phenyl-morpholine;
89) 2-(R)-(1-(S)-(3,5-Bis(trifluoromethyl)phenyl)ethoxy)-3-(S)-phenyl-4-(3-(5-oxo-1H,4H-1,2,4-triazolo)methyl-morpholine;
90) 2-(R)-(1-(R)-(3,5-bis(trifluoromethyl)phenyl)ethoxy)-3-(S)-phenyl-4-(3-(5-oxo-1H,4H-1,2,4-triazolo)methyl-morpholine;
91) 2-(R)-(3,5-bis(trifluoromethyl)benzoyloxy)-3-(S)-(4-fluoro)phenyl-4-benzyl-morpholine;
92) 2-(R)-(1-(3,5-bis(trifluoromethyl)phenyl)ethenyloxy)-3-(S)-(4-fluoro)phenyl-4-benzyl-morpholine;
93) 2-(R)-(1-(S)-(3,5-bis(trifluoromethyl)phenyl)ethoxy)-3-(S)-(4-fluoro)phenyl-morpholine;
94) 2-(R)-(1-(R)-(3,5-bis(trifluoromethyl)phenyl)ethoxy)-3-(S)-(4-fluoro)phenyl-morpholine;
95) 2-(R)-(1-(S)-(3,5-bis(trifluoromethyl)phenyl)ethoxy)-3-(S)-(4-fluoro)phenyl-4-(3-(5-oxo-1H,4H-1,2,4-triazolo)methylmorpholine;
96) 2-(R)-(1-(R)-(3,5-bis(trifluoromethyl)phenyl)ethoxy)-3-(S)-(4-fluoro)phenyl-4-(3-(5-oxo-1H,4H-1,2,4-triazolo)methylmorpholine;
97) 2-(R)-(1-(R)-(1-(3-(methyl)naphthyl))ethoxy)-3-(S)-phenyl-4-(3-(1,2,4-triazolo)methyl-morpholine;

98) 2-(R)-(1-(R)-(1-(3-(methyl)naphthyl))ethoxy)-3-(S)-phenyl-4-(4-(2-oxo-1,3-imidazolo)methyl-morpholine;

99) 2-(R)-(1-(R)-(3-(fluoro)-5-(trifluoromethyl)phenyl)ethoxy)-3-(S)-phenyl-morpholine;

100) 2-(R)-(1-(R)-(3-(fluoro)-5-(trifluoromethyl)phenyl)ethoxy)-3-(S)-phenyl-4-(3-(5-oxo-1H,4H-1,2,4-triazolo)methyl)morpholine;

101) 2-(R)-(1-(R)-(3-(chloro)-5-(trifluoromethyl)phenyl)ethoxy)-3-(S)-phenyl-morpholine;

102) 2-(R)-(1-(R)-(3-(chloro)-5-(trifluoromethyl)phenyl)ethoxy)-3-(S)-phenyl-4-(3-(5-oxo-1H,4H-1,2,4-triazolo)methyl)morpholine;

103) 2-(R)-(1-(R)-(3,5-(dimethyl)phenyl)ethoxy)-3-(S)-phenylmorpholine;

104) 2-(R)-(1-(R)-(3,5-(dimethyl)phenyl)ethoxy)-3-(S)-phenyl-4-(3-(5-oxo-1H,4H-1,2,4-triazolo)methyl)-morpholine;

105) 2-(R)-(1-(R)-(3-(fluoro)-5-(methyl)phenyl)ethoxy)-3-(S)-phenylmorpholine;

106) 2-(R)-(1-(R)-(3-(fluoro)-5-(methyl)phenyl)ethoxy)-3-(S)-phenyl-4-(3-(5-oxo-1H,4H-1,2,4-triazolo)methyl)-morpholine;

107) 2-(R)-(1-(R)-(3-(chloro)-5-(methyl)phenyl)ethoxy)-3-(S)-phenyl-morpholine;

108) 2-(R)-(1-(R)-(3-(chloro)-5-(methyl)phenyl)ethoxy)-3-(S)-phenyl-4-(3-(5-oxo-1H,4H-1,2,4-triazolo)methyl)-morpholine;

109) 2-(R)-(1-(R)-(3-(bromo)-5-(methyl)phenyl)ethoxy)-3-(S)-phenyl-morpholine;

110) 2-(R)-(1-(R)-(3-(bromo)-5-(methyl)phenyl)ethoxy)-3-(S)-phenyl-4-(3-(5-oxo-1H,4H-1,2,4-triazolo)methyl)-morpholine;

111) 2-(R)-(1-(R)-(3-(isopropoxy)phenyl)ethoxy)-3-(S)-phenylmorpholine;

112) 2-(R)-(1-(R)-(3-(isopropoxy)phenyl)ethoxy)-3-(S)-phenyl-4-(3-(5-oxo-1H,4H-1,2,4-triazolo)methyl)-morpholine;

113) 2-(R)-(1-(R)-(3-(isopropoxy)-5-trifluoromethyl)phenyl)ethoxy)-3-(S)-phenyl-morpholine;

114) 2-(R)-(1-(R)-(3-(isopropoxy)-5-trifluoromethyl)phenyl)ethoxy)-3-(S)-phenyl-4-(3-(5-oxo-1H,4H-1,2,4-triazolo)methyl)morpholine;

115) 2-(R)-(1-(R)-(3-(chloro)-5-(isopropoxy)phenyl)ethoxy)-3-(S)-phenyl-morpholine;

116) 2-(R)-(1-(R)-(3-(chloro)-5-(isopropoxy)phenyl)ethoxy)-3-(S)-phenyl-4-(3-(5-oxo-1H,4H-1,2,4-triazolo)methyl)-morpholine;

117) 2-(R)-(1-(R)-(3-(fluoro)-5-(isopropoxy)phenyl)ethoxy)-3-(S)-phenyl-morpholine;

118) 2-(R)-(1-(R)-(3-(fluoro)-5-(isopropoxy)phenyl)ethoxy)-3-(S)-phenyl-4-(3-(5-oxo-1H,4H-1,2,4-triazolo)methyl)-morpholine;

119) 2-(R)-(1-(R)-(1-(3-(trifluoromethyl)naphthyl))ethoxy)-3-(S)-phenyl-4-(3-(1,2,4-triazolo)methyl)-morpholine;

120) 2-(R)-(1-(R)-(1-(3-(trifluoromethyl)naphthyl))ethoxy)-3-(S)-phenyl-4-(4-(2-oxo-1,3-imidazolo)methyl)-morpholine;

121) 2-(R)-(1-(R)-(3-(t-butyl)-5-(chloro)phenyl) ethoxy)-3-(S)-phenylmorpholine;

122) 2-(R)-(1-(R)-(3-(t-butyl)-5-(chloro)phenyl)ethoxy)-3-(S)-phenyl-4-(3-(5-oxo-1H,4H-1,2,4-triazolo)methyl)-morpholine;

123) 2-(R)-(1-(R)-(3-(t-butyl)-5-(trifluoromethyl)phenyl)ethoxy)-3-(S)-phenyl-morpholine;

124) 2-(R)-(1-(R)-(3-(t-butyl)-5-(trifluoromethyl)phenyl)ethoxy)-3-(S)-phenyl-4-(3-(5-oxo-1H,4H-1,2,4-triazolo)methyl)morpholine;

125) 2-(R)-(1-(R)-(3,5-(dimethyl)-4-(fluoro)phenyl)ethoxy)-3-(S)-phenyl-morpholine;

126) 2-(R)-(1-(R)-(3,5-(dimethyl)-4-(fluoro)phenyl)ethoxy)-3-(S)-phenyl-4-(3-(5-oxo-1H,4H-1,2,4-triazolo)methyl)-morpholine;

127) 2-(R)-(1-(R)-(3,5-(dimethyl)-4-(chloro)phenyl)ethoxy)-3-(S)-phenyl-morpholine;

128) 2-(R)-(1-(R)-(3,5-(dimethyl)-4-(chloro)phenyl)ethoxy)-3-(S)-phenyl-4-(3-(5-oxo-1H,4H-1,2,4-triazolo)methyl)-morpholine;

129) 2-(R)-(1-(R)-(3,5-bis(trifluoromethyl)-4-(fluoro)phenyl)ethoxy)-3-(S)-phenyl-morpholine;

130) 2-(R)-(1-(R)-(3,5-bis(trifluoromethyl)-4-(fluoro)phenyl)ethoxy)-3-(S)-phenyl-4-(3-(5-oxo-1H,4H-1,2,4-triazolo)methyl)morpholine;

131) 2-(R)-(1-(R)-(3,5-bis(trifluoromethyl)-4-chloro)phenyl)ethoxy)-3-(S)-phenyl-morpholine;

132) 2-(R)-(1-(R)-(3,5-bis(trifluoromethyl)-4-chloro)phenyl)ethoxy)-3-(S)-phenyl-4-(3-(5-oxo-1H,4H-1,2,4-triazolo)methyl)morpholine;

133) 2-(R)-(1-(R)-(3,5-(dichloro)phenyl)ethoxy)-3-(S)-phenylmorpholine;

134) 2-(R)-(1-(R)-(3,5-(dichloro)phenyl)ethoxy)-3-(S)-phenyl-4-(3-(5-oxo-1H,4H-1,2,4-triazolo)methyl)-morpholine;

135) 2-(R)-(1-(R)-(3,5-(difluoro)phenyl)ethoxy)-3-(S)-phenylmorpholine;

136) 2-(R)-(1-(R)-(3,5-(difluoro)phenyl)ethoxy)-3-(S)-phenyl-4-(3-(5-oxo-1H,4H-1,2,4-triazolo)methyl)-morpholine;

137) 2-(R)-(1-(R)-(1-(naphthyl)ethoxy)-3-(S)-phenyl-morpholine;

138) 2-(R)-(1-(R)-(1-(naphthyl)ethoxy)-3-(S)-phenyl-4-(3-(5-oxo-1H,4H-1,2,4-triazolo)methylmorpholine;

139) 2-(R)-(1-(R)-(1-(4-(fluoro)naphthyl))ethoxy)-3-(S)-phenylmorpholine;

140) 2-(R)-(1-(R)-(1-(4-(fluoro)naphthyl))ethoxy)-3-(S)-phenyl-4-(3-(5-oxo-1H,4H-1,2,4-triazolo)methyl)-morpholine;

141) 2-(R)-(1-(R)-(1-(3-(fluoro)naphthyl))ethoxy)-3-(S)-phenylmorpholine;

142) 2-(R)-(1-(R)-(1-(3-(fluoro)naphthyl))ethoxy)-3-(S)-phenyl-4-(3-(5-oxo-1H,4H-1,2,4-triazolo)methyl)-morpholine;

143) 2-(R)-(1-(R)-(1-(3-(chloro)naphthyl))ethoxy)-3-(S)-phenylmorpholine;

144) 2-(R)-(1-(R)-(1-(3-chloro)naphthyl))ethoxy)-3-(S)-phenyl-4-(3-(5-oxo-1H,4H-1,2,4-triazolo)methyl)-morpholine;

145) 2-(R)-(1-(R)-(1-(3-(methyl)naphthyl))ethoxy)-3-(S)-phenylmorpholine;

146) 2-(R)-(1-(R)-(1-(3-(methyl)naphthyl))ethoxy)-3-(S)-phenyl-4-(3-(5-oxo-1H,4H-1,2,4-triazolo)methyl)-morpholine;

147) 2-(R)-(1-(R)-(1-(3-(trifluoromethyl)naphthyl))ethoxy)-3-(S)-phenyl-morpholine;

148) 2-(R)-(1-(R)-(1-(3-(trifluoromethyl)naphthyl))ethoxy)-3-(S)-phenyl-4-(3-(5-oxo-1H,4H-1,2,4-triazolo)methyl)-morpholine;

149) 2-(S)-(3,5-bis(trifluoromethyl)benzyloxy)-3-(S)-(4-hydroxy)phenyl-morpholine;

150) 2-(S)-(3,5-bis(trifluoromethyl)benzyloxy)-3-(S)-(4-hydroxy)phenyl-4-(3-(5-oxo-1H,4H-1,2,4-triazolo)methyl)-morpholine;

151) 2-(S)-(2-fluoro-5-trifluoromethyl)benzyloxy-3-(S)-phenylmorpholine;

152) 2-(S)-(2-fluoro-5-trifluoromethyl)benzyloxy-3-(S)-(4-fluoro)phenyl-morpholine;

153) 2-(R)-(1-(R)-(2-fluoro-5-trifluoromethyl)phenylethoxy)-3-(S)-phenyl-morpholine;
154) 2-(R)-(1-(R)-(2-fluoro-5-trifluoromethyl)phenylethoxy)-3-(S)-(4-fluoro)phenyl-morpholine;
155) 2-(S)-(2-fluoro-5-trifluoromethyl)benzyloxy-3-(S)-phenyl-4-(3-(1,2,4-triazolo)methyl)-morpholine;
156) 2-(S)-(2-fluoro-5-trifluoromethyl)benzyloxy-3-(S)-(4-fluoro)phenyl-4-(3-(1,2,4-triazolo)methyl)-morpholine;
157) 2-(R)-(1-(R)-(2-fluoro-5-trifluoromethyl)phenylethoxy)-3-(S)-phenyl-4-(3-(1,2,4-triazolo)methyl)-morpholine;
158) 2-(R)-(1-(R)-(2-fluoro-5-trifluoromethyl)phenylethoxy)-3-(S)-(4-fluoro)phenyl-4-(3-(1,2,4-triazolo)methyl)-morpholine;
159) 2-(S)-(2-fluoro-5-trifluoromethyl)benzyloxy-3-(S)-phenyl-4-(3-(5-oxo-1H,4H-1,2,4-triazolo)methyl)-morpholine;
160) 2-(S)-(2-fluoro-5-trifluoromethyl)benzyloxy-3-(S)-(4-fluoro)phenyl-4-(3-(5-oxo-1H,4H-1,2,4-triazolo)methyl)morpholine;
161) 2-(R)-(1-(R)-(2-fluoro-5-trifluoromethyl)phenylethoxy)-3-(S)-phenyl-4-(3-(5-oxo-1H,4H-1,2,4-triazolo)methyl)-morpholine;
162) 2-(R)-(1-(R)-(2-fluoro-5-trifluoromethyl)phenylethoxy)-3-(S)-(4-fluoro)phenyl-4-(3-(5-oxo-1H,4H-1,2,4-triazolo)methyl)morpholine;
163) 2-(S)-(2-fluoro-5-trifluoromethyl)benzyloxy-3-(S)-phenyl-4-(4-(2-oxo-1,3-imidazolo)methyl)-morpholine;
164) 2-(S)-(2-fluoro-5-trifluoromethyl)benzyloxy-3-(S)-(4-fluoro)phenyl-4-(4-(2-oxo-1,3-imidazolo)methyl)-morpholine;
165) 2-(R)-(1-(R)-(2-fluoro-5-trifluoromethyl)phenylethoxy)-3-(S)-phenyl-4-(4-(2-oxo-1,3-imidazolo)methyl)-morpholine;
166) 2-(R)-(1-(R)-(2-fluoro-5-trifluoromethyl)phenylethoxy)-3-(S)-(4-fluoro)phenyl-4-(4-(2-oxo-1,3-imidazolo)methyl)-morpholine;
167) 2-(S)-(2-fluoro-5-trifluoromethyl)benzyloxy-3-(S)-phenyl-4-(2-imidazolo)methyl-morpholine;
168) 2-(S)-(2-fluoro-5-trifluoromethyl)benzyloxy-3-(S)-(4-fluoro)phenyl-4-(2-imidazolo)methyl-morpholine;
169) 2-(R)-(1-(R)-(2-fluoro-5-trifluoromethyl)phenylethoxy)-3-(S)-phenyl-4-(2-imidazolo)methyl-morpholine;
170) 2-(R)-(1-(R)-(2-fluoro-5-trifluoromethyl)phenylethoxy)-3-(S)-(4-fluoro)phenyl-4-(2-imidazolo)methyl-morpholine;
171) 2-(S)-(2-fluoro-5-trifluoromethyl)benzyloxy-3-(S)-phenyl-4-(4-imidazolo)methyl-morpholine;
172) 2-(S)-(2-fluoro-5-trifluoromethyl)benzyloxy-3-(S)-(4-fluoro)phenyl-4-(4-imidazolo)methyl-morpholine;
173) 2-(R)-(1-(R)-(2-fluoro-5-trifluoromethyl)phenylethoxy)-3-(S)-phenyl-4-(4-imidazolo)methyl-morpholine;
174) 2-(R)-(1-(R)-(2-fluoro-5-trifluoromethyl)phenylethoxy)-3-(S)-(4-fluoro)phenyl-4-(4-imidazolo)methyl-morpholine;
175) 2-(S)-(2-fluoro-5-trifluoromethyl)benzyloxy-3-(S)-phenyl-4-(5-tetrazolo)methyl-morpholine;
176) 2-(S)-(2-fluoro-5-trifluoromethyl)benzyloxy-3-(S)-(4-fluoro)phenyl-4-(5-tetrazolo)methyl-morpholine;
177) 2-(R)-(1-(R)-(2-fluoro-5-trifluoromethyl)phenylethoxy)-3-(S)-phenyl-4-(5-tetrazolo)methyl-morpholine;
178) 2-(R)-(1-(R)-(2-fluoro-5-trifluoromethyl)phenylethoxy)-3-(S)-(4-fluoro)phenyl-4-(5-tetrazolo)methyl-morpholine;
179) 2-(S)-(2-fluoro-5-trifluoromethyl)benzyloxy-3-(S)-phenyl-4-(2-oxo-5H-pyrrol-4-yl)methyl-morpholine;
180) 2-(S)-(2-fluoro-5-trifluoromethyl)benzyloxy-3-(S)-(4-fluoro)phenyl-4-(2-oxo-5H-pyrrol-4-yl)methyl-morpholine;
181) 2-(R)-(1-(R)-(2-fluoro-5-trifluoromethyl)phenylethoxy)-3-(S)-phenyl-4-(2-oxo-5H-pyrrol-4-yl)methyl-morpholine;
182) 2-(R)-(1-(R)-(2-fluoro-5-trifluoromethyl)phenylethoxy)-3-(S)-(4-fluoro)phenyl-4-(2-oxo-5H-pyrrol-4-yl)methyl-morpholine;
183) 2-(S)-(2-chloro-5-trifluoromethyl)benzyloxy-3-(S)-phenylmorpholine;
184) 2-(S)-(2-chloro-5-trifluoromethyl)benzyloxy-3-(S)-(4-fluoro)phenyl-morpholine;
185) 2-(R)-(1-(R)-(2-chloro-5-trifluoromethyl)phenylethoxy)-3-(S)-phenyl-morpholine;
186) 2-(R)-(1-(R)-(2-chloro-5-trifluoromethyl)phenylethoxy)-3-(S)-(4-fluoro)phenyl-morpholine;
187) 2-(S)-(2-chloro-5-trifluoromethyl)benzyloxy-3-(S)-phenyl-4-(3-(1,2,4-triazolo)methyl-morpholine;
188) 2-(S)-(2-chloro-5-trifluoromethyl)benzyloxy-3-(S)-(4-fluoro)phenyl-4-(3-(1,2,4-triazolo)methyl)-morpholine;
189) 2-(R)-(1-(R)-(2-chloro-5-trifluoromethyl)phenylethoxy)-3-(S)-phenyl-4-(3-(1,2,4-triazolo)methyl)-morpholine;
190) 2-(R)-(1-(R)-(2-chloro-5-trifluoromethyl)phenylethoxy)-3-(S)-(4-fluoro)phenyl-4-(3-(1,2,4-triazolo)methyl)-morpholine;
191) 2-(S)-(2-chloro-5-trifluoromethyl)benzyloxy-3-(S)-phenyl-4-(3-(5-oxo-1H,4H-1,2,4-triazolo)methyl)-morpholine;
192) 2-(S)-(2-chloro-5-trifluoromethyl)benzyloxy-3-(S)-(4-fluoro)phenyl-4-(3-(5-oxo-1H,4H-1,2,4-triazolo)methyl)morpholine;
193) 2-(R)-(1-(R)-(2-chloro-5-trifluoromethyl)phenylethoxy)-3-(S)-phenyl-4-(3-(5-oxo-1H,4H-1,2,4-triazolo)methyl)-morpholine;
194) 2-(R)-(1-(R)-(2-chloro-5-trifluoromethyl)phenylethoxy)-3-(S)-(4-fluoro)phenyl-4-(3-(5-oxo-1H,4H-1,2,4-triazolo)methyl)morpholine;
195) 2-(S)-(2-chloro-5-trifluoromethyl)benzyloxy-3-(S)-phenyl-4-(4-(2-oxo-1,3-imidazolo)methyl)-morpholine;
196) 2-(S)-(2-chloro-5-trifluoromethyl)benzyloxy-3-(S)-(4-fluoro)phenyl-4-(4-(2-oxo-1,3-imidazolo)methyl)-morpholine;
197) 2-(R)-(1-(R)-(2-chloro-5-trifluoromethyl)phenylethoxy)-3-(S)-phenyl-4-(4-(2-oxo-1,3-imidazolo)methyl)-morpholine;
198) 2-(R)-(1-(R)-(2-chloro-5-trifluoromethyl)phenylethoxy)-3-(S)-(4-fluoro)phenyl-4-(4-(2-oxo-1,3-imidazolo)methyl)-morpholine;
199) 2-(S)-(2-chloro-5-trifluoromethyl)benzyloxy-3-(S)-phenyl-4-(2-imidazolo)methyl)-morpholine;
200) 2-(S)-(2-chloro-5-trifluoromethyl)benzyloxy-3-(S)-(4-fluoro)phenyl-4-(2-imidazolo)methyl)-morpholine;
201) 2-(R)-(1-(R)-(2-chloro-5-trifluoromethyl)phenylethoxy)-3-(S)-phenyl-4-(2-imidazolo)methyl)-morpholine;
202) 2-(R)-(1-(R)-(2-chloro-5-trifluoromethyl)phenylethoxy)-3-(S)-(4-fluoro)phenyl-4-(2-imidazolo)methyl)-morpholine;
203) 2-(S)-(2-chloro-5-trifluoromethyl)benzyloxy-3-(S)-phenyl-4-(4-imidazolo)methyl)-morpholine;
204) 2-(S)-(2-chloro-5-trifluoromethyl)benzyloxy-3-(S)-(4-fluoro)phenyl-4-(4-imidazolo)methyl-morpholine;
205) 2-(R)-(1-(R)-(2-chloro-5-trifluoromethyl)phenylethoxy)-3-(S)-phenyl-4-(4-imidazolo)methyl-morpholine;

206) 2-(R)-(1-(R)-(2-chloro-5-trifluoromethyl)phenylethoxy)-3-(S)-(4-fluoro)phenyl-4-(4-imidazolo)methyl-morpholine;
207) 2-(S)-(2-chloro-5-trifluoromethyl)benzyloxy-3-(S)-phenyl-4-(5-tetrazolo)methyl-morpholine;
208) 2-(S)-(2-chloro-5-trifluoromethyl)benzyloxy-3-(S)-(4-fluoro)phenyl-4-(5-tetrazolo)methyl-morpholine;
209) 2-(R)-(1-(R)-(2-chloro-5-trifluoromethyl)phenylethoxy)-3-(S)-phenyl-4-(5-tetrazolo)methyl-morpholine;
210) 2-(R)-(1-(R)-(2-chloro-5-trifluoromethyl)phenylethoxy)-3-(S)-(4-fluoro)phenyl-4-(5-tetrazolo)methyl-morpholine;
211) 2-(S)-(2-chloro-5-trifluoromethyl)benzyloxy-3-(S)-phenyl-4-(2-oxo-5H-pyrrol-4-yl)methyl-morpholine;
212) 2-(S)-(2-chloro-5-trifluoromethyl)benzyloxy-3-(S)-(4-fluoro)phenyl-4-(2-oxo-5H-pyrrol-4-yl)methyl-morpholine;
213) 2-(R)-(1-(R)-(2-chloro-5-trifluoromethyl)phenylethoxy)-3-(S)-phenyl-4-(2-oxo-5 H -pyrrol-4-yl)methyl-morpholine;
214) 2-(R)-(1-(R)-(2-Chloro-5-trifluoromethyl)phenylethoxy)-3-(S)-(4-fluoro)phenyl-4-(2-oxo-5H-pyrrol-4-yl)methyl-morpholine;
215) 2-(S)-(3-methyl)benzyloxy-3-(S)-phenyl-morpholine;
216) 2-(S)-(3-methyl)benzyloxy-3-(S)-(4-fluoro)phenyl-morpholine;
217) 2-(R)-(1-(R)-(3-methyl)phenylethoxy)-3-(S)-phenyl-morpholine;
218) 2-(R)-(1-(R)-(3-methyl)phenylethoxy)-3-(S)-(4-fluoro)phenyl-morpholine;
219) 2-(S)-(3-methyl)benzyloxy-3-(S)-phenyl-4-(3-(1,2,4-triazolo)methyl)-morpholine;
220) 2-(S)-(3-methyl)benzyloxy-3-(S)-(4-fluoro)phenyl-4-(3-(1,2,4-triazolo)methyl)-morpholine;
221) 2-(R)-(1-(R)-(3-methyl)phenylethoxy)-3-(S)-phenyl-4-(3-(1,2,4-triazolo)methyl)-morpholine;
222) 2-(R)-(1-(R)-(3-methyl)phenylethoxy)-3-(S)-(4-fluoro)phenyl-4-(3-(1,2,4-triazolo)methyl)-morpholine;
223) 2-(S)-(3-methyl)benzyloxy-3-(S)-phenyl-4-(3-(5-oxo-1,2,4-triazolo)methyl)-morpholine;
224) 2-(S)-(3-methyl)benzyloxy-3-(S)-(4-fluoro)phenyl-4-(3-(5-oxo-1,2,4-triazolo)methyl)-morpholine;
225) 2-(R)-(1-(R)-(3-methyl)phenylethoxy)-3-(S)-phenyl-4-(3-(5-oxo-1,2,4-triazolo)methyl)-morpholine;
226) 2-(R)-(1-(R)-(3-methyl)phenylethoxy)-3-(S)-(4-fluoro)phenyl-4-(3-(5-oxo-1,2,4-triazolo)methyl)-morpholine;
227) 2-(S)-(3-methyl)benzyloxy-3-(S)-phenyl-4-(4-(2-oxo-1,3-imidazolo)methyl)-morpholine;
228) 2-(S)-(3-methyl)benzyloxy-3-(S)-(4-fluoro)phenyl-4-(4-(2-oxo-1,3-imidazolo)methyl)-morpholine;
229) 2-(R)-(1-(R)-(3-methyl)phenylethoxy)-3-(S)-phenyl-4-(4-(2-oxo-1,3-imidazolo)methyl)-morpholine;
230) 2-(R)-(1-(R)-(3-methyl)phenylethoxy)-3-(S)-(4-fluoro)phenyl-4-(4-(2-oxo-1,3-imidazolo)methyl)-morpholine;
231) 2-(S)-(3-methyl)benzyloxy-3-(S)-phenyl-4-(2-imidazolo)methylmorpholine;
232) 2-(S)-(3-methyl)benzyloxy-3-(S)-(4-fluoro)phenyl-4-(2-imidazolo)methyl-morpholine;
233) 2-(R)-(1-(R)-(3-methyl)phenylethoxy)-3-(S)-phenyl-4-(2-imidazolo)methyl-morpholine;
234) 2-(R)-(1-(R)-(3-methyl)phenylethoxy)-3-(S)-(4-fluoro)phenyl-4-(2-imidazolo)methyl-morpholine;
235) 2-(S)-(3-methyl)benzyloxy-3-(S)-phenyl-4-(4-imidazolo)methyl-morpholine;
236) 2-(S)-(3-methyl)benzyloxy-3-(S)-(4-fluoro)phenyl-4-(4-imidazolo)methyl-morpholine;
237) 2-(R)-(1-(R)-(3-methyl)phenylethoxy)-3-(S)-phenyl-4-(4-imidazolo)methyl-morpholine;
238) 2-(R)-(1-(R)-(3-methyl)phenylethoxy)-3-(S)-(4-fluoro)phenyl-4-(4-imidazolo)methyl-morpholine;
239) 2-(S)-(3-methyl)benzyloxy-3-(S)-phenyl-4-(5-tetrazolo)methyl-morpholine;
240) 2-(S)-(3-methyl)benzyloxy-3-(S)-(4-fluoro)phenyl-4-(5-tetrazolo)methyl-morpholine;
241) 2-(R)-(1-(R)-(3-methyl)phenylethoxy)-3-(S)-phenyl-4-(5-tetrazolo)methyl-morpholine;
242) 2-(R)-(1-(R)-(3-methyl)phenylethoxy)-3-(S)-(4-fluoro)phenyl-4-(5-tetrazolo)methyl-morpholine;
243) 2-(S)-(3-methyl)benzyloxy-3-(S)-phenyl-4-(2-oxo-5H-pyrrol-4-yl)methyl-morpholine;
244) 2-(S)-(3-methyl)benzyloxy-3-(S)-(4-fluoro)phenyl-4-(2-oxo-5H-pyrrol-4-yl)methyl-morpholine;
245) 2-(R)-(1-(R)-(3-methyl)phenylethoxy)-3-(S)-phenyl-4-(2-oxo-5H-pyrrol-4-yl)methyl-morpholine;
246) 2-(R)-(1-(R)-(3-methyl)phenylethoxy)-3-(S)-(4-fluoro)phenyl-4-(2-oxo-5H-pyrrol-4-yl)methyl-morpholine;
247) 2-(S)-(3-bromo)benzyloxy-3-(S)-phenyl-morpholine;
248) 2-(S)-(3-bromo)benzyloxy-3-(S)-(4-fluoro)phenyl-morpholine;
249) 2-(R)-(1-(R)-(3-bromo)phenylethoxy)-3-(S)-phenyl-morpholine;
250) 2-(R)-(1-(R)-(3-bromo)phenylethoxy)-3-(S)-(4-fluoro)phenyl-morpholine;
251) 2-(S)-(3-bromo)benzyloxy-3-(S)-phenyl-4-(3-(1,2,4-triazolo)methyl-morpholine;
252) 2-(S)-(3-bromo)benzyloxy-3-(S)-(4-fluoro)phenyl-4-(3-(1,2,4-triazolo)methyl-morpholine;
253) 2-(R)-(1-(R)-(3-bromo)phenylethoxy)-3-(S)-phenyl-4-(3-(1,2,4-triazolo)methyl-morpholine;
254) 2-(R)-(1-(R)-(3-bromo)phenylethoxy)-3-(S)-(4-fluoro)phenyl-4-(3-(1,2,4-triazolo)methyl-morpholine;
255) 2-(S)-(3-bromo)benzyloxy-3-(S)-phenyl-4-(3-(5-oxo-1H,4H-1,2,4-triazolo)methyl-morpholine;
256) 2-(S)-(3-bromo)benzyloxy-3-(S)-(4-fluoro)phenyl-4-(3-(5-oxo-1H,4H-1,2,4-triazolo)methyl-morpholine;
257) 2-(R)-(1-(R)-(3-bromo)phenylethoxy)-3-(S)-phenyl-4-(3-(5-oxo-1H,4Ho 1,2,4-triazolo)methyl)-morpholine;
258) 2-(R)-(1-(R)-(3-bromo)phenylethoxy)-3-(S)-(4-fluoro)phenyl-4-(3-(5-oxo-1H,4H-1,2,4-triazolo)methyl)-morpholine;
259) 2-(S)-(3-bromo)benzyloxy-3-(S)-phenyl-4-(4-(2-oxo-1,3-imidazolo)methyl)-morpholine;
260) 2-(S)-(3-bromo)benzyloxy-3-(S)-(4-fluoro)phenyl-4-(4-(2-oxo-1,3-imidazolo)methyl)-morpholine;
261) 2-(R)-(1-(R)-(3-bromo)phenylethoxy)-3-(S)-phenyl-4-(4-(2-oxo-1,3-imidazolo)methyl)-morpholine;
262) 2-(R)-(1-(R)-(3-bromo)phenylethoxy)-3-(S)-(4-fluoro)phenyl-4-(4-(2-oxo-1,3-imidazolo)methyl)-morpholine;
263) 2-(S)-(3-bromo)benzyloxy-3-(S)-phenyl-4-(2-imidazolo)methyl-morpholine;
264) 2-(S)-(3-bromo)benzyloxy-3-(S)-(4-fluoro)phenyl-4-(2-imidazolo)methyl-morpholine;
265) 2-(R)-(1-(R)-(3-bromo)phenylethoxy)-3-(S)-phenyl-4-(2-imidazolo)methyl-morpholine;
266) 2-(R)-(1-(R)-(3-bromo)phenylethoxy)-3-(S)-(4-fluoro)phenyl-4-(2-imidazolo)methyl-morpholine;
267) 2-(S)-(3-bromo)benzyloxy-3-(S)-phenyl-4-(4-imidazolo)methyl-morpholine;
268) 2-(S)-(3-bromo)benzyloxy-3-(S)-(4-fluoro)phenyl-4-(4-imidazolo)methyl-morpholine;

269) 2-(R)-(1-(R)-(3-bromo)phenylethoxy)-3-(S)-phenyl-4-(4-imidazolo)methyl-morpholine;
270) 2-(R)-(1-(R)-(3-bromo)phenylethoxy)-3-(S)-(4-fluoro)phenyl-4-(4-imidazolo)methyl-morpholine;
271) 2-(S)-(3-bromo)benzyloxy-3-(S)-phenyl-4-(5-tetrazolo)methyl-morpholine;
272) 2-(S)-(3-bromo)benzyloxy-3-(S)-(4-fluoro)phenyl-4-(5-tetrazolo)methyl-morpholine;
273) 2-(R)-(1-(R)-(3-bromo)phenylethoxy)-3-(S)-phenyl-4-(5-tetrazolo)methyl-morpholine;
274) 2-(R)-(1-(R)-(3-bromo)phenylethoxy)-3-(S)-(4-fluoro)phenyl-4-(5-tetrazolo)methyl-morpholine;
275) 2-(S)-(3-bromo)benzyloxy-3-(S)-phenyl-4-(2-oxo-5H-pyrrol-4-yl)methyl-morpholine;
276) 2-(S)-(3-bromo)benzyloxy-3-(S)-(4-fluoro)phenyl-4-(2-oxo-5H-pyrrol-4-yl)methyl-morpholine;
277) 2-(R)-(1-(R)-(3-bromo)phenylethoxy)-3-(S)-phenyl-4-(2-oxo-5H-pyrrol-4-yl)methyl-morpholine;
278) 2-(R)-(1-(R)-(3-bromo)phenylethoxy)-3-(S)-(4-fluoro)phenyl-4-(2-oxo-5H-pyrrol-4-yl)methyl-morpholine;
279) 2-(S)-(3-chloro)benzyloxy-3-(S)-phenyl-morpholine;
280) 2-(S)-(3-chloro)benzyloxy-3-(S)-(4-fluoro)phenyl-morpholine;
281) 2-(R)-(1-(R)-(3-chloro)phenylethoxy)-3-(S)-phenyl-morpholine;
282) 2-(R)-(1-(R)-(3-chloro)phenylethoxy)-3-(S)-(4-fluoro)phenyl-morpholine;
283) 2-(S)-(3-chloro)benzyloxy-3-(S)-phenyl-4-(3-(1,2,4-triazolo)methyl)-morpholine;
284) 2-(S)-(3-chloro)benzyloxy-3-(S)-(4-fluoro)phenyl-4-(3-(1,2,4-triazolo)methyl)-morpholine;
285) 2-(R)-(1-(R)-(3-chloro)phenylethoxy)-3-(S)-phenyl-4-(3-(1,2,4-triazolo)methyl)-morpholine;
286) 2-(R)-(1-(R)-(3-chloro)phenylethoxy)-3-(S)-(4-fluoro)phenyl-4-(3-(1,2,4-triazolo)methyl)-morpholine;
287) 2-(S)-(3-chloro)benzyloxy-3-(S)-phenyl-4-(3-(5-oxo-1H,4H-1,2,4-triazolo)methyl)-morpholine;
288) 2-(S)-(3-chloro)benzyloxy-3-(S)-(4-fluoro)phenyl-4-(3-(5-oxo-1H,4H-1,2,4-triazolo)methyl)-morpholine;
289) 2-(R)-(1-(R)-(3-chloro)phenylethoxy)-3-(S)-phenyl-4-(3-(5-oxo-1H,4H-1,2,4-triazolo)methyl)-morpholine;
290) 2-(R)-(1-(R)-(3-chloro)phenylethoxy)-3-(S)-(4-fluoro)phenyl-4-(3-(5-oxo-1H,4H-1,2,4-triazolo)methyl)-morpholine;
291) 2-(S)-(3-chloro)benzyloxy-3-(S)-phenyl-4-(4-(2-oxo-1,3-imidazolo)methyl)-morpholine;
292) 2-(S)-(3-chloro)benzyloxy-3-(S)-(4-fluoro)phenyl-4-(4-(2-oxo-1,3-imidazolo)methyl)-morpholine;
293) 2-(R)-(1-(R)-(3-chloro)phenylethoxy)-3-(S)-phenyl-4-(4-(2-oxo-1,3-imidazolo)methyl)-morpholine;
294) 2-(R)-(1-(R)-(3-chloro)phenylethoxy)-3-(S)-(4-fluoro)phenyl-4-(4-(2-oxo-1,3-imidazolo)methyl)-morpholine;
295) 2-(S)-(3-chloro)benzyloxy-3-(S)-phenyl-4-(2-imidazolo)methyl-morpholine;
296) 2-(S)-(3-chloro)benzyloxy-3-(S)-(4-fluoro)phenyl-4-(2-imidazolo)methyl-morpholine;
297) 2-(R)-(1-(R)-(3-chloro)phenylethoxy)-3-(S)-phenyl-4-(2-imidazolo)methyl-morpholine;
298) 2-(R)-(1-(R)-(3-chloro)phenylethoxy)-3-(S)-(4-fluoro)phenyl-4-(2-imidazolo)methyl-morpholine;
299) 2-(S)-(3-chloro)benzyloxy-3-(S)-phenyl-4-(4-imidazolo)methyl-morpholine;
300) 2-(S)-(3-chloro)benzyloxy-3-(S)-(4-fluoro)phenyl-4-(4-imidazolo)methyl-morpholine;
301) 2-(R)-(1-(R)-(3-chloro)phenylethoxy)-3-(S)-phenyl-4-(4-imidazolo)methyl-morpholine;
302) 2-(R)-(1-(R)-(3-chloro)phenylethoxy)-3-(S)-(4-fluoro)phenyl-4-(4-imidazolo)methyl-morpholine;
303) 2-(S)-(3-chloro)benzyloxy-3-(S)-phenyl-4-(5-tetrazolo)methyl-morpholine;
304) 2-(S)-(3-chloro)benzyloxy-3-(S)-(4-fluoro)phenyl-4-(5-tetrazolo)methyl-morpholine;
305) 2-(R)-(1-(R)-(3-chloro)phenylethoxy)-3-(S)-phenyl-4-(5-tetrazolo)methyl-morpholine;
306) 2-(R)-(1-(R)-(3-chloro)phenylethoxy)-3-(S)-(4-fluoro)phenyl-4-(5-tetrazolo)methyl-morpholine;
307) 2-(S)-(3-chloro)benzyloxy-3-(S)-phenyl-4-(2-oxo-5H-pyrrol-4-yl)methyl-morpholine;
308) 2-(S)-(3-chloro)benzyloxy-3-(S)-(4-fluoro)phenyl-4-(2-oxo-5H-pyrrol-4-yl)methyl-morpholine;
309) 2-(R)-(1-(R)-(3-chloro)phenylethoxy)-3-(S)-phenyl-4-(2-oxo-5H-pyrrol-4-yl)methyl-morpholine;
310) 2-(R)-(1-(R)-(3-chloro)phenylethoxy)-3-(S)-(4-fluoro)phenyl-4-(2-oxo-5H-pyrrol-4-yl)methyl-morpholine;
311) 2-(S)-(3-trifluoromethyl)benzyloxy-3-(S)-phenyl-morpholine;
312) 2-(S)-(3-trifluoromethyl)benzyloxy-3-(S)-(4-fluoro)phenyl-morpholine;
313) 2-(R)-(1-(R)-(3-trifluoromethyl)phenylethoxy)-3-(S)-phenyl-morpholine;
314) 2-(R)-(1-(R)-(3-trifluoromethyl)phenylethoxy)-3-(S)-(4-fluoro)phenyl-morpholine;
315) 2-(S)-(3-trifluoromethyl)benzyloxy-3-(S)-phenyl-4-(3-1H,4H-1,2,4-triazolo)methyl-morpholine;
316) 2-(S)-(3-trifluoromethyl)benzyloxy-3-(S)-(4-fluoro)phenyl-4-(3-1H,4H-1,2,4-triazolo)methyl-morpholine;
317) 2-(R)-(1-(R)-(3-trifluoromethyl)phenylethoxy)-3-(S)-phenyl-4-(3-1H,4H-1,2,4-triazolo)methyl-morpholine;
318) 2-(R)-(1-(R)-(3-trifluoromethyl)phenylethoxy)-3-(S)-(4-fluoro)phenyl-4-(3-(1,2,4-triazolo)methyl-morpholine;
319) 2-(S)-(3-trifluoromethyl)benzyl oxy-3-(S)-phenyl-4-(3-(5-oxo)-1H,4H-1,2,4-triazolo)methyl)-morpholine;
320) 2-(S)-(3-trifluoromethyl)benzyloxy-3-(S)-(4-fluoro)phenyl-4-(3-(5-oxo-1H,4H-1,2,4-triazolo)methyl)-morpholine;
321) 2-(R)-(1-(R)-(3-trifluoromethyl)phenylethoxy)-3-(S)-phenyl-4-(3-(5-oxo-1H,4H-1,2,4-triazolo)methyl)-morpholine;
322) 2-(R)-(1-(R)-(3-trifluoromethyl)phenylethoxy)-3-(S)-(4-fluoro)phenyl-4-(3-(5-oxo-1H,4H-1,2,4-triazolo)methyl)-morpholine;
323) 2-(S)-(3-trifluoromethyl)benzyloxy-3-(S)-phenyl-4-(4-(2-oxo-1,3-imidazolo)methyl)-morpholine;
324) 2-(S)-(3-trifluoromethyl)benzyloxy-3-(S)-(4-fluoro)phenyl-4-(4-(2-oxo-1,3-imidazolo)methyl)-morpholine;
325) 2-(R)-(1-(R)-(3-trifluoromethyl)phenylethoxy)-3-(S)-phenyl-4-(4-(2-oxo-1,3-imidazolo)methyl)-morpholine;
326) 2-(R)-(1-(R)-(3-trifluoromethyl)phenylethoxy)-3-(S)-(4-fluoro)phenyl-4-(4-(2-oxo-1,3-imidazolo)methyl)-morpholine;
327) 2-(S)-(3-trifluoromethyl)benzyloxy-3-(S)-phenyl-4-(2-imidazolo)methyl-morpholine;
328) 2-(S)-(3-trifluoromethyl)benzyloxy-3-(S)-(4-fluoro)phenyl-4-(2-imidazolo)methyl-morpholine;
329) 2-(R)-(1-(R)-(3-trifluoromethyl)phenylethoxy)-3-(S)-phenyl-4-(2-imidazolo)methyl-morpholine;
330) 2-(R)-(1-(R)-(3-trifluoromethyl)phenylethoxy)-3-(S)-(4-fluoro)phenyl-4-(2-imidazolo)methyl-morpholine;
331) 2-(S)-(3-trifluoromethyl)benzyloxy-3-(S)-phenyl-4-(4-imidazolo)methyl-morpholine;
332) 2-(S)-(3-trifluoromethyl)benzyloxy-3-(S)-(4-fluoro)phenyl-4-(4-imidazolo)methyl-morpholine;
333) 2-(R)-(1-(R)-(3-trifluoromethyl)phenylethoxy)-3-(S)-phenyl-4-(4-imidazolo)methyl-morpholine;
334) 2-(R)-(1-(R)-(3-trifluoromethyl)phenylethoxy)-3-(S)-(4-fluoro)phenyl-4-(4-imidazolo)methyl-morpholine;

335) 2-(S)-(3-trifluoromethyl)benzyloxy-3-(S)-phenyl-4-(5-tetrazolo)methyl-morpholine;
336) 2-(S)-(3-trifluoromethyl)benzyloxy-3-(S)-(4-fluoro)phenyl-4-(5-tetrazolo)methyl-morpholine;
337) 2-(R)-(1-(R)-(3-trifluoromethyl)phenylethoxy)-3-(S)-phenyl-4-(5-tetrazolo)methyl-morpholine;
338) 2-(R)-(1-(R)-(3-trifluoromethyl)phenylethoxy)-3-(S)-(4-fluoro)phenyl-4-(5-tetrazolo)methyl-morpholine;
339) 2-(S)-(3-trifluoromethyl)benzyloxy-3-(S)-phenyl-4-(2-oxo-5H-pyrrol-4-yl)methyl-morpholine;
340) 2-(S)-(3-trifluoromethyl)benzyloxy-3-(S)-(4-fluoro)phenyl-4-(2-oxo-5H-pyrrol-4-yl)methyl-morpholine;
341) 2-(R)-(1-(R)-(3-trifluoromethyl)phenylethoxy)-3-(S)-phenyl-4-(2-oxo-5H-pyrrol-4-yl)methyl-morpholine;
342) 2-(R)-(1-(R)-(3-trifluoromethyl)phenylethoxy)-3-(S)-(4-fluoro)phenyl-4-(2-oxo-5H-pyrrol-4-yl)methyl-morpholine;
343) 2-(S)-(3-t-butyl)benzyloxy-3-(S)-phenyl-morpholine;
344) 2-(S)-(3-t-butyl)benzyloxy-3-(S)-(4-fluoro)phenyl-morpholine;
345) 2-(R)-(1-(R)-(3-t-butyl)phenylethoxy)-3-(S)-phenyl-morpholine;
346) 2-(R)-(1-(R)-(3-t-butyl)phenylethoxy)-3-(S)-(4-fluoro)phenyl-morpholine;
347) 2-(S)-(3-t-butyl)benzyloxy-3-(S)-phenyl-4-(3-(1,2,4-triazolo)methyl-morpholine;
348) 2-(S)-(3-t-butyl)benzyloxy-3-(S)-(4-fluoro)phenyl-4-(3-(1,2,4-triazolo)methyl-morpholine;
349) 2-(R)-(1-(R)-(3-t-butyl)phenylethoxy)-3-(S)-phenyl-4-(3-(1,2,4-triazolo)methyl-morpholine;
350) 2-(R)-(1-(R)-(3-t-butyl)phenylethoxy)-3-(S)-(4-fluoro)phenyl-4-(3-(1,2,4-triazolo)methyl-morpholine;
351) 2-(S)-(3-t-butyl)benzyloxy-3-(S)-phenyl-4-(3-(5-oxo-1H,4H-1,2,4-triazolo)methyl-morpholine;
352) 2-(S)-(3-t-butyl)benzyloxy-3-(S)-(4-fluoro)phenyl-4-(3-(5-oxo-1H,4H-1,2,4-triazolo)methyl-morpholine;
353) 2-(R)-(1-(R)-(3-t-butyl)phenylethoxy)-3-(S)-phenyl-4-(3-(5-oxo-1H,4H-1,2,4-triazolo)methyl)-morpholine;
354) 2-(R)-(1-(R)-(3-t-butyl)phenylethoxy)-3-(S)-(4-fluoro)phenyl-4-(3-(5-oxo-1H,4H-1,2,4-triazolo)methyl)-morpholine;
355) 2-(S)-(3-t-butyl)benzyloxy-3-(S)-phenyl-4-(4-(2-oxo-1,3-imidazolo)methyl-morpholine;
356) 2-(S)-(3- t-butyl)benzyloxy-3-(S)-(4-fluoro)phenyl-4-(4-(2-oxo-1,3-imidazolo)methyl-morpholine;
357) 2-(R)-(1-(R)-(3-t-butyl)phenylethoxy)-3-(S)-phenyl-4-(4-(2-oxo-1,3-imidazolo)methyl-morpholine;
358) 2-(R)-(1-(R)-(3-t-butyl)phenylethoxy)-3-(S)-(4-fluoro)phenyl-4-(4-(2-oxo-1,3-imidazolo)methyl-morpholine;
359) 2-(S)-(3-t-butyl)benzyloxy-3-(S)-phenyl-4-(2-imidazolo)methyl-morpholine;
360) 2-(S)-(3-t-butyl)benzyloxy-3-(S)-(4-fluoro)phenyl-4-(2-imidazolo)methyl-morpholine;
361) 2-(R)-(1-(R)-(3-t-butyl)phenylethoxy)-3-(S)-phenyl-4-(2-imidazolo)methyl-morpholine;
362) 2-(R)-(1-(R)-(3-t-butyl)phenylethoxy)-3-(S)-(4-fluoro)phenyl-4-(2-imidazolo)methyl-morpholine;
363) 2-(S)-(3-t-butyl)benzyloxy-3-(S)-phenyl-4-(4-imidazolo)methyl-morpholine;
364) 2-(S)-(3-t-butyl)benzyloxy-3-(S)-(4-fluoro)phenyl-4-(4-imidazolo)methyl-morpholine;
365) 2-(R)-(1-(R)-(3-t-butyl)phenylethoxy)-3-(S)-phenyl-4-(4-imidazolo)methyl-morpholine;
366) 2-(R)-(1-(R)-(3-t-butyl)phenylethoxy)-3-(S)-(4-fluoro)phenyl-4-(4-imidazolo)methyl-morpholine;
367) 2-(S)-(3-t-butyl)benzyloxy-3-(S)-phenyl-4-(5-tetrazolo)methyl-morpholine;
368) 2-(S)-(3-t-butyl)benzyloxy-3-(S)-(4-fluoro)phenyl-4-(5-tetrazolo)methyl-morpholine;
369) 2-(R)-(1-(R)-(3-t-butyl)phenylethoxy)-3-(S)-phenyl-4-(5-tetrazolo)methyl-morpholine;
370) 2-(R)-(1-(R)-(3-t-butyl)phenylethoxy)-3-(S)-(4-fluoro)phenyl-4-(5-tetrazolo)methyl-morpholine;
371) 2-(S)-(3-t-butyl)benzyloxy-3-(S)-phenyl-4-(2-oxo-5H-pyrrol-4-yl)methyl-morpholine;
372) 2-(S)-(3-t-butyl)benzyloxy-3-(S)-(4-fluoro)phenyl-4-(2-oxo-5H-pyrrol-4-yl)methyl-morpholine;
373) 2-(R)-(1-(R)-(3-t-butyl)phenylethoxy)-3-(S)-phenyl-4-(2-oxo-5H-pyrrol-4-yl)methyl-morpholine;
374) 2-(R)-(1-(R)-(3-t-butyl)phenylethoxy)-3-(S)-(4-fluoro)phenyl-4-(2-oxo-5H-pyrrol-4-yl)methyl-morpholine;
375) 4-(4-(imidazolo)methyl)-2-(3-(tert-butyl)-5-(trifluoromethyl)benzyloxy)-3-phenyl-morpholine;
376) 2-(R)-(2,5-bis(trifluoromethyl)benzoyloxy)-3-(S)-(4-fluorophenyl)-4-benzyl-morpholine;
377) 2-(R)-(1-(2,5-bis(trifluoromethyl)phenyl)ethenyloxy)-3-(S)-(4-fluorophenyl)-4-benzyl-morpholine;
378) 2-(R)-(1-(R)-(2,5-bis(trifluoromethyl)phenyl)ethoxy)-3-(S)-(4-fluorophenyl)-morpholine;
379) 2-(R)-(1-(R)-(2,5-bis(trifluoromethyl)phenyl)ethoxy)-3-(S)-(4-fluorophenyl)-4-(3-(5-oxo-1H,4H-1,2,4-triazolo)methyl)morpholine;
380) 2-(R)-(1-(R)-(2,5-bis(trifluoromethyl)phenyl)ethoxy)-3-(S)-(4-fluorophenyl)-4-(3-(1,2,4-triazolo)methyl)-morpholine;
381) 2-(R)-(1-(R)-(2,5-bis(trifluoromethyl)phenyl)ethoxy)-3-(S)-(4-fluorophenyl)-4-(4-(2-oxo-1,3-imidazolo)methyl)-morpholine;
382) 2-(R)-(1-(R)-(3-(thiomethyl)phenyl)ethoxy)-3-(S)-phenyl-morpholine;
383) 2-(R)-(1-(R)-(3-(thiomethylphenyl)ethoxy)-3-(S)-phenyl-4-(3-(5-oxo-1H,4H-1,2,4-triazolo)methyl)-morpholine;
384) 2-(R)-(1-(R)-(3-(thiomethylphenyl)ethoxy)-3-(S)-phenyl-4-(3-(1,2,4-triazolo)methyl)-morpholine;
385) 2-(R)-(1-(R)-(3-(thiomethylphenyl)ethoxy)-3-(S)-phenyl-4-(4-(2-oxo-1,3-imidazolo)methyl)-morpholine;
386) 2-(R)-(1-(R)-(3-(thiomethyl)-5-(trifluoromethyl)phenyl)ethoxy)-3-(S)-phenyl-morpholine;
387) 2-(R)-(1-(R)-(3-(thiomethyl-5-(trifluoromethyl)phenyl)ethoxy)-3-(S)-phenyl-4-(3-(5-oxo-1H,4H-1,2,4-triazolo)methyl)-morpholine;
388) 2-(R)-(1-(R)-(3-(thiomethyl-5-(trifluoromethyl)phenyl)ethoxy)-3-(S)-phenyl-4-(3-(1,2,4-triazolo)methyl)-morpholine;
389) 2-(R)-(1-(R)-(3-(thiomethyl-5-(trifluoromethyl)phenyl)ethoxy)-3-(S)-phenyl-4-(4-(2-oxo-1,3-imidazolo)methyl)-morpholine;
390) 2-(R)-(1-(R)-(2,2-(dimethyl)-5-(thiomethyl)-2,3-dihydrobenzofuran-7-yl)ethoxy)-3-(S)-phenyl-morpholine;
391) 2-(R)-(1-(R)-(2,2-(dimethyl)-5-(thiomethyl)-2,3-dihydrobenzofuran-7-yl)ethoxy)-3-(S)-phenyl-4-(3-(5-oxo-1H,4H-1,2,4-triazolo)methyl)-morpholine;
392) 2-(R)-(1-(R)-(2,2-(dimethyl)-5-(thio methyl)-2,3-dihydrobenzofuran-7-yl)ethoxy)-3-(S)-phenyl-4-(3-(1,2,4-triazolo)methyl)-morpholine;
393) 2-(R)-(1-(R)-(2,2-(dimethyl)-5-(thiomethyl)-2,3-dihydrobenzofuran-7-yl)ethoxy)-3-(S)-phenyl-4-(2-oxo-1,3-imidazolo)methyl)-morpholine;
394) 2-(R)-(1-(R)-(3,5-(dimethoxy)phenyl)ethoxy)-3-(S)-phenylmorpholine;
395) 2-(R)-(1-(R)-(3,5-(dimethoxy)phenyl)ethoxy)-3-(S)-phenyl-4-(3-(5-oxo-1H,4H-1,2,4-triazolo)methyl)-morpholine;

396) 2-(R)-(1-(R)-(3,5-(dimethoxy)phenyl)ethoxy)-3-(S)-phenyl-4-(3-(1,2,4-triazolo)methyl)-morpholine;
397) 2-(R)-(1-(R)-(3,5-(dimethoxy)phenyl)ethoxy)-3-(S)-phenyl-4-(4-(2-oxo-1,3-imidazolo)methyl)-morpholine;
398) 2-(R)-(1-(R)-(3-(fluoro)-5-(trifluoromethyl)phenyl)-ethoxy)-3-(S)-(4-fluorophenyl)-morpholine;
399) 2-(R)-(1-(R)-(3-(fluorophenyl)-5-(trifluoromethyl)ethoxy)-3-(S)-(4-fluorophenyl)-4-(3-(5-oxo-1H,4H-1,2,4-triazolo)methyl)morpholine;
400) 2-(R)-(1-(R)-(3-(fluorophenyl)-5-(trifluoromethyl)ethoxy)-3-(S)-(4-fluorophenyl)-4-(3-(1,2,4-triazolo)methyl)-morpholine;
401) 2-(R)-(1-(R)-(3-(fluorophenyl)-5-(trifluoromethyl)ethoxy)-3-(S)-(4-fluorophenyl)-4-(4-(2-oxo-1,3-imidazolo)methyl)-morpholine;
402) 2-(R)-(1-(R)-(3-(chloro)-5-(trifluoromethyl)phenyl)-ethoxy)-3-(S)-(4-fluorophenyl)-morpholine;
403) 2-(R)-(1-(R)-(3-(chlorophenyl)-5-(trifluoromethyl)ethoxy)-3-(S)-(4-fluoro)phenyl-4-(3-(5-oxo-1H,4H-1,2,4-triazolo)methyl)morpholine;
404) 2-(R)-(1-(R)-(3-(chlorophenyl)-5-(trifluoromethyl)ethoxy)-3-(S)-(4-fluoro)phenyl-4-(3-(1,2,4-triazolo)methyl)-morpholine;
405) 2-(R)-(1-(R)-(3-(chlorophenyl)-5-(trifluoromethyl)ethoxy)-3-(S)-(4-fluoro)phenyl-4-(4-(2-oxo-1,3-imidazolo)methyl)-morpholine;
406) 2-(R)-(1-(R)-(3,5-(dimethyl)phenyl)ethoxy)-3-(S)-(4-fluoro)phenyl-morpholine;
407) 2-(R)-(1-(R)-(3,5-(dimethyl)phenyl)ethoxy)-3-(S)-(4-fluoro)phenyl-4-(3-(5-oxo-1H,4H-1,2,4-triazolo)methyl)morpholine;
408) 2-(R)-(1-(R)-(3,5-(dimethyl)phenyl)ethoxy)-3-(S)-(4-fluoro)phenyl-4-(3-(1,2,4-triazolo)methyl)-morpholine;
409) 2-(R)-(1-(R)-(3,5-(dimethyl)phenyl)ethoxy)-3-(S)-(4-fluoro)phenyl-4-(4-(2-oxo-1,3-imidazolo)methyl)-morpholine;
410) 2-(R)-(1-(R)-(3-(fluoro)-5-(methyl)phenyl)ethoxy)-3-(S)-(4-fluoro)phenyl-morpholine;
411) 2-(R)-(1-(R)-(3-(fluoro)-5-(methyl)phenyl)ethoxy)-3-(S)-(4-fluoro)phenyl-4-(3-(5-oxo-1H,4H-1,2,4-triazolo)methyl)morpholine;
412) 2-(R)-(1-(R)-(3-(fluoro)-5-(methyl)phenyl)ethoxy)-3-(S)-(4-fluoro)phenyl-4-(3-(1,2,4-triazolo)methyl)-morpholine;
413) 2-(R)-(1-(R)-(3-(fluoro)-5-(methyl)phenyl)ethoxy)-3-(S)-(4-fluoro)phenyl-4-(4-(2-oxo-1,3-imidazolo)methyl)-morpholine;
414) 2-(R)-(1-(R)-(3-(chloro)-5-(methyl)phenyl)ethoxy)-3-(S)-(4-fluoro)phenyl-morpholine;
415) 2-(R)-(1-(R)-(3-(chloro)-5-(methyl)phenyl)ethoxy)-3-(S)-(4-fluoro)phenyl-4-(3-(5-oxo-1H,4H-1,2,4-triazolo)methyl)morpholine;
416) 2-(R)-(1-(R)-(3-(chloro)-5-(methyl)phenyl)ethoxy)-3-(S)-(4-fluoro)phenyl-4-(3-(1,2,4-triazolo)methyl)-morpholine;
417) 2-(R)-(1-(R)-(3-(chloro)-5-(methyl)phenyl)ethoxy)-3-(S)-(4-fluoro)phenyl-4-(4-(2-oxo-1,3-imidazolo)methyl)-morpholine;
418) 2-(R)-(1-(R)-(3-(bromo)-5-(methyl)phenyl)ethoxy)-3-(S)-(4-fluoro)phenyl-morpholine;
419) 2-(R)-(1-(R)-(3-(bromo)-5-(methyl)phenyl)ethoxy)-3-(S)-(4-fluoro)phenyl-4-(3-(5-oxo-1H,4H-1,2,4-triazolo)methyl)morpholine;
420) 2-(R)-(1-(R)-(3-(bromo)-5-(methyl)phenyl)ethoxy)-3-(S)-(4-fluoro)phenyl-4-(3-(1,2,4-triazolo)methyl)-morpholine;
421) 2-(R)-(1-(R)-(3-(bromo)-5-(methyl)phenyl)ethoxy)-3-(S)-(4-fluoro)phenyl-4-(4-(2-oxo-1,3-imidazolo)methyl)-morpholine;
422) 2-(R)-(1-(R)-(3-(isopropoxy)phenyl)ethoxy)-3-(S)-(4-fluoro)phenyl-morpholine;
423) 2-(R)-(1-(R)-(3-(isopropoxy)phenyl)ethoxy)-3-(S)-(4-fluoro)phenyl-4-(3-(5-oxo-1H,4H-1,2,4-triazolo)methyl)morpholine;
424) 2-(R)-(1-(R)-(3-(isopropoxy)phenyl)ethoxy)-3-(S)-(4-fluoro)phenyl-4-(3-(1,2,4-triazolo)methyl)-morpholine;
425) 2-(R)-(1-(R)-(3-(isopropoxy)phenyl)ethoxy)-3-(S)-(4-fluoro)phenyl-4-(4-(2-oxo-1,3-imidazolo)methyl)-morpholine;
426) 2-(R)-(1-(R)-(3-(isopropoxy)-5-(trifluoromethyl)phenyl)ethoxy)-3-(S)-(4-fluoro)phenyl-morpholine;
427) 2-(R)-(1-(R)-(3-(isopropoxy)-5-(trifluoromethyl)phenyl)ethoxy)-3-(S)-(4-fluoro)phenyl-4-(3-(5-oxo-1H,4H-1,2,4-triazolo)methyl)-morpholine;
428) 2-(R)-(1-(R)-(3-(isopropoxy)-5-(trifluoromethyl)phenyl)ethoxy)-3-(S)-(4-fluoro)phenyl-4-(3-(1,2,4-triazolo)methyl)-morpholine;
429) 2-(R)-(1-(R)-(3-(isopropoxy)-5-(trifluoromethyl)phenyl)ethoxy)-3-(S)-(4-fluoro)phenyl-4-(4-(2-oxo-1,3-imidazolo)methyl)morpholine;
430) 2-(R)-(1-(R)-(3-(chloro)-5-(isopropoxy)phenyl)ethoxy)-3-(S)-(4-fluoro)phenyl-morpholine;
431) 2-(R)-(1-(R)-(3-(chloro)-5-(isopropoxy)phenyl)ethoxy)-3-(S)-(4-fluoro)phenyl-4-(3-(5-oxo-1H,4H-1,2,4-triazolo)methyl)morpholine;
432) 2-(R)-(1-(R)-(3-(chloro)-5-(isopropoxy)phenyl)ethoxy)-3-(S)-(4-fluoro)phenyl-4-(3-(1,2,4-triazolo)methyl)-morpholine;
433) 2-(R)-(1-(R)-(3-(chloro)-5-(isopropoxy)phenyl)ethoxy)-3-(S)-(4-fluoro)phenyl-4-(4-(2-oxo-1,3-imidazolo)methyl)-morpholine;
434) 2-(R)-(1-(R)-(3-(fluoro)-5-(isopropoxy)phenyl)ethoxy)-3-(S)-(4-fluoro)phenyl-morpholine;
435) 2-(R)-(1-(R)-(3-(fluoro)-5-(isopropoxy)phenyl)ethoxy)-3-(S)-(4-fluoro)phenyl-4-(3-(5-oxo-1H,4H-1,2,4-triazolo)methyl)morpholine;
436) 2-(R)-(1-(R)-(3-(fluoro)-5-(isopropoxy)phenyl)ethoxy)-3-(S)-(4-fluoro)phenyl-4-(3-(1,2,4-triazolo)methyl)-morpholine;
437) 2-(R)-(1-(R)-(3-(fluoro)-5-(isopropoxy)phenyl)ethoxy)-3-(S)-(4-fluoro)phenyl-4-(4-(2-oxo-1,3-imidazolo)methyl)-morpholine;
438) 2-(R)-(1-(R)-(3-(t-butyl)-5-(chlorophenyl)ethoxy)-3-(S)-(4-fluoro)phenyl-morpholine;
439) 2-(R)-(1-(R)-(3-(t-butyl)-5-(chlorophenyl)ethoxy)-3-(S)-(4-fluoro)phenyl-4-(3-(5-oxo-1H,4H-1,2,4-triazolo)methyl)morpholine;
440) 2-(R)-(1-(R)-(3-(t-butyl)-5-(chlorophenyl)ethoxy)-3-(S)-(4-fluoro)phenyl-4-(3-(1,2,4-triazolo)methyl)-morpholine;
441) 2-(R)-(1-(R)-(3-(t-butyl)-5-(chlorophenyl)ethoxy)-3-(S)-(4-fluoro)phenyl-4-(4-(2-oxo-1,3-imidazolo)methyl)-morpholine;
442) 2-(R)-(1-(R)-(3-(t-butyl)-5-(trifluoromethyl)phenyl)ethoxy)-3-(S)-(4-fluoro)phenyl-morpholine;
443) 2-(R)-(1-(R)-(3-(t-butyl)-5-(trifluoromethyl)phenyl)ethoxy)-3-(S)-(4-fluoro)phenyl-4-(3-(5-oxo-1H,4H-1,2,4-triazolo)methyl)morpholine;
444) 2-(R)-(1-(R)-(3-(t-butyl)-5-(trifluoromethyl)phenyl)ethoxy)-3-(S)-(4-fluoro)phenyl-4-(3-(1,2,4-triazolo)methyl)-morpholine;
445) 2-(R)-(1-(R)-(3-(t-butyl)-5-(trifluoromethyl)phenyl)ethoxy)-3-(S)-(4-fluoro)phenyl-4-(4-(2-oxo-1,3-imidazolo)methyl)morpholine;
446) 2-(R)-(1-(R)-(3,5-(dimethyl)-4-(fluoro)phenyl)ethoxy)-3-(S)-(4-fluoro)phenyl-morpholine;

447) 2-(R)-(1-(R)-(3,5-(dimethyl)-4-(fluoro)phenyl)ethoxy)-3-(S)-(4-fluoro)phenyl-4-(3-(5-oxo-1H,4H-1,2,4-triazolo)methyl)morpholine;
448) 2-(R)-(1-(R)-(3,5-(dimethyl)-4-(fluoro)phenyl)ethoxy)-3-(S)-(4-fluoro)phenyl-4-(3-(1,2,4-triazolo)methyl)-morpholine;
449) 2-(R)-(1-(R)-(3,5-(dimethyl)-4-(fluoro)phenyl)ethoxy)-3-(S)-(4-fluoro)phenyl-4-(4-(2-oxo-1,3-imidazolo)methyl)-morpholine;
450) 2-(R)-(1-(R)-(3,5-(dimethyl)-4-(chloro)phenyl)ethoxy)-3-(S)-(4-fluoro)phenyl-morpholine;
451) 2-(R)-(1-(R)-(3,5-(dimethyl)-4-(chloro)phenyl)ethoxy)-3-(S)-(4-fluoro)phenyl-4-(3-(5-oxo-1H,4H-1,2,4-triazolo)methyl)morpholine;
452) 2-(R)-(1-(R)-(3,5-(dimethyl)-4-(chloro)phenyl)ethoxy)-3-(S)-(4-fluoro)phenyl-4-(3-(1,2,4-triazolo)methyl)-morpholine;
453) 2-(R)-(1-(R)-(3,5-(dimethyl)-4-(chloro)phenyl)ethoxy)-3-(S)-(4-fluoro)phenyl-4-(4-(2-oxo-1,3-imidazolo)methyl)-morpholine;
454) 2-(R)-(1-(R)-(3,5-bis(trifluoromethyl)-4-(fluoro)phenyl)ethoxy)-3-(S)-(4-fluoro)phenyl-morpholine;
455) 2-(R)-(1-(R)-(3,5-bis(trifluoromethyl)-4-(fluoro)phenyl)ethoxy)-3-(S)-(4-fluoro)phenyl-4-(3-(5-oxo-1H,4H-1,2,4-triazolo)methyl)-morpholine;
456) 2-(R)-(1-(R)-(3,5-bis(trifluoromethyl)-4-(fluoro)phenyl)ethoxy)-3-(S)-(4-fluoro)phenyl-4-(3-(1,2,4-triazolo)methyl)-morpholine;
457) 2-(R)-(1-(R)-(3,5-bis(trifluoromethyl)-4-(fluoro)phenyl)ethoxy)-3-(S)-(4-fluoro)phenyl-4-(4-(2-oxo-1,3-imidazolo)methyl)morpholine;
458) 2-(R)-(1-(R)-(3,5-bis(trifluoromethyl)-4-(chloro)phenyl)ethoxy)-3-(S)-(4-fluoro)phenyl-morpholine;
459) 2-(R)-(1-(R)-(3,5-bis(trifluoromethyl)-4-(chloro)phenyl)ethoxy)-3-(S)-(4-fluoro)phenyl-4-(3-(5-oxo-1H,4H-1,2,4-triazolo)methyl)-morpholine;
460) 2-(R)-(1-(R)-(3,5-bis(trifluoromethyl)-4-(chloro)phenyl)ethoxy)-3-(S)-(4-fluoro)phenyl-4-(3-(1,2,4-triazolo)methyl)-morpholine;
461) 2-(R)-(1-(R)-(3,5-bis(trifluoromethyl)-4-(chloro)phenyl)ethoxy)-3-(S)-(4-fluoro)phenyl-4-(4-(2-oxo-1,3-imidazolo)methyl)morpholine;
462) 2-(R)-(1-(R)-(3,5-(dichloro)phenyl)ethoxy)-3-(S)-(4-fluoro)phenyl-morpholine;
463) 2-(R)-(1-(R)-(3,5-(dichloro)phenyl)ethoxy)-3-(S)-(4-fluoro)phenyl-4-(3-(5-oxo-1H,4H-1,2,4-triazolo)methyl)morpholine;
464) 2-(R)-(1-(R)-(3,5-(dichloro)phenyl)ethoxy)-3-(S)-(4-fluoro)phenyl-4-(3-(1,2,4-triazolo)methyl)-morpholine;
465) 2-(R)-(1-(R)-(3,5-(dichloro)phenyl)ethoxy)-3-(S)-(4-fluoro)phenyl-4-(4-(2-oxo-1,3-imidazolo)methyl)-morpholine;
466) 2-(R)-(1-(R)-(3,5-(difluoro)phenyl)ethoxy)-3-(S)-(4-fluoro)phenyl-morpholine;
467) 2-(R)-(1-(R)-(3,5-(difluoro)phenyl)ethoxy)-3-(S)-(4-fluoro)phenyl-4-(3-(5-oxo-1H,4H-1,2,4-triazolo)methyl)morpholine;
468) 2-(R)-(1-(R)-(3,5-(difluoro)phenyl)ethoxy)-3-(S)-(4-fluoro)phenyl-4-(3-(1,2,4-triazolo)methyl)-morpholine;
469) 2-(R)-(1-(R)-(3,5-(difluoro)phenyl)ethoxy)-3-(S)-(4-fluoro)phenyl-4-(4-(2-oxo-1,3-imidazolo)methyl)-morpholine;
470) 2-(R)-(1-(R)-(1-(naphthyl)ethoxy)-3-(S)-(4-fluoro)phenylmorpholine;
471) 2-(R)-(1-(R)-(1-(naphthyl)ethoxy)-3-(S)-(4-fluoro)phenyl-4-(3-(5-oxo-1H,4H-1,2,4-triazolo)methyl)-morpholine;
472) 2-(R)-(1-(R)-(1-(naphthyl)ethoxy)-3-(S)-(4-fluoro)phenyl-4-(3-(1,2,4-triazolo)methyl)-morpholine;
473) 2-(R)-(1-(R)-(1-(naphthyl)ethoxy)-3-(S)-(4-fluoro)phenyl-4-(4-(2-oxo-1,3-imidazolo)methyl)-morpholine;
474) 2-(R)-(1-(R)-(1-(4-(fluoro)naphthyl))ethoxy)-3-(S)-(4-fluoro)phenyl-morpholine;
475) 2-(R)-(1-(R)-(1-(4-(fluoro)naphthyl))ethoxy)-3-(S)-(4-fluoro)phenyl-4-(3-(5-oxo-1H,4H-1,2,4-triazolo)methyl)morpholine;
476) 2-(R)-(1-(R)-(1-(4-(fluoro)naphthyl))ethoxy)-3-(S)-(4-fluoro)phenyl-4-(3-(1,2,4-triazolo)methyl)-morpholine;
477) 2-(R)-(1-(R)-(1-(4-(fluoro)naphthyl))ethoxy)-3-(S)-(4-fluoro)phenyl-4-(4-(2-oxo-1,3-imidazolo)methyl)-morpholine;
478) 2-(R)-(1-(R)-(1-(3-(fluoro)naphthyl))ethoxy)-3-(S)-(4-fluoro)phenyl-morpholine;
479) 2-(R)-(1-(R)-(1-(3-(fluoro)naphthyl))ethoxy)-3-(S)-(4-fluoro)phenyl-4-(3-(5-oxo-1H,4H-1,2,4-triazolo)methyl)morpholine;
480) 2-(R)-(1-(R)-(1-(3-(fluoro)naphthyl))ethoxy)-3-(S)-(4-fluoro)phenyl-4-(3-(1,2,4-triazolo)methyl)-morpholine;
481) 2-(R)-(1-(R)-(1-(3-(fluoro)naphthyl))ethoxy)-3-(S)-(4-fluoro)phenyl-4-(4-(2-oxo-1,3-imidazolo)methyl)-morpholine;
482) 2-(R)-(1-(R)-(1-(3-(chloro)naphthyl))ethoxy)-3-(S)-(4-fluoro)phenyl-morpholine;
483) 2-(R)-(1-(R)-(1-(3-(chloro)naphthyl))ethoxy)-3-(S)-(4-fluoro)phenyl-4-(3-(5-oxo-1H,4H-1,2,4-triazolo)methyl)morpholine;
484) 2-(R)-(1-(R)-(1-(3-(chloro)naphthyl))ethoxy)-3-(S)-(4-fluoro)phenyl-4-(3-(1,2,4-triazolo)methyl)-morpholine;
485) 2-(R)-(1-(R)-(1-(3-(chloro)naphthyl))ethoxy)-3-(S)-(4-fluoro)phenyl-4-(4-(2-oxo-1,3-imidazolo)methyl)-morpholine;
486) 2-(R)-(1-(R)-(1-(3-(methyl)naphthyl))ethoxy)-3-(S)-(4-fluoro)phenyl-morpholine;
487) 2-(R)-(1-(R)-(1-(3-(methyl)naphthyl))ethoxy)-3-(S)-(4-fluoro)phenyl-4-(3-(5-oxo-1H,4H-1,2,4-triazolo)methyl)morpholine;
488) 2-(R)-(1-(R)-(1-(3-(methyl)naphthyl))ethoxy)-3-(S)-(4-fluoro)phenyl-4-(3-(1,2,4-triazolo)methyl)-morpholine;
489) 2-(R)-(1-(R)-(1-(3-(methyl)naphthyl))ethoxy)-3-(S)-(4-fluoro)phenyl-4-(4-(2-oxo-1,3-imidazolo)methyl)-morpholine;
490) 2-(R)-(1-(R)-(1-(3-(trifluoromethyl)naphthyl))ethoxy)-3-(S)-(4-fluoro)phenyl-morpholine;
491) 2-(R)-(1-(R)-(1-(3-(trifluoromethyl)naphthyl))ethoxy)-3-(S)-(4-fluoro)phenyl-4-(3-(5-oxo-1H,4H-1,2,4-triazolo)methyl)morpholine;
492) 2-(R)-(1-(R)-(1-(3-(trifluoromethyl)naphthyl))ethoxy)-3-(S)-(4-fluoro)phenyl-4-(3-(1,2,4-triazolo)methyl)-morpholine;
493) 2-(R)-(1-(R)-(1-(3-(trifluoromethyl)naphthyl))ethoxy)-3-(S)-(4-fluoro)phenyl-4-(4-(2-oxo-1,3-imidazolo)methyl)-morpholine;
494) 2-(R)-(1-(R)-(3-(thiomethyl)phenyl)ethoxy)-3-(S)-(4-fluoro)phenyl-morpholine;
495) 2-(R)-(1-(R)-(3-(thiomethylphenyl)ethoxy)-3-(S)-(4-fluoro)phenyl-4-(3-(5-oxo-1H,4H-1,2,4-triazolo)methyl)morpholine;
496) 2-(R)-(1-(R)-(3-(thiomethylphenyl)ethoxy)-3-(S)-(4-fluoro)phenyl-4-(3-(1,2,4-triazolo)methyl)-morpholine;
497) 2-(R)-(1-(R)-(3-(thiomethylphenyl)ethoxy)-3-(S)-(4-fluoro)phenyl-4-(4-(2-oxo-1,3-imidazolo)methyl)-morpholine;

498) 2-(R)-(1-(R)-(3-(thiomethyl)-5-(trifluoromethyl) phenyl)ethoxy)-3-(S)-(4-fluoro)phenyl-morpholine;

499) 2-(R)-(1-(R)-(3-(thiomethyl-5-(trifluoromethyl) phenyl)ethoxy)-3-(S)-(4-fluoro)phenyl-4-(3-(5-oxo-1H,4H-1,2,4-triazolo)methyl)-morpholine;

500) 2-(R)-(1-(R)-(3-(thiomethyl-5-(trifluoromethyl) phenyl)ethoxy)-3-(S)-(4-fluoro)phenyl-4-(3-(1,2,4-triazolo)methyl)-morpholine;

501) 2-(R)-(1-(R)-(3-(thiomethyl-5-(trifluoromethyl) phenyl)ethoxy)-3-(S)-(4-fluoro)phenyl-4-(4-(2-oxo-1,3-imidazolo)methyl)morpholine;

502) 2-(R)-(1-(R)-(2,2-(dimethyl)-5-(thiomethyl)-2,3-dihydrobenzofuran-7-yl)ethoxy)-3-(S)-(4-fluoro)phenyl-morpholine;

503) 2-(R)-(1-(R)-(2,2-(dimethyl)-5-(thiomethyl)-2,3-dihydrobenzofuran-7-yl)ethoxy)-3-(S)-(4-fluoro)phenyl-4-(3-(5-oxo-1H,4H-1,2,4-triazolo)methyl)-morpholine;

504) 2-(R)-(1-(R)-(2,2-(dimethyl)-5-(thiomethyl)-2,3-dihydrobenzofuran-7-yl)ethoxy)-3-(S)-(4-fluoro)phenyl-4-(3-(1,2,4-triazolo)methyl)-morpholine;

505) 2-(R)-(1-(R)-(2,2-(dimethyl)-5-(thiomethyl)-2,3-dihydrobenzofuran-7-yl)ethoxy)-3-(S)-(4-fluoro)phenyl-4-(4-(2-oxo-1,3-imidazolo)methyl)-morpholine;

506) 2-(R)-(1-(R)-(3,5-(dimethoxy)phenyl)ethoxy)-3-(S)-(4-fluoro)phenyl-morpholine;

507) 2-(R)-(1-(R)-(3,5-(dimethoxy)phenyl)ethoxy)-3-(S)-(4-fluoro)phenyl-4-(3-(5-oxo-1H,4H-1,2,4-triazolo) methyl)morpholine;

508) 2-(R)-(1-(R)-(3,5-(dimethoxy)phenyl)ethoxy)-3-(S)-(4-fluoro)phenyl-4-(3-(1,2,4-triazolo)methyl)-morpholine;

509) 2-(R)-(1-(R)-(3,5-(dimethoxy)phenyl)ethoxy)-3-(S)-(4-fluoro)phenyl-4-(4-(2-oxo-1,3-imidazolo)methyl)-morpholine;

510) 2-(R)-(1-(R)-(phenyl)ethoxy)-3-(S)-phenyl-morpholine;

511) 2-(R)-(1-(R)-(phenyl)ethoxy)-3-(S)-phenyl-4-(3-(5-oxo-1H,4H-1,2,4-triazolo)methyl)-morpholine;

512) 2-(R)-(1-(R)-(phenyl)ethoxy)-3-(S)-phenyl-4-(3-(1,2,4-triazolo)methyl)-morpholine;

513) 2-(R)-(1-(R)-(phenyl)ethoxy)-3-(S)-phenyl-4-(4-(2-oxo-1,3-imidazolo)methyl)-morpholine;

514) 2-(R)-(1-(R)-(phenyl)ethoxy)-3-(S)-(4-fluoro)phenyl morpholine;

515) 2-(R)-(1-(R)-(phenyl)ethoxy)-3-(S)-(4-fluoro)phenyl-4-(3-(5-oxo-1H,4H-1,2,4-triazolo)methyl)-morpholine;

516) 2-(R)-(1-(R)-(phenyl)ethoxy)-3-(S)-(4-fluoro)phenyl-4-(3-(1,2,4-triazolo)methyl)-morpholine;

517) 2-(R)-(1-(R)-(phenyl)ethoxy)-3-(S)-(4-fluoro)phenyl-4-(4-(2-oxo-1,3-imidazolo)methyl)-morpholine;

518) 2-(R)-(1-(R)-(3-(fluoro)phenyl)ethoxy)-3-(S)-phenyl-morpholine;

519) 2-(R)-(1-(R)-(3-(fluoro)phenyl)ethoxy)-3-(S)-phenyl-4-(3-(5-oxo-1H,4H-1,2,4-triazolo)methyl)-morpholine;

520) 2-(R)-(1-(R)-(3-(fluoro)phenyl)ethoxy)-3-(S)-phenyl-4-(3-(1,2,4-triazolo)methyl)-morpholine;

521) 2-(R)-(1-(R)-(3-(fluoro)phenyl)ethoxy)-3-(S)-phenyl-4-(4-(2-oxo-1,3-imidazolo)methyl)-morpholine;

522) 2-(R)-(1-(R)-(3-(fluoro)phenyl)ethoxy)-3-(S)-(4-fluoro)phenylmorpholine;

523) 2-(R)-(1-(R)-(3-(fluoro)phenyl)ethoxy)-3-(S)-(4-fluoro)phenyl-4-(3-(5-oxo-1H,4H-1,2,4-triazolo)methyl)-morpholine;

524) 2-(R)-(1-(R)-(3-(fluoro)phenyl)ethoxy)-3-(S)-(4-fluoro)phenyl-4-(3-(1,2,4-triazolo)methyl)-morpholine;

525) 2-(R)-(1-(R)-(3-(fluoro)phenyl)ethoxy)-3-(S)-(4-fluoro)phenyl-4-(4-(2-oxo-1,3-imidazolo)methyl)-morpholine;

526) 2-(R)-(1-(R)-(4-(fluoro)phenyl)ethoxy)-3-(S)-phenyl-morpholine;

527) 2-(R)-(1-(R)-(4-(fluoro)phenyl)ethoxy)-3-(S)-phenyl-4-(3-(5-oxo-1H,4H-1,2,4-triazolo)methyl)-morpholine;

528) 2-(R)-(1-(R)-(4-(fluoro)phenyl)ethoxy)-3-(S)-phenyl-4-(3-(1,2,4-triazolo)methyl)-morpholine;

529) 2-(R)-(1-(R)-(4-(fluoro)phenyl)ethoxy)-3-(S)-phenyl-4-(4-(2-oxo-1,3-imidazolo)methyl)-morpholine;

530) 2-(R)-(1-(R)-(4-(fluoro)phenyl)ethoxy)-3-(S)-(4-fluoro)phenylmorpholine;

531) 2-(R)-(1-(R)-(4-(fluoro)phenyl)ethoxy)-3-(S)-(4-fluoro)phenyl-4-(3-(5-oxo-1H,4H-1,2,4-triazolo)methyl)-morpholine;

532) 2-(R)-(1-(R)-(4-(fluoro)phenyl)ethoxy)-3-(S)-(4-fluoro)phenyl-4-(3-(1,2,4-triazolo)methyl)-morpholine;

533) 2-(R)-(1-(R)-(4-(fluoro)phenyl)ethoxy)-3-(S)-(4-fluoro)phenyl-4-(4-(2-oxo-1,3-imidazolo)methyl)-morpholine;

534) 2-(R)-(1-(R)-(3,5-bis(trifluoromethyl)phenyl)ethoxy)-3-(S)-(3-fluoro)phenyl-morpholine;

535) 2-(R)-(1-(R)-(3,5-bis(trifluoromethyl)phenyl)ethoxy)-3-(S)-(3-fluoro)phenyl-4-(3-(5-oxo-1H,4H-1,2,4-triazolo)methyl)morpholine;

536) 2-(R)-(1-(R)-(3,5-bis(trifluoromethyl)phenyl)ethoxy)-3-(S)-(3-fluoro)phenyl-4-(3-(1,2,4-triazolo)methyl)-morpholine;

537) 2-(R)-(1-(R)-(3,5-bis(trifluoromethyl)phenyl)ethoxy)-3-(S)-(3-fluoro)phenyl-4-(4-(2-oxo-1,3-imidazolo)methyl)-morpholine;

538) 2-(R)-(1-(R)-(3,5-bis(trifluoromethyl)phenyl)ethoxy)-3-(S)-(3,4-difluoro)phenyl-morpholine;

539) 2-(R)-(1-(R)-(3,5-bis(trifluoromethyl)phenyl)ethoxy)-3-(S)-(3,4-difluoro)phenyl-4-(3-(5-oxo-1H,4H-1,2,4-triazolo)methyl)morpholine;

540) 2-(R)-(1-(R)-(3,5-bis(trifluoromethyl)phenyl)ethoxy)-3-(S)-(3,4-difluoro)phenyl-4-(3-(1,2,4-triazolo)methyl)-morpholine;

541) 2-(R)-(1-(R)-(3,5-bis(trifluoromethyl)phenyl)ethoxy)-3-(S)-(3,4-difluoro)phenyl-4-(4-(2-oxo-1,3-imidazolo) methyl)-morpholine;

542) 2-(R)-(1-(R)-(3,5-bis(trifluoromethyl)phenyl)ethoxy)-3-(S)-(3,4-dichloro)phenyl-morpholine;

543) 2-(R)-(1-(R)-(3,5-bis(trifluoromethyl)phenyl)ethoxy)-3-(S)-(3,4-dichloro)phenyl-4-(3-(5-oxo-1H,4H-1,2,4-triazolo)methyl)morpholine;

544) 2-(R)-(1-(R)-(3,5-bis(trifluoromethyl)phenyl)ethoxy)-3-(S)-(3,4-dichloro)phenyl-4-(3-(1,2,4-triazolo)methyl)-morpholine;

545) 2-(R)-(1-(R)-(3,5-bis(trifluoromethyl)phenyl)ethoxy)-3-(S)-(3,4-dichloro)phenyl-4-(4-(2-oxo-1,3-imidazolo) methyl)-morpholine;

546) 2-(R)-(1-(R)-(3,5-bis(trifluoromethyl)phenyl)ethoxy)-3-(S)-(3,4-dimethyl)phenyl-morpholine;

547) 2-(R)-(1-(R)-(3,5-bis(trifluoromethyl)phenyl)ethoxy)-3-(S)-(3,4-dimethyl)phenyl-4-(3-(5-oxo-1H,4H-1,2,4-triazolo)methyl)morpholine;

548) 2-(R)-(1-(R)-(3,5-bis(trifluoromethyl)phenyl)ethoxy)-3-(S)-(3,4-dimethyl)phenyl-4-(3-(1,2,4-triazolo)methyl)-morpholine;

549) 2-(R)-(1-(R)-(3,5-bis(trifluoromethyl)phenyl)ethoxy)-3-(S)-(3,4-dimethyl)phenyl-4-(4-(2-oxo-1,3-imidazolo) methyl)-morpholine;

550) 2-(R)-(1-(R)-(3,5-bis(trifluoromethyl)phenyl)ethoxy)-3-(S)-3,4-methylenedioxyphenyl-morpholine;

551) 2-(R)-(1-(R)-(3,5-bis(trifluoromethyl)phenyl)ethoxy)-3-(S)-3,4-methylenedioxyphenyl-4-(3-(5-oxo-1H,4H-1,2,4-triazolo)methyl)morpholine;

552) 2-(R)-(1-(R)-(3,5-bis(trifluoromethyl)phenyl)ethoxy)-3-(S)-3,4-methylenedioxyphenyl-4-(3-(1,2,4-triazolo)methyl)-morpholine;
553) 2-(R)-(1-(R)-(3,5-bis(trifluoromethyl)phenyl)ethoxy)-3-(S)-3,4-methylenedioxyphenyl-4-(4-(2-oxo-1,3-imidazolo)methyl)morpholine;
554) 2-(R)-(1-(R)-(3,5-bis(trifluoromethyl)phenyl)ethoxy)-3-(S)-(2-naphthyl)-morpholine;
555) 2-(R)-(1-(R)-(3,5-bis(trifluoromethyl)phenyl)ethoxy)-3-(S)-(2-naphthyl)-4-(3-(5-oxo-1H,4H-1,2,4-triazolo)methyl)-morpholine;
556) 2-(R)-(1-(R)-(3,5-bis(trifluoromethyl)phenyl)ethoxy)-3-(S)-(2-naphthyl)-4-(3-(1,2,4-triazolo)methyl)-morpholine;
557) 2-(R)-(1-(R)-(3,5-bis(trifluoromethyl)phenyl)ethoxy)-3-(S)-(2-naphthyl)-4-(4-(2-oxo-1,3-imidazolo)methyl)-morpholine;
558) 2-(R)-(1-(R)-(3-(fluorophenyl)-5-(trifluoromethyl)ethoxy)-3-(S)-phenyl-4-(3-(1,2,4-triazolo)methyl)-morpholine;
559) 2-(R)-(1-(R)-(3-(fluorophenyl)-5-(trifluoromethyl)ethoxy)-3-(S)-phenyl-4-(4-(2-oxo-1,3-imidazolo)methyl)-morpholine;
560) 2-(R)-(1-(R)-(3-(chlorophenyl)-5-(trifluoromethyl)ethoxy)-3-(S)-phenyl-4-(3-(1,2,4-triazolo)methyl)-morpholine;
561) 2-(R)-(1-(R)-(3-(chlorophenyl)-5-(trifluoromethyl)ethoxy)-3-(S)-phenyl-4-(4-(2-oxo-1,3-imidazolo)methyl)-morpholine;
562) 2-(R)-(1-(R)-(3,5-(dimethyl)phenyl)ethoxy)-3-(S)-phenyl-4-(3-(1,2,4-triazolo)methyl)-morpholine;
563) 2-(R)-(1-(R)-(3,5-(dimethyl)phenyl)ethoxy)-3-(S)-phenyl-4-(4-(2-oxo-1,3-imidazolo)methyl)-morpholine;
564) 2-(R)-(1-(R)-(3-(fluoro)-5-(methyl)phenyl)ethoxy)-3-(S)-phenyl-4-(3-(1,2,4-triazolo)methyl)-morpholine;
565) 2-(R)-(1-(R)-(3-(fluoro)-5-(methyl)phenyl)ethoxy)-3-(S)-phenyl-4-(4-(2-oxo-1,3-imidazolo)methyl)-morpholine;
566) 2-(R)-(1-(R)-(3-(chloro)-5-(methyl)phenyl)ethoxy)-3-(S)-phenyl-4-(3-(-1H,4H-1,2,4-triazolo)methyl)-morpholine;
567) 2-(R)-(1-(R)-(3-(chloro)-5-(methyl)phenyl)ethoxy)-3-(S)-phenyl-4-(4-(2-oxo-1,3-imidazolo)methyl)-morpholine;
568) 2-(R)-(1-(R)-(3-(bromo)-5-(methyl)phenyl)ethoxy)-3-(S)-phenyl-4-(3-(1,2,4-triazolo)methyl)-morpholine;
569) 2-(R)-(1-(R)-(3-(bromo)-5-(methyl)phenyl)ethoxy)-3-(S)-phenyl-4-(4-(2-oxo-1,3-imidazolo)methyl)-morpholine;
570) 2-(R)-(1-(R)-(3-(isopropoxy)phenyl)ethoxy)-3-(S)-phenyl-4-(3-(1,2,4-triazolo)methyl)-morpholine;
571) 2-(R)-(1-(R)-(3-(isopropoxy)phenyl)ethoxy)-3-(S)-phenyl-4-(4-(2-oxo-1,3-imidazolo)methyl)-morpholine;
572) 2-(R)-(1-(R)-(3-(isopropoxy)-5-(trifluoromethyl)phenyl)ethoxy)-3-(S)-phenyl-4-(3-(-1H,4H-1,2,4-triazolo)methyl)-morpholine;
573) 2-(R)-(1-(R)-(3-(isopropoxy)-5-(trifluoromethyl)phenyl)ethoxy)-3-(S)-phenyl-4-(4-(2-oxo-1,3-imidazolo)methyl)-morpholine;
574) 2-(R)-(1-(R)-(3-(chloro)-5-(isopropoxy)phenyl)ethoxy)-3-(S)-phenyl-4-(3-(-1H,4H-1,2,4-triazolo)methyl)-morpholine;
575) 2-(R)-(1-(R)-(3-(chloro)-5-(isopropoxy)phenyl)ethoxy)-3-(S)-phenyl-4-(4-(2-oxo-1,3-imidazolo)methyl)-morpholine;
576) 2-(R)-(1-(R)-(3-(fluoro)-5-(isopropoxy)phenyl)ethoxy)-3-(S)-phenyl-4-(3-(-1H,4H-1,2,4-triazolo)methyl)-morpholine;
577) 2-(R)-(1-(R)-(3-(fluoro)-5-(isopropoxy)phenyl)ethoxy)-3-(S)-phenyl-4-(4-(2-oxo-1,3-imidazolo)methyl)-morpholine;
578) 2-(R)-(1-(R)-(3-(t-butyl)-5-(chloro)phenyl)ethoxy)-3-(S)-phenyl-4-(3-(-1H,4H-1,2,4-triazolo)methyl)-morpholine;
579) 2-(R)-(1-(R)-(3-(t-butyl)-5-(chloro)phenyl)ethoxy)-3-(S)-phenyl-4-(4-(2-oxo-1,3-imidazolo)methyl)-morpholine;
580) 2-(R)-(1-(R)-(3-(t-butyl)-5-(trifluoromethyl)phenyl)ethoxy)-3-(S)-phenyl-4-(3-(-1H,4H-1,2,4-triazolo)methyl)-morpholine;
581) 2-(R)-(1-(R)-(3-(t-butyl)-5-(trifluoromethyl)phenyl)ethoxy)-3-(S)-phenyl-4-(4-(2-oxo-1,3-imidazolo)methyl)-morpholine;
582) 2-(R)-(1-(R)-(3,5-(dimethyl)-4-(fluoro)phenyl)ethoxy)-3-(S)-phenyl-4-(3-(1,2,4-triazolo)methyl)-morpholine;
583) 2-(R)-(1-(R)-(3,5-(dimethyl)-4-(fluoro)phenyl)ethoxy)-3-(S)-phenyl-4-(4-(2-oxo-1,3-imidazolo)methyl)-morpholine;
584) 2-(R)-(1-(R)-(3,5-(dimethyl)-4-(chloro)phenyl)ethoxy)-3-(S)-phenyl-4-(3-(-1H,4H-1,2,4-triazolo)methyl)-morpholine;
585) 2-(R)-(1-(R)-(3,5-(dimethyl)-4-(chloro)phenyl)ethoxy)-3-(S)-phenyl-4-(4-(2-oxo-1,3-imidazolo)methyl)-morpholine;
586) 2-(R)-(1-(R)-(3,5-bis(trifluoromethyl)-4-(fluoro)phenyl)ethoxy)-3-(S)-phenyl-4-(3-(-1H,4H-1,2,4-triazolo)methyl)-morpholine;
587) 2-(R)-(1-(R)-(3,5-bis(trifluoromethyl)-4-(fluoro)phenyl)ethoxy)-3-(S)-phenyl-4-(4-(2-oxo-1,3-imidazolo)methyl)-morpholine;
588) 2-(R)-(1-(R)-(3,5-bis(trifluoromethyl)-4-(chloro)phenyl)ethoxy)-3-(S)-phenyl-4-(3-(-1H,4H-1,2,4-triazolo)methyl)-morpholine;
589) 2-(R)-(1-(R)-(3,5-bis(trifluoromethyl)-4-(chloro)phenyl)ethoxy)-3-(S)-phenyl-4-(4-(2-oxo-1,3-imidazolo)methyl)-morpholine;
590) 2-(R)-(1-(R)-(3,5-(dichloro)phenyl)ethoxy)-3-(S)-phenyl-4-(3-(-1H,4H-1,2,4-triazolo)methyl)-morpholine;
591) 2-(R)-(1-(R)-(3,5-(dichloro)phenyl)ethoxy)-3-(S)-phenyl-4-(4-(2-oxo-1,3-imidazolo)methyl)-morpholine;
592) 2-(R)-(1-(R)-(3,5-(difluoro)phenyl)ethoxy)-3-(S)-phenyl-4-(3-(1,2,4-triazolo)methyl)-morpholine;
593) 2-(R)-(1-(R)-(3,5-(difluoro)phenyl)ethoxy)-3-(S)-phenyl-4-(4-(2-oxo-1,3-imidazolo)methyl)-morpholine;
594) 2-(R)-(1-(R)-(1-(naphthyl)ethoxy)-3-(S)-phenyl-4-(3-(1,2,4-triazolo)methyl)-morpholine;
595) 2-(R)-(1-(R)-(1-(naphthyl)ethoxy)-3-(S)-phenyl-4-(4-(2-oxo-1,3-imidazolo)methyl)-morpholine;
596) 2-(R)-(1-(R)-(1-(4-(fluoro)naphthyl))ethoxy)-3-(S)-phenyl-4-(3-(1,2,4-triazolo)methyl)-morpholine;
597) 2-(R)-(1-(R)-(1-(4-(fluoro)naphthyl))ethoxy)-3-(S)-phenyl-4-(4-(2-oxo-1,3-imidazolo)methyl)-morpholine;
598) 2-(R)-(1-(R)-(1-(3-(fluoro)naphthyl))ethoxy)-3-(S)-phenyl-4-(3-(1,2,4-triazolo)methyl)-morpholine;
599) 2-(R)-(1-(R)-(1-(3-(fluoro)naphthyl))ethoxy)-3-(S)-phenyl-4-(4-(2-oxo-1,3-imidazolo)methyl)-morpholine;
600) 2-(R)-(1-(R)-(1-(3-(chloro)naphthyl))ethoxy)-3-(S)-phenyl-4-(3-(1,2,4-triazolo)methyl)-morpholine;
601) 2-(R)-(1-(R)-(1-(3-(chloro)naphthyl))ethoxy)-3-(S)-phenyl-4-(4-(2-oxo-1,3-imidazolo)methyl)-morpholine;

and pharmaceutically acceptable salts thereof.

Representative examples of the nomenclature employed herein are given below:

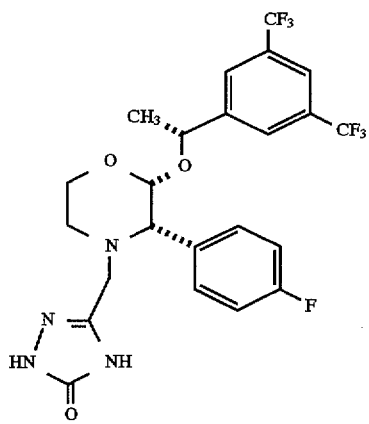

96) 2-(R)-(1-(R)-(3,5-bis(trifluoromethyl)phenyl)
ethoxy)-3-(S)-(4-fluoro)phenyl-4-(3-(5-oxo-1H,4H-
1,2,4-triazolo)methyl-morpholine;

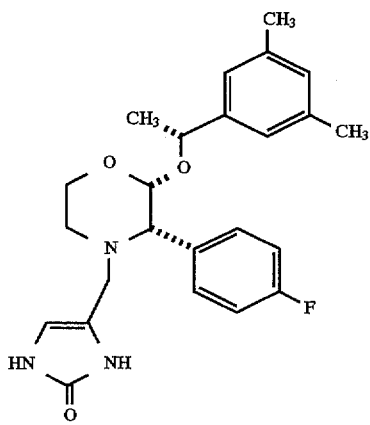

449) 2-(R)-(1-(R)-(3,5-(dimethyl)-4-(fluoro)phenyl)
ethoxy)-3-(S)-(4-fluoro)phenyl-4-(4-(2-oxo-1,3-
imidazolo)methyl)-morpholine;

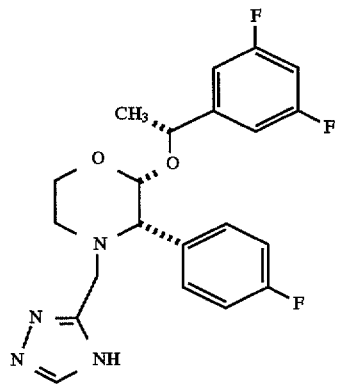

468) 2-(R)-(1-(R)-(3,5-(difluoro)phenyl)ethoxy)-3-
(S)-(4-fluoro)phenyl-4-(3-(1,2,4-triazolo)methyl)-
morpholine.

Specific compounds within the scope of the present invention include:

(1) 2-(S)-(3,5-bis(trifluoromethyl)benzyloxy)-3-(S)-phenyl-
4-(3-(5-oxo-1H,4H-1,2,4-triazolo)methyl)morpholine
N-oxide;

(2) 2-(R)-(1-(R)-(3,5-bis(trifluoromethyl)phenyl)ethoxy)-3-
(S)-(4-fluoro)-phenyl-4-(3-(4-monophosphoryl-5-oxo-
1H,-1,2,4-triazolo)methyl)morpholine;

(3) 2-(R)-(1-(R)-(3,5-bis(trifluoromethyl)phenyl)ethoxy)-3-
(S)-(4-fluoro)-phenyl-4-(3-(1-monophosphoryl-5-oxo-
1H,-1,2,4-triazolo)methyl)morpholine;

(4) 2-(R)-(1-(R)-(3,5-bis(trifluoromethyl)phenyl)ethoxy)-3-
(S)-(4-fluoro)-phenyl-4-(3-(2-monophosphoryl-5-oxo-
1H,-1,2,4-triazolo)methyl)morpholine;

(5) 2-(R)-(1-(R)-(3,5-bis(trifluoromethyl)phenyl)ethoxy)-3-
(S)-(4-fluoro)-phenyl-4-(3-(5-oxyphosphoryl-1H,-1,2,4-
triazolo)methyl)morpholine;

(6) 2-(S)-(1-(R)-(3,5-bis(trifluoromethyl)phenyl)ethoxy)-3-
(S)-(4-fluoro)-phenyl-4-(3-(1-phosphoryl-5-oxo-4H-1,2,
4-triazolo)methyl)morpholine;

or a pharmaceutically acceptable salt thereof.

Particularly prefered compounds include those wherein the pharmaceutically acceptable salt is the bis(N-methyl-D-glucamine) salt.

Specific compounds within the scope of the present invention also include:

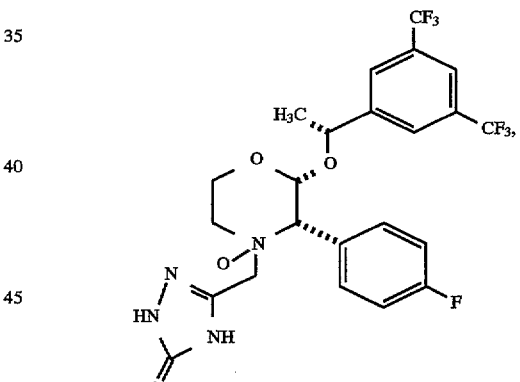

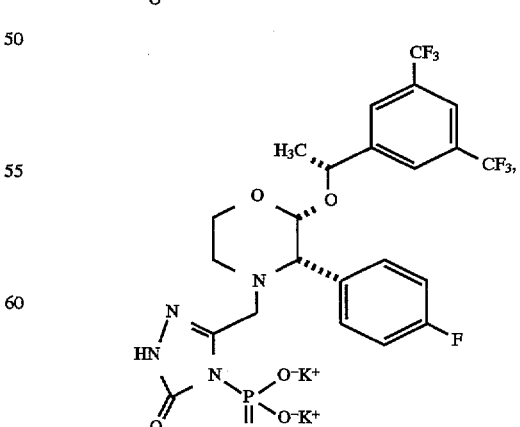

41
-continued
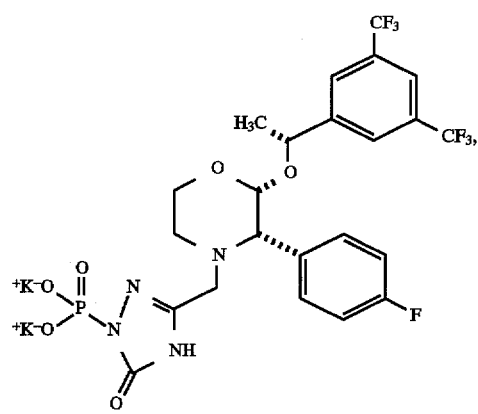
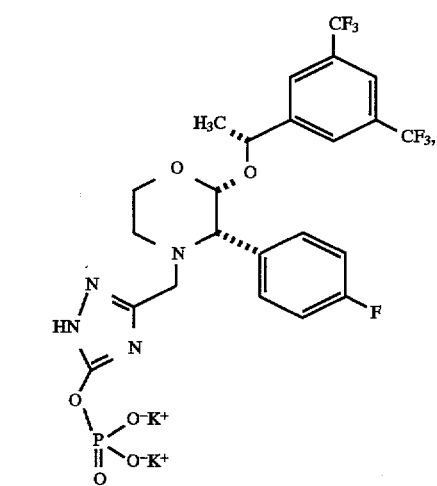
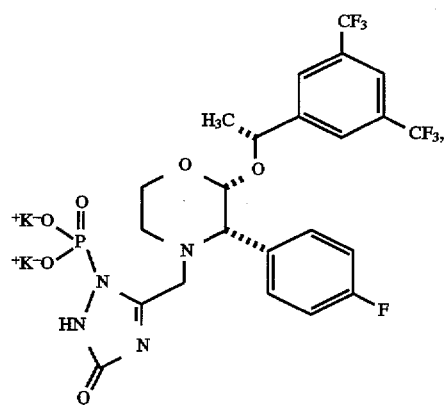
42
-continued
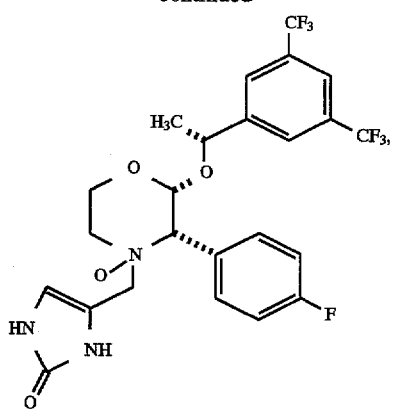
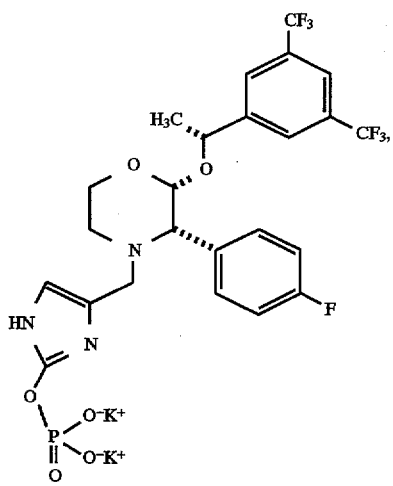
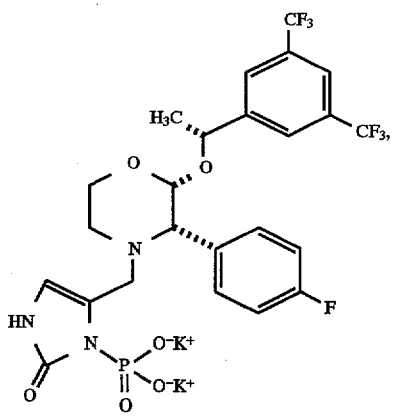

-continued

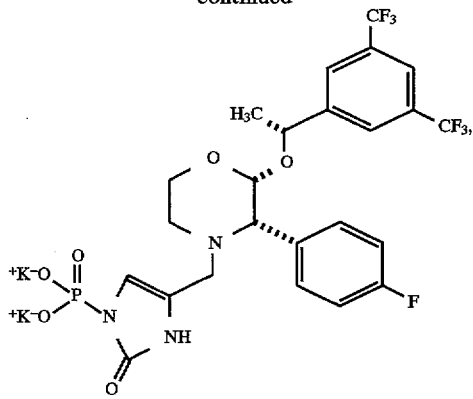

wherein K⁺ is a pharmaceutically acceptable counterion.

A particularly preferred compound within the scope of the present invention is 2-(R)-(1-(R)-(3,5-bis(trifluoro-methyl) phenyl)ethoxy)-3-(S)-(4-fluoro)phenyl-4-(3-(1-phosphoryl-5-oxo-4H-1,2,4-triazolo)methylmorpholine, or a pharmaceutically acceptable salt thereof, and a specific particularly preferred compound within the scope of the present invention is 2-(R)-(1-(R)-(3,5-bis(trifluoromethyl)phenyl)ethoxy) -3-(S)-(4-fluoro)phenyl-4-(3-(1-phosphoryl-5-oxo-4H-1,2, 4-triazolo)methylmorpholine, bis(N-methyl-D-glucamine).

TACHYKININ ANTAGONISM ASSAY

The compounds of this invention are useful for antagonizing tachykinins, in particular substance P and neurokinin A in the treatment of gastrointestinal disorders, central nervous system disorders, inflammatory diseases, pain or migraine and asthma in a mammal in need of such treatment. This activity can be demonstrated by the following assay.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100 U/ml penicillin-streptomycin, and 90% DMEM media (GIBCO, Grand Island, N.Y.) in 5% $CO_2$ at 37° C. for three days before the binding assay.

B. Stable Expression in CHO

To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer suplemented with 0.625 mg/ml Herring sperm DNA at 300 V and 950 uF using the IBI GENEZAPPER (IBI). The transfected cells were incubated in CHO media [10% fetal calf serum, 100 U/ml pennicilin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 ul of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter.

The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1N HCl is added. Each well is sonicated at 4° C. and extracted with $CHCl_3$/methanol (1:1). The aqueous phase is applied to a 1 ml Dowex AG 1×8 ion exchange column. The column is washed with 0.1N formic acid followed by 0.025M ammonium formate-0.1N formic acid. The inositol monophosphate is eluted with 0.2M ammonium formate-0.1N formic acid and quantitated by beta counter.

The compounds of Formula I as exemplified in the Examples below have been found to displace radioactive ligand for the neurokinin-1 receptor at a concentration range of 0.01 nM to 1.0 μM.

The activity of the present compounds may also be demonstrated by the assay disclosed by Lei, et al., *British J. Pharmacol.*, 105, 261–262 (1992).

The compounds of the present invention are useful in the prevention and treatment of a wide variety of clinical conditions which are characterized by the presence of an excess of tachykinin, in particular substance P, activity. These conditions may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as multiple sclerosis (MS) and amyotrophic lateral sclerosis (ALS; Lou Gehrig's disease) and other neuropathological disorders such as peripheral neuropathy, for example AIDS related neuropathy, diabetic neuropathy, chemotherapy-induced neuropathy, and postherpetic and other neuralgias; small cell carcinomas such as small cell lung cancer; respiratory diseases, particularly those associated with excess mucus secretion, such as chronic obstructive airways disease, bronchopneumonia, chronic bronchitis, acute bronchitis, diffuse panbronchilitis, emphysema, cystic fibrosis, asthma, and bronchospasm; airways disease modulated by neurogenic inflammation; laryngopharhngitis; bronchiectasis; conoisis; whooping cough; pulmonary tuberculosis; diseases associated with decreased glandular secretions, including lacrimation, such as Sjogren's syndrome, hyperlipoproteinemias IV and V, hemochromatosis, sarcoidosis, or amyloidosis; iritis; inflammatory diseases such as inflammatory bowel disease, inflammatory intestinal disease, psoriasis, fibrositis, ocular intimation, osteoarthritis, rheumatoid arthritis, pruritis, and sunburn; hepatitis; allergies such as eczema and rhinitis; hypersensitivity disorders such as poison ivy; ophthalmic diseases such as conjunctivitis, vernal conjunctivitis, dry eye syndrome, and the like; ophthalmic conditions associated with cell proliferation such as proliferative vitreoretinopathy; cutaneous diseases such as contact dermatitis, atopic dermatitis, urticaria, and other eczematoid dermatitis; hemodialysis-associated itching; lichen planus; oedema, such as oedema caused by thermal injury; addiction disorders such as alcoholism; mental disease, particularly anxiety and depression; stress related somatic disorders; reflex sympathetic dystrophy such as shoulder/hand syndrome; dysthymic disorders; tenalgia attended to hypedipidemia; post-operative neuroma, particularly of mastectomy; vulvar vestibulitis; amniogenesis; adverse immunological reactions such as rejection of transplanted tissues and disorders related to immune enhancement or suppression, such as systemic lupus erythmatosus; gastrointestinal (GI) disorders, including inflammatory disorders, and diseases of the GI tract, such as gastritis, gastroduodenal ulcers, gastric carcinomas, gastric lymphomas, disorders associated with the neuronal control of viscera such as ulcerative colitis, Crohn's disease, irritable bowel syndrome, nausea, and emesis, including acute, delayed, post-operative, late-phase, and anticipatory emesis, such as emesis or nausea induced by for example chemotherapy, radiation, surgery, migraine, toxins, such as metabolic or microbial toxins, viral or bacterial infections, pregnancy, vestibular disorder, motion, mechanical stimulation, gastrointestinal obstruction, reduced gastrointestinal motility, visceral pain, psychological stress or disturbance, high altitude, weightlessness, opioid analgesics, intoxication, resulting for example from consumption of alcohol, and variations in intercranial pressure, in particular, for example, drug or radiation induced emesis or post-operative nausea and vomiting; disorders of bladder function such as cystitis, bladder detrusor hyperreflexia, and incontinence; fibrosing and collagen diseases such as scleroderma and eosinophilic fascioliasis; disorders of blood flow caused by vasodilation and vasospastic diseases such as angina, migraine and Reynaud's disease; and pain or nociception, for example, chronic pain or that attributable to or associated with any of the foregoing conditions especially the transmission of pain in migraine, or such as headache, toothache, cancerous pain, back pain, and superficial pain on congelation, burn, herpes zoster or diabetic neuropathy. Hence, these compounds may be readily adapted to therapeutic use for the treatment of physiological disorders associated with an excessive stimulation of tachykinin receptors, especially neurokinin-1, and as neurokinin-1 antagonists in the control and/or treatment of any of the aforesaid clinical conditions in mammals, including humans.

The compounds of the present invention are also of value in the treatment of a combination of the above conditions, in particular in the treatment of combined post-operative pain and post-operative nausea and vomiting.

The compounds of the present invention are particularly useful in the treatment of nausea or emesis, including acute, delayed, post-operative, late-phase, and anticipatory emesis, such as emesis or nausea induced by for example chemotherapy, radiation, surgery, migraine, toxins, such as metabolic or microbial toxins, viral or bacterial infections, pregnancy, vestibular disorder, motion, mechanical stimulation, gastrointestinal obstruction, reduced gastrointestinal motility, visceral pain, psychological stress or disturbance, high altitude, weightlessness, opioid analgesics, intoxication, resulting for example from consumption of alcohol, and variations in intercranial pressure. Most especially, this compound is of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulfonates and other compounds with an alkylating action such as nitrosoureas, cisplatin, and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for example, by D. J. Stewart in "Nausea and Vomiting: Recent Research and Clinical Advances", Eds. J. Kucharczyk, et al., CRC Press Inc., Boca Raton, Fla., U.S.A. (1991), pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, and chlorambucil [R. J. Gralla, et al., *Cancer Treatment Reports*, 68(1), 163–172 (1984)].

The compounds of the present invention are also of use in the treatment of emesis induced by radiation including radiation therapy such as in the treatment of cancer, or radiation sickness, and in the treatment of post-operative nausea and vomiting.

The compounds of the present invention are also of use in the prevention or treatment of disorders of the central nervous system such as anxiety, psychosis and schizophrenia; neurodegenerative disorders such as senile dementia of the Alzheimer type, Alzheimer's disease and Down's syndrome; respiratory diseases, particularly those associated with excess mucus secretion, such as chronic obstructive airways disease, broncho-pneumonia, chronic bronchitis, cystic fibrosis and asthma, and bronchospasm; inflammatory diseases such as inflammatory bowel disease, osteoarthritis and rheumatoid arthritis; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; and pain or nociception, for example, that attributable to or associated with any of the foregoing conditions or the transmission of pain in migraine (both prophylaxis and acute treatment).

As calcium channel blocking agents some of the compounds of the present invention are useful in the prevention of treatment of clinical conditions which benefit from inhibition of the transfer of calcium ions across the plasma membrane of cells. These include diseases and disorders of the heart and vascular system such as angina pectoris, myocardial infarction, cardiac arrhythmia, cardiac hypertrophy, cardiac vasospasm, hypertension, cerebrovascular spasm and other ischemic disease. Furthermore, these compounds may be capable of lowering elevated intraocular pressure when administered topically to the hypertensive eye in solution in a suitable ophthalmic vehicle. Also, these compounds may be useful in the reversal of multidrug resistance in tumor cells by enhancing the efficacy of chemotherapeutic agents. In addition, these compounds may have activity in blocking calcium channels in insect brain membranes and so may be useful as insecticides.

The compounds of the present invention are particularly useful in the treatment of pain or nociception and/or inflammation and disorders associated therewith such as, for example: neuropathy, such as diabetic or peripheral neuropathy and chemotherapy-induced neruopathy; postherpetic and other neuralgias; asthma; osteoarthritis; rheumatoid arthritis; and especially migraine. The compounds of the present invention are also particularly useful in the treatment of diseases characterized by neurogenic mucus secretion, especially cystic fibrosis.

For the treatment of certain conditions it may be desirable to employ a compound of the present invention in conjunction with another pharmacologically active agent. For example, a compound of the present invention may be presented together with another therapeutic agent as a combined preparation for simultaneous, separate, or sequential use for the relief of emesis. Such combined preparations may be, for example, in the form of a twin pack. A preferred combination comprises a compound of the present invention with a chemotherapeutic agent such as an alkylating agent, antimetabolite, mitotic inhibitor, or cytotoxic antibiotic, as described above. In general, the currently available dosage forms of the known therapeutic agents for use in such combinations will be suitable.

Similarly, for the treatment of respiratory diseases, such as asthma, a compound of the present invention may be used in conjunction with a bronchodilator, such as a $\beta_2$-adrenergic receptor agonist or a tachykinin antagonist which acts at neurokinin-2 receptors. Suitable $\beta_2$-adrenergic receptor agonist include: Bambuterol (U.S. Pat. No. 4,419,364 issued to Draco on Dec. 6, 1983); Bitolterol mesylate (U.S. Pat. No. 4,138,581 issued to Sterling Feb. 6, 1979); Brosaterol (U.S. Pat. No. 4,276,299 issued to Zambon Jun. 30, 1981 and U.S. Pat. No. 4,520,200 issued to Zambon May 28, 1985); Carbuterol (U.S. Pat. No. 3,763,232 issued to Smith Kline Oct. 2, 1973); Clenbuterol (U.S. Pat. No. 3,536,712 issued to Boehringer Ingelheim Oct. 27, 1970); Cimaterol (U.S. Pat. No. 4,407,819 issued to American Cyanamid Oct. 4, 1983); Docarpamine (U.S. Pat. No. 4,228,183 issued to Tanabe Oct. 14, 1980); Dopexamine (U.S. Pat. No. 4,645,768 issued to Fisons Feb. 24, 1987); Formoterol (U.S. Pat. No. 3,994,974 issued to Yamanouchi Nov. 30, 1976); Mabuterol (U.S. Pat. No. 4,119,710 issued to Boehringer Ingelheim Oct. 10, 1978); Pirbuterol hydrochloride (U.S. 3,700,681 issued to Pfizer Oct. 24, 1972); Procaterol hydrochloride (U.S. Pat. No. 4,026,897 issued to Otsuka May 31, 1977); Ritodrine hydrochloride (U.S. Pat. No. 3,410,944 issued to North American Philips Nov. 12, 1968); or Salmeterol (U.S. Pat. No. 4,992,474 issued to Glaxo Feb. 21, 1991 and U.S. Pat. No. 5,091,422 issued to Glaxo Feb. 25, 1992).

Also, for the treatment of conditions that require antagonism of both neurokinin-1 and neurokinin-2, including disorders associated with bronchoconstriction and/or plasma extravasation in airways, such as asthma, chronic bronchitis, airways disease, or cystic fibrosis; neuropathy, such as diabetic or peripheral neuropathy and chemotherapy-induced neuropathy; osteoarthritis; rheumatoid arthritis; and migraine, a compound of the present invention may be used in conjunction with a tachykinin antagonist which acts at neurokinin-2 receptors, or with tachykinin receptor antagonist which acts at both neurokinin-1 and neurokinin-2 receptors.

Likewise, a compound of the present invention may be employed with a leucotriene antagonist, such a leucotriene $D_4$ antagonist, exemplified by those disclosed in Patent Pub. EP O,480,717, published Apr. 15, 1992; Patent Pub. EP O 604,114, published June 1994; U.S. Pat. No. 5,270,324, issued Dec. 14, 1993; and U.S. Pat. No. 4,859,692, issued Aug. 22, 1989. This combination is particularly useful in the treatment of respiratory diseases such as asthma, chronic bronchitis and cough.

A compound of the present invention further may be used in combination with a corticosteroid such as Dexamethasone, Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712.

Similarly, for the prevention or treatment of emesis a compound of the present invention may be used in conjunction with other anti-emetic agents, especially $5HT_3$ receptor antagonists, such as ondansetron, granisetron, tropisetron, decadron, and zatisetron, or $GABA_B$ receptor agonists, such as baclofen. Likewise, for the prevention or treatment of migraine a compound of the present invention may be used in conjunction with other anti-migraine agents, such as ergotamines or $5HT_1$ agonists, especially sumatriptan.

Likewise, for the treatment of behavioral hyperalgesia, a compound of the present invention may be used in conjunction with an antagonist of N-methyl D-aspartate (NMDA), such as dizocilpine. For the prevention or treatment of inflammatory conditions in the lower urinary tract, especially cystitis, a compound of the present invention may be used in conjunction with an antiinflammatory agent, such as a bradykinin receptor antagonist. The compound of the present invention and the other pharmacologically active agent may be administered to a patient simultaneously, sequentially or in combination.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non- toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solution, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For the treatment of the clinical conditions and diseases noted above, the compounds of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The compounds of this invention may be administered to patients (animals and human) in need of such treatment in dosages that will provide optimal pharmaceutical efficacy. The dose will vary from patient to patient depending upon the nature and severity of disease, the patient's weight, special diets then being followed by a patient, concurrent medication, and other factors which those skilled in the art will recognize.

In the treatment of a condition associated with an excess of tachykinins, an appropriate dosage level will generally be about 0.001 to 50 mg per kg patient body weight per day which may be administered in single or multiple doses. Preferably, the dosage level will be about 0.01 to about 25 mg/kg per day; more preferably about 0.05 to about 10 mg/kg per day. For example, in the treatment of conditions involving the neurotransmission of pain sensations, a suitable dosage level is about 0.001 to 25 mg/kg per day, preferably about 0.05 to 10 mg/kg per day, and especially about 0.1 to 5 mg/kg per day. A compound may be administered on a regimen of 1 to 4 times per day, preferably once or twice per day. In the treatment of emesis using an injectable formulation, a suitable dosage level is about 0.001 to 10 mg/kg per day, preferably about 0.005 to 5 mg/kg per day, and especially about 0.05 to 5 mg/kg per day. A compound may be administered on a regimen of 1 to 4 times per day, preferably once or twice per day.

Several methods for preparing the compounds of this invention are illustrated in the following Schemes and Examples wherein wherein $R^2, R^3, R^6, R^7, R^8, R^{11}, R^{12}, R^{13}$, A, B, p, Y and Z are as defined above.

TABLE 1

| ABBREVIATIONS USED IN SCHEMES AND EXAMPLES | |
|---|---|
| Reagents: | |
| Et$_3$N | triethylamine |
| Ph$_3$P | triphenylphosphine |
| TFA | trifluoroacetic acid |
| NaOEt | sodium ethoxide |
| DCC | N,N'-dicyclohexylcarbodiimide |
| DCU | N,N'-dicyclohexylurea |
| CDI | 1,1'-carbonyldiimidazole |
| MCPBA | m-chloroperbenzoic acid |
| DBU | 1,8-diazabicyclo[5.4.0]undec-7-ene |
| Cbz—Cl | benzyl chloroformate |
| ACE—Cl | alpha-chloroethyl chloroformate |
| iPr$_2$NEt or DIEA | N,N-diisopropylethylamine |
| NHS | N-hydroxysuccinimide |
| DIBAL | diisobutylaluminum hydride |
| Me$_2$SO$_4$ | dimethyl sulfate |
| HOBt | 1-hydroxybenzotriazole hydrate |
| EDAC | 1-ethyl-3-(3-dimethylaminopropyl)carbodiimide hydrochloride |
| Solvents: | |
| DMF | dimethylformamide |
| THF | tetrahydrofuran |
| MeOH | methanol |
| EtOH | ethanol |
| AmOH | n-amyl alcohol |
| AcOH | acetic acid |
| MeCN | acetonitrile |

TABLE 1-continued

ABBREVIATIONS USED IN SCHEMES AND EXAMPLES

| | |
|---|---|
| DMSO | dimethylsulfoxide |

Others:

| | |
|---|---|
| Ph | phenyl |
| Ar | aryl |
| Me | methyl |
| Et | ethyl |
| iPr | isopropyl |
| Am | n-amyl |
| Cbz | carbobenzyloxy (benzyloxy-carbonyl) |
| BOC | tert-butoxycarbonyl |
| PTC | phase transfer catalyst |
| cat. | catalytic |
| FAB-MS | fast atom bombardment mass spectrometry |
| rt | room temperature |
| LG | leaving group (Cl, Br, I, OTs, OMs, OTf, etc.) |

SCHEME 1

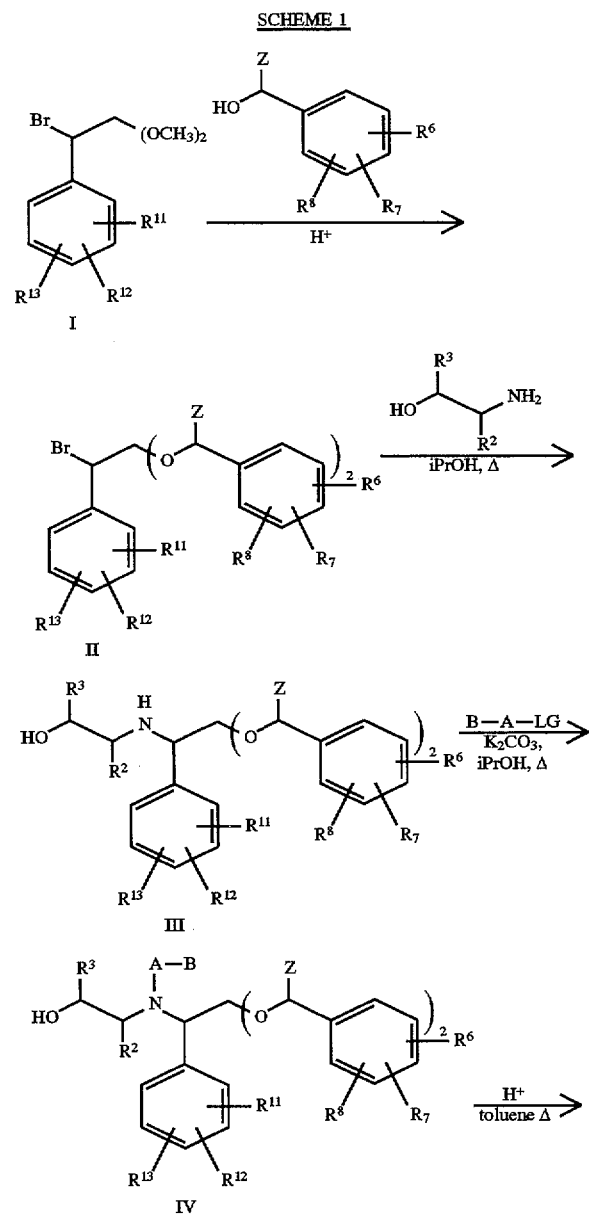

SCHEME 1 (continued)

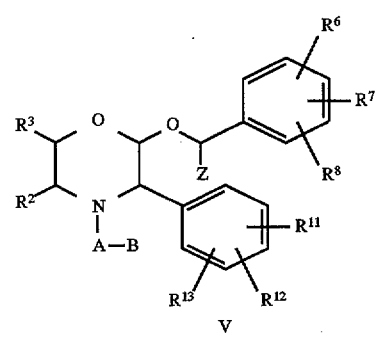

SCHEME 2

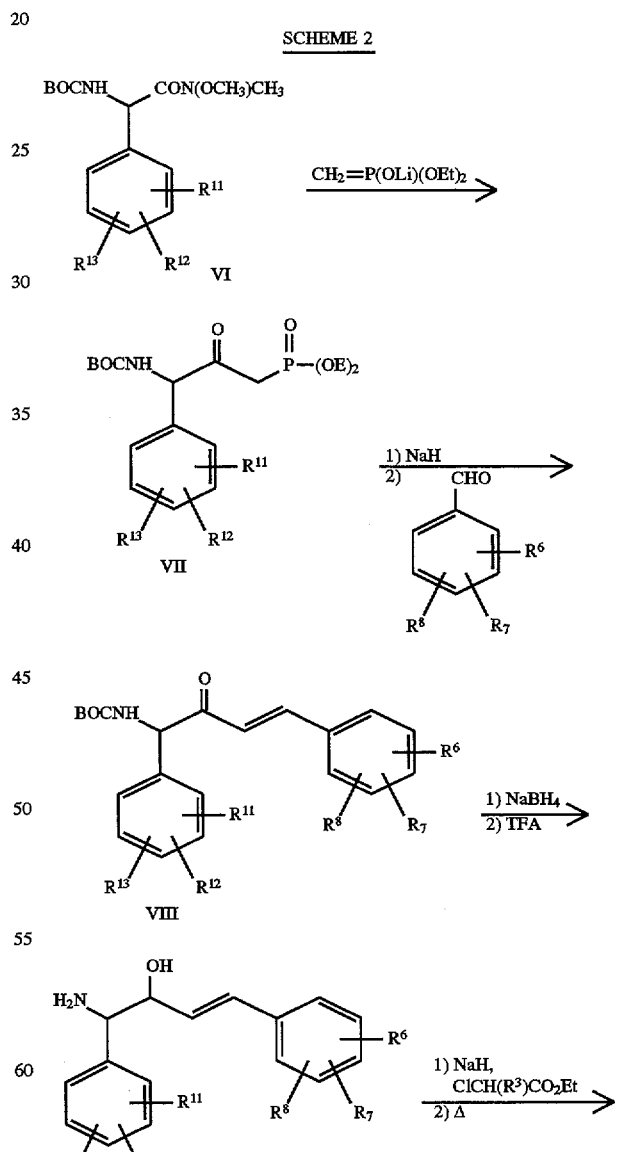

-continued
SCHEME 2
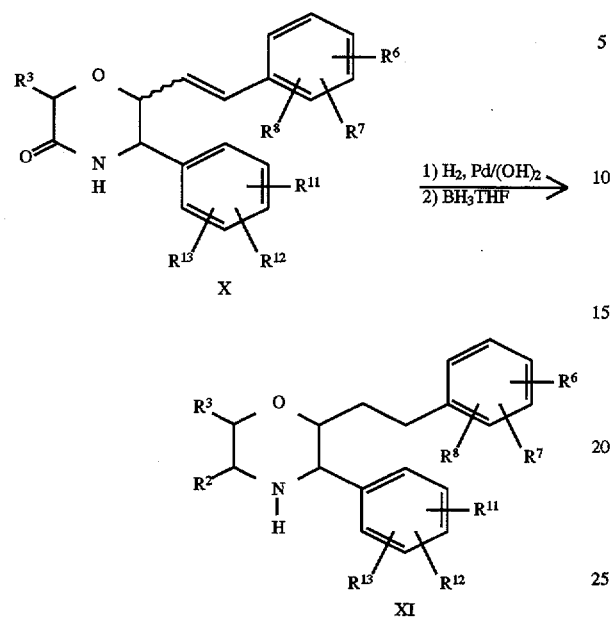
SCHEME 3
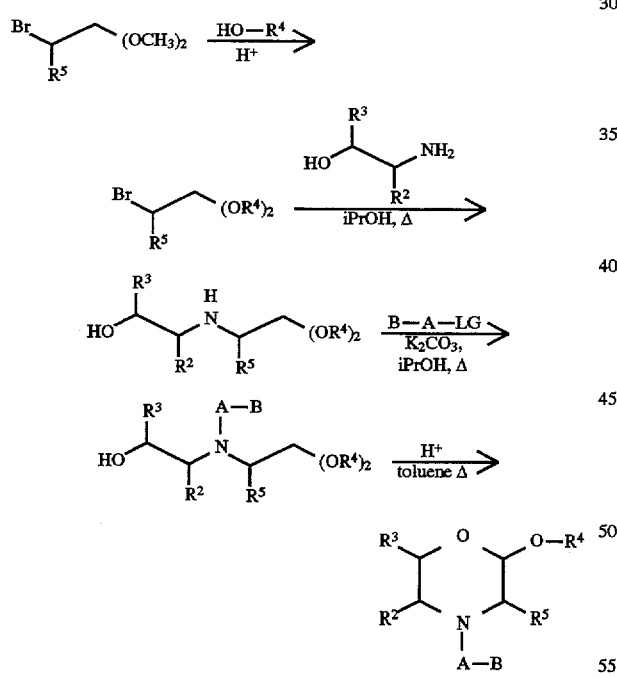
-continued
SCHEME 4
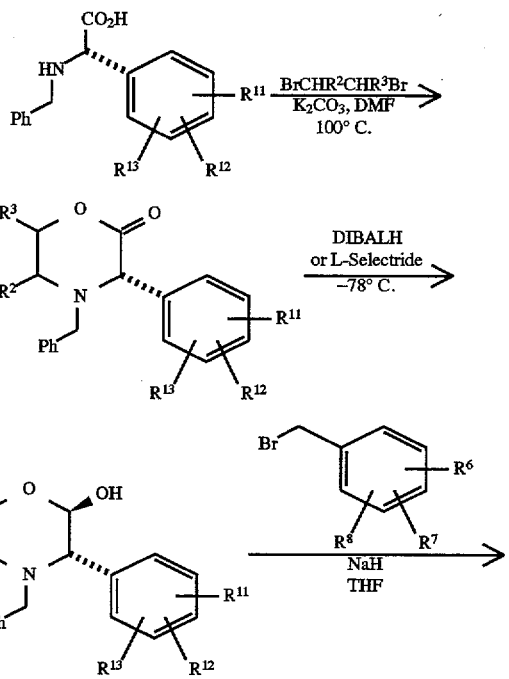
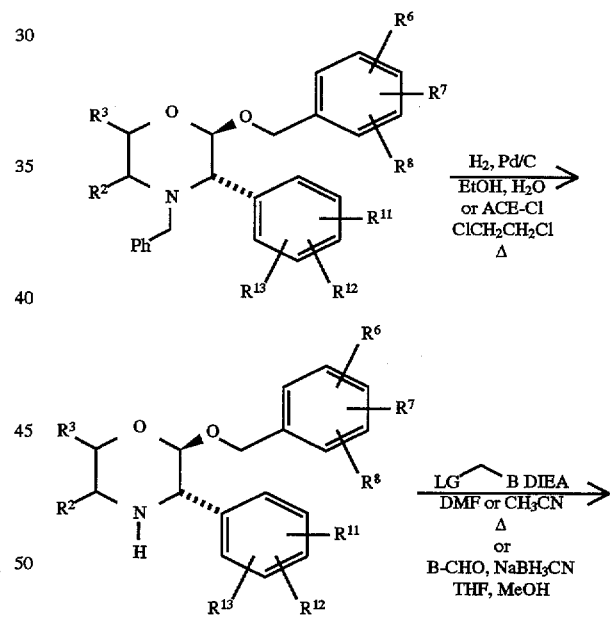
SCHEME 4
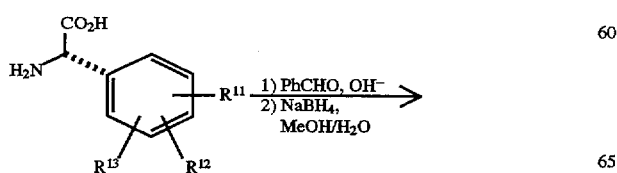

SCHEME 5
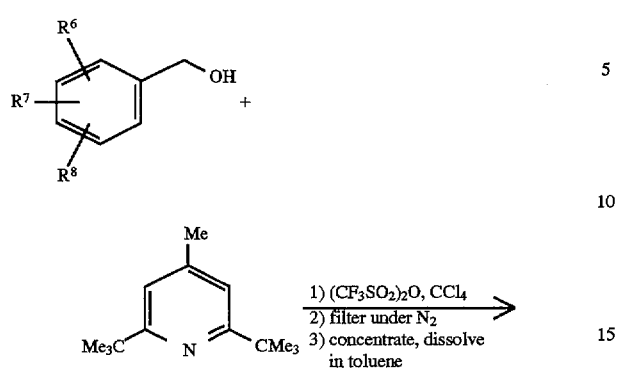
SCHEME 6
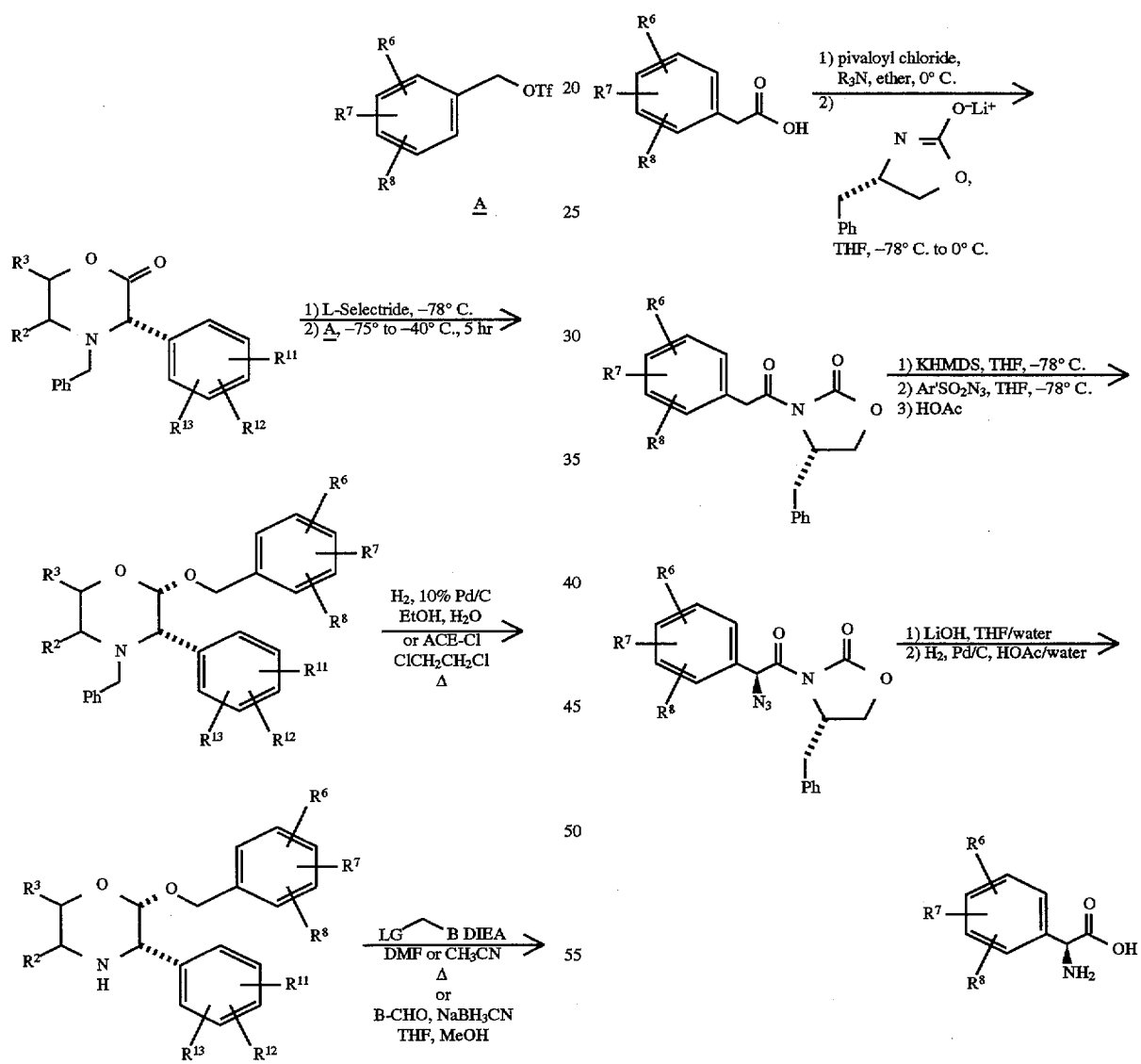

SCHEME 7
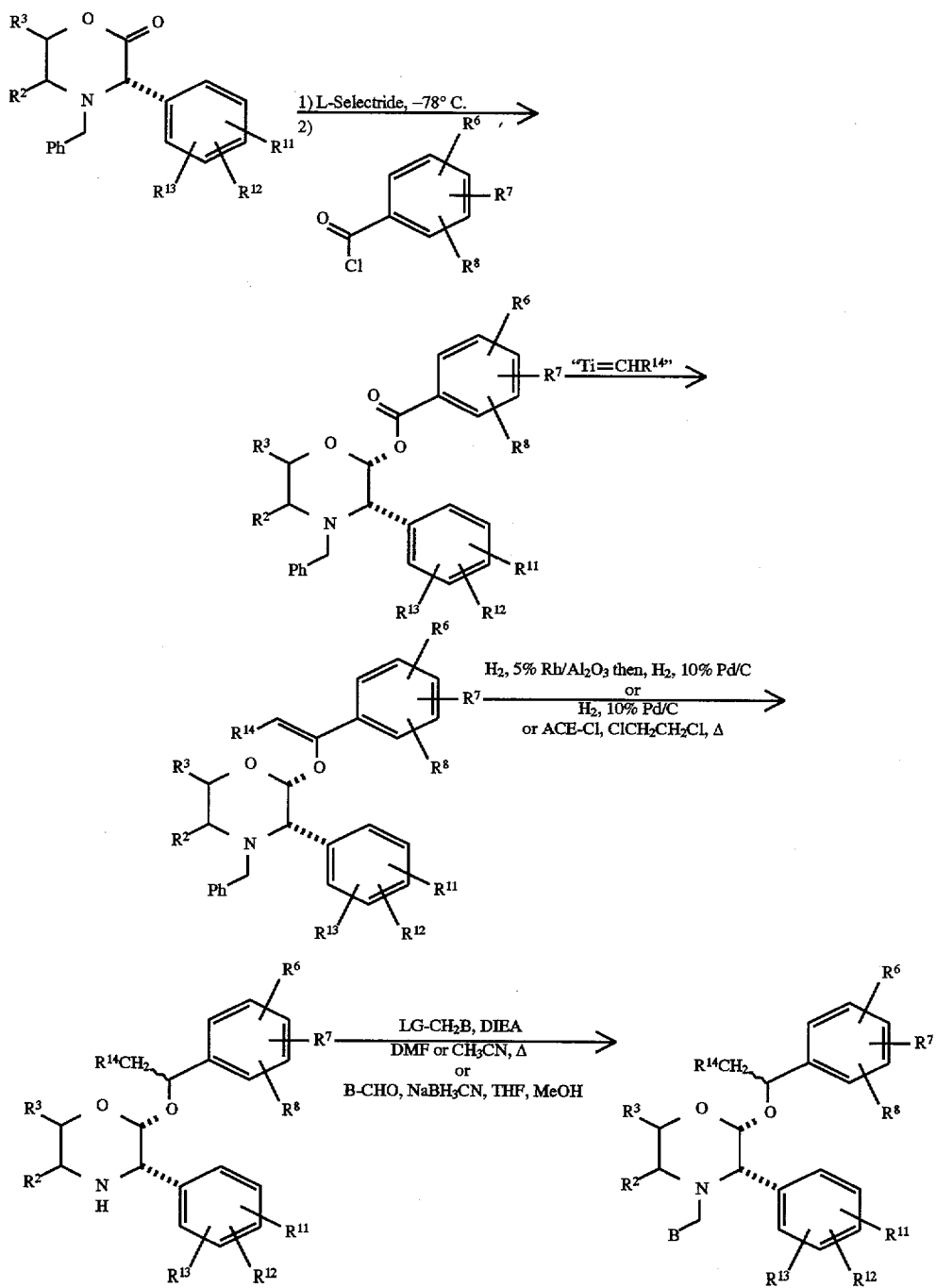

SCHEME 8

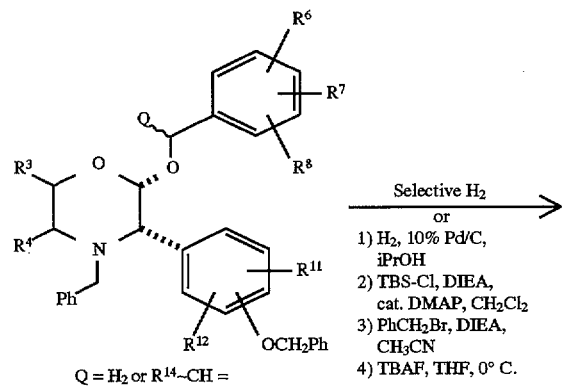

Q = H$_2$ or R$^{14}$—CH =

Selective H$_2$
or
1) H$_2$, 10% Pd/C, iPrOH
2) TBS-Cl, DIEA, cat. DMAP, CH$_2$Cl$_2$
3) PhCH$_2$Br, DIEA, CH$_3$CN
4) TBAF, THF, 0° C.

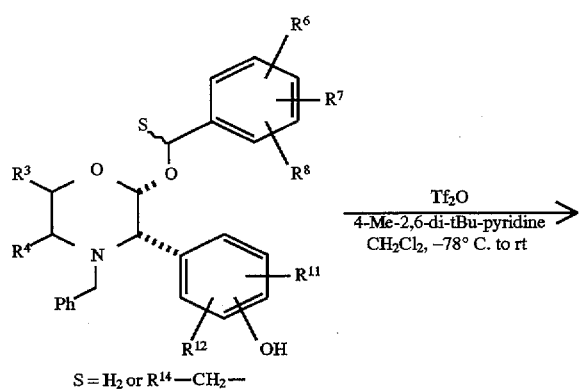

S = H$_2$ or R$^{14}$—CH$_2$—

Tf$_2$O
4-Me-2,6-di-tBu-pyridine
CH$_2$Cl$_2$, −78° C. to rt

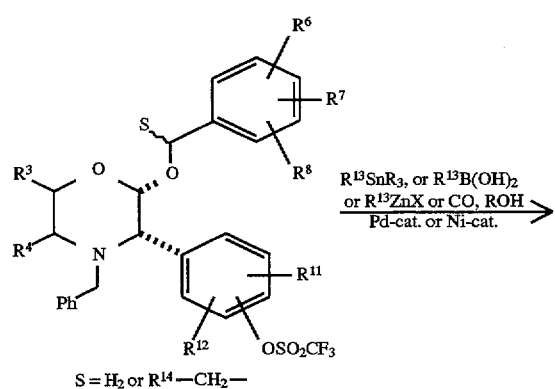

S = H$_2$ or R$^{14}$—CH$_2$—

R$^{13}$SnR$_3$, or R$^{13}$B(OH)$_2$
or R$^{13}$ZnX or CO, ROH
Pd-cat. or Ni-cat.

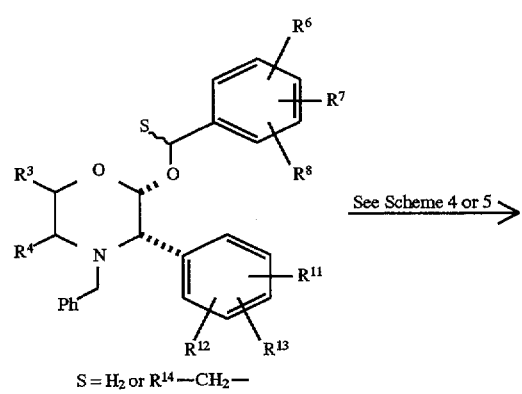

S = H$_2$ or R$^{14}$—CH$_2$—

See Scheme 4 or 5

-continued
SCHEME 8

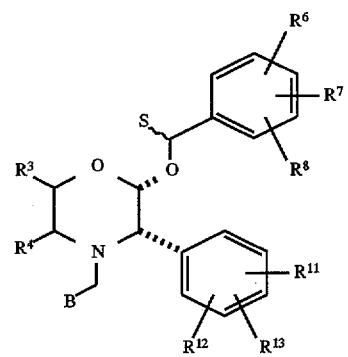

SCHEME 9

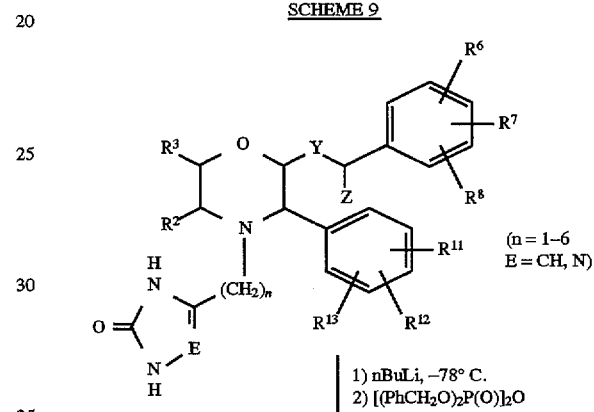

(n = 1–6
E = CH, N)

1) nBuLi, −78° C.
2) [(PhCH$_2$O)$_2$P(O)]$_2$O

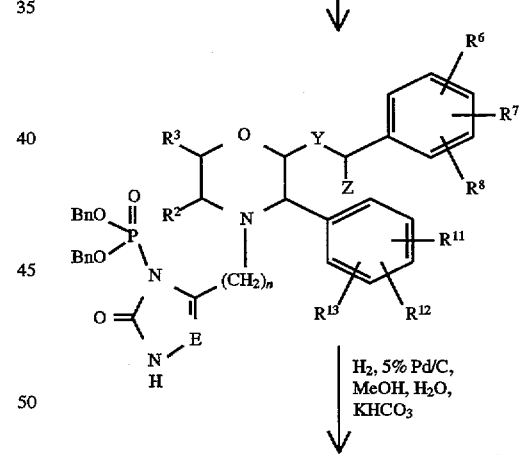

H$_2$, 5% Pd/C,
MeOH, H$_2$O, KHCO$_3$

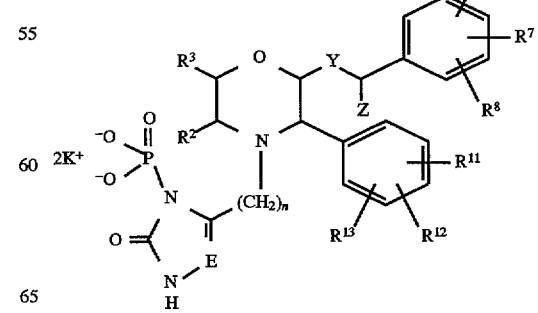

2K$^+$

SCHEME 10
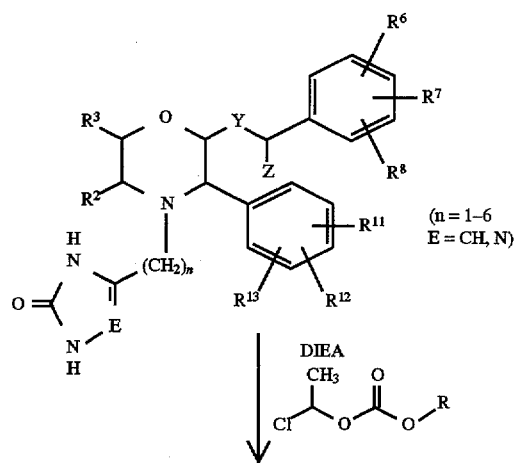
(n = 1–6
E = CH, N)
DIEA
-continued
SCHEME 10
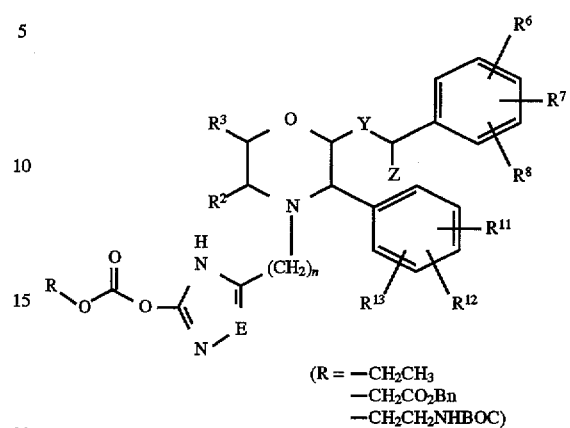
(R = —CH$_2$CH$_3$
—CH$_2$CO$_2$Bn
—CH$_2$CH$_2$NHBOC)
SCHEME 11
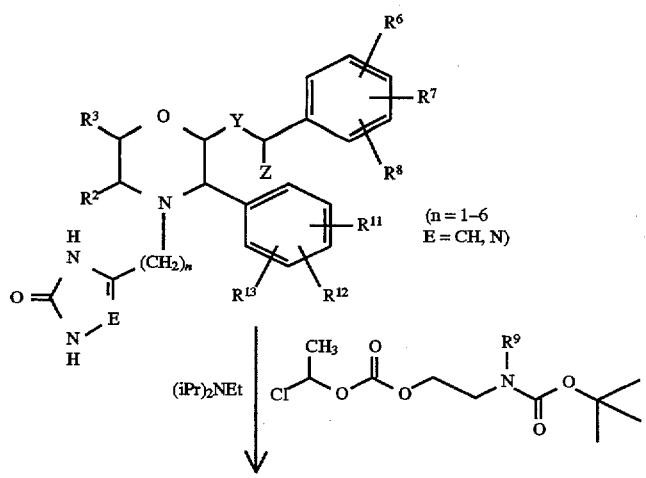
(n = 1–6
E = CH, N)
(iPr)$_2$NEt -continued
SCHEME 11
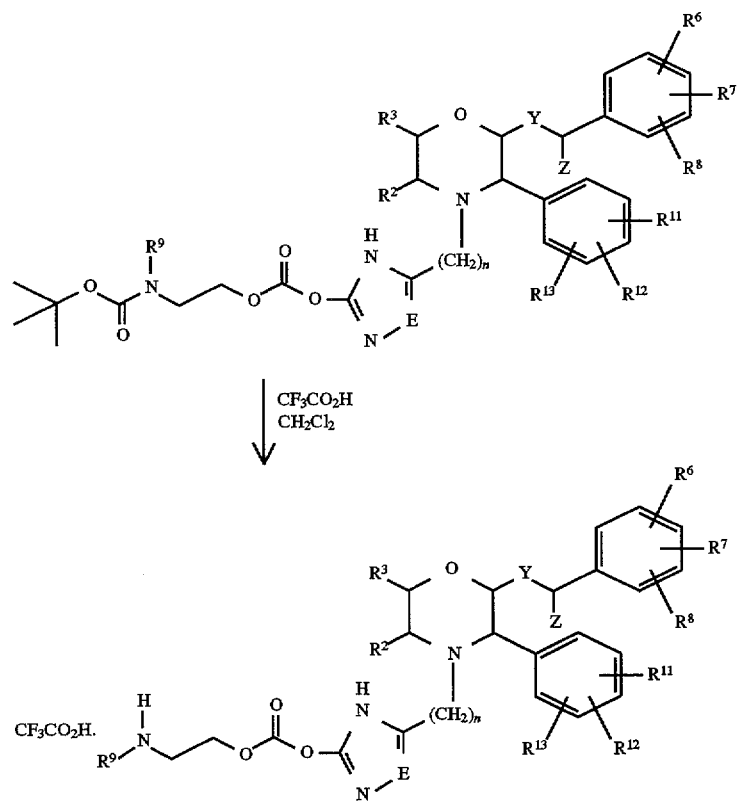
SCHEME 12
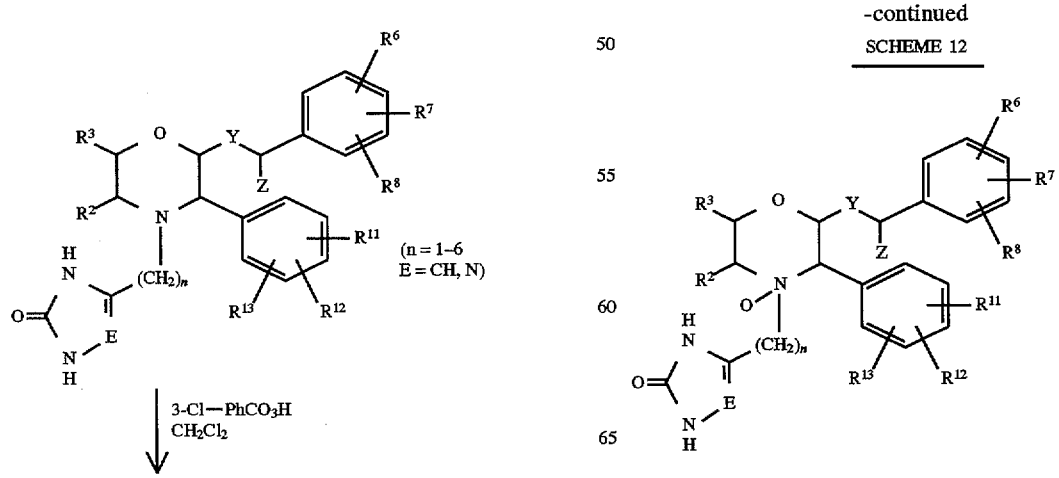
(n = 1–6
E = CH, N)
-continued
SCHEME 12

SCHEME 13
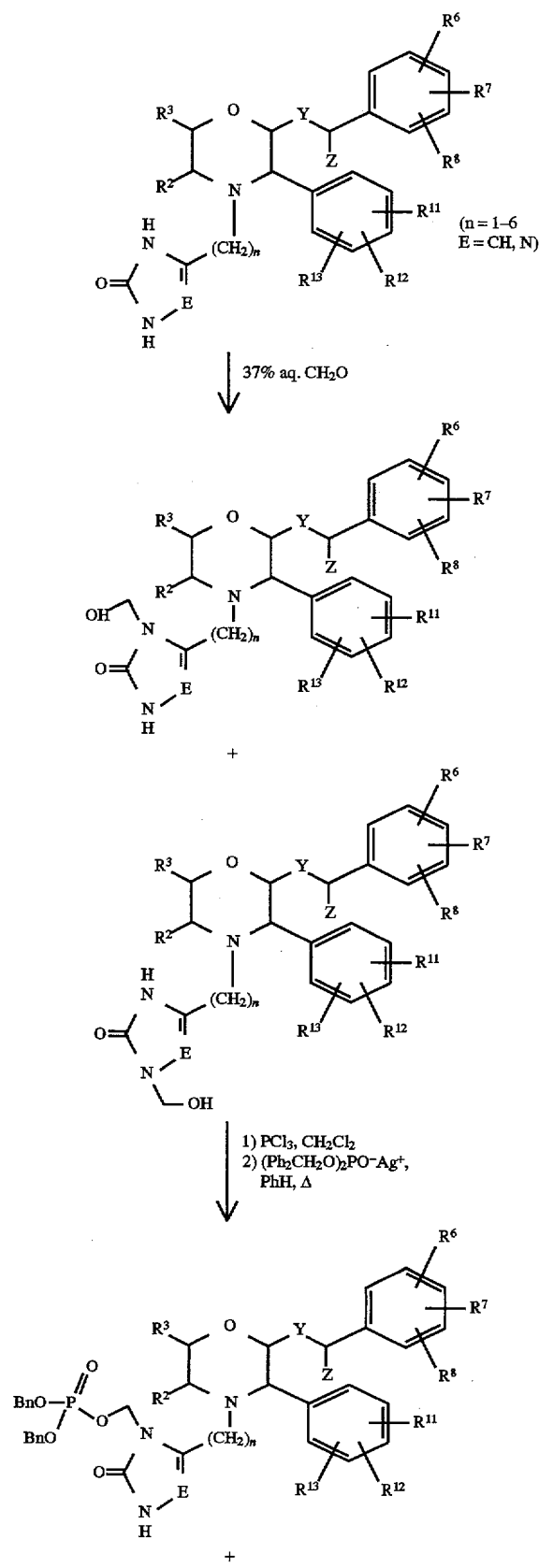
(n = 1-6
E = CH, N)
37% aq. CH₂O
1) PCl₃, CH₂Cl₂
2) (PhCH₂O)₂PO⁻Ag⁺, PhH, Δ
-continued
SCHEME 13
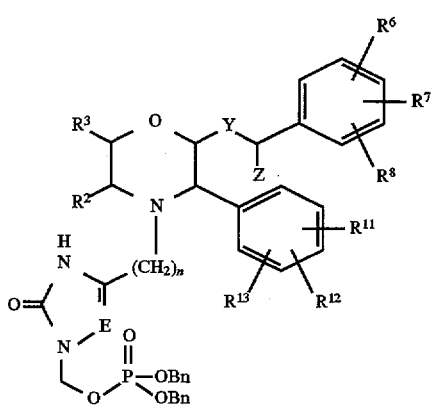
SCHEME 14
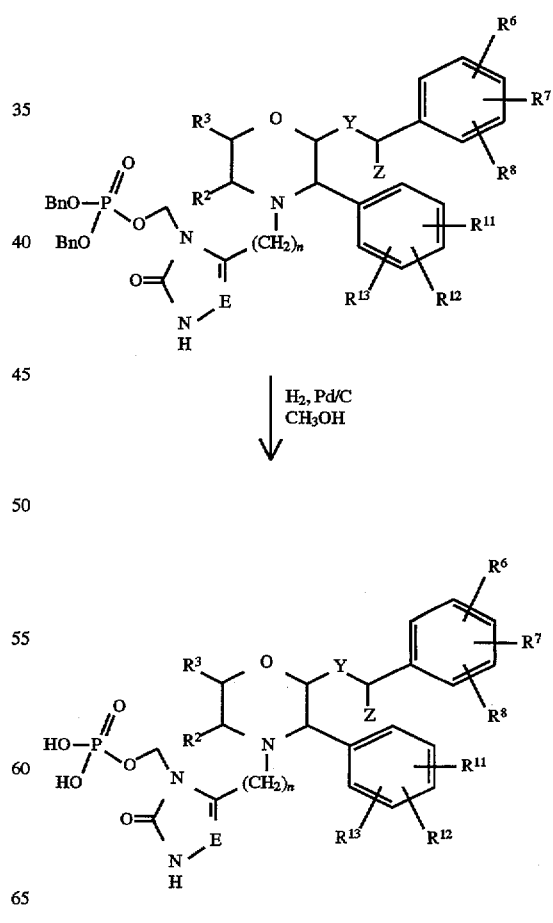
H₂, Pd/C
CH₃OH

SCHEME 15

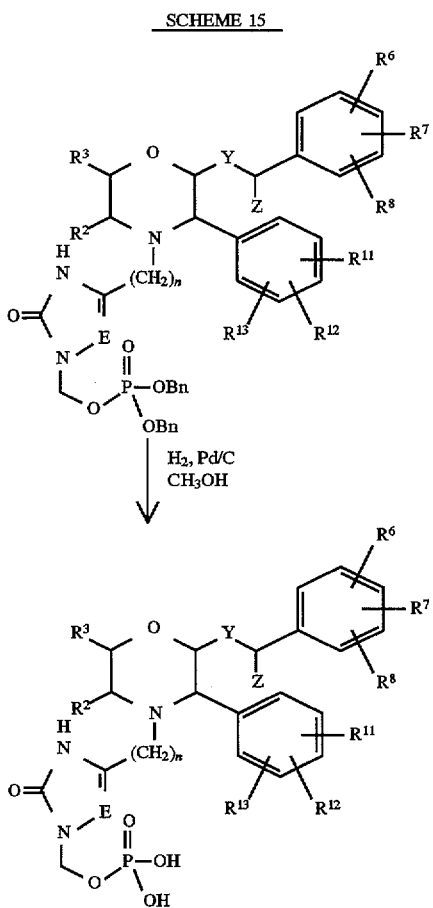

The compounds of the present invention in which Y=O may be prepared by the general route outlined in Scheme 1. Thus, the appropriately substituted α-bromo-phenylacetaldehyde, dimethyl acetal I (prepared using the method of Jacobs in *Journal of the American Chemical Society*, 1953, 75, 5500) may be convened to the dibenzyl acetal II by stirring I and a slight excess of a benzyl alcohol in the presence of an acid catalyst with concomitant removal of methanol. Alkylation of a substituted amino alcohol by benzyl bromide II may give N-alkyl amino alcohol III; use of a chiral amino alcohol would result in the formation of diastereomers and these may be separated at this (or at a later) stage using standard chromatographic methods. N-Alkylation or N-acylation of III may give the dialkyl- or acyl/alkyl-amino alcohol IV in which the group A—B may serve as a protecting group or be used as or elaborated into a substituent in the final target compound. Cyclization to give substituted morpholine V may be realized by warming a solution of IV and an acid catalyst. Diastereomers of V that may be formed may be separated using standard chromatographic methods. If A—B is a protecting group, it may be removed using known procedures (Greene, T. W., Wuts, P. G. M. Protective Groups in Organic Synthesis, 2nd ed., John Wiley & Sons, Inc., New York, 1991). If the preparation of I–V results in the formation of enantiomers, these may be resolved by alkylating or acylating V (A—B=H) with a chiral auxiliary, separating the diastereomers thus formed using known chromatographic methods, and removing the chiral auxiliary to give the enantiomers of V. Alternatively, the diastereomers of V may be separated via fractional crystallization from a suitable solvent of the diastereomeric salts formed by V and a chiral organic acid.

The compounds of the present invention in which Y=CH$_2$ may be prepared by the general route outlined in Scheme 2. Thus, the N-methoxy-N-methyl amide of a protected phenyl glycine VI (prepared from the carboxylic acid via the mixed anhydride according to the procedure of Rapoport in *Journal of Organic Chemistry*, 1985, 50, 3972) may be used to acylate the lithium enolate of methyl diethylphosphonate to give the ketophosphonate VII. The sodium salt of VII may be condensed with an appropriately substituted benzaldehyde to give the α,β-unsaturated ketone VIII. Reduction of the ketone and removal of the t-butylcarbamate protecting group may give amino alcohol IX; diastereomers that may form may be separated at this (or at a later) stage using standard chromatographic techniques. Williamson etherification of IX using a substituted chloroacetate, followed by warming, may result in the formation of morpholinone X. Reduction of the double bond and amide carbonyl may be accomplished in a straightforward manner to give the substituted morpholine XI. If the preparation of VI–XI results in the formation of enantiomers, these may be resolved by alkylating or acylating XI (A—B=H) with a chiral auxiliary, separating the diastereomers thus formed using known chromatographic methods, and removing the chiral auxiliary to give the enantiomers of XI. Alternatively, the diastereomers of XI may be separated via fractional crystallization from a suitable solvent of the diastereomeric salts formed by XI and a chiral organic acid. If it is desired that A—B is other than H, the morpholine nitrogen of XI may be further functionalized using standard methods for the alkylation or acylation of secondary amines. If it is desired that R$^2$ is other than H, morpholinone X may be elaborated into the carbinolcarbamate (A—B=RO$_2$C, R$^2$=OH), an intermediate that could be alkylated and would allow for variation in R$^2$.

The compounds of the present invention in which Y=O may also be prepared by the general route outlined in Scheme 3. Thus, the appropriately substituted a-bromo-acetaldehyde, dimethyl acetal (prepared using the method of Jacobs in *Journal of the American Chemical Society*, 1953, 75, 5500) may be converted to the acetal by stirring and a slight excess of the appropriate alcohol in the presence of an acid catalyst with concommitant removal of methanol. Alkylation of a substituted amino alcohol by a bromide may give the N-alkyl amino alcohol; use of a chiral amino alcohol would result in the formation of diastereomers and these may be separated at this (or at a later) stage using standard chromatographic methods. N-Alkylation or N-acylation may give the dialkyl- or acyl/alkyl-amino alcohol in which the group A—B may serve as a protecting group or be used as or elaborated into a substituent in the final target compound. Cyclization to give substituted morpholine may be realized by warming a solution with an acid catalyst. Diastereomers that may be formed may be separated using standard chromatographic methods. If A—B is a protecting group, it may be removed using known procedures (Greene, T. W., Wuts, P. G. M. Protective Groups in Organic Synthesis, 2nd ed., John Wiley & Sons, Inc., New York, 1991). If the preparation of such compounds results in the formation of enantiomers, these may be resolved by alkylating or acylating the final product (A—B=H) with a chiral auxiliary, separating the diastereomers thus formed using known chromatographic methods, and removing the chiral auxiliary to give the desired enantiomers. Alternatively, the diastereomers may be separated via fractional crystallization from a suitable solvent of the diastereomeric salts formed by the compound of a chiral organic acid.

One method of synthesizing enantiomerically pure substituted morpholines is illustrated in Scheme 4. Protection of enantiomerically pure phenylglycine as the N-benzyl derivative followed by double alkylation with a 1,2-dibromoethane derivative leads to the morpholinone. Reduction with an active hydride reagent such as diisobutyl aluminum hydride, lithium aluminum hydride, lithium tri(sec-butyl)-borohydride (L-Selectride®) or other reducing agents leads predominantly to the 2,3-trans morpholine derivatives. Alkylation of the alcohol, removal of the protecting group on nitrogen (for example, with a palladium hydrogenation catalyst or with 1-chloroethyl chloroformate (Olofson in *J. Org. Chem.*, 1984, 2081 and 2795), and alkylation of the nitrogen (wherein in A—B—CH$_2$— or A—B—CHO= appropriate definitions of A—B are present) produces the 2,3-trans compounds.

One method of producing enantiomerically pure 2,3-cis morpholines is illustrated in Scheme 5. In the first step, formation of the trifluoromethane-sulfonate ester of the appropiate benzyl alcohol (especially benzyl alcohols which are substituted with electron-withdrawing groups such as —NO$_2$, —F, —Cl, —Br, —COR, —CF$_3$, etc) is carried out in the presence of an unreactive base, in an inert solvent. Other leaving groups such as iodide, mesylate, tosylate, p-nitrophenylsulfonate and the like may also be employed. Appropriate bases include 2,6-di-t-butylpyridine, 2,6-di-t-butyl-4-methyl-pyridine, diisopropylethylamine, potassium carbonate, sodium carbonate, and the like. Suitable solvents include toluene, hexanes, benzene, carbon tetrachloride, dichloromethane, chloroform, dichloroethane, and the like and mixtures thereof. The filtered solution of the triflate is then added to a solution of the intermediate formed when the morpholinone is contacted with an active hydride reagent such as diisobutyl aluminum hydride, lithium aluminum hydride, or lithium tri(sec-butyl)-borohydride (L-Selectride®) at low temperature, preferably from −78° C. to −20° C. After several hours at low temperature, workup and purification provides predominantly 2,3-cis substituted products, which may be carried on to final compounds as shown in Scheme 5.

Enantiomerically pure phenylglycines substituted on the phenyl ring may be prepared by the procedure shown in Scheme 6 (D. A. Evans, et al, *J. Am. Chem. Soc.*, 1990, 112, 4011).

Methods for preparing the nitrogen alkylating agents A—B—CH$_2$-LG (wherein "LG" indicates an appropriately suitable leaving group) used in Scheme 4 and Scheme 5 are based on known literature methods (for A—B=3-(1,2,4-triazolyl) or 5-(1,2,4-triazol-3-one)-yl and LG=Cl, see Yanagisawa, I.; Hirata, Y.; Ishii, Y. *Journal of Medicinal Chemistry*, 27, 849 (1984); for A—B=4-((2H)-imidazol-2-one)-yl or 5-(4-ethoxycarbonyl-(2H)-imidazol-2-one)-yl and X=Br, see Ducschinsky, R., Dolan, L. A. *Journal of the American Chemical Society*, 70, 657 (1948)).

One method of producing enantiomerically pure 2,3-cis morpholines that are substituted at the α-position of the C2 benzyl ether is shown in Scheme 7. Thus, a substituted 2-morpholinone (prepared as described in Scheme 4) is reacted with an active hydride reagent, such as diisobutylaluminum hydride, lithium aluminum hydride, or lithium tri(sec-butyl)borohydrdide and the resulting reaction intermediate is quenched with a substituted benzoyl halide, anhydride, or other activated acyl transfer reagent. Aqueous work-up affords the 2-benzoyloxy compound shown in Scheme 7. This compound is converted to the corresponding enol ether using a "titanium ylide" generated from reagents such as μ-chloro-μ-methylene-[bis(cyclopentadienyl) titanium]dimethylamluminum ("Tebbe Reagent", Tebbe, F. N., Parshall, G. W., Reddy, G. S., *Journal of the American Society*, 100, 3611 (1978)), dimethyl titanocene (Petasis, N. A., Bzowej, E. I., *Journal of the American Chemical Society*, 112, 6392 (1990)) or the reagent prepared by the reduction of 1,1-dibromoalkanes with zinc and titanium tetrachloride in the presence of N,N,N',N'-tetramethylethylenediamine (Takai, K. et. al., *Journal of Organic Chemistry*, 52, 4412 (1987)). The resulting enol ether is reduced to its saturated analog by hydrogenation in the presence of a rhodium based catalyst, such as rhodium on alumina or on carbon; if concomitant removal of the N-benzyl group on the morpholine nitrogen is desired, the hydrogenation may be carried out in the presence of palladium on carbon catalyst. If diastereomers are obtained at this juncture, they may be separated using chromatographic methods or by recrystallization of the mixture of diastereomers. Elaboration of the morpholines so obtained to the final product is carried out in manners analogous to those described in Schemes 4 and 5.

Methods by which the substitution on the C-3 phenyl ring of the morpholines of the present invention may be introduced or altered is shown in Scheme 8. Thus, a substituted morpholine may be prepared as described in Scheme 4, 5, or 7 from an enantiomerically pure benzyloxy-substituted aryl glycine (prepared as described in the literature (e.g. L-p-benzyloxyphenylglycine may be prepared according to the procedure of Kamiya, et al. *Tetrahedron*, 35, 323 (1979)) or using the methods described in Scheme 6). Selective cleavage of the benzyl ether via hydrogenolysis or nonselective hydrogenolysis followed by the synthetic sequence shown in Scheme 8 may afford a suitably protected phenolic intermediate. The phenol may be converted to the corresponding aryl triflate (as shown, or using N-phenyltrifluoromethane-sulfonimide in the presence of a tertiary amine base in methylene chloride) and the triflate converted to the desired functional group using the palladium- or nickel-catalyzed methods described in Ritter, *Synthesis*, 735 (1993) (and refs. therein). Elaboration to the desired final product may be carried out as described in Scheme 4 or 5.

The parent compounds prepared above are converted to their prodrug counterparts by alkylation, acylation, phosphorylation or suffonylation to give ether, ester, phosphate or suffonate derivatives (wherein the parent compounds bear an —X substitutent as defined above) by the general procedures referenced herein, or reasonable modifications thereof.

In particular, as depicted in Scheme 9, treatment of, for example, a triazolone or imidazolone-containing tachykinin antagonist with a suitable base, such as n-butyllithium, sodium hydride, potassium hydride, lithium hexamethyldisilazide, sodium hexamethyldisilazide, potassium hexamethyldisilazide or lithium diisopropylamide in THF at low temperature followed by addition of an appropiate phosphoryl transfer reagent, for example tetrabenzyl pyrophosphate, dibenzyl phosphochloridate or dibenzyl phosphofluoridate provides an intermediate with a protected phosphoryl group. Following purification, for example by gravity silica gel chromatography or by reverse phase high pressure liquid chromatography, the dibenzyl ester may be converted into the desired product by hydrogenolysis, for example with hydrogen gas in the presence of palladium on carbon in the presence of two equivalents of a suitable salt forming agent, such as sodium bicarbonate (to prepare the disodium salt of the phosphoramidate product) or potassium bicarbonate (to prepare the dipotassium salt of the product). The product may be purified by crystallization or by normal or reverse phase chromatography.

As depicted in Scheme 10, treatment of, for example, a triazolone or imidazolone-containing tachykinin antagonist with a suitable base, such as diisopropylethylamine, 2,6-dimethylpyridine or triethylamine and 1-chloroethyl ethyl carbonate (wherein R may be ethyl, —$CH_2CO_2CH_2$phenyl, or —$CH_2CH_2$NH-BOC) in a compatible solvent such as toluene or dichloroethane, followed by heating the mixture at reflux for 12–24 hr, provides the corresponding O-alkylcarbonate product (insted of the expected N-alkoxycarbonylalkyl compound), which may be purified by flash chromatography.

Similarly, the same substrate may be treated with the functionalized carbonate given in Scheme 11 under similar conditions, such as refluxing in toluene in the presence of diisopropylethylamine, 2,6-dimethylpyridine or triethylamine to provide the N-Boc protected intermediate. Cleavage of the Boc group, for example with trifluoroacetic acid in methylene chloride or with hydrogen chloride in ethyl acetate provides the corresponding salt of the prodrug product.

Generation of the N-oxide prodrug of the aforementioned morpholine tachykinin antagonists may be achieved as shown in Scheme 12 simply by treatment with an oxygen-transfer agent, such as a peracid, such as 3-chloroperoxybenzoic acid or trifluoromethylperacetic acid, or with hydrogen peroxide or alkyl hydroperoxides such as t-butyl hydroperoxide in the presence of a transition metal catalyst, or with Caro's acid ($H_2SO_5$).

Compounds containing linking groups between the heterocycle and the phosphoryl group may also be prepared, for example as illustrated in Scheme 13 (see S. A. Varia, S. Schuller, K. B. Sloan, and V. J. Stella, *J. Pharm. Sci.*, 73, 1068–1073 (1984)). Treatment of the parent compound with an aliphatic aldehyde, for example aqueous formaldehyde, provides the corresponding hydroxymethyl derivatives, which after conversion to the chloride with phosphorus trichloride, may be treated with silver dibenzyl phosphate. The resulting protected phosphates may be separated by conventional means, for example silica gel chromatography. The purified products may then be converted to the free phosphoric acids as depicted in Schemes 14 and 15, by treatment with a reducing agent such as hydrogen gas in the presence of pallidium on carbon.

The object compounds of Formula I obtained according to the reactions as explained above may be isolated and purified in a conventional manner, for example, extraction, precipitation, fractional crystallization, recrystallization, chromatography, and the like.

The compounds of the present invention are capable of forming salts with various inorganic and organic acids and bases and such salts are also within the scope of this invention. Examples of such acid addition salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine, ornithine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

Although the reaction schemes described herein are reasonably general, it will be understood by those skilled in the art of organic synthesis that one or more functional groups present in a given compound of formula I may render the molecule incompatible with a particular synthetic sequence. In such a case an alterative route, an altered order of steps, or a strategy of protection and deprotection may be employed. In all cases the particular reaction conditions, including reagents, solvent, temperature, and time, should be chosen so that they are consistent with the nature of the functionality present in the molecule.

As one skilled in the art will recognize, Examples 1–93 describe the prepartion of various parent compounds, whereas Examples 94–96 detail the prepartion of specific prodrugs of some of the parent compounds. Accordingly, the methodology presented in Examples 94–96 is readily adapted without undue experimentation to the preparation of the compounds of the present invention, including prodrugs of the parent compounds of Examples 1–93.

The following examples are given for the purpose of illustrating the present invention and shall not be construed as being limitations on the scope or spirit of the instant invention.

EXAMPLE 1

(±)-α-Bromo-phenylacetaldehyde, 3,5-bis(trifluoromethyl)benzyl acetal

A solution of 2.50 g (10.2 mmol) of α-bromophenylacetaldehyde, dimethyl acetal, 8.00 g (32.8 mmol) of 3,5-bis(trifluoromethyl)benzyl alcohol and 0.50 g (2.6 mmol) of p-toluenesulfonic acid monohydrate in 10 mL of toluene was stirred under vacuum (35 mmHg) at rt for 3 days. The reaction mixture was partitioned between 100 mL of ether and 50 mL of saturated aqueous sodium bicarbonate solution and the layers were separated. The organic layer was washed with 25 mL of saturated aqueous sodium chloride solution, dried over magnesium sulfate, and concentrated in vacuo. Flash chromatography on 200 g of silica gel using 9:1 v/v hexane/methylene chloride as the eluant afforded 5.41 g (81%) of the title compound as a solid, mp 79°–82° C.: $^1$H NMR 4.47 and 4.62 (AB q, 2H, J=12.5), 4.78–4.93 (2H), 5.09 and 5.21 (AB q, 2H, J=7.7), 7.31–7.44 (m, 7H), 7.70 (app s, 1H), 7.82 (app s, 1H), 7.84 (app s 2H); IR (thin film) 1363, 1278, 1174, 1130, 704, 682.

Analysis Calcd for $C_{26}H_{17}BrF_{12}O_2$: C, 46.76; H, 2.23; Br, 11.64; F, 33.70. Found: C, 46.65; H, 2.56; Br, 11.94; F, 34.06.

EXAMPLE 2

(±)-N-(2-Hydroxyethyl)-phenylglycinal, 3,5-bis-(trifluoromethyl)benzyl acetal

A solution of 1.50 g (2.2 mmol) of (±)-α-bromophenylacetaldehyde, 3,5-bis(trifluoromethyl)-benzyl acetal (Example 1), 100 mg (0.67 mmol) of sodium iodide and 3 mL of ethanolamine in 6 mL of isopropanol was heated at reflux for 20 h. The solution was cooled and concentrated to ~25% the original volume in vacuo. The concentrated solution was partitioned between 50 mL of ether and 20 mL of 2N aqueous sodium hydroxide solution and the layers were separated. The organic layer was washed with 20 mL of saturated aqueous sodium chloride solution, dried over magnesium sulfate and concentrated in vacuo. Flash chromatography on 50 g of silica gel using 65:35 v/v ether/hexane as the eluant afforded 1.18 g (83%) of the title compound as an oil: $^1$H NMR 2.66 (br s, 2H), 2.61 and 2.68 (ddAB q, 2H, $J_{AB}$=12.4, $J_{2.61}$=6.8, 6.2, $J_{2.68}$=6.2, 6.2), 3.57 and 3.66 (ddAB q, 2H, $J_{AB}$=10.8, $J_{3.57}$=6.2, 6.2), $J_{3.66}$=6.8, 6.2), 4.02 (d, 1H, J=7.0), 4.37 and 4.64 (AB q, 2H, J=12.5), 4.80 and 4.87 (AB q, 2H, J=12.8), 4.87 (d, 1H, J=7.0), 7.31–7.40 (7H), 7.73 (app s, 1H), 7.81 (app s, 3H);

IR (neat)3342, 1456, 1373, 1278, 1173, 1128, 704, 682; FAB-MS 650(M+1)$^+$.

Analysis Calcd for $C_{28}H_{23}F_{12}NO_3$: C, 51.78; H, 3.57; N, 2.16; F, 35.11. Found: C, 51.80; H, 3.67; N, 2.10; F, 35.41.

EXAMPLE 3

(±)-N-(2-Hydroxyethyl)-N-(prop-2-enyl)-phenyl-glycinal, 3,5-bis(trifluoromethyl)benzyl acetal A mixture of 1.45 g (2.2 mmol) of (±)-N-(2-hydroxyethyl)-phenylglycinal, 3,5-bis-(trifluoromethyl)benzyl acetal (Example 2), 1.0 g (7.2 mmol) of potassium carbonate, 3.0 mL (35.0 mmol) of allyl bromide and 15 mL of ethanol was stirred at 60° C. for 20 h. The mixture was cooled, partitioned between 100 mL of ether and 25 mL of water and the layers were separated. The organic layer was dried over magnesium sulfate. The aqueous layer was extracted with 100 mL of ether; the ether extract was dried and combined with the original organic layer. The combined organic layers were concentrated in vacuo. Flash chromatography on 50 g of silica gel using 4:1 v/v hexane/ether as the eluant afforded 1.36 g (88%) of the title compound as an oil: $^1$H NMR 2.40 (dt, 1H, J=13.2, 2.8), 2.93–3.08 (3H), 3.30 (ddt, 1H, J=12.0, 2.8, 1.6), 3.54 (br m, 2H), 3.65 (dt, 1H, J=10.0, 2.8), 4.23 (d, 1H, J=8.4), 4.52 and 4.58 (AB q, 2H, J=12.4), 4.85 and 4.95 (AB q, 2H, J=12.4), 5.25 (d, 1H, J=9.6), 5.28 (d, 1H, J=16.4), 5.39 (d, 1H, J=8.4), 5.81 (m, 1H), 7.24–7.40 (7H), 7.68 (s 1H), 7.83 (s, 1H), 7.86 (s, 2H);

IR (neat) 3457, 1362, 1278, 1174, 1132, 1056, 759, 705, 682; FAB-MS 690(M+1)$^+$.

Analysis Calcd for $C_{31}H_{27}F_{12}NO_3$: C, 53.99; H, 3.95; N, 2.03; F, 33.07. Found: C, 54.11; H, 4.08; N, 1.78; F, 32.75.

EXAMPLE 4

(±)-2-(3,5-Bis(trifluoromethyl)benzyloxy)-3-phenylmorpholine

Step A: A solution of 850 mg (1.2 mmol) of (±)-N-(2-hydroxyethyl)-N-(prop-2-enyl)-phenyl-glycinal, 3,5-bis (trifluoromethyl)benzyl acetal (Example 3) and 700 mg (3.7 mmol) of p-toluenesulfonic acid monohydrate in 15 mL of toluene was heated at reflux for 1.5 h. The reaction mixture was cooled and partitioned between 100 mL of ether and 25 mL of saturated aqueous sodium bicarbonate solution. The layers were separated; the organic layer was washed with 25 mL of saturated aqueous sodium chloride solution, dried over magnesium sulfate, and concentrated in vacuo. Flash chromatography on 30 g of silica gel using 50:1 v/v hexane/ether as the eluant afforded 426 mg (78%) of the N-allyl morpholines which were used in the next step without further purification.

Step B: A 50 mL 2-necked flask, equipped with a stopper and a short path distillation apparatus, was charged with a solution of the N-allyl morpholines (Example 4, Step A) (540 mg, 1.2 mmol)) and 80 mg (0.09 mmol) tris (triphenylphosphine)rhodium chloride (Wilkinson's catalyst) in 25 mL of 4:1 v/v acetonitrile/water. The reaction mixture was heated to boiling and solvent was allowed to distill from the reaction mixture. The volume of the reaction mixture was maintained between 10 and 20 mL by adding solvent through the stoppered inlet. After 1 h and 4 h, the reaction was treated with additional 80 mg portions of the Wilkinson's catalyst. After 6 h, the reaction mixture cooled and partitioned between 75 mL of ether and 50 mL of water. The layers were separated and the organic layer was dried over magnesium sulfate. The aqueous layer was extracted with 75 mL of ether; the extract was dried and combined with the original organic layer. The combined organic layers were concentrated in vacuo. Flash chromatography on 35 g of silica gel using 1:1 v/v ether/hexane as the eluant afforded 200 mg of trans-isomer and 130 mg of a mixture of cis- and trans-isomers (68% total). Chromatography of the mixture on 8 g of silica gel using 4:1 v/v hexane/ether as the eluant afforded 64 mg of cis and 57 mg of a mixture of the cis- and trans-isomers of the title compound.

For trans: $^1$H NMR 2.03 (br s, 1H), 2.94 (ddd, 1H, J=11.0, 2.5, 2.5), 3.08 (dt, 1H, J=11.0, 3.2), 3.71 (d, 1H, J=7.0), 3.83 (dt, 1H, J=11.2, 2.8), 4.05 (ddd, 1H, J=11.2, 3.2, 3.2), 4.43 (d, 1H, J=7.0), 4.53 and 4.88 (AB q, 2H, J=13.3), 7.26–7.45 (7H), 7.70 (s, 1H);

IR (neat) 3333, 2859, 1456, 1374, 1278, 1173, 1131, 1082, 757, 702, 682; FAB-MS 406(M+1)$^+$.

Analysis Calcd for $C_{19}H_{17}F_6NO_2$: C, 56.30; H, 4.23; N, 3.46; F, 28.12. Found: C, 56.39; H, 4.28; N, 3.36; F, 28.32.

For cis: $^1$H NMR 2.10 (br s, 1H), 3.13 (dd, 1H, J=12.4, 3.0), 3.26 (dt, 1H, J=12.4, 3.6), 3.65 (dd, 1H, J=11.6, 3.6), 4.07 (dt, 1H, J=11.6, 3.0), 4.14 (d, 1H, J=2.4), 4.52 and 4.82 (AB q, 2H, J=13.6), 4.76 (d, 1H, J=2.4), 7.30–7.42 (6H), 7.70 (s, 1H), FAB-MS 406(M+1)$^+$.

EXAMPLE 5

(±)-2-(3,5-Bis(trifluoromethyl)benzyloxy)-3-phenyl-4-methylcarboxamido morpholine A solution of 105 mg (0.26 mmol) of the trans-isomer of (±)-2-(3,5-bis(trifluoromethyl)benzyloxy)-3-phenyl-morpholine (Example 4) and 0.09 mL (0.50 mmol) of N,N-diisopropylethylamine in 3 mL of acetonitrile was treated with 90 mg (0.50 mmol) of iodoacetamide and the resulting solution was stirred at rt for 16 h. The solution was concentrated in vacuo and the residue was partitioned between 20 mL of ethyl acetate and 10 mL of 0.5N aqueous potassium hydrogen sulfate solution. The layers were separated; the organic layer was washed with 10 mL of 5% aqueous sodium thiosulfate solution, 10 mL of saturated aqueous sodium bicarbonate solution, 10 mL of saturated aqueous sodium chloride solution, dried over magnesium sulfate and concentrated in vacuo. Flash chromatography on 5 g of silica gel using 2:1 v/v ethyl acetate/hexane as the eluant afforded 99 mg (82%) of the trans-isomer of the title compound as an oil: $^1$H NMR 2.56 (dt, 1H, J=3.2, 11.6), 2.67 and 3.16 (AB q, 2H, J=16.4), 2.96 (dt, 1H, J=12.0, 1.6), 3.30 (d, 1H, J=7.0), 3.86 (dt, 1H, J=3.2, 12.0), 4.08 (ddt, 1H, J=11.6, 3.2, 1.6), 4.48 and 4.84 (AB q, 2H, J= 13.2), 4.49 (d, 1H, J=7.0), 5.98 (br s, 1H), 6.83 (br s, 1H), 7.33 (app s, 7H), 7.70 (s, 1H);

IR (neat) 3445, 2838, 1682, 1278, 1173, 1132, 760, 704, 682; FAB-MS 463 (M+1)$^+$.

Analysis Calcd for $C_{21}H_{20}F_6NO_3$: C, 54.54; H, 4.36; N, 6.06; F, 24.65. Found: C, 54.54; H, 4.52; N, 5.61; F, 24.45.

A similar experiment was carried out on 40 mg (0.99 mmol) of the cis-isomer of (±)-2-(3,5-bis-(trifluoromethyl)benzyloxy)-3-phenyl-morpholine (Example 4) using 0.035 mL (0.2 mmol) of N,N-diisopropylethylamine and 37 mg (0.2 mmol) of iodoacetamide in the reaction. Work-up and flash chromatography afforded 30 mg (65%) of the cis-isomer of the title compound as an oil:

$^1$H NMR 2.54 and 3.04 (AB q, 2H, J=16.8), 2.63 (dt, 1H, J=3.6, 12.0), 3.04 (d, 1H, J=11.6), 3.65 (d, 1H, J=2.8), 3.71 (ddt, 1H, J=11.6, 3.2, 1.2), 4.21 (dt, 1H, J=11.6, 2.4), 4.44 and 4.89 (AB q, 2H, J=13.6), 4.71 (d, 1H, J=2.8), 5.86 (br s, 1H), 7.15 (br s, 1H), 7.27–7.45 (7H), 7.73 (s, 1H); FAB-MS 463(M+1)$^+$.

EXAMPLE 6

(±)-2-(3,5-Bis(trifluoromethyl)benzyloxy)-3-phenyl-4-(methoxycarbonylmethyl)morpholine A solution of 150 mg (0.37 mmol) of the trans-isomer of (±)-2-(3,5-bis(trifluoromethyl)benzyloxy)-3-phenyl morpholine (Example 4) and 0.18 mL (1.00 mmol) of N,N-diisopropyl-ethyl-amine in 2 mL of acetonitrile was treated with 0.095 mL (1.00 mmol) of methyl bromoacetate and the resulting solution was stirred at rt for 20 h. The solution was concentrated in vacuo and the residue was partitioned between 20 mL of ethyl acetate and 5 mL of 0.5$\underline{N}$ aqueous potassium hydrogen sulfate solution. The layers were separated; the organic layer was washed with 10 mL of saturated aqueous sodium chloride solution, dried over magnesium sulfate and concentrated in vacuo. Flash chromatography on 10 g of silica gel using 4:1 v/v hexanes/ether as the eluant afforded 164 mg (93%) of the trans-isomer of the title compound as an oil: $^1$H NMR 2.79 (dt, 1H, J=3.2, 11.2), 2.93 (dt, 1H, J=11.2, 1.6), 3.52 (d, 1H, J=7.2), 3.63 (s, 3H), 3.92 (dt, 1H, J=2.8, 11.6), 4.04 (ddd, 1H, J=11.6, 3.2, 1.6), 4.45 and 4.84 (AB q, 2H, J=13.2), 4.46 (d, 1H, J=7.2), 7.31–7.38 (m, 6H), 7.68 (s, 1H); IR (neat) 2861, 1744, 1455, 1375, 1346, 1278, 1170, 887, 759, 704, 682; FAB-MS 478(M+1)$^+$.

Analysis Calcd for $C_{22}H_{21}F_6NO_4$: C, 55.35; H, 4.43; N, 2.93; F, 23.88. Found: C, 55.74; H, 4.50; N, 2.79; F, 24.01.

EXAMPLE 7

N-Methoxy-N-methyl-(N-t-butoxycarbonyl)-phenylglycinamide

A solution of 20.0 g (79.7 mmol) of (N-t-butoxycarbonyl) phenylglycine in 150 mL of ethyl acetate at −10° C. was treated with 8.8 mL (79.7 mmol) of 4-methylmorpholine. Isobutylchloroformate (10.3 mL, 79.7 mmol) was added dropwise over 10 minutes maintaining the temperature at −10° C.; the resulting suspension was stirred cold for 15 min. The mixture was treated with 11.6 g (119.0 mmol) of N,O-Dimethyl-hydroxylamine•HCl. A second portion of 4-methylmorpholine (13.0 mL, 119.0 mmol) was added and the reaction was stirred at −10° C. for 15 min and at 25° C. for 2 h. The reaction mixture was partitioned between 100 mL of ethyl acetate and 100 mL of 10% aqueous citric acid solution and the layers were separated. The organic layer was washed with 100 mL of saturated aqueous sodium bicarbonate solution, 100 mL of saturated aqueous ammonium chloride solution, dried over magnesium sulfate and concentrated in vacuo. Crystallization from hexanes at −20° C. for 72 h afforded 8.0 g (34%) of the title compound as a solid: $^1$H NMR 1.40 (s, 9H), 3.20 (s, 3H), 3.40 (s, 3H), 5.80 (m, 2H), 7.40 (m, 5H).

EXAMPLE 8

Diethyl (2-oxo-3-t-butoxycarbamido-3-phenyl)-propylphosphonate

A solution of 7.45 mL (51.0 mmol) of diethyl methylphosphonate in tetrahydrofuran at −78° C. was treated with 31.8 mL (51.0 mmol) of 1.6$\underline{M}$ n-butyllithium in hexanes solution and the resulting mixture was stirred cold for 30 min. A solution of 4.0 g (14.0 mmol) of N-methoxy-N-methyl-(N-t-butoxycarbonyl)phenylglycinamide (Example 7) in 20 mL of tetrahydrofuran was added and the reaction was stirred at −78° C. for 15 min and at 25° C. for 15 min. The reaction was quenched with 150 mL of saturated aqueous ammonium chloride solution, diluted with 300 mL of ethyl acetate, and the layers were separated. The organic layer was dried over magnesium sulfate and concentrated in vacuo. Flash chromatography on silica gel using 7:3 v/v then 4:1 v/v ethyl acetate/hexanes as the eluant afforded 4.8 g (92%) of the title compound as an oil: $^1$H NMR 1.20–1.42 (15H), 2.84 (dd, 1H), 3.20 (dd, 1H), 4.00–4.20 (m, 4H), 5.50 (d, 1H), 5.94 (br s, 1H), 7.32 (m, 5H).

EXAMPLE 9

N-t-Butoxycarbonyl-1-phenyl-2-oxo-4-(3,5-bis(trifluoromethyl)phenyl)-but-3-enamine A solution of 4.80 g (12.5 mmol) of diethyl (2-oxo-3-t-butoxycarbamido-3-phenyl)propylphosphonate (Example 8) in 20 mL of THF was added dropwise to a suspension of 1.05 g (26.3 mmol, 60% dispersion in mineral oil) of sodium hydride in 30 mL of tetrahydrofuran at 0° C. After 15 min, 2.06 mL (12.5 mmol) of 3,5-bis(trifluoromethyl) benzaldehyde was slowly added and the resulting mixture was stirred cold for 15 min. The reaction was quenched with 50 mL of saturated aqueous ammonium chloride solution, diluted with 50 mL of ethyl acetate, and the layers were separated. The organic layer was dried over magnesium sulfate and concentrated in vacuo. Flash chromatography on silica gel using 19:1 v/v, then 9:1 v/v ethyl acetate/petroleum ether as the eluant afforded 3.30 g (56%) of the title compound as a solid: $^1$H NMR 1.40 (s, 9H), 5.38 (d, 1H), 5.90 (d, 1H), 6.80 (d, 1H), 7.39 (m, 5H), 7.70 (s, 1H), 7.84 (s, 3H).

EXAMPLE 10

1-Phenyl-2-hydroxy-4-(3,5-bis(trifluoromethyl)phenyl)-but-3-enamine•HCl

A solution of 1.00 g (2.1 mmol) of N-t-butoxycarbonyl-1-phenyl-2-oxo-4-(3,5-bis(trifluoromethyl)phenyl)-but-3-enamine (Example 8) in 30 mL of methanol at 0° C. was treated with 241 mg (6.3 mmol) of sodium borohydride. After 30 min, the reaction was quenched with 50 mL of water and concentrated in vacuo to remove the methanol. The mixture was partitioned between 100 mL of ethyl acetate and 50 mL of water and the layers were separated. The organic layer was dried over magnesium sulfate and concentrated in vacuo. Crystallization from ether/hexanes afforded 680 mg (68%) of the title compound as a 5:1 mixture of diastereomers (each protected as the t-butylcarbamate): $^1$H NMR (* indicates the resonances of the minor diastereomer) 1.40 (s, 9H), 4.60 (dd, 1H), 4.90 (br s, 1H), 5.20 (br d, 1H), 6.30 (dd, 1H), 6.40 (dd, 1H*), 6.70 (dd, 1H), 6.80 (dd, 1H*), 7.40 (m, 5H), 7.80 (m, 3H).

A solution of BOC-protected title compound in methanol (saturated with HCl) was allowed to stand for 72 h. The solution was concentrated in vacuo. Recrystallization of the resulting solid from ether/hexane afforded 500 mg (80%) of the title compound•HCl as a solid: $^1$H NMR 4.20 (br s, 1H), 4.40 (d, 1H), 6.20 (dd, 1H), 6.60 (dd, 1H), 7.30 (m 5H), 7.80 (m, 3H).

The title compound•HCl was dissolved in ethyl acetate and 1N aqueous sodium hydroxide solution. The layers were separated; the organic layer was dried over magnesium sulfate and concentrated in vacuo to afford the title compound as the free base.

EXAMPLE 11

2-(2-(3,5-Bis(trifluoromethyl)phenyl)ethenyl)-3-phenyl-5-oxo-morpholine

A solution of 1.95 g (5.2 mmol) of 1-phenyl-2-hydroxy-4-(3,5-bis(trifluoromethyl)phenyl)-but-3-enamine (Example 10) in 20 mL of toluene was added to a suspension of 250 mg (6.2 mmol, 60% dispersion in mineral oil) of sodium hydride in 30 mL of toluene and the resulting mixture was stirred at rt for 15 min. A solution of 0.60 mL (1.15 mol) of ethyl chloroacetate in 5 mL of toluene was slowly added and the resulting mixture was heated at reflux for 3 h. The reaction was cooled, quenched with 50 mL of saturated aqueous ammonium chloride solution, diluted with 50 mL of ethyl acetate and the layers were separated. The organic layer was dried over magnesium sulfate and concentrated in vacuo. Flash chromatography using ethyl acetate/hexanes (4:1 v/v, then 3:1 v/v, then 1:1 v/v) then ethyl acetate as the eluant afforded 300 mg of trans-title compound and 800 mg of cis-title compound (55% total), both as solids. For the cis-isomer: $^1$H NMR 1.20–1.40 (m, 1H), 1.50–1.62 (m, 1H), 2.60–2.98 (m, 2H), 3.86 (dt, 1H), 4.24 (d, 1H), 4.34 (dd, 1H), 4.45 (d, 1H), 6.40 (br s, 1H), 7.24 (m, 2H), 7.40 (m, 3H), 7.50 (s, 2H), 7.70 (s, 1H).

EXAMPLE 12

3-Phenyl-2-(2-(3,5-bis(trifluoromethyl)phenyl)ethyl)-morpholine

A solution of 95 mg (0.23 mmol) of 2-(2-(3,5-bis (trifluoromethyl)phenyl)ethenyl)-3-phenyl-5-oxo-morpholine (Example 11) in 10 mL of 1:1 v/v ethanol/ethyl acetate was treated with 10 mg of palladium hydroxide and the resulting mixture was stirred under an atmosphere of hydrogen for 2 h. The catalyst was faltered and the filtrate was concentrated in vacuo. The crude product was used directly without further purification.

A solution of 65 mg of the crude morpholinone was dissolved in 10 mL of tetrahydrofuran was treated with 0.84 mL of 1M borane•tetrahydrofuran complex solution in tetrahydrofuran and the resulting solution was heated at reflux for 16 h. The reaction was quenched by adding 10 mL of methanol and 70 mg of potassium carbonate and heating the resulting mixture at reflux for 3 h. All volatiles were removed in vacuo and the residue was partitioned between 20 mL of ethyl acetate and 10 mL of saturated ammonium chloride solution. The organic layer was separated, dried over sodium carbonate, and concentrated in vacuo. The residue was dissolved in saturated HCl in methanol and concentrated in vacuo. The residue was triturated with ether; the resulting solid was filtered and dried to afford 32 mg (46%) of the title compound•HCl, mp 114°–116° C.: $^1$H NMR 1.42 (m, 1H), 1.66–1.84 (m, 1H), 2.70–2.94 (m, 2H), 3.00 (m, 1H), 3.30–3.46 (m, 1H), 3.80–3.94 (m, 2H), 4.10 (m, 1H), 4.20 (d, 1H), 7.40 (m, 3H), 7.64 (m, 5H); CI-MS 402(M+1)$^+$.

EXAMPLE 13

N-Benzyl-(S)-phenylglycine

A solution of 1.51 g (10.0 mmol) of (S)-phenylglycine in 5 mL of 2N aqueous sodium hydroxide solution was treated with 1.0 mL (10.0 mmol) of benzaldehyde and stirred at room temperature for 20 minutes. The solution was diluted with 5 mL of methanol, cooled to 0° C., and carefully treated with 200 mg (5.3 mmol) of sodium borohydride. The cooling bath was removed and the reaction mixture was stirred at room temperature for 1.5 hours. The reaction was diluted with 20 mL of water and extracted with 2×25 mL of methylene chloride. The aqueous layer was acidified with concentrated hydrochloric acid to pH 6 and the solid that precipitated was filtered, washed with 50 mL of water, 50 mL of 1:1 v/v methanol/ethyl ether and 50 mL of ether, and dried to afford 1.83 g (76%) of product, mp 230°–232° C.

Analysis Calcd for $C_{15}H_{15}NO_2$: C, 74.66; H, 6.27; N, 5.81. Found: C, 74.17; H, 6.19; N, 5.86.

EXAMPLE 14

3-(S)-Phenyl-4-benzyl-2-morpholinone

A mixture of 4.00 g (16.6 mmol) of N-benzyl-(S)-phenylglycine (from Example 13), 5.00 g (36.0 mmol) of potassium carbonate, 10.0 mL of 1,2-dibromoethane and 25 mL of N,N-dimethylformamide was stirred at 100° C. for 20 hours. The mixture was cooled and partitioned between 200 mL of ethyl ether and 100 mL of water. The layers were separated and the organic layer was washed with 3×50 mL of water, dried over magnesium sulfate and concentrated in vacuo. The residue was purified by flash chromatography on 125 g of silica gel eluting with 9:1 v/v, then 4:1 v/v hexanes/ethyl ether to afford 2.41 g (54%) of the product as a solid, mp 98°–100° C.

Mass Spectrum (FAB): m/Z 268 (M+H, 100%).

$^1$H NMR (CDCl$_3$, 200 MHz, ppm): δ 2.54–2.68 (m, 1H), 2.96 (dt, J=12.8, 2.8, 1H), 3.14 (d, J=13.3, 1H), 3.75 (d, J=13.3, 1H), 4.23 (s, 1H), 4.29–4.37 (m, 1H), 4.53 (dt, J=3.2, 11.0), 7.20–7.56 (m, 10H).

Analysis Calcd for $C_{17}H_{17}NO_2$: C, 76.38; H, 6.41; N, 5.24. Found: C, 76.06; H, 6.40; N, 5.78.

EXAMPLE 15

2-(S)-(3,5-Bis(trifluoromethyl)benzyloxy)-3-(S)-phenylmorpholine

Step A: 3,5-Bis(trifluoromethyl)benzyl alcohol, trifluoromethanesulfonate ester

A solution of 1.00 g (4.1 mmole) of 3,5-bis (trifluoromethyl)benzyl alcohol and 1.05 g (5.12 mmole) of 2,6-di-t-butyl-4-methylpyridine in 45 mL of dry carbon tetrachloride under a nitrogen atmosphere was treated with 0.74 mL (4.38 mmole) of trifluoromethanesulfonic anhydride at room temperature. A white precipitate formed shortly after the addition of the anhydride. After 90 min, the slurry was filtered under nitrogen with a Schlenk filter, and the filtrate was concentrated in vacuo. The residue, which was a two-phase oil, was dissolved under nitrogen in 10 mL of dry toluene. The resulting clear solution was used immediately in Step B below.

Step B: 4-Benzyl-2-(S)-(3,5-bis(trifluoromethyl) benz-yloxy)-3-(S)-phenylmorpholine A solution of 0.500 g (1.87 mmole) of N-benzyl-3-(S)-phenylmorpholin-2-one (from Example 14) in 10 mL of dry THF was cooled to −75° C. under nitrogen and was treated dropwise with 2.06 mL (2.06 mmole) of a 1M solution of lithium tri(sec-butyl)-borohydride (L-Selectride®) in THF. After stirring the solution at −75° C. for 30 min, a solution of 3,5-bis(trifluoromethyl)benzyl alcohol, trifluoromethanesulfonate ester in toluene was added by cannula so that the internal temperature was maintained below −60° C. The resulting solution was stirred at −75° C. for 1 hr and then between −38° C. and −50° C. for 2 hr. The solution was then poured into a mixture of 25 mL of ethyl acetate and 20 mL of saturated aqueous sodium bicarbonate, and the layers were separated. The aqueous phase was extracted with 2×30 mL of ethyl acetate, the combined organic layers were dried over sodium sulfate, the mixture was filtered and the filtrate concentrated in vacuo. The residue was purified by flash chromatography on 130 g of silica eluting with 2 L of 100:5 hexanes:ethyl acetate to give 0.68 g (73%) of an oil, which by $^1$H NMR is a 20:1 mixture of cis:trans morpholines.

$^1$H NMR (CDCl$_3$, 400 MHz, ppm): δ major (cis) isomer: 2.37 (td, J=12, 3.6, 1H), 2.86 (app t, J=13, 2H), 3.57 (d, J=2.6, 1H), 3.63 (dq, J=11.3, 1.6, 1H), 3.89 (d, J=13.3, 1H), 4.12 (td, J=11.6, 2.4, 1H), 4.40 (d, J=13.6, 1H), 4.69 (d, J=2.9, 1H), 4.77 (d, J=13.6), 7.2–7.4 (m, 8H), 7.43 (s, 2H), 7.55 (br d, 2H), 7.69 (s, 1H).

Step C: 2-(S)-(3,5-Bis(trifluoromethyl)benzyloxy)-3-(S)-phenylmorpholine

A mixture of 0.68 g (1.37 mmole) of 4-benzyl-2-(S)-(3,5-bis(trifluoromethyl)benzyloxy)-3-(S)-phenylmorpholine and 280 mg of 10% Pd/C in 36 mL of 97:3 ethanol:water was stirred under one atmosphere of hydrogen for 15 hr. The mixture was filtered through Celite, the filter cake was washed generously with ethanol, and the filtrated was concentrated in vacuo. The residue was purified by flash chromatography on 68 g of silica eluting with 1 L of 33:67 hexanes:diethyl ether, then 1 L of 25:75 hexanes:diethyl ether to give 0.443 g (80%) of an oil, which by $^1$H NMR was pure cis morpholine.

$^1$H NMR (CDCl$_3$, 400 MHz, ppm): δ 1.8 (br s, 1H), 3.10 (dd, J=12.5, 2.9, 1H), 3.24 (td, J=12.2, 3.6, 1H), 3.62 (dd, J=11.3, 2.5, 1H), 4.04 (td, J=11.7, 3, 1H), 4.11 (d, J=2.4, 1H), 4.49 (d, J=13.5, 1H), 4.74 (d, J=2.5, 1H), 4.80 (d, J=13.3, 1H), 7.25–7.40 (m, 5H), 7.40 (s, 2H), 7.68 (s, 1H).

Analysis Calcd for $C_{19}H_{17}F_6NO_2$: C, 56.30; H, 4.23; N, 3.46; F, 28.12. Found: C, 56.20; H, 4.29; N, 3.34; F, 27.94.

EXAMPLE 16

2(R)-3,5-Bis(trifluoromethyl)benzyloxy)-3(R)-phenyl-morpholine

The title compound was prepared from (R)-phenylglycine employing the procedures of Examples 13, 14 and 15.

EXAMPLE 17

4-(3-(1,2,4-Triazolo)methyl)-2-(S)-(3,5-bis(trifluoromethyl)benzyloxy)-3-(S)-phenylmorpholine Step A: N-Formyl-2-chloroacetamidrazone A solution of 5 g (66.2 mmole) of chloroacetonitrile in 30 mL of dry methanol was cooled to 0° C. under nitrogen and was treated with 0.1 g (1.8 mmole) of sodium methoxide. The mixture was allowed to warm to room temperature and was stirred for 30 min, and 0.106 mL (1.8 mmole) of acetic acid was added. To the resulting mixture was then added 3.9 g (64.9 mmole) of formic hydrazide, and the material was stirred for 30 min. The reaction mixture was concentrated in vacuo to a solid, and was used as such in Step B below.

Step B: 4-(3-(1,2,4-Triazolo)methyl)-2-(S)-(3,5-bis-(trifluoromethyl)benzyloxy)-3-(S)-phenyl-morpholine A solution of 0.295 g (0.73 mmole) of 2-(S)-(3,5-bis (trifluoromethyl)benzyloxy)-3-(S)-phenylmorpholine (from Example 15) in 10 mL of dry DMF was treated with 0.302 g (2.18 mmole) of anhydrous potassium carbonate and then 0.168 g (1.24 mmole) of N-formyl-2-chloroacetamidrazone (from Example 17, Step A) and the suspension was stirred at 60° C. for 4 hr. The mixture was then heated to 120° C. for 4.5 hr. After cooling, the reaction was diluted with 80 mL of ethyl acetate and the organic layer was washed with 3×20 mL of water. The organic layer was dried over magnesium sulfate, filtered and concentrated in vacuo. The residue was purified by flash chromatography on 67 g of silica eluting with 1.5 L of 100:2 methylene chloride:methanol to give 0.22 g of a yellow solid, which was recrystallized from hexanes/methylene chloride to give 0.213 g (60%) of a white crystalline solid, mp 134°–135° C.

Mass Spectrum (FAB): m/Z 487 (M+H, 100%), 259 (35%), 243 (65%), 227 (40%), 174 (25%).

$^1$H NMR (CDCl$_3$, 400 MHz, ppm): δ 2.67 (td, J=11.9, 3.4, 1H), 2.90 (br d, J=11.7, 1H), 3.43 (d, J=15.2, 1H), 3.66 (app dd, J=13, 1.9, 2H), 3.88 (d, J=15.1, 1H), 4.17 (td, J=11.7, 2.3, 1H), 4.42 (d, J=13.5, 1H), 4.69 (d, J=2.6, 1H), 4.77 (d, J=13.5, 1H), 7.30–7.50 (m, 7H), 7.70 (s, 1H), 7.94 (s, 1H).

EXAMPLE 18

4-(3-(5-Oxo-1H,4H-1,2,4-triazolo)methyl)-2-(S)-(3,5-bis(trifluoromethyl)benzyloxy)-3-(S)-phenylmorpholine Step A: N-Methylcarboxy-2-chloroacetamidrazone A solution of 5.0 g (66.2 mmol) of chloroacetonitrile in 35 mL of dry methanol was cooled to 0° C. and was treated with 0.105 g (1.9 mmol) of sodium methoxide. The ice-bath was removed and the mixture was alowed to stir at room temperature for 30 minutes. To the reaction was then added 0.110 mL (1.9 mmol) of acetic acid and then 5.8 g (64.9 mmol) of methyl hydrazinecarboxylate. After stirring 30 minutes at room temperature, the suspension was concentrated in vacuo, and placed on the high-vac line overnight, to give 10.5 g (98%) of a yellow powder, which was employed in Step C below.

$^1$H NMR (CD$_3$OD, 400 MHz, ppm): δ 3.71 (s, 3H), 4.06 (s, 2H).

Step B: 4-(2-(N-Methylcarboxy-acetamidrazono)-2-(S)-(3,5-bis(trifluoromethyl)benzyloxy)-3-(S)-phenylmorpholine A solution of 2.30 g (5.7 mmol) of 2-(S)-(3,5-bis (trifluoromethyl)benzyloxy)-3-(S)-phenylmorpholine (from Example 15), 1.13 g (6.8 mmol) of N-methylcarboxy-2-chloroacetamidrazone (from Step A), and 1.50 mL (8.6 mmol) N,N-diisopropylethylamine in 25 mL of acetonitrile was stirred at room temperature for 20 hours. The product, which had preciptated, was filtered, washed with 5 mL of ice cold acetonitrile and dried to give 1.83 g of a white solid. The filtrate was concentrated in vacuo and the residue was partitioned between 50 mL of methylene chloride and 20 mL of water. The layers were separated and the organic layer was dried over magnesium sulfate. The aqueous layer was extracted with 50 mL of methylene chloride; the extract was dried, combined with the original organic layer, and the combined organics were concentrated in vacuo. The residue was purified by flash chromatography on 30 g of silica gel eluting with 50:1:0.1 v/v/v methylene chloride/methanol/ammonium hydroxide to afford an additional 1.09 g of product (96% total).

Mass Spectrum (FAB): m/Z 535 (M+H, 100%), 462 (16%), 291 (30%), 226 (35%), 173 (25%).

$^1$H NMR (CDCl$_3$, 400 MHz, ppm): δ 2.53 (dt, J=3.5, 12.2, 1H), 2.59 (d, J=14.6, 1H), 2.94 (d, J=11.8, 1H), 3.37 (d, J=14.6, 1H), 3.58 (d, J=2.8), 1H), 3.62–3.72 (m, 1H), 3.75 (s, 3H), 4.16 (dt, J=2.2, 11.8, 1H), 4.44 (d, J=13.2, 1H), 4.70 (d, J=2.8, 1H), 4.79 (d, J=13.2), 5.55 (br s, 2H), 7.30–7.46 (m, 7H), 7.72 (s, 1H).

Step C: 2-(S)-(3,5-Bis(trifluoromethyl)benzyloxy)-4-(3-(5-oxo-1H,4H-1,2,4-triazolo)methyl)-3-(S)-phenylmorpholine A solution of 2.89 g (5.4 mmol) of 4-(2-(N-methylcarboxyacetamidrazono)-2-(S)-(3,5-bis(trifluoromethyl) benzyloxy)-3-(S)-phenylmorpholine (from Step B) in 36 mL of xylenes was heated at reflux for 1.5 hours. The solution was cooled and concentrated in vacuo. The residue was taken up in 50 mL of 3:1 v/v hexanes/ethyl acetate which caused crystallization of the product. The product was filtered and dried to afford 1.85 g of a solid. Recrystallization of the solid from 30 mL of 4:1 v/v hexanes/ethyl acetate afforded 1.19 g of pure product as a white solid, mp=156°–157° C. All of the crystallization liquors were combined and concentrated in vacuo. The residue was purified by flash chromatography on 30 g of silica gel eluting with 50:1:0.1 v/v/v methylene chloride/methanol/ammonium hydroxide to afford an additional 0.69 g of a solid. Three recrystallizations from 20 mL of 4:1 v/v hexanes/ethyl acetate afforded an additional 0.39 g of pure product as a white solid (58% total).

Mass Spectrum (FAB): m/Z 503 (M+H), 259 (55%), 226 (40%), 160 (30%).

$^1$H NMR (CDCl$_3$, 400 MHz, ppm): δ 2.57 (app t, J=9.6, 1H), 2.87–2.97 (m, 2H), 3.58–3.71 (m, 3H), 4.18 (app t, J=10.4, 1H), 4.46 (d, J=13.6), 4.68 (d, J=2.8, 1H), 4.85 (d, J=13.6, 1H), 7.30–7.45 (m, 7H), 7.64 (s, 1H), 10.40 (br s, 1H), 10.73 (br s, 1H).

EXAMPLE 19

N-(2-(R)-Hydroxypropyl)-phenylglycinal, 3,5-bis (tri-fluoromethyl)benzyl acetal

A mixture of 1.00 g (1.5 mmol) of (±)-a-bromophenylacetaldehyde, 3,5-bis(trifluoromethyl)-benzyl acetal (from Example 12), 1.25 mL of (R)-1-amino-2-propanol, 225 mg (1.5 mmol) of sodium iodide, and 3.75 mL of isopropanol was heated at reflux for 20 h. The solution was cooled and concentrated to ~25% the original volume in vacuo. The concentrated solution was partitioned between 50 mL of ether and 20 mL of 2N aqueous sodium hydroxide solution and the layers were separated. The organic layer was washed with 20 mL of saturated aqueous sodium chloride solution, dried over magnesium sulfate and concentrated in vacuo. Flash chromatography on 50 g of silica gel using 65:35 v/v ether/hexane as the eluant afforded 948 mg (95%) of the product as a 1:1 mixture of inseparable diastereomers.

Mass Spectrum (FAB): m/Z 664 (M+H, 25%), 420 (20%), 226 (100%).

EXAMPLE 20

N-(2-(S)-Hydroxypropyl)-phenylglycinal, 3,5-bis (tri-fluoromethyl)benzyl acetal

Substitution of (S)-1-amino-2-propanol for (R)-1-amino-2-propanol in an experiment identical to the preceding example afforded 940 mg (95%) of the product as a 1:1 mixture of diastereomers.

EXAMPLE 21

N-(2-(R)-Hydroxypropyl)-N-(prop-2-enyl)-(R)-phenyl-glycinal, 3,5-bis(trifluoromethyl)benzyl acetal and N-(2-(R)-Hydroxypropyl)-N-(prop-2-enyl)-(S)-phenyl-glycinal, 3,5-bis(trifluoromethyl) benzyl acetal A mixture of 933 mg (1.40 mmol) of N-(2-(R)-hydroxypropyl)-phenylglycinal, 3,5-bis(trifluoromethyl)-benzyl acetal (from Example 19), 1 mL of allyl bromide, 600 mg (4.3 mmol) of potassium carbonate, and 5 mL of ethanol was stirred at 60° C. for 20 hours. The mixture was cooled, partitioned between 100 mL of ethyl ether and 25 mL of water and the layers were separated. Flash chromatography on 50 g of silica gel using 20:1 v/v ether/hexanes as the eluant afforded 380 mg of the (R,R)-amino alcohol (R$_f$=0.72 with 3:2 v/v ether/hexanes as the eluent), 220 mg of the (R,S)-amino alcohol (R$_f$=0.62 with 3:2 v/v ether/hexanes as the eluant), and 285 mg of a mixture of the disastereomeric amino alcohols.

For the (R,R)-amino alcohol:

Mass Spectrum (FAB): m/Z 704(M+H).

IR (neat) 3476, 2932, 1624, 1454, 1361, 1278, 1175, 1132, 760, 704, 682.

$^1$H NMR (CDCl$_3$, 400 MHz, ppm) 1.12 (d, 3H, J=6.4), 2.19 and 2.62 (dAB q, 2H, J$_{AB}$=13.0, J$_{2.19}$=2.3, J$_{2.62}$=10.4), 2.97 (dd, 1H, J=14.0, 8.8), 3.25–3.30 (m, 1H), 3.76 (s, 1H), 3.77–3.85 (m, 1H), 4.21 (d, 1H, J=8.8), 4.49 and 4.55 (AB q, 2H, J=12.4), 4.86 and 4.92 (AB q, 2H, J=12.4), 5.27–5.33 (m, 2H), 5.39 (d, 1H, J=8.8), 5.79–5.89 (m, 1H), 7.21–7.26 (m, 4H), 7.35-7.40 (m, 3H), 7.67 (s, 1H), 7.81 (s, 1H), 7.85 (s, 2H).

Analysis Calcd for C$_{32}$H$_{29}$F$_{12}$NO$_3$: C, 54.63; H, 4.15; N, 1.99; F, 32.41. Found: C, 54.72; H, 3.94; N, 1.95; F, 32.17.

For the (R,S)-amino alcohol:

Mass Spectrum (FAB): m/Z 704(M+1).

IR (neat) 3451, 2931, 1624, 1454, 1362, 1277, 704, 683.

$^1$H NMR (CDCl$_3$, 400 MHz, ppm) 1.09 (d, 3H, J=6.0), 2.48 and 2.71 (dAB q, 2H, J$_{AB}$=13.2, J$_{2.48}$=9.6, J$_{2.62}$=3.6), 3.05 (dd, 1H, J=14.4, 6.8), 3.34–3.39 (m, 1H), 3.35 (s, 1H), 3.76–3.81 (m, 1H), 4.21 (d, 1H, J=8.4), 4.50 and 4.54 (AB q, 2H, J=12.8), 4.86 and 4.96 (AB q, 2H, J=12.4), 5.10–5.17 (m, 2H), 5.39 (d, 1H, J=8.4), 5.68–5.78 (m, 1H), 7.23–7.32 (m, 4H), 7.34–7.39 (m, 3H), 7.69 (s, 1H), 7.83 (s, 1H), 7.86 (s, 2H).

Analysis Calcd for C$_{32}$H$_{29}$F$_{12}$NO$_3$: C, 54.63; H, 4.15; N, 1.99; F, 32.41. Found: C, 54.80; H, 4.16; N, 1.90; F, 32.36.

EXAMPLE 22

N-(2-(S)-Hydroxypropyl)-N-(prop-2-enyl)-(S)-phenyl-glycinal, 3,5-bis(trifluoromethyl)benzyl acetal and N-(2-(S)-Hydroxypropyl)-N-(prop-2-enyl)-(R)-phenyl-glycinal, 3,5-bis(trifluoromethyl) benzyl acetal Substitution of 880 mg (1.33 mmol) of N-(2-(S)-hydroxypropyl)-phenylglycinal, 3,5-bis(trifluoro-methyl)

benzyl acetal (Example 20) for the N-(2-(R)-hydroxypropyl)-phenylglycinal, 3,5-bis(trifluoromethyl)benzyl acetal in the procedures of the preceding example afforded 281 mg of the (S,S)-amino alcohol ($R_f$=0.72 with 3:2 v/v ether/hexanes as the eluant), 367 mg of the (S,R)-amino alcohol ($R_f$=0.62 with 3:2 v/v ether/hexanes as the eluant), and 197 mg of a mixture of the diasteriomeric amino alcohols.

EXAMPLE 23

2-(R)-(3,5-Bis(trifluoromethyl)benzyloxy)-3-(R)-phenyl-6-(R)-methyl morpholine and 2-(S)-(3,5-Bis-(trifluoromethyl)benzyloxy)-3-(R)-phenyl-6-(R)-methyl morpholine Step A: 2-(R)-(3,5-Bis(trifluoromethyl)benzyloxy)-3-(R)-phenyl-4-(2-propenyl)-6-(R)-methyl morpholine and 2-(S)-(3,5-bis(trifluoro-methyl)-benzyloxy)-3-(R)-phenyl-4-(2-propenyl)-6-(R)-methyl morpholine A solution of 355 mg (0.50 mmol) of N-(2-(R)-hydroxypropyl)-N-(2-propenyl)-(R)-phenylglycinal, 3,5-bis (trifluoromethyl)benzyl acetal (from Example 21) and 285 mg (1.5 mmol) of p-toluensulfonic acid monohydrate in 5 mL of toluene was heated at reflux for 40 min. The solution was cooled and partitioned between 40 mL of ether and 15 mL of saturated aqueous sodium bicarbonate solution. The layers were separated; the organic layer was washed with 10 mL of saturated aqueous sodium chloride solution, dried over magnesium sulfate, and concentrated in vacuo. Flash chromatography on 10 g of silica gel using 19:1 v/v hexanes/ether as the eluant afforded 122 mg of (2R,3R,6R) product ($R_f$=0.53 with 4:1 v/v hexanes/ether as the eluant) and 62 mg of the (2S,3R,6R) product ($R_f$=0.23 with 4:1 v/v hexanes/ether as the eluant).

For the (2R,3R,6R) product:

Mass Spectrum (FAB): m/Z 460 (M+H, 65%)

$^1$H NMR (CDCl$_3$, 400 MHz, ppm) 1.35 (d, 3H, J=6.4), 2.53 and 2.63 (dAB q, 2H, $J_{AB}$=12.0, $J_{2.53}$=3.2, $J_{2.63}$=6.8), 2.83–2.96 (m, 2H), 3.60 (d, 1H, J=4.0), 4.27–4.32 (m, 1H), 4.57 and 4.84 (AB q, 2H, J=13.2), 4.87 (d, 1H, J=4.0), 5.08–5.13 (m, 2H), 5.76–5.86 (m, 1H), 7.31–7.37 (m, 3H), 7.50–7.52 (m, 2H), 7.58 (s, 2H), 7.71 (s, 1H).

For the (2S,3R,6R) product:

Mass Spectrum (FAB): m/Z 460 (M+H, 65%)

$^1$H NMR (CDCl$_3$, 400 MHz, ppm) 1.37 (d, 3H, J=6.8), 2.48–2.50 (m, 2H), 2.74 and 3.01 (dtAB q, 2H, J=6.4, 1.2, 12.4) 3.84 (d, 1H, J=3.6), 3.92–3.99 (m, 1H), 4.70 and 4.93 (AB q, 2H, J=13.6), 4.97 (d, 1H, J=3.6), 5.08–5.14 (m, 2H), 5.74–5.84 (m, 1H), 7.28–7.36 (m, 3H), 7.43–7.46 (m, 2H), 7.64 (s, 2H), 7.75 (s, 1H).

Step B: 2-(R)-(3,5-Bis(trifluoromethyl)benzyloxy)-3-(R)-phenyl-6-(R)-methyl morpholine A solution of 115 mg (0.25 mmol) of the 2-(R)-(3,5-bis (trifluoromethyl)benzyloxy)-3-(R)-phenyl-4-(2-propenyl)-6-(R)-methyl morpholine (from Example 23, Step A) and 230 mg (0.25 mmol) of tris(triphenylphosphine)rhodium chloride in 15 mL of 4:1 v/v acetonitrile/water was heated at reflux for 30 min. The reaction was cooled and partitioned between 50 mL of ethyl acetate and 15 mL of water. The layers were separated and the organic layer was dried over magnesium sulfate. The aqueous layer was extracted with 2×25 mL of ethyl acetate; the extracts were dried and combined with the original organic layer. The combined organics were concentrated in vacuo. The residue was filtered through a pad of silica gel (~20 g) using 2:1 v/v ether/hexanes as the solvent. The filtrate was concentrated; flash chromatography on 5 g of silica gel using 17:3 v/v hexanes/ether as the eluant afforded 67 mg (64%) of 2-(R)-(3,5-bis(trifluoromethyl)benzyloxy)-3-(R)-phenyl-6-(R)-methyl morpholine as an oil.

Mass Spectrum (FAB): m/Z 420 (M+H, 90%)

$^1$H NMR (CDCl$_3$, 400 MHz, ppm) 1.21 (d, 3H, J=6.4), 2.02 (br s, 1H), 2.67 and 2.77 (dAB q, 2H, $J_{AB}$=13.2, $J_{2.67}$=8.8, $J_{2.77}$=3.2), 3.89 (d, 1H, J=2.4), 4.07–4.15 (m, 1H), 4.68 and 4.90 (AB q, 2H, J=12.8), 5.03 (d, 1H, J=2.4), 7.28–7.38 (m, 3H), 7.51–7.53 (m, 2H), 7.77 (s, 2H), 7.79 (s, 1H).

Step C: 2-(S)-(3,5-Bis(trifluoromethyl)benzyloxy)-3-(R)-phenyl-6-(R)-methyl morpholine A similar reaction was carried out using 55 mg (0.12 mmol) of 2-(S)-(3,5-bis(trifluoromethyl)benzyloxy)-3-(R)-phenyl-4-(2-propenyl)-6-(R)-methyl morpholine (from Example 23, Step A) and 111 mg (0.12 mmol) of tris (triphenylphosphine)rhodium chloride in 12 mL of 4:1 v/v acetonitrile/water. Flash chromatography on 4 g of silica gel using 50:1 v/v methylene chloride/acetonitrile as the eluant afforded 14 mg (28%) of 2-(S)-(3,5-bis(trifluoromethyl)-benzyloxy)-3-(R)-phenyl-6-(R)-methyl morpholine as an oil.

Mass Spectrum (FAB): m/Z 420 (M+H, 90%)

$^1$H NMR (CDCl$_3$, 400 MHz, ppm) 1.39 (d, 3H, J=6.8), 1.92 (br s, 1H), 2.84 and 2.95 (dAB q, 2H, $J_{AB}$=12.8, $J_{2.84}$=6.4, $J_{2.95}$=3.6), 3.93–4.00 (m, 1H), 4.07 (d, 1H, J=2.8), 4.68 and 4.95 (AB q, 2H, J=13.2), 4.93 (d, 1H, J=2.8), 7.28–7.37 (m, 3H), 7.48–7.52 (m, 2H), 7.55 (s, 2H), 7.72 (s, 1H).

EXAMPLE 24

2-(S)-(3,5-Bis(trifluoromethyl)benzyloxy)-3-(S)-phenyl-6-(S)-methyl morpholine and 2-(R)-(3,5-Bis-(trifluoromethyl)benzyloxy)-3-(S)-phenyl-6-(S)-methyl morpholine Substitution of 350 mg of N-(2-(S)-hydroxy-propyl)-N-(2-propenyl)-(S)-phenylglycinal, 3,5-bis-(trifluoromethyl) benzyl acetal (from Example 22) for N-(2-(R)-hydroxypropyl)-N-(2-propenyl)-(R)-phenyl-glycinal, 3,5-bis(trifluoromethyl)benzyl acetal in an experiment similar to the preceding example afforded 50 mg of 2-(S)-(3,5-bis (trifluoromethhyl)benzyloxy)-3-(S)-phenyl-6-(S)-methyl morpholine and 14 mg of 2-(S)-(3,5-bis(trifluoromethyl) benzyloxy)-3-(S)-phenyl-6-(S)-methyl morpholine.

EXAMPLE 25

2-(R)-(3,5-Bis(trifluoromethyl)benzyloxy)-3-(S)-phenyl-6-(R)-methyl morpholine and 2-(S)-(3,5-Bis-(trifluoromethyl)benzyloxy)-3-(S)-phenyl-6-(R)-methyl morpholine Step A: 2-(R)-(3,5-Bis(trifluoromethyl)benzyloxy)-3-(S)-phenyl-4-(2-propenyl)-6-(R)-methyl morpholine and 2-(S)-(3,5-bis(trifluoro-methyl)-benzyloxy)-3-(S)-phenyl-4-(2-propenyl)-6-(R)-methyl morpholine The title compounds were prepared in a manner similar to Example 23, Step A. Cyclization of 300 mg (0.43 mmol)

N-(2-(R)-hydroxypropyl)-N-(prop-2-enyl)-(S)-phenylglycinal, 3,5-bis(trifluoromethyl)benzyl acetal (from Example 23) was effected using 246 mg (1.29 mmol) of p-toluenesulfonic acid monohydrate and 5 mL of toluene. Flash chromatography on 8 g of silica gel using 20:1 v/v hexanes/ether as the eluant afforded 149 mg (75%) of the products as inseparable diastereomers.

Mass Spectrum (FAB): m/Z 460 (M+H, 65%).

Step B: 2-(R)-(3,5-Bis(trifluoromethyl)benzyloxy)-3-(S)-phenyl-6-(R)-methyl morpholine and 2-(S)-(3, 5-Bis(trifluoromethyl)benzyloxy)-3-(S)-phenyl-6-(R)-methyl morpholine A solution of 150 mg (0.33 mmol) of 2-(R)-(3,5-bis (trifluoromethyl)benzyloxy)-3-(S)-phenyl-4-(2-propenyl)-6-(R)-methyl morpholine and 2-(S)-(3,5-bis-(trifluoromethyl)-benzyloxy)-3-(S)-phenyl-4-(2-propenyl)-6-(R)-methyl morpholine (from Example 25, Step A) and 318 mg (0.32 mmol) of tris(triphenyl-phosphine)-rhodium chloride in 20 mL of 4:1 v/v acetonitrile/water was heated at reflux for 1 h. Flash chromatography on 5 g of silica gel using 9:1 v/v hexanes/ether as the eluant afforded 35 mg of the products as a mixture and 26 mg of 2-(R)-(3,5-bis-(trifluoromethyl)benzyloxy)-3-(S)-phenyl-6-(R)-methyl morpholine ($R_f$=0.22 with 3:2 v/v hexanes/ether as the eluant). Chromatography of the mixture on 5 g of silica gel using 20:1 v/v afforded 14 mg of 2-(S)-(3,5-bis (trifluoromethyl)benzyloxy)-3-(S)-phenyl-6-(R)-methyl morpholine ($R_f$=0.14 with 3:2 v/v hexanes/ether as the eluant) and 17 mg of 2-(R)-(3,5-bis(trifluoromethyl) benzyloxy)-3-(S)-phenyl-6-(R)-methyl morpholine (41% total yield).

For the (2R,3S,6R) product:

Mass Spectrum (FAB): m/Z 420 (M+H, 90%)

$^1$H NMR (CDCl$_3$, 400 Mhz. ppm) 1.30 (d, 3H, J=6.4), 1.74 (br s, 1H), 2.73 and 2.98 (dAB q, 2H, $J_{AB}$=11.6, $J_{2.73}$=10.0, $J_{2.98}$=2.4), 3.65 (d, 1H, J=7.2), 3.89–3.94 (m, 1H), 4.45 (d, 1H, J=7.2), 4.53 and 4.90 (AB q, 2H, J=13.2), 7.28–7.38 (m, 3H), 7.41–7.43 (m, 2H), 7.45 (s, 2H), 7.70 (s, 1H).

For the (2S,3S,6R) product:

Mass Spectrum (FAB): m/Z 420 (M+H, 90%)

$^1$H NMR (CDCl$_3$, 400 Mhz. ppm) 1.20 (d, 3H, J=6.4), 2.04 (br s, 1H), 2.84 and 3.15 (dAB q, 2H, $J_{AB}$=12.8, $J_{2.84}$=10.8, $J_{3.15}$=2.8), 4.08 (d, 1H, J=2.8), 4.08–4.15 (m, 1H), 4.53 and 4.80 (AB q, 2H, J=13.2), 4.79 (d, 1H, J=2.8), 7.28–7.38 (m, 5H), 7.43 (s, 2H), 7.70 (s, 1H).

EXAMPLE 26

2-(S)-(3,5-Bis(trifluoromethyl)benzyloxy)-3-(R)-phenyl-6-(S)-methyl morpholine and 2-(R)-(3,5-Bis-(trifluoromethyl)benzyloxy)-3-(R)-phenyl-6-(S)-methyl morpholine Substitution of 250 mg of N-(2-(S)-hydroxy-propyl)-N-(2-propenyl)-(S)-phenylglycinal, 3,5-bis-(trifluoromethyl) benzyl acetal (from Example 22) for N-(2-(R)-hydroxypropyl)-N-(2-propenyl)-(R)-phenyl-glycinal, 3,5-bis(trifluoromethyl)benzyl acetal in an experiment similar to the preceding example afforded 42 mg of 2-(S)-(3,5-bis (trifluoromethyl)benzyloxy)-3-(R)-phenyl-6-(S)-methyl morpholine and 17 mg of 2-(S)-(3,5-bis(trifluoro-methyl) benzyloxy)-3-(R)-phenyl-6-(S)-methyl morpholine.

EXAMPLE 27

2-(R)-(3,5-Bis(trifluoromethyl)benzyloxy)-3-(S)-phenyl-5-(R)-methyl morpholine, 2-(S)-(3,5-Bis-(tri-fluoromethyl)benzyloxy)-3-(S)-phenyl-5-(R)-methyl morpholine, 2-(R or S)-(3,5-Bis (trifluoromethyl)benzyloxy)-3-(R)-phenyl-5-(R)-methylmorpholine, and 2-(S or R)-(3,5-Bis (trifluoromethyl)benzyloxy)-3-(R)-phenyl-5-(R)-methylmorpholine Execution of the sequence described in Example 19 substituting (R)-2-amino-1-propanol for (R)-1-amino-2-propanol provided a mixture of 55 mg of high $R_f$ material and 56 mg of low $R_f$ material. The high $R_f$ material was processed according to Example 23, Step A above to provide 10 mg of high $R_f$ material (2-(R)-(3,5-Bis(trifluoromethyl) benzyloxy)-3-(S)-phenyl-5-(R)-methyl morpholine and 7 mg of low $R_f$ material (2-(S)-(3,5-Bis(trifluoromethyl) benzyloxy)-3-(S)-phenyl-5-(R)-methyl morpholine. The low $R_f$ material (after being combined with an additional 30 mg of material) was processed according to Example 23, Step A to provide 24 mg of high $R_f$ material (2-(R or S)-(3,5-Bis(trifluoromethyl)benzyloxy)-3-(R)-phenyl-5-(R)-methyl-morpholine and 18 mg of low $R_f$ material (2-(S or R)-(3,5-Bis(trifluoromethyl)benzyloxy)-3-(R)-phenyl-5-(R)-methylmorpholine.

2-(R)-(3,5-Bis(trifluoromethyl)benzyloxy)-3-(S)-phenyl-5-(R)-methyl morpholine

Mass Spectrum (FAB): m/Z 420 (M+H, 100%), 227 (50%), 192 (75%), 176 (65%).

NMR (CDCl$_3$, 400 MHz, ppm): δ 0.98 (d, 3H, J=6.3 Hz), 3.16–3.20 (m, 1H), 3.43–3.47 (m, 1H), 3.79 (d, 1H, J=7.5 Hz), 3.91 (dd, 1H, J=3.2 &11.5 Hz), 4.51 (d, 2H, J=13.4 Hz), 4.85 (d, 1H, J=13.2 Hz), 7.29–7.45 (m, 7H), 7.67 (s, 1H).

2-(S)-(3,5-Bis(trifluoromethyl)benzyloxy)-3-(S)-phenyl-5-(R)-methyl morpholine

Mass Spectrum (FAB): m/Z 420 (M+H, 48%), 227 (35%), 192 (39%), 176 (100%).

NMR (CDCl$_3$, 400 MHz, ppm): δ 1.10 (d, 3H, J=6.4 Hz), 3.23–3.26 (m, 1H), 3.56–3.61 (m, 2H), 4.17 (d, 1H, J=2.3 Hz), 4.51 (d, 1H, J=13.7 Hz), 4.71 (d, 1H, J=2.4 Hz), 4.78 (d, 1H, J=13.5 Hz), 7.28–7.39 (m, 7H), 7.68 (s, 1H).

2-(R or S)-(3,5-Bis(trifluoromethyl)benzyloxy)-3-(R)-phenyl-5-(R)-methyl morpholine Mass Spectrum (FAB): m/Z 281 (35%), 221 (55%), 207 (45%), 192 (40%), 147 (100%).

NMR (CDCl$_3$, 400 MHz, ppm): δ 1.13 (d, 3H, J=6.6 Hz), 3.10–3.14 (m, 1H), 3.66 (dd, 1H, J=6.6 & 11.4 Hz), 3.76 (dd, 1H, J=3.5 & 11.2 Hz), 4.04 (d, 1H, J=4.0 Hz), 4.61 (d, 1H, J=13.2 Hz), 4.74 (d, 1H, J=3.9 Hz), 4.89 (d, 1H, 13.2 Hz), 7.26–7.35 (m, 3H), 7.47–7.49 (m, 2H), 7.64 (s, 1H), 7.74 (s, 1H).

2-(R or S)-(3,5-Bis(trifluoromethyl)benzyloxy)-3-(R)-phenyl-5-(R)-methyl morpholine NMR (CDCl$_3$, 400 MHz, ppm): δ 1.36 (d, 3H, J=6.7 Hz), 3.27–3.31 (m, 1H), 3.39 (dd, 1H, J=2.2 & 11.3 Hz), 4.16 (dd, 1H, J=3.2 & 11.0 Hz), 4.37 (d, 1H, J=2.3 Hz), 4.53 (d, 1H, J=13.5 Hz), 4.75 (d, 1H, J=2.5 Hz), 4.81 (d, 1H, 13.6 Hz), 7.26–7.35 (m, 3H), 7.26–7.43 (m, 7H), 7.68 (s, 1H).

EXAMPLE 28

2-(R or S)-(3,5-Bis(trifluoromethyl)-benzyloxy)-3-(S)-phenyl-5-(S)-methylmorpholine, 2-(S or R)-(3, 5-(-Bis-(trifluoromethyl)benzyloxy)-3-(S)-phenyl-5-(S)-methyl-morpholine, and 2-(R)-(3,5-Bis (trifluoromethyl)benzyl-oxy)-3-(R)-phenyl-5-(S)-methylmorpholine Execution of the sequence described in Example 19 substituting (S)-2-amino-1-propanol for (R)-1-amino-2- propanol provided a mixture of 78 mg of high $R_f$ material and 70 mg of low $R_f$ material. The high $R_f$ material was processed according to Example 23, Step A above to provide less than 1 mg of high $R_f$ material (2-(R)-(3,5-Bis (trifluoromethyl)benzyloxy)-3-(S)-phenyl-5-(S)-methylmorpholine) and 9 mg of low $R_f$ material (2-(S)-(3,5-Bis(trifluoromethyl)benzyloxy)-3-(S)-phenyl-5-(S)-methyl morpholine. The low $R_f$ material was processed according to Example 23, Step A to provide 20 mg of high $R_f$ material (2-(R or S)-(3,5-Bis(trifluoromethyl)benzyloxy)-3-(S)-phenyl-5-(S)-methylmorpholine and 14 mg of low $R_f$ material (2-(S or R)-(3,5-Bis(trifluoromethyl)benzyloxy)-3-(S)-phenyl-5-(S)-methylmorpholine.

2-(R or S)-(3,5-Bis(trifluoromethyl)benzyloxy)-3-(S)-phenyl-5-(S)-methyl morpholine Mass Spectrum (FAB): m/Z 420 (M+H, 60%), 227 (68%), 192 (56%), 176 (100%).

NMR (CDCl$_3$, 400 MHz, ppm): δ 1.12 (d, 3H, J=6.6 Hz), 3.09–3.14 (m, 1H), 3.65 (dd, 1H, J=6.6 & 11.0 Hz), 3.75 (dd, 1H, J=3.6 & 11.1 Hz), 4.04 (d, 1H, J=3.9 Hz), 4.61 (d, 1H, J=13.2 Hz), 4.73 (d, 1H, J= 3.9 Hz), 4.89 (d, 1H, 13.2 Hz), 7.28–7.35 (m, 3H), 7.47 (d, 2H, 7.0 Hz), 7.64 (s, 1H), 7.74 (s, 1H).

2-(S or R)-(3,5-Bis(trifluoromethyl)benzyloxy)-3-(S)-phenyl-5-(S)-methyl morpholine Mass Spectrum (FAB): m/Z 420 (M+H, 50%), 227 (45%), 192 (40%), 176 (100%).

NMR (CDCl$_3$, 400 MHz, ppm): δ0 1.36 (d, 3H, J=6.9 Hz), 3.27–3.29 (m, 1H), 3.39 (dd, 1H, J=2.2 & 11.1 Hz), 4.15 (dd, 1H, J=3.3 & 11.1 Hz), 4.37 (d, 1H, J=2.5 Hz), 4.52 (d, 1H, J=13.3 Hz), 4.75 (d, 1H, J=2.4 Hz), 4.81 (d, 1H, 13.5 Hz), 7.28–7.43 (m, 7H), 7.68 (s, 1H).

2-(R)-(3,5-Bis(trifluoromethyl)benzyloxy)-3-(R)-phenyl-5-(S)-methyl morpholine

NMR (CDCl$_3$, 400 MHz, ppm): δ 1.10 (d, 3H, J=6.4 Hz), 3.22–3.25 (m, 1H), 3.55–3.60 (m, 2H), 4.17 (d, 1H, J=2.3 Hz), 4.51 (d, 1H, J=13.5 Hz), 4.71 (d, 1H, J=2.4 Hz), 4.77 (d, 1H, J=13.6 Hz), 7.28–7.38 (m, 7H), 7.67 (s, 1H).

EXAMPLE 29

2-(R)-(3,5-Bis(trifluoromethyl)benzyloxy)-3-(S)-phenyl-5-(R)-phenylmorpholine, 2-(S)-(3,5-Bis(trifluoromethyl)benzyloxy)-3-(S)-phenyl-5-(R)-phenyl-morpholine, and 2-(R or S)-(3,5-Bis (trifluoromethyl)-benzyloxy)-3-(R)-phenyl-5-(R)-phenylmorpholine Execution of the sequence described in Example 19 substituting (R)-2-amino-2-phenylethanol for (R)-1-amino-2-propanol provided a mixture of 62 mg of high $R_f$ material and 52 mg of low $R_f$ material. The high $R_f$ material was processed according to Example 23, Step A above to provide 16 mg of high $R_f$ material (2-(R)-(3,5-B is(trifluoromethyl) benzyloxy)-3-(S)-phenyl-5-(R)-phenylmorpholine and 4 mg of low $R_f$ material (2-(S)-(3,5-Bis(trifluoromethyl) benzyloxy)-3-(S)-phenyl-5-(R)-phenylmorpholine. The low $R_f$ material was processed according to Example 23, Step A to provide 4 mg of product (2-(R or S)-(3,5-Bis (trifluoromethyl)benzyl-oxy)-3-(R)-phenyl-5-(R)-phenylmorpholine.

2-(R)-(3,5-Bis(trifluoromethyl)benzyloxy)-3-(S)-phenyl-5-(R)-phenylmorpholine

NMR (CDCl$_3$, 400 MHz, ppm): δ 3.62 (t, 1H, J=10.7 & 21.5 Hz), 3.93 (d, 1H, J=7.4 Hz), 3.99 (dd, 1H, J=3.1 & 11.2 Hz), 4.18 (dd, 1H, J=3.0 & 10.2 Hz), 4.46 (d, 1H, J=7.4 Hz), 4.53 (d, 1H, J=13.5 Hz), 4.89 (d, 1H, J=13.3 Hz), 7.28–7.55 (m, 12H), 7.69 (s, 1H).

2-(S)-(3,5-Bis(trifluoromethyl)benzyloxy)-3-(S)-phenyl-5-(R)-phenylmorpholine

NMR (CDCl$_3$, 400 MHz, ppm): δ 3.67 (dd, 1H, J=3.5 & 11.0 Hz), 3.89 (d, 1H, J=10.8 & 21.6 Hz), 4.25 (dd, 1H, J=3.3 & 11.0 Hz), 4.34 (d, 1H, J=2.2 Hz), 4.52 (d, 1H, J=13.8 Hz), 4.78–4.87 (m, 2H), 7.28–7.51 (m, 12H), 7.69 (s, 1H).

2-(R or S)-(3,5-Bis(trifluoromethyl)benzyloxy)-3-(R)-phenyl-5-(R)-phenylmorpholine NMR (CDCl$_3$, 400 MHz, ppm): δ 4.10–4.25 (m, 2H), 4.30–4.38 (m, 1H), 4.48–4.54 (m, 1H), 4.59–4.66 (m, 1H), 4.86–5.00 (m, 2H), 7.25–7.74 (m, 13H).

EXAMPLE 30

2-(S)-(3,5-Bis(trifluoromethyl)benzyloxy)-3-(R)-phenyl-5-(S)-phenylmorpholine, 2-(R)-(3,5-Bis(trifluoromethyl)benzyloxy)-3-(R)-phenyl-5-(S)-phenyl-morpholine, 2-(R or S)-(3,5-Bis-(trifluoromethyl)benzyloxy)-3-(S)-phenyl-5-(S)-phenyl-morpholine, and 2-(R or S)-(3,5-Bis (trifluoromethyl)benzyloxy)-3-(S)-phenyl-5-(S)-phenylmorpholine Execution of the sequence described in Example 19 substituting (S)-2-amino-2-phenylethanol for (R)-1-amino-2-propanol provided a mixture of 75 mg of high $R_f$ material and 64 mg of low $R_f$ material. The high $R_f$ material was processed according to Example 23, Step A above to provide 23 mg of high $R_f$ material (2-(S)-(3,5-Bis(trifluoromethyl) benzyloxy)-3-(R)-phenyl-5-(S)-phenylmorpholine [L-740, 930]) and 7 mg of low $R_f$ material (2-(R)-(3,5-Bis (trifluoromethyl)benzyloxy)-3-(R)-phenyl-5-(S)-phenylmorpholine. The low $R_f$ material was processed according to Example 23, Step A to provide 26 mg of higher $R_f$ material (2-(R or S)-(3,5-Bis(trifluoromethyl)benzyloxy)-3-(S)-phenyl-5-(S)-phenylmorpholine and 6 mg of lower $R_f$ material (2-(R or S)-(3,5-Bis(trifluoro-methyl)benzyloxy)-3-(S)-phenyl-5-(S)-phenylmorpholine.

2-(S)-(3,5-Bis(trifluoromethyl)benzyloxy)-3-(R)-phenyl-5-(S)-phenylmorpholine

NMR (CDCl$_3$, 400 MHz, ppm): δ 3.60–3.74 (m, 1H), 3.94 (d, 1H, J=7.6 Hz), 4.00 (dd, 1H, J=3.2 & 11.3 Hz), 4.18–4.21 (m, 1H), 4.50–4.55 (m, 2H,), 4.89 (m, 1H), 7.26–7.55 (m, 12H), 7.69 (s, 1H).

2-(R)-(3,5-Bis(trifluoromethyl)benzyloxy)-3-(R)-phenyl-5-(S)-phenylmorpholine

NMR (CDCl$_3$, 400 MHz, ppm): δ 3.68 (dd, 1H, J=3.0 & 11.0 Hz), 3.88–3.94 (m, 1H), 4.26–4.30 (m, 1H), 4.36 (s, 1H), 4.52 (d, 1H, J=13.5 Hz), 4.77–4.86 (m, 2H), 7.27–7.51 (m, 12H), 7.69 (s, 1H).

2-(R or S)-(3,5-Bis(trifluoromethyl)benzyloxy)-3-(S)-phenyl-5-(S)-phenylmorpholine NMR (CDCl$_3$, 400 MHz, ppm): δ 3.93–3.95 (m, 1H), 4.06–4.21 (m, 2H), 4.38–4.42 (m, 1H), 4.59–4.68 (m, 2H), 4.83–4.94 (m, 2H), 7.25–7.81 (m, 13H).

2-(R or S)-(3,5-Bis(trifluoromethyl)benzyloxy)-3-(S)-phenyl-5-(S)-phenylmorpholine NMR (CDCl$_3$, 400 MHz, ppm): δ 3.43–3.59 (m, 2H), 3.82 (d, 1H, J=7.2 Hz), 4.25 (d, 1H, J=12.5 Hz), 4.52–4.63 (m, 3H), 4.80–4.90 (br s, 1H), 7.11–7.81 (m, 13H).

EXAMPLE 31

2-(S)-(3,5-bis(trifluoromethyl)benzyloxy)-6-(R)-methyl-3-(S)-phenyl-4-(3-(1,2,4-triazolo)methyl)-morpholine According to the procedure given in Example 17, Step B, 98 mg (0.24 mmole) of 2-(S)-(3,5-bis-(trifluoromethyl)benzyloxy)-3-(S)-phenyl-6-(R)-methyl morpholine (from Example 25 above), 38 mg (0.28 mmole) of N-formyl-2-chloroacetamidrazone (from Example 17, Step A above) and 97 mg (0.7 mmole) of anhydrous potassium carbonate gave, after flash chromatography on 28 g of silica eluting with 1 L of 100:4:0.5 methylene chloride:methanol:ammonia water, a light yellow solid which after recrystallization from hexanes/methylene chloride provided 77 mg (66%) of 2-(S)-(3,5-bis(trifluoromethyl)benzyloxy)-6-(R)-methyl-3-(S)-phenyl-4-(3-(1,2,4-triazolo)methyl)morpholine as a white powder.

NMR (CDCl$_3$, 400 MHz, ppm): δ 1.17 (d, J=6.3, 3H), 2.29 (t, J=11.1, 1H), 2.92 (d, J=11.1, 1H), 3.42 (d, J=15.3, 1H), 3.58 (s, 1H), 3.88 (d, J=15.4, 1H), 4.20–4.33 (m, 1H), 4.43 (d, 13.5, 1H), 4.71 (d, J=2.4, 1H), 4.74 (d, J=13.3, 1H), 7.30–7.55 (m, 7H), 7.69 (s, 1H), 7.95 (s, 1H).

EXAMPLE 32

2-(S)-(3,5-Bis(trifluoromethyl)benzyloxy)-6-(R)-methyl-4-(3-(5-oxo-1H,4H-1,2,4-triazolo)methyl)-3-(S)-phenylmorpholine A mixture of 96 mg (0.23 mmole) of 2-(S)-(3,5-bis(trifluoromethyl)benzyloxy)-3-(S)-phenyl-6-(R)-methyl morpholine (from Example 25 above), 46 mg (0.28 mmole) of N-methylcarboxy-2-chloroacetamidrazone and 95 mg (0.69 mmole) of anhydrous potassium carbonate in 3 mL of dry DMF was stirred at room temperature for 20 min, at 60° C. for 90 min and then at 120° C. for 2 hr. The mixture was cooled to room temperature, taken up in 15 mL of ethyl acetate and was washed with 3×10 mL of water. The combined aqueous layers were back-extracted with 10 mL of ethyl acetate, the combined organic layers were washed with 10 mL of brine, dried over sodium sulfate, filtered and concentrated in vacuo. The residue was purified by flash chromatography on 28 g of silica eluting with 1 L of 100:4 methylene chloride:methanol to give 65 mg (55%) of 2-(S)-(3,5-bis(trifluoromethyl)benzyl-oxy)-6-(R)-methyl-4-(3-(5-oxo-1H,4H-1,2,4-triazolo)methyl)-3-(S)-phenylmorpholine as a light yellow powder.

NMR (CDCl$_3$, 400 MHz, ppm): δ 1.18 (d, J=6.2, 3H), 2.15 (t, J=11.1, 1H), 2.89 (d, J=14, 2H), 3.49 (d, J=2.2, 1H), 3.61 (d, J=14.4, 1H), 4.20–4.30 (m, 1H), 4.45 (d, J=13.6, 1H), 4.67 (d, J=2.5, 1H), 4.79 (d, J=13.5, 1H), 7.25–7.50 (m, 7H), 7.62 (s, 1H), 10.07 (s, 1H), 10.35 (s, 1H).

EXAMPLE 33

2-(S)-(3,5-Bis(trifluoromethyl)benzyloxy)-3-(R)-phenylmorpholine

Step A: 4-Benzyl-2-(S)-hydroxy-3-(R)-phenylmorpholine

A solution of 3.72 g (13.9 mmol) of 4-benzyl-3-(R)-phenyl-2-morpholinone, prepared from (R)-phenyl-glycine as described in Example 14, in 28 mL of CH$_2$Cl$_2$ was cooled in a −78° C. bath under a N$_2$ atmosphere and 14 mL of a 1.5M solution of DIBAL-H (21 mmol) in toluene were added. After stirring the resulting solution for 0.5 h, it was allowed to warm to −50° C. and mantained at this temperature for 0.5 h. The reaction mixture was quenched by adding 10 mL of aqueous potassium sodium tartarate. The mixture was diluted with CH$_2$Cl$_2$ and the layers were separated. The aqueous layer was extracted 3 times with CH$_2$Cl$_2$. The CH$_2$Cl$_2$ layers were washed with brine, dried over Na$_2$SO$_4$ and filtered. Concentration of the filtrate furnished 3.32 g (88%) of 4-benzyl-2-(S)-hydroxy-3-(R)-phenylmorpholine suitable for use in the next step.

NMR (CDCl$_3$) 2.28 (m, 1H), 2.71 (m, 1H), 2.91 (d, J=13 Hz, 1H), 3.09 (d, J=6 Hz, 1H), 3.69 (d, J=13 Hz, 1H), 3.82 (td, J=10 Hz and 2 Hz, 1H), 3.91 (d, J=10 Hz, 1H), 4.73 (t, J=6 Hz, 1H), 7.2–7.52 (m, 10H).

Step B: 4-Benzyl-2-(S)-(3,5-bis(trifluoromethyl)benzyloxy)-3-(R)phenylmorpholine To a suspension of 0.592 g (14.8 mmol) of NaH in 30 mL of dry THF at 0° C. was added 3.32 g (12.3 mmol) of 4-benzyl-2-(S)-hydroxy-3-(R)-phenyl-morpholine prepared in step A. After 15 min 0.915 g of tetrabutylammonium iodide (2.47 mmol) and 2.4 mL (13 mmol) of 3,5-bis(trifluoromethyl)benzyl bromide were added. The resulting mixture was stirred at ice-bath temperature for 1 h, then poured into saturated NaHCO$_3$ solution and extracted with ethyl acetate (EtOAc). The organic layers were combined, washed with brine, dried over Na$_2$SO$_4$ and filtered. The filtrate was concentrated in vacuo and the resiue was chromatographed on a Waters Prep500 HPLC system using 50% EtOAc/Hexane to isolate 3.6 g (59%) of 4-Benzyl-2-(S)-(3,5-bis(trifluoromethyl)benzyloxy)-3-(R)-phenylmorpholine.

$^1$H NMR (CDCl$_3$) 2.3 (td, J=11 Hz and 3Hz, 1H), 2.71 (d, J=11 Hz, 1H), 2.90 (d, J=13 Hz, 1H), 3.22 (d, J=7.3 Hz, 1H), 3.75 (m, 2H), 3.93 (m, 1H), 4.43 (d, J=13 Hz, 1H), 4.45 (d, J=7.3 Hz, 1H), 4.82 (d, J=13 Hz, 1H), 7.19–7.5 (m, 12H), 7.67 (s, 1H).

Step C: 2-(S)-(3,5-Bis(trifluoromethyl)benzyloxy)-3-(R)-phenylmorpholine

A solution of 3.6 g (7.27 mmol) of 4-benzyl-2-(S)-(3,5-bis(trifluoromethyl)benzyloxy)-3-(R)-phenylmorpholine in 100 mL of ethanol and 5 mL of water, containing 0.72 g of 10% Pd/C was hydrogenated on a Parr apparatus for 36 h. The catalyst was filtered and thoroughly washed with EtOAc. The filtrate was concentrated and the residue was partitioned between water and EtOAc. The EtOAc layer was washed with brine, dried over Na$_2$SO$_4$, filtered and concentrated. The residue was purified by flash chromatography using a gradient of 10–60% EtOAc/hexane to isolate 2.05 g (70%) of 2-(S)-(3,5-bis(trifluoromethyl)benzyloxy)-3-(R)-phenylmorpholine.

$^1$H NMR (CDCl$_3$) 1.92 (br s, 1H), 2.91 (m, 1H), 3.05 (td, J=11 Hz and 3 Hz, 1H), 3.68 (d, J=7 Hz, 1H), 3.81 (td, J=11 Hz and 3 Hz, 1H), 4.01 (m, 1H), 4.44 (d, J=7Hz), 4.5 (d, J=13 Hz, 1H), 4.85 (d, J=13 Hz, 1H), 7.28–7.42 (m, 7H), 7.67 (s, 1H).

EXAMPLE 34

4-(3-(1,2,4-Triazolo)methyl)-2-(S)-(3,5-bis(trifluoromethyl)benzyloxy)-3-(R)-phenylmorpholine The title compound was prepared by the procedure of Example 17, step B employing the product of Example 33, step C as a starting material.

$^1$H NMR (CDCl$_3$) 1.75 (br s, 1H), 2.61 (td, J=12 Hz and 2 Hz, 1H), 2.83 (d, J=12 Hz, 1H), 3.33 (d, J=7 Hz, 1H), 3.48

(d, J=15 Hz, 1H), 3.78 (d, J=15 Hz, 1H), 3.85 (m, 1H), 3.99 (m, 1H), 4.44 (d, J=13 Hz, 1H), 4.49 (d, J=7 Hz, 1H), 4.81 (d, J=13 Hz, 1H), 7.23–7.45 (m, 7H), 7.67 (s, 1H), 7.96 (s, 1H).

EXAMPLE 35

4-(3-(5-Oxo-1H,4H-1,2,4-triazolo)methyl)-2-(S)-(3,5-bis-(trifluoromethyl)benzyloxy)-3-(R)-phenyl-morpholine The title compound was prepared by the procedure of Example 18, steps B & C employing the product of Example 33, step C as a starting material.

EXAMPLE 36

4-(2-(Imidazolo)methyl)-2-(S)-(3,5-bis(trifluoromethyl)benzyloxy)-3-(S)-phenylmorpholine A solution of 101 mg (0.25 mmol) of 2-(S)-(3,5-bis (trifluoromethyl)benzyloxy)-3-(S)-phenylmorpholine (Example 15), 98 mg (1.0 mmol) of imidazole-2-carboxaldehyde, and 5 drops of glacial acetic acid in 3 ml of methanol was treated with 1.5 ml of 1M sodium cyanoborohydride solution in THF. After 16 hr, the reaction was quenched with 5 ml of saturated aqueous sodium bicarbonate solution and partitioned between 40 ml of ethyl acetate and 20 ml of water. The organic layer was separated, dried over magnesium sulfate, and concentrated in vacuo. Flash chromatography on 8 g of silica gel using 0:1:0.1 methylene chloride/methanol/amonium hydroxide as the eluent afforded 54 mg (44% yield) of the title compound as a white solid.

$^1$H NMR (CDCl$_3$) 2.60 (dt, J=3.2 Hz and 12.4 Hz, 1H), 2.85 (d, J=12.4 Hz, 1H), 3.28 (d, J=14.4 Hz, 1H), 3.59 (d, J=2.8 Hz, 1H), 3.66 (dd, J=2.0, 11.6 Hz, 1H), 3.84 (d, J=14.4 Hz, 1H), 3.94 (app s, 2H), 4.14 (dt, J=2.0, 12.0 Hz, 1H), 4.43 (d, J=13.6 Hz, 1H), 4.71 (d, J=2.8 Hz, 1H), 4.78 (d, J=13.6 Hz, 1H), 6.99 (app s, 2H), 7.25–7.48 (m, 6H), 7.72 (s, 1H). Mass spectrum (FAB): m/z 486 (100%, M+H)

EXAMPLE 37

4-(2-(Imidazolo)methyl)-2-(S)-(3,5-bis(trifluoromethyl)benzyloxy)-3-(R)-phenylmorpholine The title compound was prepared by the procedure of Example 36 employing appropriate starting materials.

$^1$H NMR (CDCl$_3$) 2.53 (td, J=11 Hz and 3 Hz, 1H), 2.74 (d, J=12 Hz, 1H), 3.23 (d, J=7 Hz, 1H), 3.32 (d, J=15 Hz, 1H), 3.66 (d, J=15 Hz, 1H), 3.77 (td, J=11 Hz and 2 Hz, 1H), 3.99 (m, 1H), 4.44 (m, 2H), 4.8 (d, J=13 Hz, 1H), 6.94 (s, 2H), 7.2–7.45 (m, 7H), 7.67 (s, 1H).

EXAMPLE 38

4-(5-(Imidazolo)methyl)-2-(S)-(3,5-bis(trifluoromethyl)benzyloxy)-3-(R)-phenylmorpholine The title compound was prepared by the procedure of Example 36 employing appropriate starting materials.

$^1$H NMR (CDCl$_3$) 2.47 (td, J=12 Hz and 3 Hz, 1H), 2.83 (d, J=12 Hz, 1H), 3.2 (m, 2H), 3.61 (d, J=14 Hz, 1H), 3.79 (td, J=12 Hz and 2 Hz, 1H), 3.96 (m, 1H), 4.44 (m, 2H), 4.80 (d, J=13 Hz, 1H), 6.81 (s, 1H), 7.28–7.45 (m, 7H), 7.60 (s, 1H), 7.66 (s, 1H).

EXAMPLE 39

4-(Aminocarbonylmethyl)-2-(S)-(3,5-bis(trifluoromethyl)benzyloxy)-3-(R)-phenylmorpholine The title compound was prepared by the procedure of Example 15 employing appropriate starting materials.

$^1$H NMR (CDCl$_3$) 2.54 (td, J=11 Hz and 2 Hz, 1H), 2.64 (d, J=17 Hz, 1H), 2.93 (d, J 12 Hz, 1H), 3.14 (d, J=17 Hz, 1H), 3.27 (d, J=7 Hz, 1H), 3.83 (td, J=11 Hz and 2 Hz, 1H), 4.05 (m, 1H), 4.46 (m, 2H), 4.81 (d, J=13 Hz, 1H), 5.62 (br s, 1H), 6.80 (br s, 1H), 7.28–7.32 (m, 7H), 7.67 (s, 1H).

EXAMPLES 40–43

4-(3-(1,2,4-Triazolo)methyl)-2-(3-(tert-butyl)-5-methylbenzyloxy)-3-phenyl-morpholine, 4-(3-(5-Oxo-1H,4H-1,2,4-triazolo)methyl)-2-(3-(tert-butyl)-5-methylbenzyloxy)-3-phenyl-morpholine, 4-(2-(Imidazolo)methyl)-2-(3-(tert-butyl)-5-methyl-benzyloxy)-3-phenylmorpholine, 4-(4-(Imidazolo)-methyl)-2-(3-(tert-butyl)-5-methylbenxyloxy)-3-phenyl-morpholine The title compounds are each prepared by the procedures of Examples 15, 17 & 18 employing appropriately substituted starting materials and reagents.

EXAMPLE 44

2-(S)-(3,5-Dichlorobenzyloxy)-3-(S)-phenylmorpholine

Step A: 3,5-Dichlorobenzyl alcohol, trifluoromethanesulfonate ester

A solution of 6.09 g (34.4 mmole) of 3,5-dichlorobenzyl alcohol and 8.48 g (41.3 mmole) of 2,6-di-t-butyl-4-methylpyridine in 280 mL of dry carbon tetrachloride under a nitrogen atmosphere was treated with 5.95 mL (35.4 mmole) of trifluoromethanesulfonic anhydride at room temperature. A white precipitate formed shortly after the addition of the anhydride. After 90 min, the slurry was filtered under nitrogen with a Schlenk filter, and the filtrate was concentrated in vacuo. The residue, which was a two-phase oil, was dissolved under nitrogen in 60 mL of dry toluene. The resulting solution was used immediately in Step B below.

Step B: 4-Benzyl-2-(S)-(3,5-dichlorobenzyloxy)-3-(S)-phenylmorpholine

A solution of 5.11 g (19.1 mmole) of N-benzyl-3-(S)-phenylmorpholin-2-one (from Example 14) in 100 mL of dry THF was cooled to −75° C. under nitrogen and was treated dropwise with 20.5 mL (20.5 mmole) of a 1M solution of lithium tri(sec-butyl)borohydride (L-Selectride®) in THF. After stirring the solution at −75° C. for 30 min, a solution of 3,5-dichlorobenzyl alcohol, trifluoromethanesulfonate ester in toluene (from Example 44, Step A) was added by cannula so that the internal temperature was maintained below −60° C. The resulting solution was stirred between −38° C. and −50° C. for 9 hr, and was then treated with 14 mL of aqueous ammonia and stored at −20° C. for 12 hours. The solution was then poured into a mixture of 50 mL of ethyl acetate and 100 mL of water, and the layers were separated. The aqueous phase was extracted with 2×100 mL of ethyl acetate, each extract was washed with brine, the combined organic layers were dried over sodium sulfate, the mixture was filtered and the filtrate concentrated in vacuo. The residue was purified by flash chromatography on 235 g of silica eluting with 1.5 L of 100:2 hexanes:ethyl acetate, then 1.5 L of 100:3 hexanes:ethyl acetate and then 1.9 L of 100:5 hexanes:ethyl acetate to give 4.4 g (54%) of an oil, which by $^1$H NMR is a 8:1 mixture of cis:trans morpholines.

Mass Spectrum (FAB): m/Z 430,428,426 (M+H, ~60%), 268 (M—ArCH$_2$, 100%), 252 (M—ArCH$_2$O, 75%), 222 (20%), 159 (45%).

$^1$H NMR (CDCl$_3$, 400 MHz, ppm): δ major (cis) isomer: 2.32 (td, J=12, 3.6, 1H), 2.84 (app t, J=13, 2H), 3.52 (d, J=2.6, 1H), 3.55 (dq, J=11.3, 1.6, 1H), 3.91 (d, J=13.3, 1H), 4.12 (td, J=11.6, 2.4, 1H), 4.29 (d, J=13.6, 1H), 4.59 (d, J=2.9, 1H), 4.60 (d, J=13.6), 6.70 (s, 2H), 7.13 (t, J=1.9, 1H), 7.2–7.6 (m, 8H), 7.53 (br d, 2H).

Step C: 2-(S)-(3,5-Dichlorobenzyloxy)-3-(S)-phenyl-morpholine

A solution of 0.33 g (0.77 mmole) of 4-benzyl-2-(S)-(3,5-dichlorobenzyloxy)-3-(S)-phenylmorpholine (from Example 44, Step B) and 0.22 g (1.54 mmole) of 1-chloroethyl chloroformate in 4.5 mL of 1,2-dichloroethane was placed in a pressure vial which was lowered into an oil bath which was heated to 110° C. After stirring for 60 hr the solution was cooled and concentrated in vacuo. The residue was dissolved in 7 mL of methanol and the resulting solution was heated at reflux for 30 min. The mixture was cooled and treated with several drops of concentrated aqueous ammonia and the solution was concentrated. The residue was partly purified by flash chromatography on 67 g of silica eluting with 1.5 L of 100:1 methylene chloride:methanol, and the rich cuts were purified by flash chromatography on 32 g of silica eluting with 50:50 hexanes:ethyl acetate and then 50:50:5 hexanes:ethyl acetate:methanol to give 0.051 g (20%) of an oil, which by $^1$H NMR was pure cis morpholine.

Mass Spectrum (FAB): m/Z 468,466,464 (max 8%)), 338,340 (M+H, 25%), 178 (20%), 162 (100%), 132 (20%), $^1$H NMR (CDCl$_3$, 400 MHz, ppm): δ 1.89 (br s, 1H), 3.08 (dd, J=12.5, 2.9, 1H), 3.23 (td, J=12.2, 3.6, 1H), 3.59 (dd, J=11.3, 2.5, 1H), 4.03 (td, J=11.7, 3, 1H), 4.09 (d, J=2.4, 1H), 4.37 (d, J=13.5, 1H), 4.62 (d, J=13.3, 1H), 4.67 (d, J=2.5, 1H), 6.72 (d, J=1.8, 2H), 7.14 (t, J=1.8, 1H), 7.25–7.40 (m, 5H).

EXAMPLE 45

2-(S)-(3,5-dichlorobenzyloxy)-4-(3-(5-oxo-1,2,4-triazolo)methyl)-3-(S)-phenylmorpholine Step A: N-Methylcarboxy-2-chloroacetamidrazone A solution of 5.0 g (66.2 mmol) of chloroacetonitrile in 35 mL of dry methanol was cooled to 0° C. and was treated with 0.105 g (1.9 mmol) of sodium methoxide. The ice-bath was removed and the mixture was alowed to stir at room temperature for 30 minutes. To the reaction was then added 0.110 mL (1.9 mmol) of acetic acid and then 5.8 g (64.9 mmol) of methyl hydrazinecarboxylate. After stirring 30 minutes at room temperature, the suspension was concentrated in vacuo, and placed on the high-vac line overnight, to give 10.5 g (98%) of a yellow powder, a portion of which was employed in Step C below.

Step B: 4-(2-(N-Methylcarboxy-acetamidrazono)-2-(S)-(3,5-dichlorobenzyloxy)-3-(S)-phenylmorpholine A solution of 0.050 g (0.15 mmol) of 2-(S)-(3,5-dichlorobenzyloxy)-3-(S)-phenylmorpholine (from Example 44, Step C), 0.034 g (0.21 mmol) of N-methylcarboxy-2-chloroacteamidrazone (from Step A), and 0.044 mL (0.25 mmol) N,N-diisopropylethylamine in 1 mL of acetonitrile was stirred at room temperature for 3 hours. The mixture was partitioned between 20 mL of methylene chloride and 10 mL of water. The layers were separated, the organic layer was dried over sodium sulfate and was then concentrated in vacuo. The residue was purified by flash chromatography on 35 g of silica eluting with 1 L of 50:1: methylene chloride/methanol then 500 mL of 25:1:0.05 methylene chloride:methanol:aqueous ammonia to give 70 mg (~100%) of the product as a white solid.

Mass Spectrum (FAB): m/Z 469 (M+H, 60%), 467 (M+H, 100%),291 (40%), 160 (20%), 158 (25%).

$^1$H NMR (CDCl$_3$, 400 MHz, ppm): δ 2.48 (td, J=3.5, 12.2, 1H), 2.53 (d, J=14.6, 1H), 2.90 (d, J=11.8, 1H), 3.37 (d, J=14.6, 1H), 3.52 (d, J=2.8, 1H), 3.62 (dm, J=11.4, 1H), 3.75 (s, 3H), 4.14 (td, J=2.2, 11.8, 1H), 4.28 (d, J=13.5, 1H), 4.58 (d, J=13.6), 4.60 (d, J=2.8, 1H), 5.45 (br s, 2H), 6.74 (d, J=1.9, 2H), 7.15 (t, J=1.9, 1H), 7.30–7.46 (m, 6H).

Step C: 2-(S)-(3,5-Dichlorobenzyloxy)-4-(3-(5-oxo-1,2,4-triazolo)methyl)-3-(S)-phenylmorpholine A solution of 0.069 g (0.15 mmol) of 4-(2-(N-methylcarboxyacetamidrazono)-2-(S)-(3,5-dichlorobenzyloxy)-3-(S)-phenylmorpholine (from Step B) in 6 mL of xylenes was heated at reflux for 2 hours. The solution was cooled and concentrated in vacuo. The residue was purified by flash chromatography on 35 g of silica gel eluting with 500 mL of 50:1:0.1 methylene chloride/methanol/aqueous ammonia then 500 mL of 20:1:0.1 methylene chloride/methanol/aqueous ammonia to give 56 mg (88%) of the product as a white powder.

Mass Spectrum (FAB): m/Z 437 (M+H, 65%), 435 (M+H, 100%), 259 (85%), 161 (55%).

$^1$H NMR (CDCl$_3$, 400 MHz, ppm): δ 2.53 (t, J=11.7, 3.6, 1H), 2.88 (d,J=11.6, 1H), 2.96 (d, J=14.3, 1H), 3.54 (d, J=2.6, 1H), 3.63 (dd, J=11.6, 1.9, 1H), 3.68 (d, J=14.6, 1H), 4.16 (t, J=11.7, 2.2, 1H), 4.30 (d, J=13.6, 1H), 4.58 (d, J=2.7, 1H), 4.67 (d, J=13.6, 1H), 6.65 (d, J=1.8, 2H), 7.07 (t, J=1.9, 1H), 7.29–7.44 (m, 5H), 10.25 (br s, 1H), 10.75 (br s, 1H).

EXAMPLE 46

2-(S)-(3,5-Bis(trifluoromethyl)benzyloxy)-4-(methoxy-carbonylmethyl)-3-(S)-phenylmorpholine A solution of 300 mg (0.74 mmole) of 2-(S)-(3,5-bis(trifluoromethyl)benzyloxy)-3-(S)-phenyl-morpholine (from Example 15, Step C) and 0.35 mL (2.0 mmole) of DIEA in 5 mL of acetonitrile was treated with 0.19 mL (2.0 mmole) of methyl bromoacetate and the mixture was stirred for 16 hr at room temperature. The solution was then concentrated in vacuo and the residue partitioned between 30 mL of ether and 15 mL of 0.5N aqueous KHSO$_4$. The layers were separated and the organic phase was washed with 10 mL of brine and dried over magnesium sulfate. Following filtration, the organic phase was concentrated in vacuo and the residue purified by flash chromatography on 20 g of silica eluting with 80:20 hexanes:ether to give 351 mg (99%) of the product. [a]$_D$=+147.3° (c=1.6, CHCl$_3$).

Mass Spectrum (FAB): m/Z 478 (M+H, 40%), 477 (65%), 418 (50%), 250 (95%), 234 (90%), 227 (100%).

$^1$H NMR (CDCl$_3$, 400 MHz, ppm): δ 3.02 (br d, 2H), 3.13 (d, J=16.9, 1H), 3.36 (d, J=16.8), 3.62 (s, 3H), 3.69 (dt, J=11.7, 2.2, 1H), 4.03 (br s, 1H), 4.23–4.32 (m, 1H), 4.44 (d, J=13.3, 1H), 4.68, (d, J=2.6, 1H), 4.81 (d, J=13.5, 1H), 7.30–7.38 (m, 3H), 7.4–7.5 (m, 3H), 7.70 (s, 1H).

Analysis Calcd for C$_{22}$H$_{21}$F$_6$NO$_4$: C, 55.35; H, 4.43; N, 2.93; F, 23.88 Found: C, 55.09; H, 4.43; N, 2.83; F, 24.05

EXAMPLE 47

2-(S)-(3,5-Bis(trifluoromethyl)benzyloxy)-4-(carboxymethyl)-3-(S)-phenylmorpholine A solution of 0.016 g (0.034 mmole) of 2-(S)-(3,5-Bis(trifluoromethyl)benzyloxy)-4-(methoxy-carbonylmethyl)-

3-(S)-phenylmorpholine (from Example 46) in 2 mL of THF and 0.5 mL of water was treated with 0.027 mL (0.067 mmole) of 2.5N aqueous sodium hydroxide and the mixture was stirred at room temperature for 5 hr. The mixture was treated with 2 drops of 2N aqueous HCl and 3 mL of water and the solution was extracted with 15 mL of 1:1 hexanes:ethyl acetate. The organic phase was dried over magnesium sulfate, filtered and concentrated in vacuo. The residue was purified by flash chromatography on 13 g of silica fluting with 250 mL of 100:3:0.1 methylene chloride:methanol:acetic acid then 100 mL of 50:2:0.1 methylene chloride:methanol:acetic acid to give 0.014 g (90%) of an oil.

Mass Spectrum (FAB): m/Z 464 (M+H, 90%), 420 (M—$CO_2$, 10%), 227 ($ArCH_2$, 35%), 220 (M—$OCH_2Ar$, 100%), 161 (20%).

$^1$H NMR ($CDCl_3$, 400 MHz, ppm): δ 2.9 (app d, 2H), 3.03 (d, 1H), 3.33 (d, 1H), 3.72 (d, 1H), 3.90 (d, 1H), 4.25 (t, 1H), 4.44 (d, 1H), 4.71 (d, 1H), 4.79 (d, 1H), 7.3–7.4 (m, 5H), 7.44 (s, 2H), 7.71 (s, 1H).

EXAMPLE 48

2-(S)-(3,5-Bis(trifluoromethyl)benzyloxy)-4-((2-aminoethyl)aminocarbonylmethyl)-3-(S)-phenylmorpholine hydrochloride A solution of 54 mg (0.11 mmole) of 2-(S)-(3,5-bis (trifluoromethyl)benzyloxy)-4-(carboxymethyl)-3-(S)-phenylmorpholine (from Example 46) and 0.15 mL of ethylenediamine (2.3 mmole) in 1 mL of methanol was stirred at 55° C. for 48 hr. The mixture was concentrated and the residue purified by flash chromatography on 16 g of silica eluting with 500 mL of 50:4:0.1 methylene chloride:methanol:aqueous ammonia to provide 57 mg (100%) of an oil. The oil was dissolved in ether and was treated with ether saturated with gaseous HCl. After concentration in vacuo, 58 mg (95%) of a rigid oil was obtained.

Mass Spectrum (FAB; free base): m/Z 506 (M+H, 100%), 418 (15%), 262(35%), 227 (30%), 173 (40%)

$^1$H NMR ($CDCl_3$, 400 MHz, ppm): δ 2.56 (d, J=15.5, 1H), 2.59 (td, J=12.0, 3.6, 1H), 2.82 (t, J=6.5, 2H), 2.96 (d, J=11.8, 1H), 3.21 (d, J=15.8, 1H), 3.25–3.40 (m, 2H), 3.65 (d, J=2.6, 1H), 3.67 (app dt, J=11.4, ~2, 1H), 4.18 (td, J=11.8, 2.6, 1H), 4.33 (d, J=13.5, 1H),4.69 (d, J=2.7, 1H), 4.79 (d, J=13.5, 1H), 7.25–7.40 (m, 5H), 7.46 (s, 2H), 7.59 (br t, 1H), 7.71 (s, 1H).

EXAMPLE 49

2-(S)-(3,5-Bis(trifluoromethyl)benzyloxy)-4-((3-amino-propyl)amino carbonylmethyl)-3-(S)-phenylmorpholine hydrochloride A solution of 59 mg (0.12 mmole) of 2-(S)-(3,5-bis (trifluoromethyl)benzyloxy)-4-(carboxymethyl)-3-(S)-phenylmorpholine (from Example 46) and 0.21 mL of 1,3-propylenediamine (2.5 mmole) in 1 mL of methanol was stirred at 55° C. for 72 hr. The mixture was concentrated and the residue purified by flash chromatography on 16 g of silica eluting with 500 mL of 10:1:0.05 methylene chloride:methanol:aqueous ammonia to provide 56 mg (88%) of an oil. The oil was dissolved in methylene chloride and was treated with methylene chloride saturated with gaseous HCl. After concentration in vacuo, a white paste was obtained.

Mass Spectrum (FAB; free base): m/Z 520 (M+H, 100%), 418 (10%), 276(30%), 227 (20%), 174 (30%)

$^1$H NMR ($CDCl_3$, 400 MHz, ppm): δ 1.64 (pentet, J=6.6, 2H), 2.53 (d, J=15.5, 1H), 2.58 (td, J=12.0, 3.6, 1H), 2.73 (t, J=6.5, 2H), 2.92 (d, J=11.8, 1H), 3.19 (d, J=15.8, 1H), 3.25–3.40 (m, 2H), 3.62 (d, J=2.6, 1H), 3.65 (app dt, J=11.4, ~2, 1H), 4.16 (td, J=11.8, 2.6, 1H), 4.41 (d, J=13.5, 1H),4.68 (d, J=2.7, 1H), 4.79 (d, J=13.5, 1H), 7.25–7.40 (m, 5H), 7.45 (s, 2H), 7.57 (br t, 1H), 7.70 (s, 1H).

EXAMPLE 50

4-benzyl-5-(S),6-(R)-dimethyl-3-(S)-phenylmorpholinone and 4-benzyl-5-(R),6-(S)-dimethyl-3-(S)-phenylmorpholine To a suspension of 1.7 g (7.0 mmole) of N-benzyl-(S)-phenylglycine (Example 13) in 15 ml of methylene chloride at 0° C. was added 6.9 ml (13.9 mmole) of trimethylaluminum (2.0M in toluene). After one hour at 0° C., 0.625 ml (7.0 mmole) of (±)-trans-2,3-epoxy butane (dissolved in 2.0 ml of methylene chloride) was added dropwise and then allowed to stir at 22° C. for 16 hours. The reaction was then transferred to another flask containing 30 ml of 1:1 hexane:methylene chloride and 30 ml of 1M potassium sodium tartrate and stirred at 22° C. for 2 hours. The layers were separated, and the aqueous layer was extracted with methylene chloride (3×100 ml). The combined organic layers were washed with 25 ml of a saturated sodium chloride solution, dried over anhydrous sodium sulfate, filtered, and concentrated in vacuo.

The crude alcohol was dissolved in 25 ml of toluene, treated with 93 mg (0.49 mmole) of p-toluenesulfonic acid and heated at 50° C. for 20 hours. The reaction was then cooled and concentrated in vacuo. The residue was partitioned between 15 ml of diethyl ether and 10 ml of saturated sodium bicarbonate. The layers were separated, and the organic layer was washed with water (3×10 ml). The combined organic layers were washed with 25 ml of a saturated sodium chloride solution, dried over anhydrous magnesium sulfate, filtered, and concentrated in VacuO. Flash chromatography on 145 g of silica gel using 1:4 v/v ethyl acetate/hexane as the eluant afforded 567 mg of the high $R_f$ lactone (Isomer A) and 388 mg of the low $R_f$ lactone (Isomer B).

$^1$H-NMR (400 MHz, $CDCl_3$) δ Isomer A: 1.04 (d, 3H, J=8.0 Hz), 1.24 (d, 3H, J=8.0 Hz), 2.92 (br qd, 1H), 3.41 (d, 1H, J=16.0 Hz), 3.62 (d, 1H, J=16.0 Hz), 4.38 (s, 1H), 4.96 (br qd, 1H), 7.20–7.42 (m, 8H), 7.58–7.64 (m, 2H); Isomer B: 1.04 (d, 3H, J=10.0 Hz), 1.39 (d, 3H, J=10.0 Hz), 3.06 (br qd, 1H), 3.53 (d, 1H, J=16.0 Hz), 3.81 (d, 1H, J=16.0 Hz), 4.33 (s, 1H), 4.67 (br qd, 1H), 7.18–7.50 (m, 10H). Mass Spectrum (FAB): m/z Isomer A: 296 (M+H, 100%), 294 (50%); Isomer B: 296 (M+H, 100%), 294 (50%).

EXAMPLE 51

2-(R)-(3,5-Bis(trifluoromethyl)benzyloxy)-[5-(S),6-(R) or 5-(R),6-(S)-dimethyl]-3-(S)-phenylmorpholinone Step A: 4-Benzyl-2-(R)-(3,5-bis(trifluoromethyl)-benzyloxy)-[5-(S),6-(R) or 5-(R),6-(S)-dimethyl]-3-(S)-phenylmorpholinone According to the procedure in Example 15, Step B, 251 mg (0.85 mmole) of Isomer A from Example 50 (4-benzyl-[5-(S),6-(R) or 5-(R)-6-(S)-dimethyl]-3-(S)-phenylmorpholinone) provided 238 mg (53%) of the product as an oil.

$^1$H-NMR (400 MHz, $CDCl_3$) δ 1.03 (d, 3H, J=6.7 Hz), 1.13 (d, 3H, J=6.6 Hz), 2.61 (qd, 1H, J=2.2 & 6.6 Hz), 3.26 (d, 1H, J=13.9 Hz), 3.55 (d, 1H, J=13.9 Hz), 3.63 (d, 1H,

J=7.6 Hz), 4.01 (qd, 1H, J=2.3 & 6.6 Hz), 4.44 (d, 1H, J=13.1 Hz), 4.53 (d, 1H, J=7.7 Hz), 4.71 (s, 1H), 4.85 (d, 1H, J=13.2 Hz), 7.20–7.35 (m, 9H), 7.46–7.48 (m, 2H), 7.67 (s, 1H), 7.81 (s, 1H).

Mass Spectrum (FAB): m/z 523 (M+H, 100%), 296 (95%), 280 (40%), 227 (50%).

Step B: 2-(R)-(3,5-Bis(trifluoromethyl)benzyloxy)-[5-(S),6-(R) or 5-(R),6-(S)-dimethyl]-3-(S)-phenylmorpholinone According to the procedure in Example 15, Step C, 260 mg of starting material from Step A [derived from Isomer A in Example 50 (4-Benzyl-2-(R)-(3,5-bis(trifluoromethyl)benzyloxy)-[5-(S),6-(R) or 5-(R),6-(S)-dimethyl]-3-(S)-phenylmorpholinone)] provided 122 mg (57%) of the product as an oil.

$^1$H-NMR (400 MHz, CDCl$_3$) δ 1.19 (d, 3H, J=6.5 Hz), 1.27 (d, 3H, J=6.7 Hz), 2.97 (qd, 1H, J=2.9 & 6.9 Hz), 3.96 (d, 1H, J=7.7 Hz), 4.08–4.11 (m, 2H), 4.39 (d, 1H, J=7.7 Hz), 4.50 (d, 1H, J=13.3 Hz), 4.88 (d, 1H, J=13.2 Hz), 7.27–7.33 (m, 3H), 7.40–7.42 (m, 4H), 7.67 (s, 1H). Mass Spectrum (FAB): m/z 434 (M+H, 45%), 227 (35%), 206 (40%), 190 (100%).

EXAMPLE 52

2-(S)-(3,5-Bis(trifluoromethyl)benzyloxy)-[5-(R),6-(S) or 5-(S),6-(R)-dimethyl]-3-(S)-phenylmorpholinone Step A: 4-Benzyl-2-(S)-(3,5-bis(trifluoromethyl)benzyloxy)-[5-(R),6-(S) or 5(S),6-(R)-dimethyl]-3-(S)-phenylmorpholinone According to the procedure in Example 15, Step B, 449 mg (1.52 mmole) of Isomer B from Example 50 (4-benzyl-[5-(R),6-(S) or 5-(S)-6-(R)-dimethyl]-3-(S)-phenylmorpholinone) provided 400 mg (51%) of the product as an oil.

$^1$H-NMR (400 MHz, CDCl$_3$) δ 0.90 (d, 3H, J=6.8 Hz), 1.37 (d, 3H, J=6.6 Hz), 2.86–2.89 (br qd, 1H), 3.47 (d, 1H, J=15.0 Hz), 3.82–3.85 (m, 2H), 3.99–4.02 (br qd, 1H), 4.45 (d, 1H, J=13.6 Hz), 4.81 (d, 1H, J=2.0 Hz), 4.87 (d, 1H, J=13.5 Hz), 7.17–7.83 (m, 13H).

Step B: 2-(S)-(3,5-Bis(trifluoromethyl)benzyloxy)-[5-(S),6-(R) or 5-(R),6-(S)-dimethyl]-3-(S)-phenylmorpholinone According to the procedure in Example 15, Step C, 400 mg of starting material from Step A [derived from Isomer B in Example 50 (4-Benzyl-2-(S)-(3,5-bis(trifluoromethyl)benzyloxy)-[5-(R),6-(S) or 5-(S),6-(R)-dimethyl]-3-(S)-phenylmorpholinone)]provided 230 mg (69%) of the product as an oil.

$^1$H-NMR (400 MHz, CDCl$_3$) δ 1.08 (d, 3H, J=6.7 Hz), 1.38 (d, 3H, J=7.0 Hz), 3.41–3.45 (br qd, 1H), 3.85–3.89 (br qd, 1H), 4.16 (d, 1H, J=2.9 Hz), 4.49 (d, 1H, J=13.6 Hz), 4.71 (d, 1H, J=2.9 Hz), 4.82 (d, 1H, J=13.6 Hz), 7.25–7.36 (m, 7H), 7.66 (s, 1H).

Mass Spectrum (FAB): m/z 434 (M+H, 35%), 227 (40%), 206 (40%), 190 (100%).

EXAMPLE 53

2-(R)-(3,5-Bis(trifluoromethyl)benzyloxy)-4-(3-(1,2,4-triazolo)methyl)-[5-(S),6-(R) or 5-(R),6-(S)-dimethyl]-3-(S)-phenylmorpholinione A mixture of 62 mg (0.14 mmole) of 2-(R)-(3,5-Bis(trifluoromethyl)benzyloxy)-[5-(S),6-(R) or 5-(R),6-(S)-dimethyl]-3-(S)-phenylmorpholinone (from Example 51, Step B), 62 mg (0.45 mmole) of anhydrous potassium carbonate and 26 mg (0.19 mmole) of N-formyl-2-chloroacetamidrazone (from Example 17, Step A) in 2.0 ml of N,N-dimethylformamide was heated to 60° C. for 2 hours and then 118° C. for 1.5 hours. The mixture was then allowed to cool to room temperature and then quenched with 5 mls of water and diluted with 15 mls of ethyl acetate. The layers were separated and the organic layer was washed with ethyl acetate (2×10 mls). The combined organic layers were washed with 10 mls of brine, dried over anhydrous magnesium sulfate, filtered, and concentrated in vacuo. Flash chromatography on 42 g of silica gel using 95:5 v/v methylene chloride/methanol as the eluant afforded 42 mg (57%) of a clear oil.

$^1$H-NMR (400 MHz, CDCl$_3$) δ 1.13 (d, 3H, J=6.5 Hz), 1.19 (d, 3H, J=6.5 Hz), 2.65 (qd, 1H, J=1.9 & 6.5 Hz), 3.58 (d, 1H, J=15.5 Hz), 3.65 (d, 1H, J=7.7 Hz), 3.75 (d, 1H, J=15.4 Hz), 4.06 (qd, 1H, J=2.2 & 6.6 Hz), 4.45 (d, 1H, J=13.2 Hz), 4.54 (d, 1H, J=7.7 Hz), 4.84 (d, 1H, J=13.2 Hz), 7.28–7.37 (m, 7H), 7.67 (s, 1H), 7.89 (s, 1H). Mass Spectrum (FAB): m/z 516 (M+H, 52%), 287 (28%), 271 (100%), 227 (40%), 202 (38%).

EXAMPLE 54

2-(R)-(3,5-Bis(trifluoromethyl)benzyloxy)-4-(3-(5-oxo-1,2,4-triazolo)methyl)-[5-(S),6-(R) or 5-(R),6-(S)-dimethyl]-3-(S)-phenylmorpholinone A solution of 96 mg (0.22 mmole) of 2-(R)-(3,5-Bis(trifluoromethyl)benzyloxy)-[5-(S),6-(R) or 5-(R),6-(S)-dimethyl]-3-(S)-phenylmorpholinone (from Example 51, Step B), 92 mg (0.66 mmole) of potassium carbonate and 48 mg (0.29 mmole) of N-methylcarboxy-2-chloroacetamidrazone (from Example 18, Step A) in 4 mL of DMF was heated at 60° C. for 1.5 hr and at 120° C. for 3.5 hr. The mixture was cooled to room temperature and was partitioned between 15 mL of water and 25 mL of ethyl acetate. The aqueous layer was extracted with 3×10 mL of ethyl acetate, the combined organic layers were washed with 10 mL of brine, dried over sodium sulfate, filtered and concentrated in vacuo. The residue was partly purified by flash chromatography on 42 g of silica gel using 2 L of 98:2 v/v methylene chloride/methanol as the eluant and the rich cuts were purified under the same conditions to give 38 mg (33%) of a clear oil.

$^1$H-NMR (400 MHz, CDCl$_3$) δ 1.09 (d, 3H, J=6.5 Hz), 1.20 (d, 3H, J=6.6 Hz), 2.64 (qd, 1H, J=2.4 & 6.6 Hz), 3.33 (s, 1H), 3.56 (d, 1H, J=7.6 Hz), 4.11 (qd, 1H, J=2.4 & 6.6 Hz), 4.41 (d, 1H, J=13.2 Hz), 4.57 (d, 1H, J=7.7 Hz), 4.82 (d, 1H, J=13.2 Hz), 7.25–7.30 (m, 5H), 7.40 (d, 2H, J=5.7 Hz), 7.65 (s, 1H), 9.46 (s, 1H), 10.51 (s, 1H).

Mass Spectrum (FAB): m/z 531 (M+H, 98%), 287 (100%), 227 (80%), 189 (65%).

EXAMPLE 55

2-(S)-(3,5-Bis(trifluoromethyl)benzyloxy)-4-(3-(1,2,4-triazolo)methyl)-[5-(R),6-(S) or 5-(S),6-(R)-dimethyl]-3-(S)-phenylmorpholinone According to the procedure in Example 53, 75 mg (0.17 mmole) of 2-(S)-(3,5-Bis(trifluoromethyl)-benzyloxy)-[5-(R),6-(S) or 5-(S),6-(R)-dimethyl]-3-(S)-phenylmorpholinone (from Example 52, Step B) provided, after flash chromatography on 73 g of silica gel using 98:2 v/v methylene chloride/methanol as the eluant, 46 mg (52%) of a yellow oil.

¹H-NMR (400 MHz, CDCl₃) δ 1.04 (d, 3H, J=6.6 Hz), 1.46 (d, 3H, J=6.7 Hz), 3.05–3.08 (m, 1H), 3.74–3.81 (m, 2H), 3.91–3.95 (m, 2H), 4.41 (d, 1H, J=13.2 Hz), 4.69 (d, 1H, J=3.2 Hz), 4.82 (d, 1H, J=13.5 Hz), 7.31–7.35 (m, 5H), 7.43–7.45 (m, 2H), 7.68 (s, 1H), 7.91 (s, 1H).

Mass Spectrum (EI): m/z 432 (36%), 287 (60%), 270 (65%), 227 (30%), 187 (48%), 83 (100%).

EXAMPLE 56

2-(S)-(3,5-Bis(trifluoromethyl)benzyloxy)-4-(3-(5-oxo-1,2,4-triazolo)methyl)-[5-(R),6-(S) or 5-(S),6-(R)-dimethyl]-3-(S)-phenylmorpholinone According to the procedure in Example 54, 86 mg (0.2 mmole) of 2-(S)-(3,5-Bis(trifluoromethyl)-benzyloxy)-[5-(R),6-(S) or 5-(S),6-(R)-dimethyl]-3-(S)-phenylmorpholinone (from Example 47, Step B) provided, after flash chromatography on 73 g of silica gel using 95:5 v/v methylene chloride/methanol as the eluant, 32 mg (30%) of a yellow oil.

¹H-NMR (400 MHz, CDCl₃) δ 1.03 (d, 3H, J=6.7 Hz), 1.40 (d, 3H, J=6.8 Hz), 3.00 (qd, 1H, J=3.8 & 6.8 Hz), 3.44 (d, 1H, J=16.1 Hz), 3.63 (d, 1H, J=16.0 Hz), 3.82 (d, 1H, J=3.3 Hz), 3.95 (qd, 1H, J=3.7 & 6.7 Hz), 4.43 (d, 1H, J=13.5 Hz), 4.73 (d, 1H, J=3.3 Hz), 4.84 (d, 1H, J=13.6 Hz), 7.28–7.47 (m, 7H), 7.68 (s, 1H), 9.52 (d, 2H).

Mass Spectrum (FAB): m/z 531 (M+H, 100%), 287 (55%), 227 (25%), 147 (50%).

EXAMPLE 57

2-(S)-(3,5-Bis(trifluoromethyl)benzyloxy)-4-(2-(1-(4-benzyl)piperidino)ethyl)-3-(S)-phenylmorpholine To a solution of 2-(S)-(3,5-bis(trifluoro-methyl)benzyloxy)-3-(S)-phenylmorpholine (50 mg, 0.12 mmol) and 4-benzyl-1-(2-chloroethyl)piperidine hydrochloride (50 mg, 0.18 mmol) in acetonitrile (0.5 mL) was added diisopropylethylamine (0.065 mL, 0.36 mmol) at room temperature. After 60 hours, TLC (5% MeOH/2% Et₃N/93% EtOAc) indicated that the reaction was only partially complete. The reaction was diluted with methylene chloride and washed with water, then brine, dried over sodium sulfate and evaporated. Prep TLC (5% MeOH/2% Et₃N/93% EtOAc) afforded 36 mg (50%) of the title compound as an oil.

¹H-NMR (400 MHz, CDCl₃) δ 1.1–1.4 (m, 2H), 1.4–1.65 (2 m, 4H), 1.65–2.05 (m, 3H), 2.05–2.3 (m, 1H), 2.35–2.5 (m and d, J=7 Hz, 3H), 2.55 (br t, J=11 Hz, 1H), 2.65–2.8 (m, 2H), 3.09 (d, J=11 Hz, 1H), 3.50 (d, J=2.5 Hz, 1H), 3.66 (dd, J=2 and 11 Hz, 1H), 4.15 (dt, J=2 and 12 Hz, 1H), 4.38 and 4.75 (AB q, J=13 Hz, 2H), 4.61 (d, J=2.5 Hz, 1H), 7.06 (d, J=7 Hz, 2H), 7.15 (t, J=7 Hz, 1H), 7.2–7.35 (m, 5H), 7.36 (m, 4H), 7.75 (s, 1H).

EXAMPLE 58

(S)-(4-Fluorophenyl)glycine

Via Chiral Synthesis:

Step A: 3-(4-Fluorophenyl)acetyl-4-(S)-benzyl-2-oxazolidinone

An oven-dried, 1 L 3-necked flask, equipped with a septum, nitrogen inlet, thermometer, and a magnetic stirring bar, was flushed with nitrogen and charged with a solution of 5.09 g (33.0 mmol) of 4-fluorophenylacetic acid in 100 mL of anhydrous ether. The solution was cooled to −10° C. and treated with 5.60 mL (40.0 mmol) of triethylamine followed by 4.30 mL (35.0 mmol) of trimethylacetyl chloride. A white precipitate formed immediately. The resulting mixture was stirred at −10° C. for 40 minutes, then cooled to −78° C.

An oven-dried, 250 mL round bottom flask, equipped with a septum and a magnetic stirring bar, was flushed with nitrogen and charged with a solution of 5.31 g (30.0 mmol) of 4-(S)-benzyl-2-oxazolidinone in 40 mL of dry THF. The solution was stirred in a dry ice/acetone bath for 10 minutes, then 18.8 mL of 1.6M n-butyllithium solution in hexanes was slowly added. After 10 minutes, the lithiated oxazolidinone solution was added, via cannula, to the mixture in the 3-necked flask. The cooling bath was removed from the resulting mixture and the temperature was allowed to rise to 0° C. The reaction was quenched with 100 mL of saturated aqueous ammonium chloride solution, transferred to a 1 L flask, and the ether and THF were removed in vacuo. The concentrated mixture was partitioned between 300 mL of methylene chloride and 50 mL of water and the layers were separated. The organic layer was washed with 200 mL of 2N aqueous hydrochloric acid solution, 300 mL of saturated aqueous sodium bicarbonate solution, dried over magnesium sulfate and concentrated in vacuo. Flash chromatography on 400 g of silica gel using 3:2 v/v hexanes/ether as the eluant afforded 8.95 g of an oil that slowly solidified on standing. Recrystallization from 10:1 hexanes/ether afforded 7.89 g (83%) of the title compound as a white solid, mp 64°–66° C. Mass Spectrum (FAB): m/Z 314 (M+H, 100%), 177 (M—ArCH₂CO+H, 85%). ¹H-NMR (400 MHz, CDCl₃): δ 2.76 (dd, 1H, J=13.2, 9.2), 3.26 (dd, J=13.2, 3.2), 4.16–4.34 (m, 4H), 4.65–4.70 (m, 1H), 7.02–7.33 (m, 9H). Analysis: Calcd for C₁₈H₁₆FNO₃: C, 69.00; H, 5.15; N, 4.47; F, 6.06 Found: C, 68.86; H, 5.14; N, 4.48; F, 6.08

Step B: 3-((S)-Azido-(4-fluorophenyl))acetyl-4-(S)-benzyl-2-oxazolidinone

An oven-dried, 1 L 3-necked flask, equipped with a septum, nitrogen inlet, thermometer, and a magnetic stirring bar, was flushed with nitrogen and charged with a solution of 58.0 mL of 1M potassium bis(trimethylsilyl)amide solution in toluene and 85 mL of THF and was cooled to −78° C. An oven-dried, 250 mL round-bottomed flask, equipped with a septum and a magnetic stirring bar, was flushed with nitrogen and charged with a solution of 7.20 g (23.0 mmol) of 3-(4-fluorophenyl)acetyl-4-(S)-benzyl-2-oxazolidinone (from Example 58, Step A) in 40 mL of THF. The acyl oxazolidinone solution was stirred in a dry ice/acetone bath for 10 minutes, then transferred, via cannula, to the potassium bis(trimethylsilyl)amide solution at such a rate that the internal temperature of the mixture was maintained below −70° C. The acyl oxazolidinone flask was rinsed with 15 mL of THF and the rinse was added, via cannula, to the reaction mixture and the resulting mixture was stirred at −78° C. for 30 minutes. An oven-dried, 250 mL round-bottomed flask, equipped with a septum and a magnetic stirring bar, was flushed with nitrogen and charged with a solution of 10.89 g (35.0 mmol) of 2,4,6-triisopropylphenylsulfonyl azide in 40 mL of THF. The azide solution was stirred in a dry ice/acetone bath for 10 minutes, then transferred, via cannula, to the reaction mixture at such a rate that the internal temperature of the mixture was maintained below −70° C. After 2 minutes, the reaction was quenched with 6.0 mL of glacial acetic acid, the cooling bath was removed and the mixture was stirred at room temperature for 18 hours. The quenched reaction mixture was partitioned between 300 mL of ethyl acetate and 300 mL of 50% saturated aqueous sodium bicarbonate solution. The organic layer was separated, dried over magnesium sulfate, and concentrated in vacuo. Flash chromatography on 500 g of silica gel using 2:1 v/v, then 1:1 v/v hexanes/methylene chloride as the eluant afforded 5.45 g (67%) of the title compound as an oil.

IR Spectrum (neat, cm$^{-1}$): 2104, 1781, 1702.

$^1$H-NMR (400 MHz, CDCl$_3$): δ 2.86 (dd, 1H, J=13.2, 9.6), 3.40 (dd, 1H, J=13.2, 3.2), 4.09–4.19 (m, 2H), 4.62–4.68 (m, 1H), 6.14 (s, 1H), 7.07–7.47 (m, 9H).

Analysis: Calcd for C$_{18}$H$_{15}$FN$_4$O$_3$: C, 61.01; H, 4.27; N, 15.81; F, 5.36 Found: C, 60.99; H, 4.19; N, 15.80; F, 5.34

Step C: (S)-Azido-(4-fluorophenyl)acetic acid

A solution of 5.40 g (15.2 mmol) of 3-((S)-azido-(4-fluorophenyl))acetyl-4-(S)-benzyl-2-oxazolidinone (from Example 58, Step B) in 200 mL of 3:1 v/v THF/water was stirred in an ice bath for 10 minutes. 1.28 g (30.4 mmol) of lithium hydroxide monohydrate was added in one portion and the resulting mixture was stirred cold for 30 minutes. The reaction mixture was partitioned between 100 mL of methylene chloride and 100 mL of 25% saturated aqueous sodium bicarbonate solution and the layers were separated. The aqueous layer was washed with 2×100 mL of methylene chloride and acidified to pH with 2N aqueous hydrochloric acid solution. The resulting mixture was extracted with 2×100 mL of ethyl acetate; the extracts were combined, washed with 50 mL of saturated aqueous sodium chloride solution, dried over magnesium sulfate, and concentrated in vacuo to afford 2.30 g (77%) of the title compound as an oil that was used in the following step without further purification.

IR Spectrum (neat, cm–1): 2111, 1724. $^1$H-NMR (400 MHz, CDCl$_3$): δ 5.06 (s, 1H), 7.08–7.45 (m, 4H), 8.75 (br s, 1H).

Step D: (S)-4-Fluorophenyl)glycine

A mixture of 2.30 g (11.8 mmol) of (S)-azido-(4-fluorophenyl)acetic acid (from Example 58, Step C), 250 mg 10% palladium on carbon catalyst and 160 mL 3:1 v/v water/acetic acid was stirred under an atmosphere of hydrogen for 18 hours. The reaction mixture was filtered through Celite and the flask and filter cake were rinsed well with ~1 L of 3:1 v/v water/acetic acid. The filtrate was concentrated in vacuo to about 50 mL of volume. 300 mL of toluene was added and the mixture concentrated to afford a solid. The solid was suspended in 1:1 v/v methanol/ether, filtered and dried to afford 1.99 g (100%) of the title compound.

$^1$H-NMR (400 MHz, D$_2$O+NaOD): δ 3.97 (s, 1H), 6.77 (app t, 2H, J=8.8), 7.01 (app t, 2H, J=5.6).
Via Resolution:

Step A': 4-Fluorophenylacetyl chloride

A solution of 150 g (0.974 mol) of 4-fluorophenylacetic acid an 1 mL of N,N-dimethylformamide in 500 mL of toluene at 40° C. was treated with 20 mL of thionyl chloride and heated to 40° C. An additional 61.2 mL of thionyl chloride was added dropwise over 1.5 hours. After the addition, the solution was heated at 50° C. for 1 hour, the solvent was removed in vacuo and the residual oil was distilled at reduced pressure (1.5 mmHg) to afford 150.4 g (89.5%) of the title compound, bp=68°–70° C.

Step B': Methyl 2-bromo-2-(4-fluoro)phenylacetate

A mixture of 150.4 g (0.872 mol) of 4-fluorophenylacetyl chloride (from Example 58, Step A') and 174.5 g (1.09 mol) of bromine was irradiated at 40°–50° C. with a quartz lamp for 5 hours. The reaction mixture was added dropwise to 400 mL of methanol and the solution was stirred for 16 hours. The solvent was removed in vacuo and the residual oil was distilled at reduced pressure (1.5 mmHg) to afford 198.5 g (92%) of the title compound, bp=106°–110° C.

Step C': Methyl (±)-(4-fluorophenyl)glycine

A solution of 24.7 g (0.1 mol) of methyl 2-bromo-2-(4-fluoro) phenylacetate (from Example 58, Step B') and 2.28 g (0.01 mol) of benzyl triethylammonium chloride in 25 mL of methanol was treated with 6.8 g (0.105 mol) of sodium azide and the resulting mixture was stirred 20 hours at room temperature. The reaction mixture was filtered; the filtrate was diluted with 50 mL of methanol and hydrogenated in the presence of 0.5 g of 10% Pd/C at 50 psi for 1 hour. The solution was filtered and the solvent removed in vacuo. The residue was partitioned between 10% aqueous sodium carbonate solution and ethyl acetate. The organic phase was washed with water, saturated aqueous sodium chloride solution, dried over magnesium sulfate and concentrated in vacuo to afford 9.8 g of the title compound as an oil.

Step D': Methyl (S)-(4-fluorophenyl)glycinate

A solution of 58.4 g of methyl (±)-4-fluorophenylglycinate (from Example 58, Step C') in 110 mL of 7:1 v/v ethanol/water was mixed with a solution of 28.6 g (0.0799 mol) of O,O'-(±)-dibenzoyltartaric acid ((+)-DBT) (28.6 g, 0.0799 mol) in 110 mL of 7:1 v/v ethanol:water and the resulting solution was allowed to age at room temperature. Ethyl acetate (220 ml) was added after crystallization was complete and the resulting mixture was cooled to –20° C. and filtered to afford 32.4 g of methyl (S)-(4-fluorophenyl) glycinate, (+)-DBT salt (ee=93.2%). The mother liquors were concentrated in vacuo and the free base was liberated by partitioning between ethyl acetate and aqueous sodium carbonate solution. A solution of free base, so obtained, in 110 mL of 7:1 v/v ethanol/water was mixed with a solution of 28.6 g (0.0799 mol) of O,O'-(–)-dibenzoyltartaric acid ((–)-DBT) (28.6 g, 0.0799mol) in 110 mL of 7:1 v/v ethanol:water and the resulting solution was allowed to age at room temperature. Ethyl acetate (220 ml) was added after crystallization was complete and the resulting mixture was cooled to –20° C. and filtered to afford 47.0 g of methyl (R)-(4-fluorophenyl) glycinate, (–)-DBT salt (ee=75.8%). Recycling of the mother liquors and addition of (+)-DBT gave a second crop of 7.4 g of (S)-(4-fluorophenyl) glycinate, (+)-DBT salt (ee=96.4%). The two crops of the (S)-amino ester (39.8 g) were combined in 200 mL of 7:1 v/v ethanol/water, heated for 30 minutes and cooled to room temperature. Addition of ethyl acetate, cooling, and filtration afforded 31.7 g of (S)-(4-fluorophenyl) glycinate, (+)-DBT salt (ee>98%). Enatiomeric excesses was determined by chiral HPLC (Crownpak CR(+) 5% MeOH in aqHClO$_4$ pH2 1.5 ml/min 40° C. 200 mm).

A mixture of 17.5 g of (S)-(4-fluorophenyl) glycinate, (+)-DBT salt and 32 mL of 5.5N HCl (32 ml) was heated at reflux for 1.5 hours. The reaction mixture was concentrated in vacuo and the residue was dissolved in 40 mL of water. The aqueous solution was washed 3×30 mL of ethyl acetate and the layers were separated. The pH of the aqueous layer was adjusted to 7 using ammonium hydroxide and the precipitated solid was filtered to afford 7.4 g of the title compound (ee=98.8%).

EXAMPLE 59

3-(S)-(4-Fluorophenyl)-4-benzyl-2-morpholinone

Step A: N-Benzyl (S)-4-fluorophenyl)glycine

A solution of 1.87 g (11.05 mmol) of (S)-(4-fluorophenyl) glycine (from Example 58) and 1.12 mL (11.1 mmol) of benzaldehyde in 11.1 mL of 1N aqueous sodium hydroxide solution and 11 mL of methanol at 0° C. was treated with 165 mg (4.4 mmol) of sodium borohydride. The cooling bath was removed and the resulting mixture was stirred at room temperature for 30 minutes. Second portions of benzaldehyde (1.12 mL (11.1 mmol)) and sodium borohydride 165 mg (4.4 mmol) were added to the reaction mixture and stirring was continued for 1.5 hours. The reaction mixture was partitioned between 100 mL of ether and 50 mL of water and the layers were separated. The aqueous layer was separated and filtered to remove a small amount of insoluble material. The filtrate was acidified to pH 5 with 2N aqueous hydrochloric acid solution and the solid that had precipitated was filtered, rinsed well with water, then ether, and dried to afford 1.95 g of the title compound. $^1$H-NMR (400 MHz, D$_2$O+NaOD): δ 3.33 (AB q, 2H, J=8.4), 3.85 (s, 1H), 6.79–7.16 (m, 4H).

Step B: 3-(S)-(4-Fluorophenyl)-4-benzyl-2-morpholinone

A mixture of 1.95 g (7.5 mmol) of N-benzyl (S)-(4-fluorophenyl)glycine, 3.90 mL (22.5 mmol) of N,N-diisopropylethylamine, 6.50 mL (75.0 mmol) of 1,2-dibromoethane and 40 mL of N,N-dimethylformamide was stirred at 100° C. for 20 hours (dissolution of all solids occurred on warming). The reaction mixture was cooled and concentrated in vacuo. The residue was partitioned between 250 mL of ether and 100 mL of 0.5N potassium hydrogen sulfate solution and the layers were separated. The organic layer was washed with 100 mL of saturated aqueous sodium bicarbonate solution, 3×150 mL of water, dried over magnesium sulfate, and concentrated in vacuo. Flash chromatography on 125 g of silica gel using 3:1 v/v hexanes/ether as the eluant afforded 1.58 g (74%) of the title compound as an oil.

$^1$H-NMR (400 MHz, CDCl$_3$): δ 2.65 (dt, 1H, J=3.2, 12.8), 3.00 (dt, 1H, J=12.8, 2.8), 3.16 (d, 1H, J=13.6), 3.76 (d, 1H, J=13.6), 4.24 (s, 1H), 4.37 (dt, 1H, J=13.2, 3.2), 4.54 (dt, 1H, J=2.8, 13.2), 7.07–7.56 (m, 9H).

EXAMPLE 60

2-(S)-(3,5-Bis(trifluoromethyl)benzyloxy)-3-(S)-(4-fluorophenyl)-4-benzylmorpholine The title compound was prepared in 72% yield from 3-(S)-(4-fluorophenyl)-4-benzyl-2-morpholinone (from Example 59) using procedures analogous to those in Example 15, Steps A and B.

$^1$H-NMR (200 MHz, CDCl$_3$): δ 2.37 (dt, 1H, J=3.6, 11.8), 2.83–2.90 (m, 2H), 3.55–3.63 (m, 2H), 3.85 (d, 1H, J=13.4), 4.14 (dt, 1H, J=2.0, 11.8), 4.44 (d, 1H, J=13.6), 4.66 (d, 1H, J=2.8), 4.79 (d, 1H, J=13.4), 7.00–7.70 (12H).

EXAMPLE 61

2-(S)-(3,5-Bis(trifluoromethyl)benzyloxy)-3-(S)-(4-fluorophenyl)morpholinone

The title compound was prepared in 70% yield from 2-(S)-(3,5-bis(trifluoromethyl)benzyloxy)-3-(S)-(4-fluorophenyl)-4-benzylmorpholine (from Example 60) using a procedure analogous to that in Example 15, Step C. Mass Spectrum (FAB): m/Z 424 (M+H, 40%).

$^1$H-NMR (400 MHz, CDCl$_3$): δ 1.80 (br s, 1H), 3.11 (app dd, 1H, J=2.2, 12.4), 3.25 (dt, 1H, J=3.6, 12.4), 3.65 (app dd, 1H, J=3.6, 11.4), 4.05 (dt, 1H, J=2.2, 11.8), 4.11 (d, 1H, J=2.2), 4.53 (d, 1H, J=13.6), 4.71 (d, 1H, J=2.2), 4.83 (d, 1H, J=13.6), 7.04 (t, 2H, J=7.2), 7.33–7.37 (m, 2H), 7.42 (s, 2H), 7.72 (s, 1H).

EXAMPLE 62

2-(S)-(3,5-Bis(trifluoromethyl)benzyloxy)-3-(S)-(4-fluorophenyl)-4-(3-(5-oxo-1H,4H-1,2,4-triazolo)methylmorpholoine The title compound was prepared in 69% yield from 2-(S)-(3,5-bis(trifluoromethyl)benzyloxy)-3-(S)-(4-fluorophenyl)morpholine (from Example 61) using a procedure analogous to that in Example 18. Mass Spectrum (FAB): m/Z 521 (M+H, 100%).

$^1$H-NMR (400 MHz, CDCl$_3$): δ 2.55 (dt, 1H, J=3.6, 12.0), 2.91 (d, 1H, J=11.6), 2.93 (d, 1H, J=14.4), 3.57 (d, 1H, J=2.8), 3.59 (d, 1H, J=14.4), 3.67–3.70 (m, 1H), 4.18 (dt, 1H, J=2.4, 11.6), 4.48 (d, 1H, J=13.6), 4.65 (d, 1H, J=2.8), 4.84 (d, 1H, J=13.6), 7.07 (t, 2H, J=8.4), 7.40 (s, 2H), 7.45–7.48 (m, 2H), 7.68 (s, 1H), 10.04 (br s, 1H), 10.69 (br s, 1H).

Analysis: Calcd for C$_{22}$H$_{19}$F$_7$N$_4$O$_3$: C, 50.78; H, 3.68; N, 10.77; F, 25.55 Found: C, 50.89; H, 3.76; N, 10.62; F, 25.56

EXAMPLE 63

2-(S)-(3,5-Bis(trifluoromethyl)benzyloxy)-4-((3-pyridyl)methyl carbonyl)-3-(R)-phenylmorpholine A solution of 55 mg (0.315 mmol) of 4-pyridylacetic acid in 1 mL of CH$_2$Cl$_2$, containing 0.079 mL (0.715 mmol) of N-methylmorpholine, 53 mg (0.37 mmol) of HOBt and 73 mg (0.37 mmol) of EDC was stirred for 10 min. A solution of 2-(S)-(3,5-bis(trifluoromethyl)benzyloxy)-3-(R)-phenylmorpholine (from Example 33) in 1 mL of CH$_2$Cl$_2$ was added. After stirring the mixture for 2 h, it was partitioned between water and CH$_2$Cl$_2$. The organic layer was washed with water, brine and dried by filtering through Na$_2$SO$_4$. The filtrate was concentrated and the residue was purified by flash chromatography using 70% EtOAc/hexane to furnish 152 mg (100% yield) of the product.

$^1$H-NMR (400 MHz, CDCl$_3$): δ 3.0–3.85 (m, 5H), 3.95 & 4.4 (br s, 1H), 4.66 (d, J=13 Hz, 1H), 4.82 (d, J=13 Hz, 1H), 5.0 & 5.9 (br s, 1H), 5.23 (s, 1H), 7.1–7.65 (m, 7H), 7.8 (m, 3H), 8.43 (br s, 2H).

EXAMPLE 64

2-(S)-(3,5-Bis(trifluoromethyl)benzyloxy)-4-(methoxycarbonylpentyl)-3-(R)-phenylmorpholine To a solution of 0.259 g (0.64 mmol) of 2-(S)-(3,5-bis (trifluoromethyl)benzyloxy)-3-(R)-phenylmorpholine (from example 33) in 2 mL of DMF were added 0.16 g (0.77 mmol) of methyl 6-bromohexanoate, 0.155 g (1.12 mmol) of K$_2$CO$_3$ and 2 crystals of nBu$_4$NI. The resulting solution was heated in a 60° C. bath for 36 h, at which time a tlc indicated incomplete reaction. The bath temperature was raised to 100° C. After 3 h the reaction mixture was cooled and diluted with EtOAc. The EtOAc solution was washed with water (2×), brine and dried over Na$_2$SO$_4$. The filtrate was concentrated and the residue was chromatographed using 30% EtOAc/hexane to isolate 220 mg (65%) of the product.

$^1$H-NMR (400 MHz, CDCl$_3$): δ 1.0–1.4 (m, 4H), 1.47 (m, J=8 Hz, 2H), 1.95 (m, 1H), 2.2 (t, J=8 Hz, 2H), 2.35 (m, 2H), 2.9 (d, J=13 Hz, 1H), 3.07 (d, J=7 Hz, 1H), 3.62 (s, 3H), 3.81 (td, J=8 Hz and 2 Hz, 1H), 4.04 (dd, J=10 Hz and 2 Hz, 1H), 4.36 (d, J=7 Hz, 1H), 4.4 (d, J=13 Hz, 1H), 4.79 (d, J=13 Hz, 1H), 7.2–7.4 (m, 7H), 7.66 (s, 1H).

EXAMPLE 65

2-(S)-(3,5-Bis(trifluoromethyl)benzyloxy)-4-(carboxypentyl)-3-(R)-phenylmorpholine A solution of 0.15 g (0.28 mmol) of 2-(S)-(3,5-Bis (trifluoromethyl)benzyloxy)-4-(methoxycarbonylpentyl)-3-

(R)-phenylmorpholine (from Example 64) in 3 mL of MeOH was saponified by treating with 0.5 mL of 5N NaOH for 40 min at 65° C. The solution was cooled, concentrated and the residue was diluted with water. The aqueous solution was adjusted to pH 6 by adding 2N HCl and it was extracted with EtOAc. The organic layer was washed with brine, dried and concentrated. The residue upon chromatography on a flash column with 50% EtOAc/hexane furnished 0.13 g (89%) of the product.

$^1$H-NMR (400 MHz, CDCl$_3$): δ 1.0–1.5 (m, 4H), 1.5 (m, 2H), 2.2 (m, 2H), 2.35 (m, 2H), 2.9 (d, J=13 Hz, 1H), 3.08 (d, J=7 Hz, 1H), 3.82 (t, J=8 Hz, 1H), 4.09 (d, J=7 Hz, 1H), 4.38 (s, 1H), 4.4 (d, J=13 Hz, 1H), 4.79 (d, J=13 Hz, 1H), 7.2–7.4 (m, 7H), 7.66 (s, 1H).

EXAMPLE 66

2-(S)-(3,5-Bis(trifluoromethyl)benzyloxy)-4-(methylaminocarbonylpentyl)-6-oxo-hexyl)-3-(R)-phenylmorpholine A solution of 116 mg (0.22 mmol) of 2-(S)-(3,5-Bis(trifluoromethyl)benzyloxy)-4-(carboxypentyl)3-(R)-phenylmorpholine (from Example 65) in 1 mL of CH$_2$Cl$_2$ was treated with 40 mg (0.29 mmol) of HOBt, 57 mg (0.29 mmol) of EDC and 0.037 mL of N-methylmorpholine. After 10 min 0.027 mL (0.3 mmol) of aqueous methylamine (40%) was added and the resulting mixture was stirred for 4 h. The reaction mixture was diluted with water and extracted with CH$_2$Cl$_2$. The combined CH$_2$Cl$_2$ layer was washed with water, brine and dried over Na$_2$SO$_4$, and the filtrate was concentrated. Purification of the residue on a flash column with EtOAc furnished 0.10 g of the product.

$^1$H-NMR (400 MHz, CDCl$_3$): δ 1.0–1.4 (m, 4H), 1.47 (m, 2H), 1.95 (m, 1H), 2.04 (t, J=8 Hz, 2H), 2.35 (m, 2H), 2.74 (d, J=5 Hz, 3H), 2.89(d, J=12 Hz, 1H) 3.08 (d, J=7 Hz, 1H), 3.81 (t, J=7 Hz, 1H), 4.02 (d, J=11 Hz, 1H), 4.36 (d, J=7 Hz, 1H), 4.39 (d, J=13 Hz, 1H), 4.79 (d, J=13 Hz, 1H), 5.03 (br s, 1H), 7.2–7.4 (m, 7H), 7.65 (s, 1H).

EXAMPLE 67

2-(R)-(3,5-Bis(trifluoromethyl)benzoyloxy)-3-(S)-phenyl-4-benzyl morpholine

A solution of 2.67 g (10.0 mmol) of 3-(S)-phenyl-4-benzyl-2-morpholinone (from Example 14) in 40 mL of dry THF was cooled to −78° C. The cold solution was treated with 12.5 mL of 1.0$\underline{M}$ L-Selectride®, solution in THF, maintaining the internal reaction temperature below −70° C. Alternatively, only a 6% excess of L-Selectride® may be required. The resulting solution was stirred cold for 45 minutes and the reaction was charged with 3.60 mL (20.0 mmol) of 3,5-bis(trifluoro-methyl)benzoyl chloride. The resulting yellow mixture was stirred cold for 30 minutes and the reaction was quenched with 50 mL of saturated aqueous sodium bicarbonate solution. Alternatively, acetic acid may be used for the quench. The quenched mixture was partitioned between 300 mL of ether and 50 mL of water and the layers were separated. The organic layer was dried over magnesium sulfate. The aqueous layer was extracted with 300 mL of ether; the extract was dried and combined with the original organic layer. The combined organics were concentrated in vacuo. Flash chromatography on 150 g of silica gel using 37:3 v/v hexanes/ether as the eluant afforded 4.06 g (80%) of the title compound as a solid.

$^1$H NMR (CDCl$_2$, 200 MHz, ppm): δ 2.50 (dt, J=3.4, 12.0, 1H), 2.97 (app d, J=12.0, 1H), 2.99 (d, J=13.6, 1H), 3.72–3.79 (m, 1H), 3.82 (d, J=2.6, 1H), 4.00 (d, J=13.6, 1H), 4.20 (dt, J=2.4, 11.6), 6.22 (d, J=2.6, 1H), 7.22–7.37 (m, 7H), 7.57 (app d, J=6.8, 2H), 8.07 (s, 1H), 8.47 (s, 2H).

Analysis Calcd for C$_{26}$H$_{21}$F$_6$NO$_3$: C, 61.29; H, 4.16; N, 2.75; F, 22.38. Found: C, 61.18; H, 4.14; N, 2.70; F, 22.13.

EXAMPLE 68

2-(R)-(1-(3,5-Bis(trifluoromethyl)phenyl) ethenyloxy)-3-(S)-phenyl-4-benzyl morpholine Step A: Dimethyl titanocene A solution of 2.49 g (10.0 mmol) of titanocene dichloride in 50 mL of ether in the dark at 0° C. was treated with 17.5 mL of 1.4$\underline{M}$ methyllithium solution in ether maintaining the internal temperature below 5° C. The resulting yellow/orange mixture was stirred at room temperature for 30 minutes and the reaction was quenched by slowly adding 25 g of ice. The quenched reaction mixture was diluted with 50 mL of ether and 25 mL of water and the layers were separated. The organic layer was dried over magnesium sulfate and concentrated in vacuo to afford 2.03 g (98%) of the title compound as a light-sensitive solid. Alternatively, dimethyl titanocene may be prepared from methyl magnesium chloride. The dimethyl titanocene could be stored as a solution in toluene at 0° C. for at least 2 weeks without apparent chemical degradation. $^1$H NMR (CDCl$_2$, 200 MHz, ppm): δ −0.15 (s, 6H), 6.06 (s, 10H).

Step B: 2-(R)-(1-(3,5-Bis(trifluoromethyl)phenyl) ethenyloxy)-3-(S)-phenyl-4-benzyl morpholine A solution of 2.50 g (4.9 mmol) of 2-(R)-(3,5-bis(trifluoro-methyl)benzoyloxy)-3-(S)-phenyl-4-benzyl morpholine from Example 67) and 2.50 g (12.0 mmol) of dimethyl titocene (from Example 68, Step A) in 35 mL of 1:1 v/v THF/toluene was stirred in an oil bath at 80° C. for 16 hours. The reaction mixture was cooled and concentrated in vacuo. Flash chromatography on 150 g of silica gel using 3:1 v/v hexanes/methylene chloride as the eluant afforded 1.71 g (69%) of the title compound as a solid. Alternatively, the product may be isolated by crystallization from methanol, following precipitation of titanium residues. Mass Spectrum (FAB): m/Z 508 (M+H, 25%).

$^1$H NMR (CDCl$_3$, 400 MHz, ppm): δ 2.42 (dt, J=3.6, 12.0, 1H), 2.89 (app d, J=11.6), 2.92 (d, J=13.6, 1H), 3.61–3.66 (m, 1H), 3.73 (d, J=2.8), 1H), 4.00 (d, J=13.6, 1H), 4.09 (dt, J=2.4, 11.6, 1H), 4.75 (d, J=2.8, 1H), 4.79 (d, J=2.8, 1H), 5.36 (d, J=2.4, 1H), 7.23–7.41 (m, 7H), 7.63 (app d, J=7.2, 2H), 7.79 (s, 1H), 7.91 (s, 2H).

Analysis Calcd for C$_{27}$H$_{23}$F$_6$NO$_2$: C, 63.90; H, 4.57; N, 2.76; F, 22.46. Found: C, 63.71; H, 4.53; N, 2.68; F, 22.66.

EXAMPLE 69

2-(R)-(1-(S)-(3,5-Bis(trifluoromethyl)phenyl) ethoxy)-3-(S)-phenyl morpholine and 2-(S)-(1-(R)-(3,5-Bis(trifluoromethyl)phenyl)ethoxy)-3-(S)-phenyl morpholine A mixture of 1.50 g (2.9 mmol) of 2-(R)-(1-(3,5-bis(trifluoromethyl)phenyl)ethenyloxy)-3-(S)-phenyl-4-benzyl morpholine (from Example 68) and 750 mg 10% palladium on carbon catalyst in 25 mL of 3:2 v/v isopropanol/ethyl acetate was stirred under an atmosphere of hydrogen for 48 hours. Alternatively, the hydrogenation may be conducted using 5% palladium on alumina. The catalyst was filtered onto a pad of Celite; the reaction flask and filter pad were rinsed with 500 mL of ethyl acetate. The filtrate was concentrated in vacuo. Flash chromatography on 60 g of silica gel using 2:1 v/v hexanes/ether, then 2:1 v/v hexanes/ether afforded 106 mg of 2-(R)-(1-(S)-(3,5-bis(trifluoromethyl)phenyl)ethoxy)-3-(S)-phenyl morpholine and 899 mg of 2-(R)-(1-(R)-(3,5-bis(trifluoromethyl)phenyl)ethoxy)-3-(S)-phenyl morpholine, both as oils (84% total yield).

For 2-(R)-(1-(R)-(3,5-Bis(trifluoromethyl)phenyl)ethoxy)-3-(S)-phenyl morpholine:

Mass Spectrum (CI): m/Z 420 ($M^+$, 20%), 178 (100%).

$^1$H NMR (CDCl$_3$, 400 MHz, ppm): δ 1.46 (d, J=6.8), 1.92 (br s, 1H), 3.13 (dd, J=3.0, 12.6, 1H), 3.24 (dt, J=3.6, 12.6, 1H), 3.62 (rid, J=3.6, 11.2), 4.04 (d, J=2.4, 1H), 4.14 (dt, J=3.0, 11.2, 1H), 4.48 (d, J=2.4, 1H), 4.90 (q, J=6.8, 1H), 7.21–7.32 (m, 7H), 7.64 (s, 1H).

Analysis Calcd for $C_{20}H_{19}F_6NO_2$: C, 57.28; H, 4.57; N, 3.34; F, 27.18. Found: C, 57.41; H, 4.61; N, 3.29; F, 27.23.

EXAMPLE 70

2-(R)-(1-(R)-(3,5-Bis(trifluoromethyl)phenyl)ethoxy)-3-(S)-phenyl-4-(3-(5-oxo-1,2,4-triazolo)methylmorpholine Step A: 2-(R)-(1-(R)-(3,5-Bis(trifluoromethyl)phenyl)ethoxy)-3-(S)-phenyl-4-(2-(N-methylcarboxy-acetamidrazono)morpholine A solution of 945 mg (2.3 mmol) of 2-(R)-(1-(R)-(3,5-bis(trifluoromethyl)phenyl)ethoxy)-3-(S)-phenyl morpholine (from Example 69), 447 mg (2.7 mmol) of N-methylcarboxy-2-chloroacetamidrazone (from Example 45, Step A), and 0.78 mL (4.5 mmol) of N,N-diisopropylethylamine in 17 mL of acetonitrile was stirred at room temperature for 20 hours. Alternatively, the alkylation may be conducted in dimethyl sulfoxide using potassium carbonate as a base. The reaction was concentrated in vacuo and the residue was partitioned between 50 mL of methylene chloride and 25 mL of water. The organic layer was separated, dried over magnesium sulfate and concentrated in vacuo. Flash chromatography on 50 g of silica gel using 50:1:0.1 methylene chloride/methanol/ammonium hydroxide as the eluant afforded 1.12 g (90%) of the title compound as a foam.

Step B: 2-(R)-(1-(R)-(3,5-Bis(trifluoromethyl)phenyl)ethoxy)-3-(S)-phenyl-4-(3-(5-oxo-1,2,4-triazolo)methylmorpholine A solution of 1.01 g (1.8 mmol) of 2-(R)-(1-(R)-(3,5-bis(trifluoromethyl)phenyl)ethoxy)-3-(S)-phenyl-4-(2-(N-methylcarboxyacetamidrazono)morpholine (from Example 70, Step A) in 15 mL of xylenes was heated at reflux for 2 hours. Diisopropylethylamine is optionally present. The reaction was cooled and concentrated in vacuo. Flash chromatography on 50 g of silica gel using 50:1:0.1 methylene chloride/methanol/ammonium hydroxide as the eluant afforded 781 mg (76%) of the title compound as a solid. The crude product may also be isolated directly upon cooling the reaction mixture. The purified product may be afforded by crystallization from hot methanol (charcoal decolorization) and water trituration.

Mass Spectrum (FAB) m/Z 517 (M+H, 18%), 178 (100%).

$^1$H NMR (CDCl$_3$, 400 MHz, ppm): δ 1.47 (d, J=6.8), 2.01–2.05 (m, 2H), 2.55 (dt, J=3.6, 12.0, 1H), 2.91 (d, J=10.8, 1H), 2.95 (d, J=14.8, 1H), 3.49 (d, J=2.4, 1H), 3.65 (d, J=14.8, 1H), 3.69 (d, J=10.8, 1H), 4.29 (dt, J=2.4, 10.0), 4.38 (d, J=2.8, 1H), 4.88 (q, J=6.8, 1H), 7.14 (s, 2H), 7.33–7.40 (m, 5H), 7.62 (s, 1H), 9.91 (br s, 1H), 10.16 (br s, 1H).

Analysis Calcd for $C_{23}H_{22}F_6N_4O_3$: C, 53.49; H, 4.06; N, 10.85; F, 22.07. Found: C, 53.64; H, 4.33; N, 10.81; F, 22.27.

EXAMPLE 71

2-(R)-(1-(S)-(3,5-Bis(trifluoromethyl)phenyl)ethoxy)-3-(S)-phenyl-4-(3-(5-oxo-1,2,4-triazolo)methylmorpholine The title compound was prepared in 32% yield from 2-(R)-(1-(R)-(3,5-bis(trifluoromethyl)phenyl)ethoxy)-3-(S)-phenyl morpholine (from Example 69) using a procedure analogous to Example 70.

Mass Spectrum (FAB): m/Z 517 (M+H, 100%), 259 (50%).

$^1$H NMR (CDCl$_3$, 400 MHz, ppm): δ 1.09 (d, J=6.4, 3H), 2.47–2.53 (m, 1H), 2.83 (app d, J=11.6, 1H), 2.95 (d, J=14.0, 1H), 3.51–3.65 (m, 3H), 4.01 (app t, J=11.6, 1H), 4.60 (q, J=6.4, 1H), 4.84 (d, J=2.4, 1H), 7.33–7.51 (m, 5H), 7.74 (s, 2H), 7.76 (s, 1H), 9.51 (br s, 1H), 10.00 (br s, 1H).

EXAMPLE 72

2-(R)-(3,5-Bis(trifluoromethyl)benzoyloxy)-3-(S)-(4-fluoro)phenyl-4-benzyl morpholine The title compound was prepared in 83% yield from 3-(R)-(4-fluoro)phenyl-4-benzyl-2-morpholinone (from Example 59) using a procedure analogous to Example 67.

Mass Spectrum (FAB): m/Z 528 (M+H, 25%), 270 (100%).

$^1$H NMR (CDCl$_3$, 400 MHz, ppm): δ 2.50 (dt, J=3.2, 12.0, 1H), 2.96 (app d, J=12.0, 1H), 2.98 (d, J=13.6, 1H), 3.74–3.78 (m, 1H), 3.81 (d, J=2.8, 1H), 3.94 (d, J=13.6, 1H), 4.19 (tit, J=2.0, 12.0), 6.20 (d, J=2.8, 1H), 6.99 (t, J=8.4, 2H), 7.27–7.38 (m, 5H), 7.52–7.56 (m, 2H), 8.09 (s, 1H), 8.46 (s, 2H).

EXAMPLE 73

2-(R)-(1-(3,5-Bis(trifluoromethyl)phenyl)ethenyloxy)-3-(S)-(4-fluoro)phenyl-4-benzyl morpholine The title compound was prepared in 60% yield from 2-(R)-(3,5-bis(trifluoromethyl)benzoyloxy)-3-(S)-(4-fluoro)phenyl-4-benzyl morpholine (Example 72) using a procedure analogous to Example 68.

Mass Spectrum (FAB): m/Z 526 (M+H, 75%), 270 (100%).

$^1$H NMR (CDCl$_3$, 400 MHz, ppm): δ 2.42 (dt, J=3.6, 12.0), 2.90 (app d, J=12.0, 1H), 2.91 (d, J=13.6, 1H), 3.62–3.66 (m, 1H), 3.72 (d, J=2.6), 3.94 (d, J=13.6, 1H), 4.09 (dt, J=2.4, 12.0, 1H), 4.75 (d, J=3.2, 1H), 4.82 (d, J=3.2, 1H), 5.32 (d, J=2.6, 1H), 7.09 (t, J=8.8, 2H), 7.24–7.33 (m, 5H), 7.58–7.62 (m, 2H), 7.80 (s, 1H), 7.90 (s, 2H).

EXAMPLE 74

2-(R)-(1-(S)-(3,5-Bis(trifluoromethyl)phenyl)ethoxy)-3-(S)-(4-fluoro)phenyl morpholine and 2-(S)-(1-(R)-(3,5-Bis(trifluoromethyl)phenyl)ethoxy)-3-(S)-(4-fluoro)phenyl morpholine A mixture of 1.83 g (3.5 mmol) of 2-(R)-(1-(3,5-bis(trifluoromethyl)phenyl)ethenyloxy)-3-(S)-(4-fluoro)

phenyl-4-benzyl morpholine (from Example 73) and 800 mg 5% rhodium on alumina catalyst in 40 mL of absolute ethanol was stirred under an atmosphere of hydrogen for 24 hours. The catalyst was filtered onto a pad of Celite; the reaction flask and filter cake were rinsed with 200 mL of ethyl acetate. The filtrate was concentrated in vacuo and the residue was pumped under high vacuum (1 mmHg, room temperature) to dryness.

The residue was redissolved in 40 mL of isopropanol; 800 mg of 10% palladium on carbon catalyst was added and the resulting mixture was stirred under an atmosphere of hydrogen for 24 hours. The catalyst was filtered onto a pad of Celite; the reaction flask and filter cake were rinsed with 200 mL of ethyl acetate. The filtrate was concentrated in vacuo. Flash chromatography on 50 g of silica gel using 2:1 v/v hexanes/ether, then 3:2 v/v ether/hexanes as the eluant afforded 283 mg of 2-(R)-(1-(S)-(3,5-bis(trifluoromethyl) phenyl)ethoxy)-3-(S)-(4-fluoro)phenyl morpholine and 763 mg of 2-(R)-(1-(R)-(3,5-bis(trifluoromethyl)phenyl)ethoxy) -3-(S)-(4-fluoro)phenyl morpholine, both as oils (total yield 68%).

For 2-(R)-(1-(S)-(3,5-bis(trifluoromethyl)phenyl)ethoxy) -3-(S)-(4-fluoro)phenyl morpholine:

Mass Spectrum (FAB) m/Z 438 (M+H, 65%), 180 (100%).

$^1$H NMR (CDCl$_3$, 400 MHz, ppm): δ 1.47 (d, J=6.8, 3H), 1.87 (br s, 1H), 3.03 (dd, J=2.8, 12.8), 3.17 (dt, J=4.0, 12.4, 1H), 3.43–3.47 (m, 1H), 3.80 (dt, J=3.2, 11.6), 4.10 (d, J=2.2, 1H), 4.70 (q, J=6.8, 1H), 4.87 (d, J=2.2, 1H), 6.99–7.03 (m, 2H), 7.23–7.27 (m, 2H), 7.63 (s, 2H), 7.66 (s, 1H).

For 2-(R)-(1-(R)-(3,5-bis(trifluoromethyl)phenyl)ethoxy) -3-(S)-(4-fluoro)phenyl morpholine:

Mass Spectrum (FAB) m/Z 438 (M+H, 75%), 180 (100%).

$^1$H NMR (CDCl$_3$, 400 MHz, ppm): δ 1.16 (d, J=6.8), 1.80 (br s, 1H), 3.13 (dd, J=3.2, 12.4), 3.23 (dt, J=3.6, 12.4), 3.63 (dd, J=2.4, 11.2), 4.01 (d, J=2.4, 1H), 4.13 (dt, J=3.2, 12.0), 4.42 (d, J=2.4, 1H), 4.19 (q, J=6.8, 1H), 7.04–7.09 (m, 2H), 7.27–7.40 (m, 4H), 7.73 (s, 1H).

EXAMPLE 75

2-(R)-(1-(R)-(3,5-Bis(trifluoromethyl)phenyl) ethoxy)-3-(S)-(4-fluoro)phenyl-4-(3-(5-oxo-1,2,4-triazolo)methylmorpholine The title compound was prepared in 79% yield from 2-(R)-(1-(R)-(3,5-bis(trifluoromethyl)phenyl)ethoxy)-3-(S) -(4-fluoro)phenyl morpholine (from Example 74) using a procedure analogous to Example 70.

Mass Spectrum (FAB): m/Z 535 (M+H, 100%), 277 (60%).

$^1$H NMR (CDCl$_3$+CD$_3$OD, 400 MHz, ppm): δ 1.48 (d, J=6.8, 3H), 2.52 (app t, J=10.4, 1H), 2.85–2.88 (m, 2H), 3.47 (d, J=2.8, 1H), 3.63 (d, J=14.4, 1H), 3.70 (dd, J=2.0, 11.6, 1H), 4.24 (app t, J=10.8, 1H), 4.35 (d, J=2.8, 1H), 4.91 (q, J=6.8, 1H), 7.07 (app t, J=8.4, 2H), 7.15 (s, 2H), 7.37–7.40 (m, 2H), 7.65 (s, 1H).

Analysis Calcd for C$_{23}$H$_{21}$F$_7$N$_4$O$_3$: C, 51.69; H, 3.96; N, 10.48; F, 24.88. Found: C, 51.74; H, 4.04; N, 10.50; F, 24.59.

EXAMPLE 76

2-(R)-(1-(S)-(3,5-Bis(trifluoromethyl)phenyl) ethoxy)-3-(S)-(4-fluoro)phenyl-4-(3-(5-oxo-1,2,4-triazolo)methylmorpholine The title compound was prepared in 60% yield from 2-(R)-(1-(S)-(3,5-bis(trifluoromethyl)phenyl)ethoxy)-3-(S)- (4-fluoro)phenyl morpholine (from Example 74) using a procedure analogous to Example 70.

Mass Spectrum (FAB): m/Z 535 (M+H, 50%), 293 (100%).

$^1$H NMR (CDCl$_3$+CD$_3$OD, 400 MHz, ppm): δ 1.11 (d, J=6.4, 3H), 2.49 (dt, J=2.4, 11.2), 2.83 (app d, J=11.2, 1H), 2.95 (d, J=14.4, 1H), 2.48–2.58 (m, 3H), 3.99 (app t, J=9.6, 1H), 4.61 (q, J=6.4, 1H), 4.81 (d, J=2.4, 1H), 7.09 (t, J=8.8, 2H), 7.50–7.53 (m, 2H), 7.75 (app s, 3H), 10.40 (br s, 1H), 11.00 (br s, 1H).

EXAMPLE 77

2-(R)-(1-(R)-(3-(Trifluoromethyl)phenyl)ethoxy)-3- (S)-phenyl-4-(3-(5-oxo-1,2,4-triazolo) methylmorpholine Step A: 2-(R)-(1-(R)-(3-(Trifluoromethyl)phenyl) ethoxy)-3-(S)-phenyl morpholine The title compound was prepared in 25% yield from 3-(S)-phenyl-4-benzyl-2-morpholinone (from Example 14) using procedures analogous to Examples 67–69.

$^1$H NMR (CDCl$_3$, 400 MHz, ppm): δ 1.39 (d, J=6.6, 3H), 1.93 (br s, 1H), 3.10 (dd, J=3.0, 12.7, 1H), 3.20 (dt, J=3.6, 12.4, 1H), 3.58 (ddd, J=1.1, 3.8, 11.2, 1H), 4.00 (d, J=2.4, 1H), 4.12 (dt, J=3.0, 11.2, 1H), 4.44 (d, J=2.4, 1H), 4.79 (q, J=6.6, 1H), 6.72 (d, J=7.7, 1H), 7.01 (s, 1H), 7.09 (t, J=7.7, 1H), 7.18–7.25 (m, 2H), 7.25–7.3 (m, 3H), 7.34 (d, J=7.7, 1H). Analysis:

Calcd for C$_{19}$H$_{19}$F$_3$N$_1$O$_2$: C-65.14 H-5.47 N-4.00 F-16.27 Found: C-64.89 H-5.73 N-3.83 F-15.95

Step B: 2-(R)-(1-(R)-(3-(Trifluoromethyl)phenyl) ethoxy)-3-(S)-phenyl-4-(3-(5-oxo-1,2,4-triazolo) methylmorpholine The title compound was prepared in 90% yield from 2-(R)-(1-(R)-(3-(trifluoromethyl)phenyl)ethoxy)-3-(S)- phenyl morpholine (from Example 77, Step A) using a procedure analogous to Example 70.

$^1$H NMR (CDCl$_3$, 400 MHz, ppm): δ 1.40 (d, J=6.3, 3H), 2.53 (br t, J=11.2, 1H), 2.86 (app d, J=12.2, 1H), 2.94 (d, J=14.3, 1H), 3.44 (br s, 1H), 3.63 (br d, J=14, 2H), 4.27 (app t, J=11.5, 1H), 4.34 (d, J=2.1, 1H), 4.76 (q, J=6.7, 1H), 6.63 (d, J=7.7, 1H), 6.93 (s, 1H), 7.06 (t, J=7.6, 1H), 7.25–7.45 (m, 6H), 9.63 (br s, 1H), 9.74 (br s, 1H).

Analysis: Calcd for C$_{22}$H$_{22}$F$_3$N$_4$O$_3$: C-59.06 H-4.96 N-12.52 F-12.74 Found: C-58.84 H-5.17 N-12.37 F-12.50

EXAMPLE 78

2-(R)-(1-(R)-(3-(Fluoro)-5-(trifluoromethyl)phenyl) ethoxy)-3-(S)-phenyl-4-(3-(5-oxo-1,2,4-triazolo) methylmorpholine Step A: 2-(R)-(1-(R)-(3-(Fluoro)-5-(trifluoromethyl) phenyl)ethoxy)-3-(S)-phenyl-morpholine The title compound was prepared in 44% yield from 3-(S)-phenyl-4-benzyl-2-morpholinone (from Example 14) using procedures analogous to Examples 67–69.

$^1$H NMR (CDCl$_3$, 400 MHz, ppm): δ 1.38 (d, J=6.6, 3H), 1.90 (br s, 1H), 3.17 (dd, J=3.0, 12.7, 1H), 3.18 (dt, J=3.6, 12.7, 1H), 3.58 (ddd, J=1.1, 3.8, 11.2, 1H), 4.02 (d, J=2.3, 1H), 4.11 (dt, J=3.0, 11.2, 1H), 4.44 (d, J=2.3, 1H), 4.78 (q, J=6.6, 1H), 6.29 (d, J=9.2, 1H), 6.85 (s, 1H), 7.03 (d, J=8.4, 1H), 7.18–7.26 (m, 2H), 7.26–7.3 (m, 3H).

Analysis: Calcd for $C_{19}H_{18}F_4N_1O_2$: C-61.95 H-4.93 N-3.80 F-20.63 Found: C-61.78 H-5.14 N-3.71 F-20.35

Step B: 2-(R)-(1-(R)-(3-(Fluoro)-5-(trifluoromethyl) phenyl)ethoxy)-3-(S)-phenyl-4-(3-(5-oxo-1,2,4-triazolo)methylmorpholine The title compound was prepared in 77% yield from 2-(R)-(1-(R)-(3-(fluoro)-5-(trifluoromethyl)phenyl)ethoxy)-3-(S)-phenyl morpholine (from Example 78, Step A) using a procedure analogous to Example 70.

$^1$H NMR (CDCl$_3$, 400 MHz, ppm): δ 1.40 (d, J=6.3, 3H), 2.54 (br t, J=11, 1H), 2.87 (app d, J=12, 1H), 2.94 (app d, J=14, 1H), 3.47 (br s, 1H), 3.63 (br t, J=14, 2H), 4.25 (app t, J=11, 1H), 4.35 (d, J=1.5, 1H), 4.75 (q, J=6.3, 1H), 6.62 (d, J=6.7, 1H), 6.78 (s, 1H), 7.01 (d J=8.4, 1H), 7.24 (d, J=3.9, 1H), 7.35 (br s, 4H), 9.61 (br s, 1H), 9.89 (br s, 1H).

Analysis: Calcd for $C_{22}H_{21}F_4N_4O_3$: C-56.77 H-4.55 N-12.04 F-16.33 Found: C-56.57 H-4.65 N-11.94 F-16.13

EXAMPLE 79

2-(S)-(3-Fluoro-5-trifluoromethyl)benzoyloxy)-3-(S) -(4-fluoro)phenyl-4-benzyl morpholine The title compound was prepared in 57% yield from 3-(S)-(4-fluoro)phenyl-4-benzyl-2-morpholinone (from Example 59) using a procedure analogous to Example 67.

Mass Spectrum (CI): m/Z 478 (M+H, 100%)

$^1$H NMR (CDCl$_3$, 360 MHz, ppm): δ 2.50 (dt, J=3.3, 12.0, 1H), 2.96(d, J=12.0, 1H), 2.98 (d, J=13.6, 1H), 3.75 (dd,J= 1.7, 11.5, 1H), 3.80 (d, J=13.6, 1H), 3.75 (dd, J=1.7, 11.5, 1H), 3.80 (d, J=2.5, 1H), 3.92 (d, J=13.6, 1H), 4.19 (dt, J=2.1, 12.0, 1H), 6.20 (d,J=2.5, 1H), 6.99 (t, J=8.7, 2H), 7.2–7.37 (m, 5H), 7.51–7.55 (m, 3H), 7.89 (d, J=8.4, 1H), 8.09 (s, 1H).

EXAMPLE 80

2-(S)-(1-(3-Fluoro-5-trifluoromethyl)phenyl) ethenyloxy)-3-(S)-(4-fluoro)-phenyl-4-benzyl morpholine The title compound was prepared in 85% yield from 2-(S)-(3-fluoro-5-trifluoromethyl)benzoyloxy)-3-(S)-(4-fluoro)phenyl-4-benzyl morpholine (from Example 79) using a procedure analogous to Example 68.

Mass Spectrum (CI): m/Z 476 (M+H, 100%)

$^1$H NMR (CDCl$_3$, 360 MHz, ppm): δ 2.42 (dt, J=3.6, 12.0 Hz, 1H), 2.90 (d, J=12.0, 1H), 2.91 (d, J=13.6, 1H), 3.60–3.62 (m, 1H), 3.72 (d, J=2.6, 1H), 3.92 (d, J=13.6, 1H), 4.09 (dt, J=2.4, 12.0, 1H), 4.67 (d, J=2.9, 1H) 4.76 (d, J=2.9, 1H), 5.28 (d, J=2.6, 1H), 7.07 (t, J=8.7, 2H), 7.2–7.37 (m, 7H), 7.53 (s, 1H), 7.57–7.61 (m, 2H).

EXAMPLE 81

2-(S)-(1-(S)-(3-Fluoro-5-trifluoromethyl)phenyl) ethoxy)-3-(S)-(4-fluoro)phenyl morpholine and 2-(S)-(1-(R)-(3-Fluoro-5-trifluoromethyl)phenyl) ethoxy)-3-(S)-(4-fluoro)phenyl morpholine The title compounds were prepared from 2-(S)-(1-(3-fluoro-5-trifluoromethyl)phenyl)ethenyloxy)-3-(S)-(4-fluoro)-phenyl-4-benzyl morpholine (from Example 80) using a procedure analogous to Example 74, but using 10% palladium on charcoal as the catalyst.

For 2-(S)-(1-(S)-(3-Fluoro-5-trifluoromethyl)phenyl) ethoxy)-3-(S)-(4-fluoro)phenyl morpholine:

Mass Spectrum (CI): m/Z 388 (M+H, 100%)

$^1$H NMR (CDCl$_3$, 360 MHz, ppm): δ 1.12 (d, J=6.5, 1H),1.83 (s, 1H), 3.02 (d, J=10.1, 1H), 3.16 (dt, J=3.6,12.5, 1H), 3.43 (dd, J=2.7, 11.4, 1H), 3.81 (dt, J=2.9, 11.7, 1H), 4.09 (d, J=2.1, 1H), 4.62 (q, J=6.5, 1H), 4.84 (d, J=2.1, 1H), 7.05 (t, J=8.8, 2H), 7.2 (d, J=8.8, 2H), 7.32 (s, 1H), 7.38 (dd, J=5.5, 8.5, 2H).

For 2-(S)-(1-(R)-(3-Fluoro-5-trifluoromethyl)phenyl) ethoxy)-3-(S)-(4-fluoro)phenyl morpholine:

Mass Spectrum (CI): m/Z 387 (M$^+$, 100%)

$^1$H NMR (CDCl$_3$, 360 MHz, ppm): δ 1.42 (d, J=6.6, 3H), 1.91 (s, 1H), 3.11 (dd, J=3.2, 12.4, 1H), 3.22 (dt, J=3.6, 12.4, 1H), 3.58–3.62 (m, 1H), 4.01 (d, J=2.3, 1H), 4.11 (dt, J=3.2, 12.0, 1H), 4.41 (d, J=2.3, 1H), 4.80 (q, J=6.6, 1H), 6.41 (d, J=9.2, 1H), 6.86 (s, 1H), 7.02 (t, J=8.7, 2H), 7.08 (d, J=9.2, 2H), 7.21–7.26 (m, 2H).

EXAMPLE 82

2-(S)-(1-(R)-(3-Fluoro-5-trifluoromethyl)phenyl) ethoxy)-3-(S)-(4-fluoro)phenyl-4-(3-(5-oxo-1,2,4-triazolo)methyl morpholine The title compound was prepared from 2-(S)-(1-(R)-(3-fluoro-5-trifluoromethyl)phenyl)ethoxy)-3-(S)-(4-fluoro) phenyl morpholine (from Example 81) using a procedure analogous to Example 70, mp 209°–211° C.

$[α]_D$=+65.1 (c=1.0, methanol)

$^1$H NMR (CDCl$_3$, 360 MHz, ppm): δ 1.32 (d, J=6.4, 1H), 2.38 (t, J=11.9, 1H), 2.76 (d, J=13.9, 1H), 2.84 (d, J=11.5, 1H), 3.32 (s, 1H), 3.40 (d, J=13.9, 1H), 3.49 (s, 1H), 3.61 (d, J=11.2, 1H), 4.11 (t, J=11.3, 1H), 4.8 (q, J=6.4, 1H), 6.57 (d, J=9.4, 1H), 6.94 (s, 1H), 7.1 (t, J=8.7, 2H), 7.39 (d, J=8.7, 2H), 7.51 (s, 2H), 11.26 (s, 1H), 11.38 (s, 1H).

EXAMPLE 83

2-(S)-(1-(R)-(3,5-Bis(trifluoromethyl)phenyl) ethoxy)-3-(S)-(4-fluoro)phenyl-4-(4-(2-oxo-1,3-imidazolo)methyl morpholine Step A: N,N-Diacetyl-4-bromomethyl-2-imidazolone The title compound was prepared according to the procedure of Dolan and Dushinsky (*Journal of the American Chemical Society*, 70, 657 (1948)).

Step B: 2-(S)-(1-(R)-(3,5-Bis(trifluoromethyl) phenyl)ethoxy)-3-(S)-(4-fluoro)phenyl-4-(4-(2-oxo-1,3-imidazolo)methylmmorpholine A mixture of 1.00 g (2.28 mmol) of 2-(S)-(1-(R)-(3,5-bis (trifluoro-methyl)phenyl)ethoxy)-3-(S)-(4-fluoro)phenyl morpholine (from Example 74), 0.62 g (2.40 mmol) of N,N-diacetyl-4-bromomethyl-2-imidazolone (from Example 83, Step A) and 0.63 g (4.56 mmol) of potassium carbonate in 10 mL of N,N-dimethylformamide was stirred at room temperature for 15 minutes. The reaction was diluted with 100 mL of ethyl acetate and washed with water, saturated aqueous sodium chloride solution, dried over magnesium sulfate, and evaporated in vacuo. The resulting oil was dissolved in 10 mL of ethanol; the resulting solution was treated with 1.05 mL of 33% ethanolic methylamine solution and stirred at room temperature for 10 minutes. The reaction mixture was concentrated in vacuo to afford a solid. Recrystallisation from ethyl acetate/methanol afforded 0.63 g of the title compound, mp 192°–194° C.

¹H NMR (d6-DMSO, 360 MHz, ppm): δ 1.35 (d, J=6.5, 3H), 2.25 (dt, J=8.7, 1H), 2.60 (d, J=13.8, 1H), 2.89 (d, J=1 1.6, 1H), 3.28–3.36 (m, 2H), 3.62 (d, J=10.2, 1H), 4.1 (t, J=10.0, 1H), 4.31 (d, J=2.7, 1H), 4.92 (q, J=6.5, 1H), 5.97 (s, 1H), 7.06 (t, J=8.8, 2H), 7.36 (s, 2H), 7.65–7.85 (m, 2H), 7.84 (s, 1H), 9.58 (s, 1H), 9.8 (s, 1H).

EXAMPLE 84

2-(S)-(1-(R)-(3-Fluoro-5-(trifluoromethyl)phenyl) ethoxy-3-(S)-(4-fluoro)phenyl-4-(4-(2-oxo-1,3-imidazolo)methyl morpholine The title compound was prepared from 2-(S)-(1-(R)-(3-fluoro-5-trifluoromethyl)phenyl)ethoxy)-3-(S)-(4-fluoro) phenyl morpholine (from Example 82) using a procedure analogous to Example 83, mp 209°–210° C.

[α]$_D$=+92.8 (c=1.0, methanol).

¹H NMR (d$_6$-DMSO, 360 MHz, ppm) δ 1.31 (d, J=6.5, 3H), 2.24 (dt, J=3.0, 11.9, 1H), 2.6 (d, J=13.9, 1H), 3.61 (d, J=11.2, 1H), 4.1 (t, J=11.0, 1H), 4.29 (d, J=2.3, 1H), 4.8 (q, J=6.5, 1H), 6.00 (s, 1H), 6.55 (d, J=9.3, 1H), 6.94 (s, 1H), 7.11 (t, J=8.7, 2H), 7.39 (d, J=8.4, 1H), 7.51 (s, 2H), 9.59 (s, 1H), 9.84 (s, 1H).

EXAMPLE 85

2-(S)-(1-(S)-(3,5-Bis(trifluoromethyl)phenyl)ethoxy) -3-(R)-(4-fluorophenyl)-4-(3-(5-oxo-1H,4H-1,2,4-triazolo)methylmorpholine The title compound was prepared from (R)-(4-fluoro) phenylglycine using procedures analogous to Example 59, 67, 68, 69 and 70.

[α]$_D$=−67.7 (c=0.7, MeOH, 20° C.)

EXAMPLE 86

The following compounds are prepared from 3-(S)-phenyl-4-benzyl-2-morpholinone (from Example 14) or 3-(S)-(4-fluoro)phenyl-4-benzyl-2-morpholinone (from Example 59) using procedures analogous to Examples 15, 67–69 and 74. The hydrogenation of the 1-(substituted-aryl) ethenyloxy intermediates may be done with 10% palladium on carbon (Example 70) or 5% rhodium on alumina catalyst (Example 74) to give rapid reduction of the enol ether. Removal of the 4-benzyl substituent may be done catalytically under extended hydrogenation with 10% palladium on carbon or 5% rhodium on alumina catalyst or (when dehalogenation or cleavage of the ether might occur) in a second step with 1-chloroethyl chloroformate as in Example 4, Step C.

1) 2-(R)-(1-(R)-(3-(chloro)-5-(trifluoromethyl)phenyl) ethoxy)-3-(S)-phenyl-morpholine;
2) 2-(R)-(1-(R)-(3,5-(dimethyl)phenyl)ethoxy)-3-(S)-phenyl-morpholine;
3) 2-(R)-(1-(R)-(3-(fluoro)-5-(methyl)phenyl)ethoxy)-3-(S)-phenyl-morpholine;
4) 2-(R)-(1-(R)-(3-(chloro)-5-(methyl)phenyl)ethoxy)-3-(S)-phenyl-morpholine;
5) 2-(R)-(1-(R)-(3-(bromo)-5-(methyl)phenyl)ethoxy)-3-(S)-phenyl-morpholine;
6) 2-(R)-(1-(R)-(3-(isopropoxy)phenyl)ethoxy)-3-(S)-phenyl-morpholine;
7) 2-(R)-(1-(R)-(3-(isopropoxy)-5-(trifluoromethyl)phenyl) ethoxy)-3-(S)-phenyl-morpholine;
8) 2-(R)-(1-(R)-(3-(chloro)-5-(isopropoxy)phenyl)ethoxy)-3-(S)-phenyl-morpholine;
9) 2-(R)-(1-(R)-(3-(fluoro)-5-(isopropoxy)phenyl)ethoxy)-3-(S)-phenyl-morpholine;
10) 2-(R)-(1-(R)-(3-(t-butyl)phenyl)ethoxy)-3-(S)-phenyl-morpholine;
11) 2-(R)-(1-(R)-(3-(t-butyl)-5-(chloro)phenyl)ethoxy)-3-(S)-phenyl-morpholine;
12) 2-(R)-(1-(R)-(3-(t-butyl)-5-(trifluoromethyl)phenyl) ethoxy)-3-(S)-phenyl-morpholine;
13) 2-(R)-(1-(R)-(3,5-(dimethyl)-4-(fluoro)phenyl)ethoxy)-3-(S)-phenyl-morpholine
14) 2-(R)-(1-(R)-(3,5-(dimethyl)-4-(chloro)phenyl)ethoxy)-3-(S)-phenyl-morpholine;
15) 2-(R)-(1-(R)-(3,5-bis(trifluoromethyl)-4-(fluoro) phenyl)ethoxy)-3-(S)-phenyl-morpholine;
16) 2-(R)-(1-(R)-(3,5-bis(trifluoromethyl)-4-(chloro) phenyl)ethoxy)-3-(S)-phenyl-morpholine;
17) 2-(R)-(1-(R)-(3,5-(dichloro)phenyl)ethoxy)-3-(S)-phenyl-morpholine;
18) 2-(R)-(1-(R)-(3,5-(difluoro)phenyl)ethoxy)-3-(S)-phenyl-morpholine;
19) 2-(R)-(1-(R)-(1-(naphthyl)ethoxy)-3-(S)-phenyl-morpholine;
20) 2-(R)-(1-(R)-(1-(4-(fluoro)naphthyl))ethoxy)-3-(S)-phenyl-morpholine;
21) 2-(R)-(1-(R)-(1-(3-(fluoro)naphthyl))ethoxy)-3-(S)-phenyl-morpholine;
22) 2-(R)-(1-(R)-(1-(3-(chloro)naphthyl))ethoxy)-3-(S)-phenyl-morpholine;
23) 2-(R)-(1-(R)-(1-(3-(methyl)naphthyl))ethoxy)-3-(S)-phenyl-morpholine;
24) 2-(R)-(1-(R)-(1-(3-(trifluoromethyl)naphthyl))ethoxy)-3-(S)-phenyl-morpholine;
25) 2-(S)-(2-fluoro-5-trifluoromethyl)benzyloxy-3-(S)-phenyl-morpholine;
26) 2-(S)-(2-fluoro-5-trifluoromethyl)benzyloxy-3-(S)-(4-fluoro)phenyl-morpholine;
27) 2-(R)-(1-(R)-(2-fluoro-5-trifluoromethyl)phenylethoxy) -3-(S)-phenyl-morpholine;
28) 2-(R)-(1-(R)-(2-fluoro-5-trifluoromethyl)phenylethoxy) -3-(S)-(4-fluoro)phenyl-morpholine;
29) 2-(S)-(2-chloro-5-trifluoromethyl)benzyloxy-3-(S)-phenyl-morpholine;
30) 2-(S)-(2-chloro-5-trifluoromethyl)benzyloxy-3-(S)-(4-fluoro)phenyl-morpholine;
31) 2-(R)-(1-(R)-(2-chloro-5-trifluoromethyl)phenylethoxy) -3-(S)-phenyl-morpholine;
32) 2-(R)-(1-(R)-(2-chloro-5-trifluoromethyl)phenylethoxy) -3-(S)-(4-fluoro)phenyl-morpholine;
33) 2-(S)-(3-methyl)benzyloxy-3-(S)-phenyl-morpholine;
34) 2-(S)-(3-methyl)benzyloxy-3-(S)-(4-fluoro)phenyl-morpholine;
35) 2-(R)-(1-(R)-(3-methyl)phenylethoxy)-3-(S)-phenyl-morpholine;
36) 2-(R)-(1-(R)-(3-methyl)phenylethoxy)-3-(S)-(4-fluoro) phenyl-morpholine;
37) 2-(S)-(3-bromo)benzyloxy-3-(S)-phenyl-morpholine;
38) 2-(S)-(3-bromo)benzyloxy-3-(S)-(4-fluoro)phenyl-morpholine;
39) 2-(R)-(1-(R)-(3-bromo)phenylethoxy)-3-(S)-phenyl-morpholine;
40) 2-(R)-(1-(R)-(3-bromo)phenylethoxy)-3-(S)-(4-fluoro) phenyl-morpholine;
41) 2-(S)-(3-chloro)benzyloxy-3-(S)-phenyl-morpholine;
42) 2-(S)-(3-chloro)benzyloxy-3-(S)-(4-fluoro)phenyl-morpholine;
43) 2-(R)-(1-(R)-(3-chloro)phenylethoxy)-3-(S)-phenyl-morpholine;
44) 2-(R)-(1-(R)-(3-chloro)phenylethoxy)-3-(S)-(4-fluoro) phenyl-morpholine;

45) 2-(S)-(3-trifluoromethyl)benzyloxy-3-(S)-phenyl-morpholine;
46) 2-(S)-(3-trifluoromethyl)benzyloxy-3-(S)-(4-fluoro)phenyl-morpholine;
47) 2-(S)-(3-t-butyl)benzyloxy-3-(S)-phenyl-morpholine;
48) 2-(S)-(3-t-butyl)benzyloxy-3-(S)-(4-fluoro)phenyl-morpholine;
49) 2-(R)-(1-(R)-(3-(thiomethyl)phenyl)ethoxy)-3-(S)-phenyl-morpholine;
50) 2-(R)-(1-(R)-(3-(thiomethyl)-5-(trifluoromethyl)phenyl)ethoxy)-3-(S)-phenyl-morpholine;
51) 2-(R)-(1-(R)-(2,2-(dimethyl)-5-(thiomethyl)-2,3-dihydrobenzofuran-7-yl)ethoxy)-3-(S)-phenyl-morpholine;
52) 2-(R)-(1-(R)-(3,5-(dimethoxy)phenyl)ethoxy)-3-(S)-phenyl-morpholine;
53) 2-(R)-(1-(R)-(3-(trifluoromethyl)phenyl)ethoxy)-3-(S)-(4-fluoro)phenyl-morpholine;
54) 2-(R)-(1-(R)-(3-(fluoro)-5-(trifluoromethyl)phenyl)ethoxy)-3-(S)-(4-fluoro)phenyl-morpholine;
55) 2-(R)-(1-(R)-(3-(chloro)-5-(trifluoromethyl)phenyl)ethoxy)-3-(S)-(4-fluoro)phenyl-morpholine;
56) 2-(R)-(1-(R)-(3,5-(dimethyl)phenyl)ethoxy)-3-(S)-(4-fluoro)phenyl-morpholine;
57) 2-(R)-(1-(R)-(3-(fluoro)-5-(methyl)phenyl)ethoxy)-3-(S)-(4-fluoro)phenyl-morpholine;
58) 2-(R)-(1-(R)-(3-(chloro)-5-(methyl)phenyl)ethoxy)-3-(S)-(4-fluoro)phenyl-morpholine;
59) 2-(R)-(1-(R)-(3-(bromo)-5-(methyl)phenyl)ethoxy)-3-(S)-(4-fluoro)phenyl-morpholine;
60) 2-(R)-(1-(R)-(3-(isopropoxy)phenyl)ethoxy)-3-(S)-(4-fluoro)phenyl-morpholine;
61) 2-(R)-(1-(R)-(3-(isopropoxy)-5-(trifluoromethyl)phenyl)ethoxy)-3-(S)-(4-fluoro)phenyl-morpholine;
62) 2-(R)-(1-(R)-(3-(chloro)-5-(isopropoxy)phenyl)ethoxy)-3-(S)-(4-fluoro)phenyl-morpholine;
63) 2-(R)-(1-(R)-(3-(fluoro)-5-(isopropoxy)phenyl)ethoxy)-3-(S)-(4-fluoro)phenyl-morpholine;
64) 2-(R)-(1-(R)-(3-(t-butyl)phenyl)ethoxy)-3-(S)-(4-fluoro)phenyl-morpholine;
65) 2-(R)-(1-(R)-(3-(t-butyl)-5-(chloro)phenyl)ethoxy)-3-(S)-(4-fluoro)phenyl-morpholine;
66) 2-(R)-(1-(R)-(3-(t-butyl)-5-(trifluoromethyl)phenyl)ethoxy)-3-(S)-(4-fluoro)phenyl-morpholine;
67) 2-(R)-(1-(R)-(3,5-(dimethyl)-4-(fluoro)phenyl)ethoxy)-3-(S)-(4-fluoro)phenyl-morpholine;
68) 2-(R)-(1-(R)-(3,5-(dimethyl)-4-(chloro)phenyl)ethoxy)-3-(S)-(4-fluoro)phenyl-morpholine;
69) 2-(R)-(1-(R)-(3,5-bis(trifluoromethyl)-4-(fluoro)phenyl)ethoxy)-3-(S)-(4-fluoro)phenyl-morpholine;
70) 2-(R)-(1-(R)-(3,5-bis(trifluoromethyl)-4-(chloro)phenyl)ethoxy)-3-(S)-(4-fluoro)phenyl-morpholine;
71) 2-(R)-(1-(R)-(3,5-(dichloro)phenyl)ethoxy)-3-(S)-(4-fluoro)phenyl-morpholine;
72) 2-(R)-(1-(R)-(3,5-(difluoro)phenyl)ethoxy)-3-(S)-(4-fluoro)phenyl-morpholine;
73) 2-(R)-(1-(R)-(1-(naphthyl)ethoxy)-3-(S)-(4-fluoro)phenyl-morpholine;
74) 2-(R)-(1-(R)-(1-(4-(fluoro)naphthyl))ethoxy)-3-(S)-(4-fluoro)phenyl-morpholine;
75) 2-(R)-(1-(R)-(1-(3-(fluoro)naphthyl))ethoxy)-3-(S)-(4-fluoro)phenyl-morpholine;
76) 2-(R)-(1-(R)-(1-(3-(chloro)naphthyl))ethoxy)-3-(S)-(4-fluoro)phenyl-morpholine;
77) 2-(R)-(1-(R)-(1-(3-(methyl)naphthyl))ethoxy)-3-(S)-(4-fluoro)phenyl-morpholine;
78) 2-(R)-(1-(R)-(1-(3-(trifluoromethyl)naphthyl))ethoxy)-3-(S)-(4-fluoro)phenyl-morpholine;
79) 2-(R)-(1-(R)-(3-(thiomethyl)phenyl)ethoxy)-3-(S)-(4-fluoro)phenyl-morpholine;
80) 2-(R)-(1-(R)-(3-(thiomethyl)-5-(trifluoromethyl)phenyl)ethoxy)-3-(S)-(4-fluoro)phenyl-morpholine;
81) 2-(R)-(1-(R)-(2,2-(dimethyl)-5-(thiomethyl)-2,3-dihydrobenzofuran-7-yl)ethoxy)-3-(S)-(4-fluoro)phenyl-morpholine;
82) 2-(R)-(1-(R)-(3,5-(dimethoxy)phenyl)ethoxy)-3-(S)-(4-fluoro)phenyl-morpholine;
83) 2-(R)-(1-(R)-(phenyl)ethoxy)-3-(S)-phenyl-morpholine;
84) 2-(R)-(1-(R)-(phenyl)ethoxy)-3-(S)-(4-fluoro)phenyl-morpholine;
85) 2-(R)-(1-(R)-(3-(fluoro)phenyl)ethoxy)-3-(S)-phenyl-morpholine;
86) 2-(R)-(1-(R)-(3-(fluoro)phenyl)ethoxy)-3-(S)-(4-fluoro)phenyl-morpholine;
87) 2-(R)-(1-(R)-(4-(fluoro)phenyl)ethoxy)-3-(S)-phenyl-morpholine;
88) 2-(R)-(1-(R)-(4-(fluoro)phenyl)ethoxy)-3-(S)-(4-fluoro)phenyl-morpholine;
89) 2-(R)-(1-(R)-(3,5-bis(trifluoromethyl)phenyl)ethoxy)-3-(S)-(3-fluoro)phenyl-morpholine;
90) 2-(R)-(1-(R)-(3,5-bis(trifluoromethyl)phenyl)ethoxy)-3-(S)-(3,4-difluoro)phenyl-morpholine;
91) 2-(R)-(1-(R)-(3,5-bis(trifluoromethyl)phenyl)ethoxy)-3-(S)-(3,4-dichloro)phenyl-morpholine;
92) 2-(R)-(1-(R)-(3,5-bis(trifluoromethyl)phenyl)ethoxy)-3-(S)-(3,4-dimethyl)phenyl-morpholine;
93) 2-(R)-(1-(R)-(3,5-bis(trifluoromethyl)phenyl)ethoxy)-3-(S)-3,4-methylenedioxyphenyl-morpholine;
94) 2-(R)-(1-(R)-(3,5-bis(trifluoromethyl)phenyl)ethoxy)-3-(S)-(2-naphthyl)-morpholine.

EXAMPLE 87

The following compounds are prepared from the corresponding 2-(S)-(substituted-benzyloxy)-3-(S)-aryl morpholines or 2-(R)-(1-(R)-(substituted-aryl)ethoxy)-3-(S)-aryl morpholines (from Example 86) using procedures analogous to Examples 17, 18, 36, 38, 83 or, in the case of the 4-(5-tetrazolyl)methyl-substituted morpholines, by alkylation of the morpholine (from Example 86) with chloroacetonitrile in the presence of a tertiary amine base in acetonitrile, followed by formation of the final product by reacting the resulting nitrile with either sodium azide or trimethylsilylazide in an appropriate solvent.

1) 2-(R)-(1-(R)-(3-(Chloro)-5-(trifluoromethylphenyl)ethoxy)-3-(S)-phenyl-4-(3-(5-oxo-1,2,4-triazolo)methyl-morpholine;
2) 2-(R)-(1-(R)-(3,5-(Dimethyl)phenyl)ethoxy)-3-(S)-phenyl-4-(3-(5-oxo-1,2,4-triazolo)methyl-morpholine;
3) 2-(R)-(1-(R)-(3-(Fluoro)-5-(methyl)phenyl)ethoxy)-3-(S)-phenyl-4-(3-(5-oxo-1,2,4-triazolo)methyl-morpholine;
4) 2-(R)-(1-(R)-(3-(Chloro)-5-(methyl)phenyl)ethoxy)-3-(S)-phenyl-4-(3-(5-oxo-1,2,4-triazolo)methyl-morpholine;
5) 2-(R)-(1-(R)-(3-(Bromo)-5-(methyl)phenyl)ethoxy)-3-(S)-phenyl-4-(3-(5-oxo-1,2,4-triazolo)methyl-morpholine;
6) 2-(R)-(1-(R)-(3-(Isopropoxy)phenyl)ethoxy)-3-(S)-phenyl-4-(3-(5-oxo-1,2,4-triazolo)methyl-morpholine;
7) 2-(R)-(1-(R)-(3-(Isopropoxy)-5-(trifluoromethyl)phenyl)ethoxy)-3-(S)-phenyl-4-(3-(5-oxo-1,2,4-triazolo)methyl-morpholine;
8) 2-(R)-(1-(R)-(3-(Chloro)-5-(isopropoxy)phenyl)ethoxy)-3-(S)-phenyl-4-(3-(5-oxo-1,2,4-triazolo)methyl-morpholine;
9) 2-(R)-(1-(R)-(3-(Fluoro)-5-(isopropoxy)phenyl)ethoxy)-3-(S)-phenyl-4-(3-(5-oxo-1,2,4-triazolo)methyl-morpholine;

10) 2-(R)-(1-(R)-(1-(3-(trifluoromethyl)naphthyl))ethoxy)-3-(S)-phenyl-4-(3-(-1,2,4-triazolo)methyl-morpholine;
11) 2-(R)-(1-(R)-(3-(t-Butyl)-5-(chloro)phenyl)ethoxy)-3-(S)-phenyl-4-(3-(5-oxo-1,2,4-triazolo)methyl-morpholine;
12) 2-(R)-(1-(R)-(3-(t-Butyl)-5-(trifluoromethyl)phenyl)ethoxy)-3-(S)-phenyl-4-(3-(5-oxo-1,2,4-triazolo)methyl-morpholine;
13) 2-(R)-(1-(R)-(3,5-(Dimethyl)-4-(fluoro)phenyl)ethoxy)-3-(S)-phenyl-4-(3-(5-oxo-1,2,4-triazolo)methyl-morpholine;
14) 2-(R)-(1-(R)-(3,5-(Dimethyl)-4-(chloro)phenyl)ethoxy)-3-(S)-phenyl-4-(3-(5-oxo-1,2,4-triazolo)methyl-morpholine;
15) 2-(R)-(1-(R)-(3,5-Bis(trifluoromethyl)-4-(fluoro)phenyl)ethoxy)-3-(S)-phenyl-4-(3-(5-oxo-1,2,4-triazolo)methyl-morpholine;
16) 2-(R)-(1-(R)-(3,5-Bis(trifluoromethyl)-4-(chloro)phenyl)ethoxy)-3-(S)-phenyl-4-(3-(5-oxo-1,2,4-triazolo)methyl-morpholine;
17) 2-(R)-(1-(R)-(3,5-(Dichloro)phenyl)ethoxy)-3-(S)-phenyl-4-(3-(5-oxo-1,2,4-triazolo)methyl-morpholine;
18) 2-(R)-(1-(R)-(3,5-(Difluoro)phenyl)ethoxy)-3-(S)-phenyl-4-(3-(5-oxo-1,2,4-triazolo)methyl-morpholine;
19) 2-(R)-(1-(R)-(1-(Naphthyl)ethoxy)-3-(S)-phenyl-4-(3-(5-oxo-1,2,4-triazolo)methyl-morpholine;
20) 2-(R)-(1-(R)-(1-(4-(Fluoro)naphthyl))ethoxy)-3-(S)-phenyl-4-(3-(5-oxo-1,2,4-triazolo)methyl-morpholine;
21) 2-(R)-(1-(R)-(1-(3-(Fluoro)naphthyl))ethoxy)-3-(S)-phenyl-4-(3-(5-oxo-1,2,4-triazolo)methyl-morpholine;
22) 2-(R)-(1-(R)-(1-(3-(Chloro)naphthyl))ethoxy)-3-(S)-phenyl-4-(3-(5-oxo-1,2,4-triazolo)methyl-morpholine;
23) 2-(R)-(1-(R)-(1-(3-(Methyl)naphthyl))ethoxy)-3-(S)-phenyl-4-(3-(5-oxo-1,2,4-triazolo)methyl-morpholine;
24) 2-(R)-(1-(R)-(1-(3-(Trifluoromethyl)naphthyl))ethoxy)-3-(S)-phenyl-4-(3-(5-oxo-1,2,4-triazolo)methyl-morpholine;
25) 2-(S)-(2-Fluoro-5-trifluoromethyl)benzyloxy-3-(S)-phenyl-4-(3-(1,2,4-triazolo)methyl-morpholine;
26) 2-(S)-(2-Fluoro-5-trifluoromethyl)benzyloxy-3-(S)-(4-fluoro)phenyl-4-(3-(1,2,4-triazolo)methyl-morpholine;
27) 2-(R)-(1-(R)-(2-Fluoro-5-trifluoromethyl)phenylethoxy)-3-(S)-phenyl-4-(3-(1,2,4-triazolo)methyl-morpholine;
28) 2-(R)-(1-(R)-(2-Fluoro-5-trifluoromethyl)phenylethoxy)-3-(S)-(4-fluoro)phenyl-4-(3-(1,2,4-triazolo)methyl-morpholine;
29) 2-(S)-(2-Fluoro-5-trifluoromethyl)benzyloxy-3-(S)-phenyl-4-(3-(5-oxo-1,2,4-triazolo)methyl-morpholine;
30) 2-(S)-(2-Fluoro-5-trifluoromethyl)benzyloxy-3-(S)-(4-fluoro)phenyl-4-(3-(5-oxo-1,2,4-triazolo)methyl-morpholine;
31) 2-(R)-(1-(R)-(2-Fluoro-5-trifluoromethyl)phenylethoxy)-3-(S)-phenyl-4-(3-(5-oxo-1,2,4-triazolo)methyl-morpholine;
32) 2-(R)-(1-(R)-(2-chloro-5-trifluoromethyl)phenylethoxy)-3-(S)-(4-fluoro)phenyl-4-(3-(5-oxo-1,2,4-triazolo)methyl-morpholine;
33) 2-(S)-(2-Fluoro-5-trifluoromethyl)benzyloxy-3-(S)-phenyl-4-(4-(2-oxo-1,3-imidazolo)methyl-morpholine;
34) 2-(S)-(2-Fluoro-5-trifluoromethyl)benzyloxy-3-(S)-(4-fluoro)phenyl-4-(4-(2-oxo-1,3-imidazolo)methyl-morpholine;
35) 2-(R)-(1-(R)-(2-Fluoro-5-trifluoromethyl)phenylethoxy)-3-(S)-phenyl-4-(4-(2-oxo-1,3-imidazolo)methyl-morpholine;
36) 2-(R)-(1-(R)-(2-Fluoro-5-trifluoromethyl)phenylethoxy)-3-(S)-(4-fluoro)phenyl-4-(4-(2-oxo-1,3-imidazolo)methyl-morpholine;
37) 2-(S)-(2-Fluoro-5-trifluoromethyl)benzyloxy-3-(S)-phenyl-4-(2-imidazolo)methyl-morpholine;
38) 2-(S)-(2-Fluoro-5-trifluoromethyl)benzyloxy-3-(S)-(4-fluoro)phenyl-4-(2-imidazolo)methyl-morpholine;
39) 2-(R)-(1-(R)-(2-Fluoro-5-trifluoromethyl)phenylethoxy)-3-(S)-phenyl-4-(2-imidazolo)methyl-morpholine;
40) 2-(R)-(1-(R)-(2-Fluoro-5-trifluoromethyl)phenylethoxy)-3-(S)-(4-fluoro)phenyl-4-(2-imidazolo)methyl-morpholine;
41) 2-(S)-(2-Fluoro-5-trifluoromethyl)benzyloxy-3-(S)-phenyl-4-(4-imidazolo)methyl-morpholine;
42) 2-(S)-(2-Fluoro-5-trifluoromethyl)benzyloxy-3-(S)-(4-fluoro)phenyl-4-(4-imidazolo)methyl-morpholine;
43) 2-(R)-(1-(R)-(2-Fluoro-5-trifluoromethyl)phenylethoxy)-3-(S)-phenyl-4-(4-imidazolo)methyl-morpholine;
44) 2-(R)-(1-(R)-(2-Fluoro-5-trifluoromethyl)phenylethoxy)-3-(S)-(4-fluoro)phenyl-4-(4-imidazolo)methyl-morpholine;
45) 2-(S)-(2-Fluoro-5-trifluoromethyl)benzyloxy-3-(S)-phenyl-4-(5-tetrazolo)methyl-morpholine;
46) 2-(S)-(2-Fluoro-5-trifluoromethyl)benzyloxy-3-(S)-(4-fluoro)phenyl-4-(5-tetrazolo)methyl-morpholine;
47) 2-(R)-(1-(R)-(2-Fluoro-5-trifluoromethyl)phenylethoxy)-3-(S)-phenyl-4-(5-tetrazolo)methyl-morpholine;
48) 2-(R)-(1-(R)-(2-Fluoro-5-trifluoromethyl)phenylethoxy)-3-(S)-(4-fluoro)phenyl-4-(5-tetrazolo)methyl-morpholine;
49) 2-(S)-(2-Fluoro-5-trifluoromethyl)benzyloxy-3-(S)-phenyl-4-(2-oxo-5H-pyrrol-4-yl)methyl-morpholine;
50) 2-(S)-(2-Fluoro-5-trifluoromethyl)benzyloxy-3-(S)-(4-fluoro)phenyl-4-(2-oxo-5H-pyrrol-4-yl)methyl-morpholine;
51) 2-(R)-(1-(R)-(2-Fluoro-5-trifluoromethyl)phenylethoxy)-3-(S)-phenyl-4-(2-oxo-5H-pyrrol-4-yl)methyl-morpholine;
52) 2-(R)-(1-(R)-(2-Fluoro-5-trifluoromethyl)phenylethoxy)-3-(S)-(4-fluoro)phenyl-4-(2-oxo-5H-pyrrol-4-yl)methyl-morpholine;
53) 2-(S)-(2-Chloro-5-trifluoromethyl)benzyloxy-3-(S)-phenyl-4-(3-(1,2,4-triazolo)methyl-morpholine;
54) 2-(S)-(2-Chloro-5-trifluoromethyl)benzyloxy-3-(S)-(4-fluoro)phenyl-4-(3-(1,2,4-triazolo)methyl-morpholine;
55) 2-(R)-(1-(R)-(2-Chloro-5-trifluoromethyl)phenylethoxy)-3-(S)-phenyl-4-(3-(1,2,4-triazolo)methyl-morpholine;
56) 2-(R)-(1-(R)-(2-Chloro-5-trifluoromethyl)phenylethoxy)-3-(S)-(4-fluoro)phenyl-4-(3-(1,2,4-triazolo)methyl-morpholine;
57) 2-(S)-(2-Chloro-5-trifluoromethyl)benzyloxy-3-(S)-phenyl-4-(3-(5-oxo-1,2,4-triazolo)methyl-morpholine;
58) 2-(S)-(2-Chloro-5-trifluoromethyl)benzyloxy-3-(S)-(4-fluoro)phenyl-4-(3-(5-oxo-1,2,4-triazolo)methyl-morpholine;
59) 2-(R)-(1-(R)-(2-Chloro-5-trifluoromethyl)phenylethoxy)-3-(S)-phenyl-4-(3-(5-oxo-1,2,4-triazolo)methyl-morpholine;
60) 2-(R)-(1-(R)-(2-Chloro-5-trifluoromethyl)phenylethoxy)-3-(S)-(4-fluoro)phenyl-4-(3-(5-oxo-1,2,4-triazolo)methyl-morpholine;
61) 2-(S)-(2-Chloro-5-trifluoromethyl)benzyloxy-3-(S)-phenyl-4-(4-(2-oxo-1,3-imidazolo)methyl-morpholine;
62) 2-(S)-(2-Chloro-5-trifluoromethyl)benzyloxy-3-(S)-(4-fluoro)phenyl-4-(4-(2-oxo-1,3-imidazolo)methyl-morpholine;

63) 2-(R)-(1-(R)-(2-Chloro-5-trifluoromethyl)phenylethoxy)-3-(S)-phenyl-4-(4-(2-oxo-1,3-imidazolo)methyl-morpholine;
64) 2-(R)-(1-(R)-(2-Chloro-5-trifluoromethyl)phenylethoxy)-3-(S)-(4-fluoro)phenyl-4-(4-(2-oxo-1,3-imidazolo)methyl-morpholine;
65) 2-(S)-(2-Chloro-5-trifluoromethyl)benzyloxy-3-(S)-phenyl-4-(2-imidazolo)methyl-morpholine;
66) 2-(S)-(2-Chloro-5-trifluoromethyl)benzyloxy-3-(S)-(4-fluoro)phenyl-4-(2-imidazolo)methyl-morpholine;
67) 2-(R)-(1-(R)-(2-Chloro-5-trifluoromethyl)phenylethoxy)-3-(S)-phenyl-4-(2-imidazolo)methyl-morpholine;
68) 2-(R)-(1-(R)-(2-Chloro-5-trifluoromethyl)phenylethoxy)-3-(S)-(4-fluoro)phenyl-4-(2-imidazolo)methyl-morpholine;
69) 2-(S)-(2-Chloro-5-trifluoromethyl)benzyloxy-3-(S)-phenyl-4-(4-imidazolo)methyl-morpholine;
70) 2-(S)-(2-Chloro-5-trifluoromethyl)benzyloxy-3-(S)-(4-fluoro)phenyl-4-(4-imidazolo)methyl-morpholine;
71) 2-(R)-(1-(R)-(2-Chloro-5-trifluoromethyl)phenylethoxy)-3-(S)-phenyl-4-(4-imidazolo)methyl-morpholine;
72) 2-(R)-(1-(R)-(2-Chloro-5-trifluoromethyl)phenylethoxy)-3-(S)-(4-fluoro)phenyl-4-(4-imidazolo)methyl-morpholine;
73) 2-(S)-(2-Chloro-5-trifluoromethyl)benzyloxy-3-(S)-phenyl-4-(5-tetrazolo)methyl-morpholine;
74) 2-(S)-(2-Chloro-5-trifluoromethyl)benzyloxy-3-(S)-(4-fluoro)phenyl-4-(5-tetrazolo)methyl-morpholine;
75) 2-(R)-(1-(R)-(2-Chloro-5-trifluoromethyl)phenylethoxy)-3-(S)-phenyl-4-(5-tetrazolo)methyl-morpholine;
76) 2-(R)-(1-(R)-(2-Chloro-5-trifluoromethyl)phenylethoxy)-3-(S)-(4-fluoro)phenyl-4-(5-tetrazolo)methyl-morpholine;
77) 2-(S)-(2-Chloro-5-trifluoromethyl)benzyloxy-3-(S)-phenyl-4-(2-oxo-5H-pyrrol-4-yl)methyl-morpholine;
78) 2-(S)-(2-Chloro-5-trifluoromethyl)benzyloxy-3-(S)-(4-fluoro)phenyl-4-(2-oxo-5H-pyrrol-4-yl)methyl-morpholine;
79) 2-(R)-(1-(R)-(2-Chloro-5-trifluoromethyl)phenylethoxy)-3-(S)-phenyl-4-(2-oxo-5H-pyrrol-4-yl)methyl-morpholine;
80) 2-(R)-(1-(R)-(2-Chloro-5-trifluoromethyl)phenylethoxy)-3-(S)-(4-fluoro)phenyl-4-(2-oxo-5H-pyrrol-4-yl)methyl-morpholine;
81) 2-(S)-(3-Methyl)benzyloxy-3-(S)-phenyl-4-(3-(1,2,4-triazolo)methyl-morpholine;
82) 2-(S)-(3-Methyl)benzyloxy-3-(S)-(4-fluoro)phenyl-4-(3-(1,2,4-triazolo)methyl-morpholine;
83) 2-(R)-(1-(R)-(3-Methyl)phenylethoxy)-3-(S)-phenyl-4-(3-(1,2,4-triazolo)methyl-morpholine;
84) 2-(R)-(1-(R)-(3-Methyl)phenylethoxy)-3-(S)-(4-fluoro)phenyl-4-(3-(1,2,4-triazolo)methyl-morpholine;
85) 2-(S)-(3-Methyl)benzyloxy-3-(S)-phenyl-4-(3-(5-oxo-1,2,4-triazolo)methyl-morpholine;
86) 2-(S)-(3-Methyl)benzyloxy-3-(S)-(4-fluoro)phenyl-4-(3-(5-oxo-1,2,4-triazolo)methyl-morpholine;
87) 2-(R)-(1-(R)-(3-Methyl)phenylethoxy)-3-(S)-phenyl-4-(3-(5-oxo-1,2,4-triazolo)methyl-morpholine;
88) 2-(R)-(1-(R)-(3-Methyl)phenylethoxy)-3-(S)-(4-fluoro)phenyl-4-(3-(5-oxo-1,2,4-triazolo)methyl-morpholine;
89) 2-(S)-(3-Methyl)benzyloxy-3-(S)-phenyl-4-(4-(2-oxo-1,3-imidazolo)methyl-morpholine;
90) 2-(S)-(3-Methyl)benzyloxy-3-(S)-(4-fluoro)phenyl-4-(4-(2-oxo-1,3-imidazolo)methyl-morpholine;
91) 2-(R)-(1-(R)-(3-Methyl)phenylethoxy)-3-(S)-phenyl-4-(4-(2-oxo-1,3-imidazolo)methyl-morpholine;
92) 2-(R)-(1-(R)-(3-Methyl)phenylethoxy)-3-(S)-(4-fluoro)phenyl-4-(4-(2-oxo-1,3-imidazolo)methyl-morpholine;
93) 2-(S)-(3-Methyl)benzyloxy-3-(S)-phenyl-4-(2-imidazolo)methyl-morpholine;
94) 2-(S)-(3-Methyl)benzyloxy-3-(S)-(4-fluoro)phenyl-4-(2-imidazolo)methyl-morpholine;
95) 2-(R)-(1-(R)-(3-Methyl)phenylethoxy)-3-(S)-phenyl-4-(2-imidazolo)methyl-morpholine;
96) 2-(R)-(1-(R)-(3-Methyl)phenylethoxy)-3-(S)-(4-fluoro)phenyl-4-(2-imidazolo)methyl-morpholine;
97) 2-(S)-(3-Methyl)benzyloxy-3-(S)-phenyl-4-(4-imidazolo)methyl-morpholine;
98) 2-(S)-(3-Methyl)benzyloxy-3-(S)-(4-fluoro)phenyl-4-(4-imidazolo)methyl-morpholine;
99) 2-(R)-(1-(R)-(3-Methyl)phenylethoxy)-3-(S)-phenyl-4-(4-imidazolo)methyl-morpholine;
100) 2-(R)-(1-(R)-(3-Methyl)phenylethoxy)-3-(S)-(4-fluoro)phenyl-4-(4-imidazolo)methyl-morpholine;
101) 2-(S)-(3-Methyl)benzyloxy-3-(S)-phenyl-4-(5-tetrazolo)methyl-morpholine;
102) 2-(S)-(3-Methyl)benzyloxy-3-(S)-(4-fluoro)phenyl-4-(5-tetrazolo)methyl-morpholine;
103) 2-(R)-(1-(R)-(3-Methyl)phenylethoxy)-3-(S)-phenyl-4-(5-tetrazolo)methyl-morpholine;
104) 2-(R)-(1-(R)-(3-Methyl)phenylethoxy)-3-(S)-(4-fluoro)phenyl-4-(5-tetrazolo)methyl-morpholine;
105) 2-(S)-(3-Methyl)benzyloxy-3-(S)-phenyl-4-(2-oxo-5H-pyrrol-4-yl)methyl-morpholine;
106) 2-(S)-(3-Methyl)benzyloxy-3-(S)-(4-fluoro)phenyl-4-(2-oxo-5H-pyrrol-4-yl)methyl-morpholine;
107) 2-(R)-(1-(R)-(3-Methyl)phenylethoxy)-3-(S)-phenyl-4-(2-oxo-5H-pyrrol-4-yl)methyl-morpholine;
108) 2-(R)-(1-(R)-(3-Methyl)phenylethoxy)-3-(S)-(4-fluoro)phenyl-4-(2-oxo-5H-pyrrol-4-yl)methyl-morpholine;
109) 2-(S)-(3-Bromo)benzyloxy-3-(S)-phenyl-4-(3-(1,2,4-triazolo)methyl-morpholine;
110) 2-(S)-(3-Bromo)benzyloxy-3-(S)-(4-fluoro)phenyl-4-(3-(1,2,4-triazolo)methyl-morpholine;
111) 2-(R)-(1-(R)-(3-Bromo)phenylethoxy)-3-(S)-phenyl-4-(3-(1,2,4-triazolo)methyl-morpholine;
112) 2-(R)-(1-(R)-(3-Bromo)phenylethoxy)-3-(S)-(4-fluoro)phenyl-4-(3-(1,2,4-triazolo)methyl-morpholine;
113) 2-(S)-(3-Bromo)benzyloxy-3-(S)-phenyl-4-(3-(5-oxo-1,2,4-triazolo)methyl-morpholine;
114) 2-(S)-(3-Bromo)benzyloxy-3-(S)-(4-fluoro)phenyl-4-(3-(5-oxo-1,2,4-triazolo)methyl-morpholine;
115) 2-(R)-(1-(R)-(3-Bromo)phenylethoxy)-3-(S)-phenyl-4-(3-(5-oxo-1,2,4-triazolo)methyl-morpholine;
116) 2-(R)-(1-(R)-(3-Bromo)phenylethoxy)-3-(S)-(4-fluoro)phenyl-4-(3-(5-oxo-1,2,4-triazolo)methyl-morpholine;
117) 2-(S)-(3-Bromo)benzyloxy-3-(S)-phenyl-4-(4-(2-oxo-1,3-imidazolo)methyl-morpholine;
118) 2-(S)-(3-Bromo)benzyloxy-3-(S)-(4-fluoro)phenyl-4-(4-(2-oxo-1,3-imidazolo)methyl-morpholine;
119) 2-(R)-(1-(R)-(3-Bromo)phenylethoxy)-3-(S)-phenyl-4-(4-(2-oxo-1,3-imidazolo)methyl-morpholine;
120) 2-(R)-(1-(R)-(3-Bromo)phenylethoxy)-3-(S)-(4-fluoro)phenyl-4-(4-(2-oxo-1,3-imidazolo)methyl-morpholine;
121) 2-(S)-(3-Bromo)benzyloxy-3-(S)-phenyl-4-(2-imidazolo)methyl-morpholine;
122) 2-(S)-(3-Bromo)benzyloxy-3-(S)-(4-fluoro)phenyl-4-(2-imidazolo)methyl-morpholine;

123) 2-(R)-(1-(R)-(3-Bromo)phenylethoxy)-3-(S)-phenyl-4-(2-imidazolo)methyl-morpholine;
124) 2-(R)-(1-(R)-(3-Bromo)phenylethoxy)-3-(S)-(4-fluoro)phenyl-4-(2-imidazolo)methyl-morpholine;
125) 2-(S)-(3-Bromo)benzyloxy-3-(S)-phenyl-4-(4-imidazolo)methyl-morpholine;
126) 2-(S)-(3-Bromo)benzyloxy-3-(S)-(4-fluoro)phenyl-4-(4-imidazolo)methyl-morpholine;
127) 2-(R)-(1-(R)-(3-Bromo)phenylethoxy)-3-(S)-phenyl-4-(4-imidazolo)methyl-morpholine;
128) 2-(R)-(1-(R)-(3-Bromo)phenylethoxy)-3-(S)-(4-fluoro)phenyl-4-(4-imidazolo)methyl-morpholine;
129) 2-(S)-(3-Bromo)benzyloxy-3-(S)-phenyl-4-(5-tetrazolo)methyl-morpholine;
130) 2-(S)-(3-Bromo)benzyloxy-3-(S)-(4-fluoro)phenyl-4-(5-tetrazolo)methyl-morpholine;
131) 2-(R)-(1-(R)-(3-Bromo)phenylethoxy)-3-(S)-phenyl-4-(5-tetrazolo)methyl-morpholine;
132) 2-(R)-(1-(R)-(3-Bromo)phenylethoxy)-3-(S)-(4-fluoro)phenyl-4-(5-tetrazolo)methyl-morpholine;
133) 2-(S)-(3-Bromo)benzyloxy-3-(S)-phenyl-4-(2-oxo-5H-pyrrol-4-yl)methyl-morpholine;
134) 2-(S)-(3-Bromo)benzyloxy-3-(S)-(4-fluoro)phenyl-4-(2-oxo-5H-pyrrol-4-yl)methyl-morpholine;
135) 2-(R)-(1-(R)-(3-Bromo)phenylethoxy)-3-(S)-phenyl-4-(2-oxo-5H-pyrrol-4-yl)methyl-morpholine;
136) 2-(R)-(1-(R)-(3-Bromo)phenylethoxy)-3-(S)-(4-fluoro)phenyl-4-(2-oxo-5H-pyrrol-4-yl)methyl-morpholine;
137) 2-(S)-(3-Chloro)benzyloxy-3-(S)-phenyl-4-(3-(1,2,4-triazolo)methyl-morpholine;
138) 2-(S)-(3-Chloro)benzyloxy-3-(S)-(4-fluoro)phenyl-4-(3-(1,2,4-triazolo)methyl-morpholine;
139) 2-(R)-(1-(R)-(3-Chloro)phenylethoxy)-3-(S)-phenyl-4-(3-(1,2,4-triazolo)methyl-morpholine;
140) 2-(R)-(1-(R)-(3-Chloro)phenylethoxy)-3-(S)-(4-fluoro)phenyl-4-(3-(1,2,4-triazolo)methyl-morpholine;
141) 2-(S)-(3-Chloro)benzyloxy-3-(S)-phenyl-4-(3-(5-oxo-1,2,4-triazolo)methyl-morpholine;
142) 2-(S)-(3-Chloro)benzyloxy-3-(S)-(4-fluoro)phenyl-4-(3-(5-oxo-1,2,4-triazolo)methyl-morpholine;
143) 2-(R)-(1-(R)-(3-Chloro)phenylethoxy)-3-(S)-phenyl-4-(3-(5-oxo-1,2,4-triazolo)methyl-morpholine;
144) 2-(R)-(1-(R)-(3-Chloro)phenylethoxy)-3-(S)-(4-fluoro)phenyl-4-(3-(5-oxo-1,2,4-triazolo)methyl-morpholine;
145) 2-(S)-(3-Chloro)benzyloxy-3-(S)-phenyl-4-(4-(2-oxo-1,3-imidazolo)methyl-morpholine;
146) 2-(S)-(3-Chloro)benzyloxy-3-(S)-(4-fluoro)phenyl-4-(4-(2-oxo-1,3-imidazolo)methyl-morpholine;
147) 2-(R)-(1-(R)-(3-Chloro)phenylethoxy)-3-(S)-phenyl-4-(4-(2-oxo-1,3-imidazolo)methyl-morpholine;
148) 2-(R)-(1-(R)-(3-Chloro)phenylethoxy)-3-(S)-(4-fluoro)phenyl-4-(4-(2-oxo-1,3-imidazolo)methyl-morpholine;
149) 2-(S)-(3-Chloro)benzyloxy-3-(S)-phenyl-4-(2-imidazolo)methyl-morpholine;
150) 2-(S)-(3-Chloro)benzyloxy-3-(S)-(4-fluoro)phenyl-4-(2-imidazolo)methyl-morpholine;
151) 2-(R)-(1-(R)-(3-Chloro)phenylethoxy)-3-(S)-phenyl-4-(2-imidazolo)methyl-morpholine;
152) 2-(R)-(1-(R)-(3-Chloro)phenylethoxy)-3-(S)-(4-fluoro)phenyl-4-(2-imidazolo)methyl-morpholine;
153) 2-(S)-(3-Chloro)benzyloxy-3-(S)-phenyl-4-(4-imidazolo)methyl-morpholine;
154) 2-(S)-(3-Chloro)benzyloxy-3-(S)-(4-fluoro)phenyl-4-(4-imidazolo)methyl-morpholine;
155) 2-(R)-(1-(R)-(3-Chloro)phenylethoxy)-3-(S)-phenyl-4-(4-imidazolo)methyl-morpholine;
156) 2-(R)-(1-(R)-(3-Chloro)phenylethoxy)-3-(S)-(4-fluoro)phenyl-4-(4-imidazolo)methyl-morpholine;
157) 2-(S)-(3-Chloro)benzyloxy-3-(S)-phenyl-4-(5-tetrazolo)methyl-morpholine;
158) 2-(S)-(3-Chloro)benzyloxy-3-(S)-(4-fluoro)phenyl-4-(5-tetrazolo)methyl-morpholine;
159) 2-(R)-(1-(R)-(3-Chloro)phenylethoxy)-3-(S)-phenyl-4-(5-tetrazolo)methyl-morpholine;
160) 2-(R)-(1-(R)-(3-Chloro)phenylethoxy)-3-(S)-(4-fluoro)phenyl-4-(5-tetrazolo)methyl-morpholine;
161) 2-(S)-(3-Chloro)benzyloxy-3-(S)-phenyl-4-(2-oxo-5H-pyrrol-4-yl)methyl-morpholine;
162) 2-(S)-(3-Chloro)benzyloxy-3-(S)-(4-fluoro)phenyl-4-(2-oxo-5H-pyrrol-4-yl)methyl-morpholine;
163) 2-(R)-(1-(R)-(3-Chloro)phenylethoxy)-3-(S)-phenyl-4-(2-oxo-5H-pyrrol-4-yl)methyl-morpholine;
164) 2-(R)-(1-(R)-(3-Chloro)phenylethoxy)-3-(S)-(4-fluoro)phenyl-4-(2-oxo-5H-pyrrol-4-yl)methyl-morpholine;
165) 2-(S)-(3-Trifluoromethyl)benzyloxy-3-(S)-phenyl-4-(3-(1,2,4-triazolo)methylmorpholine;
166) 2-(S)-(3-Trifluoromethyl)benzyloxy-3-(S)-(4-fluoro)phenyl-4-(3-(1,2,4-triazolo)methyl-morpholine;
167) 2-(R)-(1-(R)-(3-Trifluoromethyl)phenylethoxy)-3-(S)-phenyl-4-(3-(1,2,4-triazolo)methyl-morpholine;
168) 2-(R)-(1-(R)-(3-Trifluoromethyl)phenylethoxy)-3-(S)-(4-fluoro)phenyl-4-(3-(1,2,4-triazolo)methyl-morpholine;
169) 2-(S)-(3-Trifluoromethyl)benzyloxy-3-(S)-phenyl-4-(3-(5-oxo-1,2,4-triazolo)methyl-morpholine;
170) 2-(S)-(3-Trifluoromethyl)benzyloxy-3-(S)-(4-fluoro)phenyl-4-(3-(5-oxo-1,2,4-triazolo)methyl-morpholine;
171) 2-(R)-(1-(R)-(1-(3-(trifluoromethyl)naphthyl))ethoxy)-3-(S)-phenyl-4-(3-(2-oxo-1,3-imidazolo)methyl-morpholine;
172) 2-(R)-(1-(R)-(3-Trifluoromethyl)phenylethoxy)-3-(S)-(4-fluoro)phenyl-4-(3-(5-oxo-1,2,4-triazolo)methyl-morpholine;
173) 2-(S)-(3-Trifluoromethyl)benzyloxy-3-(S)-phenyl-4-(4-(2-oxo-1,3-imidazolo)methyl-morpholine;
174) 2-(S)-(3-Trifluoromethyl)benzyloxy-3-(S)-(4-fluoro)phenyl-4-(4-(2-oxo-1,3-imidazolo)methyl-morpholine;
175) 2-(R)-(1-(R)-(3-Trifluoromethyl)phenylethoxy)-3-(S)-phenyl-4-(4-(2-oxo-1,3-imidazolo)methyl-morpholine;
176) 2-(R)-(1-(R)-(3-Trifluoromethyl)phenylethoxy)-3-(S)-(4-fluoro)phenyl-4-(4-(2-oxo-1,3-imidazolo)methyl-morpholine;
177) 2-(S)-(3-Trifluoromethyl)benzyloxy-3-(S)-phenyl-4-(2-imidazolo)methyl-morpholine;
178) 2-(S)-(3-Trifluoromethyl)benzyloxy-3-(S)-(4-fluoro)phenyl-4-(2-imidazolo)methyl-morpholine;
179) 2-(R)-(1-(R)-(3-Trifluoromethyl)phenylethoxy)-3-(S)-phenyl-4-(2-imidazolo)methyl-morpholine;
180) 2-(R)-(1-(R)-(3-Trifluoromethyl)phenylethoxy)-3-(S)-(4-fluoro)phenyl-4-(2-imidazolo)methyl-morpholine;
181) 2-(S)-(3-Trifluoromethyl)benzyloxy-3-(S)-phenyl-4-(4-imidazolo)methyl-morpholine;
182) 2-(S)-(3-Trifluoromethyl)benzyloxy-3-(S)-(4-fluoro)phenyl-4-(4-imidazolo)methyl-morpholine;
183) 2-(R)-(1-(R)-(3-Trifluoromethyl)phenylethoxy)-3-(S)-phenyl-4-(4-imidazolo)methyl-morpholine;
184) 2-(R)-(1-(R)-(3-Trifluoromethyl)phenylethoxy)-3-(S)-(4-fluoro)phenyl-4-(4-imidazolo)methyl-morpholine;
185) 2-(S)-(3-Trifluoromethyl)benzyloxy-3-(S)-phenyl-4-(5-tetrazolo)methyl-morpholine;
186) 2-(S)-(3-Trifluoromethyl)benzyloxy-3-(S)-(4-fluoro)phenyl-4-(5-tetrazolo)methyl-morpholine;

187) 2-(R)-(1-(R)-(3-Trifluoromethyl)phenylethoxy)-3-(S)-phenyl-4-(5-tetrazolo)methyl-morpholine;
188) 2-(R)-(1-(R)-(3-Trifluoromethyl)phenylethoxy)-3-(S)-(4-fluoro)phenyl-4-(5-tetrazolo)methyl-morpholine;
189) 2-(S)-(3-Trifluoromethyl)benzyloxy-3-(S)-phenyl-4-(2-oxo-5H-pyrrol-4-yl)methyl-morpholine;
190) 2-(S)-(3-Trifluoromethyl)benzyloxy-3-(S)-(4-fluoro)phenyl-4-(2-oxo-5H-pyrrol-4-yl)methyl-morpholine;
191) 2-(R)-(1-(R)-(3-Trifluoromethyl)phenylethoxy)-3-(S)-phenyl-4-(2-oxo-5H-pyrrol-4-yl)methyl-morpholine;
192) 2-(R)-(1-(R)-(3-Trifluoromethyl)phenylethoxy)-3-(S)-(4-fluoro)phenyl-4-(2-oxo-5H-pyrrol-4-yl)methyl-morpholine;
193) 2-(S)-(3-t-Butyl)benzyloxy-3-(S)-phenyl-4-(3-(1,2,4-triazolo)methyl-morpholine;
194) 2-(S)-(3-t-Butyl)benzyloxy-3-(S)-(4-fluoro)phenyl-4-(3-(1,2,4-triazolo)methyl-morpholine;
195) 2-(R)-(1-(R)-(3-t-Butyl)phenylethoxy)-3-(S)-phenyl-4-(3-(1,2,4-triazolo)methyl-morpholine;
196) 2-(R)-(1-(R)-(3-t-Butyl)phenylethoxy)-3-(S)-(4-fluoro)phenyl-4-(3-(1,2,4-triazolo)methyl-morpholine;
197) 2-(S)-(3-t-Butyl)benzyloxy-3-(S)-phenyl-4-(3-(5-oxo-1,2,4-triazolo)methyl-morpholine;
198) 2-(S)-(3-t-Butyl)benzyloxy-3-(S)-(4-fluoro)phenyl-4-(3-(5-oxo-1,2,4-triazolo)methyl-morpholine;
199) 2-(R)-(1-(R)-(3-t-Butyl)phenylethoxy)-3-(S)-phenyl-4-(3-(5-oxo-1,2,4-triazolo)methyl-morpholine;
200) 2-(R)-(1-(R)-(3-t-Butyl)phenylethoxy)-3-(S)-(4-fluoro)phenyl-4-(3-(5-oxo-1,2,4-triazolo)methyl-morpholine;
201) 2-(S)-(3-t-Butyl)benzyloxy-3-(S)-phenyl-4-(4-(2-oxo-1,3-imidazolo)methyl-morpholine;
202) 2-(S)-(3-t-Butyl)benzyloxy-3-(S)-(4-fluoro)phenyl-4-(4-(2-oxo-1,3-imidazolo)methyl-morpholine;
203) 2-(R)-(1-(R)-(3-t-Butyl)phenylethoxy)-3-(S)-phenyl-4-(4-(2-oxo-1,3-imidazolo)methyl-morpholine;
204) 2-(R)-(1-(R)-(3-t-Butyl)phenylethoxy)-3-(S)-(4-fluoro)phenyl-4-(4-(2-oxo-1,3-imidazolo)methyl-morpholine;
205) 2-(S)-(3-t-Butyl)benzyloxy-3-(S)-phenyl-4-(2-imidazolo)methyl-morpholine;
206) 2-(S)-(3-t-Butyl)benzyloxy-3-(S)-(4-fluoro)phenyl-4-(2-imidazolo)methyl-morpholine;
207) 2-(R)-(1-(R)-(3-t-Butyl)phenylethoxy)-3-(S)-phenyl-4-(2-imidazolo)methyl-morpholine;
208) 2-(R)-(1-(R)-(3-t-Butyl)phenylethoxy)-3-(S)-(4-fluoro)phenyl-4-(2-imidazolo)methyl-morpholine;
209) 2-(S)-(3-t-Butyl)benzyloxy-3-(S)-phenyl-4-(4-imidazolo)methyl-morpholine;
210) 2-(S)-(3-t-Butyl)benzyloxy-3-(S)-(4-fluoro)phenyl-4-(4-imidazolo)methyl-morpholine;
211) 2-(R)-(1-(R)-(3-t-Butyl)phenylethoxy)-3-(S)-phenyl-4-(4-imidazolo)methyl-morpholine;
212) 2-(R)-(1-(R)-(3-t-Butyl)phenylethoxy)-3-(S)-(4-fluoro)phenyl-4-(4-imidazolo)methyl-morpholine;
213) 2-(S)-(3-t-Butyl)benzyloxy-3-(S)-phenyl-4-(5-tetrazolo)methyl-morpholine;
214) 2-(S)-(3-t-Butyl)benzyloxy-3-(S)-(4-fluoro)phenyl-4-(5-tetrazolo)methyl-morpholine;
215) 2-(R)-(1-(R)-(3-t-Butyl)phenylethoxy)-3-(S)-phenyl-4-(5-tetrazolo)methyl-morpholine;
216) 2-(R)-(1-(R)-(3-t-Butyl)phenylethoxy)-3-(S)-(4-fluoro)phenyl-4-(5-tetrazolo)methyl-morpholine;
217) 2-(S)-(3-t-Butyl)benzyloxy-3-(S)-phenyl-4-(2-oxo-5H-pyrrol-4-yl)methyl-morpholine;
218) 2-(S)-(3-t-Butyl)benzyloxy-3-(S)-(4-fluoro)phenyl-4-(2-oxo-5H-pyrrol-4-yl)methyl-morpholine;
219) 2-(R)-(1-(R)-(3-t-Butyl)phenylethoxy)-3-(S)-phenyl-4-(2-oxo-5H-pyrrol-4-yl)methyl-morpholine;
220) 2-(R)-(1-(R)-(3-t-Butyl)phenylethoxy)-3-(S)-(4-fluoro)phenyl-4-(2-oxo-5H-pyrrol-4-yl)methyl-morpholine;
221) 2-(R)-(1-(R)-(3-(thiomethylphenyl)ethoxy)-3-(S)-phenyl-4-(3-(5-oxo-1,2,4-triazolo)methyl-morpholine;
222) 2-(R)-(1-(R)-(3-(thiomethylphenyl)ethoxy)-3-(S)-phenyl-4-(3-(1,2,4-triazolo)methyl-morpholine;
223) 2-(R)-(1-(R)-(3-(thiomethylphenyl)ethoxy)-3-(S)-phenyl-4-(3-(2-oxo-1,3-imidazolo)methyl-morpholine;
224) 2-(R)-(1-(R)-(3-(thiomethyl-5-(trifluoromethyl)phenyl)ethoxy)-3-(S)-phenyl-4-(3-(5-oxo-1,2,4-triazolo)methyl-morpholine;
225) 2-(R)-(1-(R)-(3-(thiomethyl-5-(trifluoromethyl)phenyl)ethoxy)-3-(S)-phenyl-4-(3-(1,2,4-triazolo)methyl-morpholine;
226) 2-(R)-(1-(R)-(3-(thiomethyl-5-(trifluoromethyl)phenyl)ethoxy)-3-(S)-phenyl-4-(3-(2-oxo-1,3-imidazolo)methyl-morpholine;
227) 2-(R)-(1-(R)-(2,2-(dimethyl)-5-(thiomethyl)-2,3-dihydrobenzofuran-7-yl)ethoxy)-3-(S)-phenyl-4-(3-(5-oxo-1,2,4-triazolo)methyl-morpholine;
228) 2-(R)-(1-(R)-(2,2-(dimethyl)-5-(thiomethyl)-2,3-dihydrobenzofuran-7-yl)ethoxy)-3-(S)-phenyl-4-(3-(1,2,4-triazolo)methyl-morpholine;
229) 2-(R)-(1-(R)-(2,2-(dimethyl)-5-(thiomethyl)-2,3-dihydrobenzofuran-7-yl)ethoxy)-3-(S)-phenyl-4-(3-(2-oxo-1,3-imidazolo)methyl-morpholine;
230) 2-(R)-(1-(R)-(3,5-(dimethoxy)phenyl)ethoxy)-3-(S)-phenyl-4-(3-(5-oxo-1,2,4-triazolo)methyl-morpholine;
231) 2-(R)-(1-(R)-(3,5-(dimethoxy)phenyl)ethoxy)-3-(S)-phenyl-4-(3-(1,2,4-triazolo)methyl-morpholine;
232) 2-(R)-(1-(R)-(3,5-(dimethoxy)phenyl)ethoxy)-3-(S)-phenyl-4-(3-(2-oxo-1,3-imidazolo)methyl-morpholine;
233) 2-(R)-(1-(R)-(3-(fluoro)-5-(trifluoromethyl)ethoxy)-3-(S)-(4-fluoro)phenyl-4-(3-(5-oxo-1,2,4-triazolo)methyl-morpholine;
234) 2-(R)-(1-(R)-(3-(fluoro)-5-(trifluoromethyl)ethoxy)-3-(S)-(4-fluoro)phenyl-4-(3-(1,2,4-triazolo)methyl-morpholine;
235) 2-(R)-(1-(R)-(3-(fluoro)-5-(trifluoromethyl)ethoxy)-3-(S)-(4-fluoro)phenyl-4-(3-(2-oxo-1,3-imidazolo)methyl-morpholine;
236) 2-(R)-(1-(R)-(3-(chloro)-5-(trifluoromethyl)ethoxy)-3-(S)-(4-fluoro)phenyl-4-(3-(5-oxo-1,2,4-triazolo)methyl-morpholine;
237) 2-(R)-(1-(R)-(3-(chloro)-5-(trifluoromethyl)ethoxy)-3-(S)-(4-fluoro)phenyl-4-(3-(1,2,4-triazolo)methyl-morpholine;
238) 2-(R)-(1-(R)-(3-(chloro)-5-(trifluoromethyl)ethoxy)-3-(S)-(4-fluoro)phenyl-4-(3-(2-oxo-1,3-imidazolo)methyl-morpholine;
239) 2-(R)-(1-(R)-(3,5-(dimethyl)phenyl)ethoxy)-3-(S)-(4-fluoro)phenyl-4-(3-(5-oxo-1,2,4-triazolo)methyl-morpholine;
240) 2-(R)-(1-(R)-(3,5-(dimethyl)phenyl)ethoxy)-3-(S)-(4-fluoro)phenyl-4-(3-(1,2,4-triazolo)methyl-morpholine;
241) 2-(R)-(1-(R)-(3,5-(dimethyl)phenyl)ethoxy)-3-(S)-(4-fluoro)phenyl-4-(3-(2-oxo-1,3-imidazolo)methyl-morpholine;
242) 2-(R)-(1-(R)-(3-(fluoro)-5-(methyl)phenyl)ethoxy)-3-(S)-(4-fluoro)phenyl-4-(3-(5-oxo-1,2,4-triazolo)methyl-morpholine;
243) 2-(R)-(1-(R)-(3-(fluoro)-5-(methyl)phenyl)ethoxy)-3-(S)-(4-fluoro)phenyl-4-(3-(1,2,4-triazolo)methyl-morpholine;

244) 2-(R)-(1-(R)-(3-(fluoro)-5-(methyl)phenyl)ethoxy)-3-(S)-(4-fluoro)phenyl-4-(3-(2-oxo-1,3-imidazolo)methyl-morpholine;

245) 2-(R)-(1-(R)-(3-(chloro)-5-(methyl)phenyl)ethoxy)-3-(S)-(4-fluoro)phenyl-4-(3-(5-oxo-1,2,4-triazolo)methyl-morpholine;

246) 2-(R)-(1-(R)-(3-(chloro)-5-(methyl)phenyl)ethoxy)-3-(S)-(4-fluoro)phenyl-4-(3-(1,2,4-triazolo)methyl-morpholine;

247) 2-(R)-(1-(R)-(3-(chloro)-5-(methyl)phenyl)ethoxy)-3-(S)-(4-fluoro)phenyl-4-(3-(2-oxo-1,3-imidazolo)methyl-morpholine;

248) 2-(R)-(1-(R)-(3-(bromo)-5-(methyl)phenyl)ethoxy)-3-(S)-(4-fluoro)phenyl-4-(3-(5-oxo-1,2,4-triazolo)methyl-morpholine;

249) 2-(R)-(1-(R)-(3-(bromo)-5-(methyl)phenyl)ethoxy)-3-(S)-(4-fluoro)phenyl-4-(3-(1,2,4-triazolo)methyl-morpholine;

250) 2-(R)-(1-(R)-(3-(bromo)-5-(methyl)phenyl)ethoxy)-3-(S)-(4-fluoro)phenyl-4-(3-(2-oxo-1,3-imidazolo)methyl-morpholine;

251) 2-(R)-(1-(R)-(3-(isopropoxy)phenyl)ethoxy)-3-(S)-(4-fluoro)phenyl-4-(3-(5-oxo-1,2,4-triazolo)methyl-morpholine;

252) 2-(R)-(1-(R)-(3-(isopropoxy)phenyl)ethoxy)-3-(S)-(4-fluoro)phenyl-4-(3-(1,2,4-triazolo)methyl-morpholine;

253) 2-(R)-(1-(R)-(3-(isopropoxy)phenyl)ethoxy)-3-(S)-(4-fluoro)phenyl-4-(3-(2-oxo-1,3-imidazolo)methyl-morpholine;

254) 2-(R)-(1-(R)-(3-(isopropoxy)-5-(trifluoromethyl)phenyl)ethoxy)-3-(S)-(4-fluoro)phenyl-4-(3-(5-oxo-1,2,4-triazolo)methyl-morpholine;

255) 2-(R)-(1-(R)-(3-(isopropoxy)-5-(trifluoromethyl)phenyl)ethoxy)-3-(S)-(4-fluoro)phenyl-4-(3-(1,2,4-triazolo)methyl-morpholine;

256) 2-(R)-(1-(R)-(3-(isopropoxy)-5-(trifluoromethyl)phenyl)ethoxy)-3-(S)-(4-fluoro)phenyl-4-(3-(2-oxo-1,3-imidazolo)methyl-morpholine;

257) 2-(R)-(1-(R)-(3-(chloro)-5-(isopropoxy)phenyl)ethoxy)-3-(S)-(4-fluoro)phenyl-4-(3-(5-oxo-1,2,4-triazolo)methyl-morpholine;

258) 2-(R)-(1-(R)-(3-(chloro)-5-(isopropoxy)phenyl)ethoxy)-3-(S)-(4-fluoro)phenyl-4-(3-(1,2,4-triazolo)methyl-morpholine;

259) 2-(R)-(1-(R)-(3-(chloro)-5-(isopropoxy)phenyl)ethoxy)-3-(S)-(4-fluoro)phenyl-4-(3-(2-oxo-1,3-imidazolo)methyl-morpholine;

260) 2-(R)-(1-(R)-(3-(fluoro)-5-(isopropoxy)phenyl)ethoxy)-3-(S)-(4-fluoro)phenyl-4-(3-(5-oxo-1,2,4-triazolo)methyl-morpholine;

261) 2-(R)-(1-(R)-(3-(fluoro)-5-(isopropoxy)phenyl)ethoxy)-3-(S)-(4-fluoro)phenyl-4-(3-(1,2,4-triazolo)methyl-morpholine;

262) 2-(R)-(1-(R)-(3-(fluoro)-5-(isopropoxy)phenyl)ethoxy)-3-(S)-(4-fluoro)phenyl-4-(3-(2-oxo-1,3-imidazolo)methyl-morpholine;

263) 2-(R)-(1-(R)-(3-(t-butyl)-5-(chloro)phenyl)ethoxy)-3-(S)-(4-fluoro)phenyl-4-(3-(5-oxo-1,2,4-triazolo)methyl-morpholine;

264) 2-(R)-(1-(R)-(3-(t-butyl)-5-(chloro)phenyl)ethoxy)-3-(S)-(4-fluoro)phenyl-4-(3-(1,2,4-triazolo)methyl-morpholine;

265) 2-(R)-(1-(R)-(3-(t-butyl)-5-(chloro)phenyl)ethoxy)-3-(S)-(4-fluoro)phenyl-4-(3-(2-oxo-1,3-imidazolo)methyl-morpholine;

266) 2-(R)-(1-(R)-(3-(t-butyl)-5-(trifluoromethyl)phenyl)ethoxy)-3-(S)-(4-fluoro)phenyl-4-(3-(5-oxo-1,2,4-triazolo)methyl-morpholine;

267) 2-(R)-(1-(R)-(3-(t-butyl)-5-(trifluoromethyl)phenyl)ethoxy)-3-(S)-(4-fluoro)phenyl-4-(3-(1,2,4-triazolo)methyl-morpholine;

268) 2-(R)-(1-(R)-(3-(t-butyl)-5-(trifluoromethyl)phenyl)ethoxy)-3-(S)-(4-fluoro)phenyl-4-(3-(2-oxo-1,3-imidazolo)methyl-morpholine;

269) 2-(R)-(1-(R)-(3,5-(dimethyl)-4-(fluoro)phenyl)ethoxy)-3-(S)-(4-fluoro)phenyl-4-(3-(5-oxo-1,2,4-triazolo)methyl-morpholine;

270) 2-(R)-(1-(R)-(3,5-(dimethyl)-4-(fluoro)phenyl)ethoxy)-3-(S)-(4-fluoro)phenyl-4-(3-(1,2,4-triazolo)methyl-morpholine;

271) 2-(R)-(1-(R)-(3,5-(dimethyl)-4-(fluoro)phenyl)ethoxy)-3-(S)-(4-fluoro)phenyl-4-(3-(2-oxo-1,3-imidazolo)methyl-morpholine;

272) 2-(R)-(1-(R)-(3,5-(dimethyl)-4-(chloro)phenyl)ethoxy)-3-(S)-(4-fluoro)phenyl-4-(3-(5-oxo-1,2,4-triazolo)methyl-morpholine;

273) 2-(R)-(1-(R)-(3,5-(dimethyl)-4-(chloro)phenyl)ethoxy)-3-(S)-(4-fluoro)phenyl-4-(3-(1,2,4-triazolo)methyl-morpholine;

274) 2-(R)-(1-(R)-(3,5-(dimethyl)-4-(chloro)phenyl)ethoxy)-3-(S)-(4-fluoro)phenyl-4-(3-(2-oxo-1,3-imidazolo)methyl-morpholine;

275) 2-(R)-(1-(R)-(3,5-bis(trifluoromethyl)-4-(fluoro)phenyl)ethoxy)-3-(S)-(4-fluoro)phenyl-4-(3-(5-oxo-1,2,4-triazolo)methyl-morpholine;

276) 2-(R)-(1-(R)-(3,5-bis(trifluoromethyl)-4-(fluoro)phenyl)ethoxy)-3-(S)-(4-fluoro)phenyl-4-(3-(1,2,4-triazolo)methyl-morpholine;

277) 2-(R)-(1-(R)-(3,5-bis(trifluoromethyl)-4-(fluoro)phenyl)ethoxy)-3-(S)-(4-fluoro)phenyl-4-(3-(2-oxo-1,3-imidazolo)methyl-morpholine;

278) 2-(R)-(1-(R)-(3,5-bis(trifluoromethyl)-4-(chloro)phenyl)ethoxy)-3-(S)-(4-fluoro)phenyl-4-(3-(5-oxo-1,2,4-triazolo)methyl-morpholine;

279) 2-(R)-(1-(R)-(3,5-bis(trifluoromethyl)-4-(chloro)phenyl)ethoxy)-3-(S)-(4-fluoro)phenyl-4-(3-(1,2,4-triazolo)methyl-morpholine;

280) 2-(R)-(1-(R)-(3,5-bis(trifluoromethyl)-4-(chloro)phenyl)ethoxy)-3-(S)-(4-fluoro)phenyl-4-(3-(2-oxo-1,3-imidazolo)methyl-morpholine;

281) 2-(R)-(1-(R)-(3,5-(dichloro)phenyl)ethoxy)-3-(S)-(4-fluoro)phenyl-4-(3-(5-oxo-1,2,4-triazolo)methyl-morpholine;

282) 2-(R)-(1-(R)-(3,5-(dichloro)phenyl)ethoxy)-3-(S)-(4-fluoro)phenyl-4-(3-(1,2,4-triazolo)methyl-morpholine;

283) 2-(R)-(1-(R)-(3,5-(dichloro)phenyl)ethoxy)-3-(S)-(4-fluoro)phenyl-4-(3-(2-oxo-1,3-imidazolo)methyl-morpholine;

284) 2-(R)-(1-(R)-(3,5-(difluoro)phenyl)ethoxy)-3-(S)-(4-fluoro)phenyl-4-(3-(5-oxo-1,2,4-triazolo)methyl-morpholine;

285) 2-(R)-(1-(R)-(3,5-(difluoro)phenyl)ethoxy)-3-(S)-(4-fluoro)phenyl-4-(3-(1,2,4-triazolo)methyl-morpholine;

286) 2-(R)-(1-(R)-(3,5-(difluoro)phenyl)ethoxy)-3-(S)-(4-fluoro)phenyl-4-(3-(2-oxo-1,3-imidazolo)methyl-morpholine;

287) 2-(R)-(1-(R)-(1-(naphthyl)ethoxy)-3-(S)-(4-fluoro)phenyl-4-(3-(5-oxo-1,2,4-triazolo)methyl-morpholine;

288) 2-(R)-(1-(R)-(1-(naphthyl)ethoxy)-3-(S)-(4-fluoro)phenyl-4-(3-(1,2,4-triazolo)methyl-morpholine;

289) 2-(R)-(1-(R)-(1-(naphthyl)ethoxy)-3-(S)-(4-fluoro)phenyl-4-(3-(2-oxo-1,3-imidazolo)methyl-morpholine;

290) 2-(R)-(1-(R)-(1-(4-(fluoro)naphthyl))ethoxy)-3-(S)-(4-fluoro)phenyl-4-(3-(5-oxo-1,2,4-triazolo)methyl-morpholine;

291) 2-(R)-(1-(R)-(1-(4-(fluoro)naphthyl))ethoxy)-3-(S)-(4-fluoro)phenyl-4-(3-(1,2,4-triazolo)methyl-morpholine;
292) 2-(R)-(1-(R)-(1-(4-(fluoro)naphthyl))ethoxy)-3-(S)-(4-fluoro)phenyl-4-(3-(2-oxo-1,3-imidazolo)methyl-morpholine;
293) 2-(R)-(1-(R)-(1-(3-(fluoro)naphthyl))ethoxy)-3-(S)-(4-fluoro)phenyl-4-(3-(5-oxo-1,2,4-triazolo)methyl-morpholine;
294) 2-(R)-(1-(R)-(1-(3-(fluoro)naphthyl))ethoxy)-3-(S)-(4-fluoro)phenyl-4-(3-(1,2,4-triazolo)methyl-morpholine;
295) 2-(R)-(1-(R)-(1-(3-(fluoro)naphthyl))ethoxy)-3-(S)-(4-fluoro)phenyl-4-(3-(2-oxo-1,3-imidazolo)methyl-morpholine;
296) 2-(R)-(1-(R)-(1-(3-(chloro)naphthyl))ethoxy)-3-(S)-(4-fluoro)phenyl-4-(3-(5-oxo-1,2,4-triazolo)methyl-morpholine;
297) 2-(R)-(1-(R)-(1-(3-(chloro)naphthyl))ethoxy)-3-(S)-(4-fluoro)phenyl-4-(3-(1,2,4-triazolo)methyl-morpholine;
298) 2-(R)-(1-(R)-(1-(3-(chloro)naphthyl))ethoxy)-3-(S)-(4-fluoro)phenyl-4-(3-(2-oxo-1,3-imidazolo)methyl-morpholine;
299) 2-(R)-(1-(R)-(1-(3-(methyl)naphthyl))ethoxy)-3-(S)-(4-fluoro)phenyl-4-(3-(5-oxo-1,2,4-triazolo)methyl-morpholine;
300) 2-(R)-(1-(R)-(1-(3-(methyl)naphthyl))ethoxy)-3-(S)-(4-fluoro)phenyl-4-(3-(1,2,4-triazolo)methyl-morpholine;
301) 2-(R)-(1-(R)-(1-(3-(methyl)naphthyl))ethoxy)-3-(S)-(4-fluoro)phenyl-4-(3-(2-oxo-1,3-imidazolo)methyl-morpholine;
302) 2-(R)-(1-(R)-(1-(3-(trifluoromethyl)naphthyl))ethoxy)-3-(S)-(4-fluoro)phenyl-4-(3-(5-oxo-1,2,4-triazolo)methyl-morpholine;
303) 2-(R)-(1-(R)-(1-(3-(trifluoromethyl)naphthyl))ethoxy)-3-(S)-(4-fluoro)phenyl-4-(3-(1,2,4-triazolo)methyl-morpholine;
304) 2-(R)-(1-(R)-(1-(3-(trifluoromethyl)naphthyl))ethoxy)-3-(S)-(4-fluoro)phenyl-4-(3-(2-oxo-1,3-imidazolo)methyl-morpholine;
305) 2-(R)-(1-(R)-(3-(thiomethylphenyl)ethoxy)-3-(S)-(4-fluoro)phenyl-4-(3-(5-oxo-1,2,4-triazolo)methyl-morpholine;
306) 2-(R)-(1-(R)-(3-(thiomethylphenyl)ethoxy)-3-(S)-(4-fluoro)phenyl-4-(3-(1,2,4-triazolo)methyl-morpholine;
307) 2-(R)-(1-(R)-(3-(thiomethylphenyl)ethoxy)-3-(S)-(4-fluoro)phenyl-4-(3-(2-oxo-1,3-imidazolo)methyl-morpholine;
308) 2-(R)-(1-(R)-(3-(thiomethyl-5-(trifluoromethyl)phenyl)ethoxy)-3-(S)-(4-fluoro)phenyl-4-(3-(5-oxo-1,2,4-triazolo)methyl-morpholine;
309) 2-(R)-(1-(R)-(3-(thiomethyl-5-(trifluoromethyl)phenyl)ethoxy)-3-(S)-(4-fluoro)phenyl-4-(3-(1,2,4-triazolo)methyl-morpholine;
310) 2-(R)-(1-(R)-(3-(thiomethyl-5-(trifluoromethyl)phenyl)ethoxy)-3-(S)-(4-fluoro)phenyl-4-(3-(2-oxo-1,3-imidazolo)methyl-morpholine;
311) 2-(R)-(1-(R)-(2,2-(dimethyl)-5-(thiomethyl)-2,3-dihydrobenzofuran-7-yl)ethoxy)-3-(S)-(4-fluoro)phenyl-4-(3-(5-oxo-1,2,4-triazolo)methyl-morpholine;
312) 2-(R)-(1-(R)-(2,2-(dimethyl)-5-(thiomethyl)-2,3-dihydrobenzofuran-7-yl)ethoxy)-3-(S)-(4-fluoro)phenyl-4-(3-(1,2,4-triazolo)methyl-morpholine;
313) 2-(R)-(1-(R)-(2,2-(dimethyl)-5-(thiomethyl)-2,3-dihydrobenzofuran-7-yl)ethoxy)-3-(S)-(4-fluoro)phenyl-4-(3-(2-oxo-1,3-imidazolo)methyl-morpholine;
314) 2-(R)-(1-(R)-(3,5-(dimethoxy)phenyl)ethoxy)-3-(S)-(4-fluoro)phenyl-4-(3-(5-oxo-1,2,4-triazolo)methyl-morpholine;
315) 2-(R)-(1-(R)-(3,5-(dimethoxy)phenyl)ethoxy)-3-(S)-(4-fluoro)phenyl-4-(3-(1,2,4-triazolo)methyl-morpholine;
316) 2-(R)-(1-(R)-(3,5-(dimethoxy)phenyl)ethoxy)-3-(S)-(4-fluoro)phenyl-4-(3-(2-oxo-1,3-imidazolo)methyl-morpholine;
317) 2-(R)-(1-(R)-(phenyl)ethoxy)-3-(S)-phenyl-4-(3-(5-oxo-1,2,4-triazolo)methyl-morpholine;
318) 2-(R)-(1-(R)-(phenyl)ethoxy)-3-(S)-phenyl-4-(3-(1,2,4-triazolo)methyl-morpholine;
319) 2-(R)-(1-(R)-(phenyl)ethoxy)-3-(S)-phenyl-4-(3-(2-oxo-1,3-imidazolo)methyl-morpholine;
320) 2-(R)-(1-(R)-(phenyl)ethoxy)-3-(S)-(4-fluoro)phenyl-4-(3-(5-oxo-1,2,4-triazolo)methyl-morpholine;
321-2-(R)-(1-(R)-(phenyl)ethoxy)-3-(S)-(4-fluoro)phenyl-4-(3-(1,2,4-triazolo)methyl-morpholine;
322) 2-(R)-(1-(R)-(phenyl)ethoxy)-3-(S)-(4-fluoro)phenyl-4-(3-(2-oxo-1,3-imidazolo)methyl-morpholine;
323) 2-(R)-(1-(R)-(3-(fluoro)phenyl)ethoxy)-3-(S)-phenyl-4-(3-(5-oxo-1,2,4-triazolo)methyl-morpholine;
324) 2-(R)-(1-(R)-(3-(fluoro)phenyl)ethoxy)-3-(S)-phenyl-4-(3-(1,2,4-triazolo)methyl-morpholine;
325) 2-(R)-(1-(R)-(3-(fluoro)phenyl)ethoxy)-3-(S)-phenyl-4-(3-(2-oxo-1,3-imidazolo)methyl-morpholine;
326) 2-(R)-(1-(R)-(3-(fluoro)phenyl)ethoxy)-3-(S)-(4-fluoro)phenyl-4-(3-(5-oxo-1,2,4-triazolo)methyl-morpholine;
327) 2-(R)-(1-(R)-(3-(fluoro)phenyl)ethoxy)-3-(S)-(4-fluoro)phenyl-4-(3-(1,2,4-triazolo)methyl-morpholine;
328) 2-(R)-(1-(R)-(3-(fluoro)phenyl)ethoxy)-3-(S)-(4-fluoro)phenyl-4-(3-(2-oxo-1,3-imidazolo)methyl-morpholine;
329) 2-(R)-(1-(R)-(4-(fluoro)phenyl)ethoxy)-3-(S)-phenyl-4-(3-(5-oxo-1,2,4-triazolo)methyl-morpholine;
330) 2-(R)-(1-(R)-(4-(fluoro)phenyl)ethoxy)-3-(S)-phenyl-4-(3-(1,2,4-triazolo)methyl-morpholine;
331) 2-(R)-(1-(R)-(4-(fluoro)phenyl)ethoxy)-3-(S)-phenyl-4-(3-(2-oxo-1,3-imidazolo)methyl-morpholine;
332) 2-(R)-(1-(R)-(4-(fluoro)phenyl)ethoxy)-3-(S)-(4-fluoro)phenyl-4-(3-(5-oxo-1,2,4-triazolo)methyl-morpholine;
332) 2-(R)-(1-(R)-(4-(fluoro)phenyl)ethoxy)-3-(S)-(4-fluoro)phenyl-4-(3-(1,2,4-triazolo)methyl-morpholine;
333) 2-(R)-(1-(R)-(4-(fluoro)phenyl)ethoxy)-3-(S)-(4-fluoro)phenyl-4-(3-(2-oxo-1,3-imidazolo)methyl-morpholine;
334) 2-(R)-(1-(R)-(3,5-bis(trifluoromethyl)phenyl)ethoxy)-3-(S)-(3-fluoro)phenyl-4-(3-(5-oxo-1,2,4-triazolo)methyl-morpholine;
335) 2-(R)-(1-(R)-(3,5-bis(trifluoromethyl)phenyl)ethoxy)-3-(S)-(3-fluoro)phenyl-4-(3-(1,2,4-triazolo)methyl-morpholine;
336) 2-(R)-(1-(R)-(3,5-bis(trifluoromethyl)phenyl)ethoxy)-3-(S)-(3-fluoro)phenyl-4-(3-(2-oxo-1,3-imidazolo)methyl-morpholine;
337) 2-(R)2-(R)-(1-(R)-(3,5-bis(trifluoromethyl)phenyl)ethoxy)-3-(S)-(3,4-difluoro)phenyl-4-(3-(5-oxo-1,2,4-triazolo)methyl-morpholine;
338) 2-(R)-(1-(R)-(3,5-bis(trifluoromethyl)phenyl)ethoxy)-3-(S)-(3,4-difluoro)phenyl-4-(3-(1,2,4-triazolo)methyl-morpholine;
339) 2-(R)-(1-(R)-(3,5-bis(trifluoromethyl)phenyl)ethoxy)-3-(S)-(3,4-difluoro)phenyl-4-(3-(2-oxo-1,3-imidazolo)methyl-morpholine;
340) 2-(R)-(1-(R)-(3,5-bis(trifluoromethyl)phenyl)ethoxy)-3-(S)-(3,4-dichloro)phenyl-4-(3-(5-oxo-1,2,4-triazolo)methyl-morpholine;
341) 2-(R)-(1-(R)-(3,5-bis(trifluoromethyl)phenyl)ethoxy)-3-(S)-(3,4-dichloro)phenyl-4-(3-(1,2,4-triazolo)methyl-morpholine;

342) 2-(R)-(1-(R)-(3,5-bis(trifluoromethyl)phenyl)ethoxy)-3-(S)-(3,4-dichloro)phenyl-4-(3-(2-oxo-1,3-imidazolo)methyl-morpholine;

343) 2-(R)-(1-(R)-(3,5-bis(trifluoromethyl)phenyl)ethoxy)-3-(S)-(3,4-dimethyl)phenyl-4-(3-(5-oxo-1,2,4-triazolo)methyl-morpholine;

344) 2-(R)-(1-(R)-(3,5-bis(trifluoromethyl)phenyl)ethoxy)-3-(S)-(3,4-dimethyl)phenyl-4-(3-(1,2,4-triazolo)methyl-morpholine;

345) 2-(R)-(1-(R)-(3,5-bis(trifluoromethyl)phenyl)ethoxy)-3-(S)-(3,4-dimethyl)phenyl-4-(3-(2-oxo-1,3-imidazolo)methyl-morpholine;

346) 2-(R)-(1-(R)-(3,5-bis(trifluoromethhyl)phenyl)ethoxy)-3-(S)-3,4-methylenedioxyphenyl-4-(3-(5-oxo-1,2,4-triazolo)methyl-morpholine;

347) 2-(R)-(1-(R)-(3,5-bis(trifluoromethhyl)phenyl)ethoxy)-3-(S)-3,4-methylenedioxyphenyl-4-(3 o (1,2,4-triazolo)methyl-morpholine;

348) 2-(R)-(1-(R)-(3,5-bis(trifluoromethyl)phenyl)ethoxy)-3-(S)-3,4-methylenedioxyphenyl-4-(3-(2-oxo-1,3-imidazolo)methyl-morpholine;

349) 2-(R)-(1-(R)-(3,5-bis(trifluoromethyl)phenyl)ethoxy)-3-(S)-(2-naphthyl)-4-(3-(5-oxo-1,2,4-triazolo)methyl-morpholine;

350) 2-(R)-(1-(R)-(3,5-bis(trifluoromethyl)phenyl)ethoxy)-3-(S)-(2-naphthyl)-4-(3-(1,2,4-triazolo)methyl-morpholine;

351) 2-(R)-(1-(R)-(3,5-bis(trifluoromethyl)phenyl)ethoxy)-3-(S)-(2-naphthyl)4-(3-(2-oxo-1,3-imidazolo)methyl-morpholine;

352) 2-(R)-(1-(R)-(3-(fluoro)-5-(trifluoromethyl)ethoxy)-3-(S)-phenyl-4-(3-(-1,2,4-triazolo)methyl-morpholine;

353) 2-(R)-(1-(R)-(3-(fluoro)-5-(trifluoromethyl)ethoxy)-3-(S)-phenyl-4-(3-(2-oxo-1,3-imidazolo)methyl-morpholine;

354) 2-(R)-(1-(R)-(3-(chloro)-5-(trifluoromethyl)ethoxy)-3-(S)-phenyl-4-(3-(-1,2,4-triazolo)methyl-morpholine;

355) 2-(R)-(1-(R)-(3-(chloro)-5-(trifluoromethyl)ethoxy)-3-(S)-phenyl-4-(3-(2-oxo-1,3-imidazolo)methyl-morpholine;

356) 2-(R)-(1-(R)-(3,5-(dimethyl)phenyl)ethoxy)-3-(S)-phenyl-4-(3-(-1,2,4-triazolo)methyl-morpholine;

357) 2-(R)-(1-(R)-(3,5-(dimethyl)phenyl)ethoxy)-3-(S)-phenyl-4-(3-(2-oxo-1,3-imidazolo)methyl-morpholine;

358) 2-(R)-(1-(R)-(3-(fluoro)-5-(methyl)phenyl)ethoxy)-3-(S)-phenyl-4-(3-(-1,2,4-triazolo)methyl-morpholine;

359) 2-(R)-(1-(R)-(3-(fluoro)-5-(methyl)phenyl)ethoxy)-3-(S)-phenyl-4-(3-(2-oxo-1,3-imidazolo)methyl-morpholine;

360) 2-(R)-(1-(R)-(3-(chloro)-5-(methyl)phenyl)ethoxy)-3-(S)-phenyl-4-(3-(-1,2,4-triazolo)methyl-morpholine;

361) 2-(R)-(1-(R)-(3-(chloro)-5-(methyl)phenyl)ethoxy)-3-(S)-phenyl-4-(3-(2-oxo-1,3-imidazolo)methyl-morpholine;

362) 2-(R)-(1-(R)-(3-(bromo)-5-(methyl)phenyl)ethoxy)-3-(S)-phenyl-4-(3-(-1,2,4-triazolo)methyl-morpholine;

363) 2-(R)-(1-(R)-(3-(bromo)-5-(methyl)phenyl)ethoxy)-3-(S)-phenyl-4-(3-(2-oxo-1,3-imidazolo)methyl-morpholine;

364) 2-(R)-(1-(R)-(3-(isopropoxy)phenyl)ethoxy)-3-(S)-phenyl-4-(3-(-1,2,4-triazolo)methyl-morpholine;

365) 2-(R)-(1-(R)-(3-(isopropoxy)phenyl)ethoxy)-3-(S)-phenyl-4-(3-(2-oxo-1,3-imidazolo)methyl-morpholine;

366) 2-(R)-(1-(R)-(3-(isopropoxy)-5-(trifluoromethyl)phenyl)ethoxy)-3-(S)-phenyl-4-(3-(-1,2,4-triazolo)methyl-morpholine;

367) 2-(R)-(1-(R)-(3-(isopropoxy)-5-(trifluoromethyl)phenyl)ethoxy)-3-(S)-phenyl-4-(3-(2-oxo-1,3-imidazolo)methyl-morpholine;

368) 2-(R)-(1-(R)-(3-(chloro)-5-(isopropoxy)phenyl)ethoxy)-3-(S)-phenyl-4-(3-(-1,2,4-triazolo)methyl-morpholine;

369) 2-(R)-(1-(R)-(3-(chloro)-5-(isopropoxy)phenyl)ethoxy)-3-(S)-phenyl-4-(3-(2-oxo-1,3-imidazolo)methyl-morpholine;

370) 2-(R)-(1-(R)-(3-(fluoro)-5-(isopropoxy)phenyl)ethoxy)-3-(S)-phenyl-4-(3-(-1,2,4-triazolo)methyl-morpholine;

371) 2-(R)-(1-(R)-(3-(fluoro)-5-(isopropoxy)phenyl)ethoxy)-3-(S)-phenyl-4-(3-(2-oxo-1,3-imidazolo)methyl-morpholine;

372) 2-(R)-(1-(R)-(3-(t-butyl)-5-(chloro)phenyl)ethoxy)-3-(S)-phenyl-4-(3-(-1,2,4-triazolo)methyl-morpholine;

373) 2-(R)-(1-(R)-(3-(t-butyl)-5-(chloro)phenyl)ethoxy)-3-(S)-phenyl-4-(3-(2-oxo-1,3-imidazolo)methyl-morpholine;

374) 2-(R)-(1-(R)-(3-(t-butyl)-5-(trifluoromethyl)phenyl)ethoxy)-3-(S)-phenyl-4-(3-(-1,2,4-triazolo)methyl-morpholine;

375) 2-(R)-(1-(R)-(3-(t-butyl)-5-(trifluoromethyl)phenyl)ethoxy)-3-(S)-phenyl-4-(3-(2-oxo-1,3-imidazolo)methyl-morpholine;

376) 2-(R)-(1-(R)-(3,5-(dimethyl)-4-(fluoro)phenyl)ethoxy)-3-(S)-phenyl-4-(3-(-1,2,4-triazolo)methyl-morpholine;

377) 2-(R)-(1-(R)-(3,5-(dimethyl)-4-(fluoro)phenyl)ethoxy)-3-(S)-phenyl-4-(3-(2-oxo-1,3-imidazolo)methyl-morpholine;

378) 2-(R)-(1-(R)-(3,5-(dimethyl)-4-(chloro)phenyl)ethoxy)-3-(S)-phenyl-4-(3-(-1,2,4-triazolo)methyl-morpholine;

379) 2-(R)-(1-(R)-(3,5-(dimethyl)-4-(chloro)phenyl)ethoxy)-3-(S)-phenyl-4-(3-(2-oxo-1,3-imidazolo)methyl-morpholine;

380) 2-(R)-(1-(R)-(3,5-bis(trifluoromethyl)-4-(fluoro)phenyl)ethoxy)-3-(S)-phenyl-4-(3-(-1,2,4-triazolo)methyl-morpholine;

381) 2-(R)-(1-(R)-(3,5-bis(trifluoromethyl)-4-(fluoro)phenyl)ethoxy)-3-(S)-phenyl-4-(3-(2-oxo-1,3-imidazolo)methyl-morpholine;

382) 2-(R)-(1-(R)-(3,5-bis(trifluoromethyl)-4-(chloro)phenyl)ethoxy)-3-(S)-phenyl-4-(3-(-1,2,4-triazolo)methyl-morpholine;

383) 2-(R)-(1-(R)-(3,5-bis(trifluoromethyl)-4-(chloro)phenyl)ethoxy)-3-(S)-phenyl-4-(3-(2-oxo-1,3-imidazolo)methyl-morpholine;

384) 2-(R)-(1-(R)-(3,5-(dichloro)phenyl)ethoxy)-3-(S)-phenyl-4-(3-(-1,2,4-triazolo)methyl-morpholine;

385) 2-(R)-(1-(R)-(3,5-(dichloro)phenyl)ethoxy)-3-(S)-phenyl-4-(3-(2-oxo-1,3-imidazolo)methyl-morpholine;

386) 2-(R)-(1-(R)-(3,5-(difluoro)phenyl)ethoxy)-3-(S)-phenyl-4-(3-(-1,2,4-triazolo)methyl-morpholine;

387) 2-(R)-(1-(R)-(3,5-(difluoro)phenyl)ethoxy)-3-(S)-phenyl-4-(3-(2-oxo-1,3-imidazolo)methyl-morpholine;

388) 2-(R)-(1-(R)-(1-(naphthyl)ethoxy)-3-(S)-phenyl-4-(3-(-1,2,4-triazolo)methyl-morpholine;

389) 2-(R)-(1-(R)-(1-(naphthyl)ethoxy)-3-(S)-phenyl-4-(3-(2-oxo-1,3-imidazolo)methyl-morpholine;

390) 2-(R)-(1-(R)-(1-(4-(fluoro)naphthyl))ethoxy)-3-(S)-phenyl-4-(3-(-1,2,4-triazolo)methyl-morpholine;

391) 2-(R)-(1-(R)-(1-(4-(fluoro)naphthyl))ethoxy)-3-(S)-phenyl-4-(3-(2-oxo-1,3-imidazolo)methyl-morpholine;

392) 2-(R)-(1-(R)-(1-(3-(fluoro)naphthyl))ethoxy)-3-(S)-phenyl-4-(3-(-1,2,4-triazolo)methyl-morpholine;

393) 2-(R)-(1-(R)-(1-(3-(fluoro)naphthyl))ethoxy)-3-(S)-phenyl-4-(3-(2-oxo-1,3-imidazolo)methyl-morpholine;

394) 2-(R)-(1-(R)-(1-(3-(chloro)naphthyl))ethoxy)-3-(S)-phenyl-4-(3-(-1,2,4-triazolo)methyl-morpholine;

395) 2-(R)-(1-(R)-(1-(3-(chloro)naphthyl))ethoxy)-3-(S)-phenyl-4-(3-(2-oxo-1,3-imidazolo)methyl-morpholine;
396) 2-(R)-(1-(R)-(1-(3-(methyl)naphthyl))ethoxy)-3-(S)-phenyl-4-(3-(-1,2,4-triazolo)methyl-morpholine; and
397) 2-(R)-(1-(R)-(1-(3-(methyl)naphthyl))ethoxy)-3-(S)-phenyl-4-(3-(2-oxo-1,3-imidazolo)methyl-morpholine.

EXAMPLE 88

2-(R)-(2,5-Bis(trifluoromethyl)benzoyloxy)-3-(S)-(4-fluorophenyl)-4-benzyl-morpholine The title compound was prepared from 3-(S)-(4-fluorophenyl)-4-benzyl-2-morpholinone (from Example 59) using a procedure analogous to Example 67.

Mass Spectrum (CI): m/Z 528 (M+H)

¹H NMR (CDCl₃, 360 MHz, ppm): δ 2.46 (dt, 1H), 2.90 (dd, 2H), 3.76 (dd, J=11.6, 2.0, 1H), 3.88 (d, J=13.6, 1H), 4.18 (t, 1H), 6.20 (d, J=2.8, 1H), 7.04 (d, J=8.4, 2H), 7.24–7.32 (m, 5H), 7.50, (m, 2H), 7.60 (s, 1H), 7.88 (dd, 2H).

EXAMPLE 89

2-(R)-(1-(2,5-Bis(trifluoromethyl)phenyl)ethenyloxy)-3-(S)-(4-fluorophenyl)-4-benzyl-morpholine The title compound was prepared from 2-(R)-(2,5-bis(trifluoromethyl)benzoyloxy)-3-(S)-(4-fluorophenyl)-4-benzyl-morpholine (from Example 88) using a procedure analogous to Example 68.

¹H NMR (CDCl₃, 250 MHz, ppm): δ 2.30 (dt, J=3.5, 11.9, 1H), 2.74 (app d, J=9.4, 1H), 2.82 (d, J=13.5, 1H), 3.55–3.60 (m, 2H), 3.72 (d, J=13.5, 1H), 4.10 (dt, J=2.4, 11.7, 1H), 4.22 (d, J=2.7, 1H), 4.67 (d, J=2.8, 1H), 5.18 (d, J=2.8, 1H), 6.90 (t, J=8.7, 2H), 7.08 (s, 1H), 7.13–7.23 (m, 5H), 7.36 (dd, J=5.6, 8.7, 2H), 7.62 (d, J=8.4, 1H), 7.72 (d, J=8.4, 1H).

EXAMPLE 90

2-(R)-(1-(R)-(2,5-Bis(trifluoromethyl)phenyl)ethoxy)-3-(S)-(4-fluorophenyl)-morpholine The title compound was prepared from 2-(R)-(1-(2,5-bis(trifluoromethyl)phenyl)ethenyloxy)-3-(S)-(4-fluorophenyl)-4-benzyl-morpholine (from Example 89) using a procedure analogous to Example 74.

Mass Spectrum (CI): m/Z 438 (M+H)

¹H NMR Spectrum (HCl salt, d₆-DMSO, 360 MHz, ppm): δ 1.47 (d, J=8.7, 3H), 3.88 (d, J=11.8, 1H), 4.20 (dt, J=3.7, 11.8, 1H), 4.50 (s, 1H), 4.58 (s, 1H), 5.17 (m, 1H), 7.04 (s, 1H), 7.23 (t, J=8.8, 2H), 7.55 (m, 2H), 7.77 (d, J=8.1, 1H), 7.88 (d, J=8.3, 1H), 10.1 (br s, 1H).

EXAMPLE 91

2-(R)-(1-(R)-(2,5-Bis(trifluoromethyl)phenyl)ethoxy)-3-(S)-(4-fluorophenyl)-4-(3-(5-oxo-1,2,4-triazolo)methyl-morpholine The title compound was prepared from 2-(R)-(1-(R)-(2,5-bis(trifluoromethyl)phenyl)ethoxy)-3-(S)-(4-fluorophenyl)-morpholine (from Example 90) using a procedure analogous to Example 70, mp 162°–168° C.

¹H NMR (d₆-DMSO, 360 MHz, ppm) δ 1.37 (d, J=6.4, 3H), 2.40 (dt, J=3.3, 11.9, 1H), 2.77 (d, J=14.0, 1H), 2.86 (d, J=11.5, 1H), 3.37 (d, J=14.4, 1H), 3.48 (d, J=2.7, 1H), 3.64 (d, J=11.0, 1H), 4.11 (t, J=9.8, 1H), 4.18 (d, J=2.8, 1H), 5.16 (q, J=6.2, 1H), 6.90 (s, 1H), 7.08 (t, J=8.8, 2H), 7.50 (br t, 1H), 7.74 (d, J=8.3, 1H), 7.85 (d, J=8.3, 1H), 11.25 s, 1H), 11.35 (s, 1H).

EXAMPLE 92

2-(R)-(1-(R)-(2,5-Bis(trifluoromethyl)phenyl)ethoxy)-3-(S)-(4-fluorophenyl)-4-(3-(1,2,4-triazolo)methyl)morpholine The title compound was prepared from 2-(R)-(1-(R)-(2,5-bis(trifluoromethyl)phenyl)ethoxy)-3-(S)-(4-fluorophenyl)-morpholine (from Example 90) using a procedure analogous to Example 17, mp 98°–100° C. Mass Spectrum (CI): m/Z 519 (M+H)

¹H NMR (d₆-DMSO, 360 MHz, ppm): δ 1.36 (d, J=6.4, 3H), 2.46 (dt, J=3.26, 11.9, 1H), 2.89 (d, J=11.0, 1H), 3.16 (d, J=13.9, 1H), 3.57–3.64 (m, 3H), 4.09 (t, J=10.5, 1H), 4.18 (d, J=2.6, 1H), 5.14 (q, J=6.4, 1H), 6.90 (s, 1H), 7.11 (t, J=8.7, 2H), 7.48 (m, 2H), 7.72 (d, J=8.3, 1H), 7.83 (d, J=8.3, 1H), 8.36 (br s), 13.8 (s, 1H).

EXAMPLE 93

2-(R)-(1-(R)-(2,5-Bis(trifluoromethyl)phenyl)ethoxy)-3-(S)-(4-fluorophenyl)-4-(4-(2-oxo-1,3-imidazolo)methyl)morpholine The title compound was prepared from 2-(R)-(1-(R)-(2,5-bis(trifluoromethyl)phenyl)ethoxy)-3-(S)-(4-fluorophenyl)-morpholine (from Example 90) using a procedure analogous to Example 83. A sample was recrystallized from aqueous ethanol, mp 203°–205° C.

¹H NMR (d₆-DMSO, 360 MHz, ppm): δ 1.35 (d, J=6.4, 3H), 2.25 (dt, J=3.1, 11.8, 1H), 2.58 (d, J=13.9, 1H), 2.88 (d, J=11.6, 1H), 3.24 (d, J=14.0, 1H), 3.35 (d, J=2.7, 1H), 3.64 (dd, J=9.6, 1H), 4.09 (t, J=9.8, 1H), 4.16 (d, J=2.7, 1H), 5.14 (q, J=6.5, 1H), 5.97 (s, 1H), 6.89 (s, 1H), 7.07 (t, J=8.7, 1H), 7.49 (m, 1H), 7.72 (d, J=8.1, 1H), 7.83 (d, J=8.3, 1H), 9.57 (s, 1H), 9.80 (s, 1H).

EXAMPLE 94

2-(S)-(3,5-Bis(trifluoromethyl)benzyloxy)-3-(S)-phenyl-4-(3-(5-oxo-1H,4H-1,2,4-triazolo)methyl)morpholine N-oxide A solution of 125 mg (0.25 mmol) of 2-(S)-(3,5-bis(trifluoromethyl)benzyloxy)-3-(S)-phenyl-4-(3-(5-oxo-1H,4H-1,2,4-triazolo)methylmorpholine in 10 mL of methylene chloride was treated with 100 mg of 80–85% 3-chloroperoxybenzoic acid and the resulting mixture was stirred at room temperature for 1 hour. The reaction mixture was concentrated in vacuo and the residue was partitioned between 25 mL of ethyl acetate and 25 mL of saturated aqueous sodium bicarbonate solution. The organic layer was separated, washed with 15 mL of 0.1N aqueous sodium hydroxide solution, dried over sodium sulfate and concentrated in vacuo to afford 142 mg of crude product. Flash chromatography on silica gel (15 mL column) using 95:5:0.5 v/v/v methylene chloride/methanol/water as the eluant afford 83 mg (64%) of the title compound. Mass Spectrum (NH₃-CI): m/Z 519 (20%, M⁺), 406 (90%), 404 (100%).

¹H NMR (CDCl₃, 500 MHz, ppm): δ 3.56–3.66 (m, 1H), 3.80 (br d, J=10.0, 1H), 3.95–4.20 (m, 3H), 4.43–4.47 (m, 1H), 4.50 (d, J=13.4, 1H), 4.86–4.94 (m, 3H), 7.32 (app s, 5H), 7.56 (s, 2H), 7.68 (s, 1H), 8.40 (br s, 1H) 12.15 (br s, 1H).

EXAMPLE 95

2-(S)-(3,5-Bis(trifluoromethyl)benzyloxy)-3-(S)-phenyl-4-(3-(4-(ethoxycarbonyloxy-1-ethyl)5-oxo-1H,-1,2,4-triazolo)methyl)morpholine A mixture of 250 mg (0.5 mmol) of 2-(S)-(3,5-bis(trifluoromethyl)benzyloxy)-3-(S)-phenyl-4-(3-(5-oxo-1H, 4H-1,2,4-triazolo)methylmorpholine, 70 mg (0.5 mmol) of N,N-diisopropylethylamine and 100 mg (1-chloroethyl) ethylcarbonate in 15 mL of dichloroethane was heated at reflux for 16 hours. TLC analysis of the reaction mixture indicated incomplete reaction; the dichloroethane solvent was replaced with toluene, 70 mg of N,N-diisopropylethylamine and 100 mg (1-chloroethyl) ethylcarbonate were added to the reaction and the resulting mixture was heated at reflux for 24 hours. At this time, an additional 70 mg of N,N-diisopropylethylamine and 100 mg (1-chloroethyl)ethylcarbonate were introduced into the reaction and the resulting mixture was heated at reflux for 24 hours. The reaction was cooled to room temperature and partitioned between 25 mL of ethyl acetate and 25 mL of saturated aqueous sodium bicarbonate solution and the layers were separated. The aqueous layer was extracted with ethyl acetate. The organic layers were combined, dried over sodium sulfate and concentrated in vacuo to afford 420 mg of crude product as a foam. Flash chromatography on silica gel (25 mL column) using 100:1 v/v, then 50:1 v/v methylene chloride/isopropanol as the eluant afforded 68 mg (22%) of the title compound.

Mass Spectrum (ESI): m/Z 619 (15%, M+1), 575 (100%).

$^1$H NMR (CDCl$_3$, 500 MHz, ppm): δ 1.38 (t, J=7.0, 3H), 2.61 (dt, J=3.0, 12.0, 1H), 2.90 (d, J=11.5, 1H), 3.03 (d, J=15.5, 1H), 3.63 (d, J=2.0, 1H), 3.66–3.71 (m, 2H), 4.20 (dt, J=2.0, 11.5, 1H), 4.41–4.45 (m, 2H), 4.48 (d, J=13.5, 1H), 4.71 (d, J=2.0, 1H), 4.81 (d, J=13.5, 1H), 7.34–7.48 (m, 5H), 7.47 (s, 2H), 7.72 (s, 1H), 10.1 (br s, 1H).

$^{13}$C NMR (CDCl$_3$, 125 MHz, ppm): δ 14.2, 25.2, 50.7, 52.6, 59.2, 64.1, 64.5, 67.7, 69.7, 97.9, 121.5, 123.1 (q, J=271), 127.2, 128.7, 129.1, 131.5 (q, J=32.9), 136.0, 140.0, 146.8, 148.4, 152.3, 163.1.

EXAMPLE 96

2-(R)-(1-(R)-(3,5-Bis(trifluoromethyl)phenyl) ethoxy)-3-(S)-(4-fluoro)phenyl-4-(3-(4-monophosphoryl-5-oxo-1H-1,2,4-triazolo)methyl) morpholine, dipotassium salt; or 2-(R)-(1-(R)-(3,5-Bis(trifluoromethyl)phenyl)ethoxy)-3-(S)-(4-fluoro)-phenyl-4-(3-(1-monophosphoryl-5-oxo-1H-1,2,4-triazolo)methyl)morpholine, dipotassium salt; or 2-(R)-(1-(R)-(3,5-Bis(trifluoromethyl)phenyl)ethoxy)-3-(S)-(4-fluoro)-phenyl-4-(3-(2-monophosphoryl-5-oxo-1H-1,2,4-triazolo)methyl)morpholine, dipotassium salt; or 2-(R)-(1-(R)-(3,5-Bis(trifluoromethyl)phenyl)ethoxy)-3-(S)-(4-fluoro)-phenyl-4-(3-(5-oxyphosphoryl-1H-1,2,4-triazolo) methyl)morpholine, dipotassium salt A solution of 450 mg (0.84 mmol) of 2-(R)-(1-(R)-(3,5-bis(trifluoro-methyl)phenyl)ethoxy)-3-(S)-(4-fluoro) phenyl-4-(3-(5-oxo-1H,,4H-1,2,4-triazolo) methylmorpholine in 20 mL of THF at 0° C. was treated with 0.84 mL of 1.0M n-butyllithium solution in hexanes. The resulting solution was stirred cold for 5 minutes and was treated with 630 mg (1.17 mmol) of tetrabenzylpyrophosphate in one portion as a solid. The cooling bath was removed and the reaction was stirred at room temperature for 45 minutes. The reaction was quenched with 25 mL of saturated aqueous sodium bicarbonate solution and was extracted with 50 mL of ethyl ether. The organic layer was separated, washed with 25 mL of saturated aqueous sodium bicarbonate solution, 25 mL of 0.5$\underline{N}$ aqueous potassium hydrogen sulfate solution, 25 mL of saturated aqueous sodium chloride solution, dried over magnesium sulfate and concentrated in vacuo. The crude dibenzyl ester was dissolved in 25 mL of methanol. A solution of 168 mg (1.68 mmol) of potassium bicarbonate was added to the ester solution and the resulting mixture was hydrogenated at 40 psi in the presence of 45 mg of 10% palladium on carbon catalyst for 75 minutes. The catalyst was filtered onto a pad of Celite; the reaction flask and falter cake were rinsed well with methanol (~200 mL), the filtrate was concentrated in vacuo and dried. The residue was partially dissolved in methanol and filtered; the filtrate was concentrated and dried. The resulting solid was recrystallized from isopropanol to afford 280 mg of crude title compound. The solid was partitioned between 40 mL of ethyl ether and 20 mL of water; mixing of the layers resulted in an emulsion. Centrifugation at 2800 rpm for 15 minutes broke the emulsion; the aqueous layer was separated and lyophilized to afford 188 mg (33%) of the compound tentatively identified as 2-(R)-(1-(R)-(3,5-bis(trifluoromethyl)phenyl)ethoxy)-3-(S)-(4-fluoro)-phenyl-4-(3-(4-monophosphoryl-5-oxo-1H-1,2,4-triazolo)methyl)-morpholine, dipotassium salt as a solid.

$^1$H NMR (CD$_3$OD, 500 MHz, ppm): δ 1.43 (d, J=6.5, 3H), 2.45 (app t, J=8.5, 1H), 2.80 (d, J=14.0, 1H), 2.92 (d, J=11.5, 1H), 3.47–3.66 (m, 4H), 4.25 (app t, J=11.5, 1H), 4.36 (d, J=1.5, 1H), 4.94 (q, J=6.6, 1H), 7.05 (t, J=8.5, 2H), 7.31(s, 2H), 7.52 (br s, 2H), 7.71 (s, 1H).

$^{13}$C NMR (CD$_3$OD, 125 MHz, ppm): δ 24.7, 52.3, 53.4, 60.5, 70.6, 73.7, 97.2, 116.1 (d, J=21.9), 122.3, 124.6 (q, J=271.0), 127.7, 132.3, 132.6, 132.8, 134.3, 145.2 (d, J=11.0), 147.5, 159.0 (d, J=10.1), 164.0 (d, J=244.4).

EXAMPLE 97

2-(R)-(1-(R)-(3,5-Bis(trifluoromethyl)-phenyl) ethoxy)-3-(S)-(4-fluoro)phenyl-4-(3-(1-phosphoryl-5-oxo-4H-1,2,4-triazolo)methylmorpholine, bis(N-methyl-D-glucamine) salt Tetrabenzylpyrophosphate was prepared in 71% yield using the procedure described by Khorana and Todd (J. Chem. Soc.,2257 (1953)). A solution of 2.00 g (3.7 mmol) of 2-(R)-(1-(R)-(3,5-bis(trifluormethyl)phenyl)ethoxy)-3-(S)-(4-fluoro)phenyl-4-(3-(1H,4H-5-oxo-1,2,4-triazolo) methylmorpholine and 2.80 g (5.2 mmol) of tetrabenzylpyrophosphate in 50 mL of dry tetrahydrofuran was cooled to 0° C. A 1.0M solution of sodium bis(trimethylsilyl)-amide ("NaHMDS", 9.4 mL, 9.4 mmol) was added to the cooled reaction mixture using a syringe pump at a rate of 1 equivalent/hour maintaining the internal temperature at 0° C. After the addition of the NaHMDS, the reaction was stirred at 0° C. for 15 minutes and quenched with 100 mL of saturated aqueous sodium bicarbonate solution. The quenched mixture was extracted with 300 mL of ethyl ether; the ether extract was washed with 100 mL of 0.5N aqueous potassium bisulfate solution, 100 mL of saturated aqueous sodium bicarbonate solution, 100 mL of saturated aqueous sodium chloride solution, dried over magnesium sulfate and concentrated in vacuo.

A solution of the crude dibenzyl ester in 50 mL of methanol, a solution of 1.45 g (7.4 mmol) of N-methyl-D-glucamine in 10 mL of water and 200 mg of 10% palladium on carbon catalyst were combined and the mixture was hydrogenated at 40 psi for 2 hours. The reaction mixture was filtered through a pad of Celite; the reaction flask and filter cake were rinsed well with methanol (400 mL). The filtrate was concentrated in vacuo. The crude product was redissolved in 25 mL of methanol; 125 mL of isopropanol was added to the solution and the resulting mixture was aged at room temperature for 30 minutes. The solid that had precipitated was filtered, washed with 75 mL of isopropanol, 75 mL of ethyl ether and air dried. The solid was partitioned between 150 mL of ethyl ether and 150 mL of water; an emulsion formed on mixing of the layers. The emulsion was transferred into 50 mL centrifuge tubes; centrifugation at 3000 rpm for 15 minutes caused separation of the layers. The organic layers were drawn off and the aqueous layers were combined, filtered and the filtrate lyophilized to afford 3.40 g of 2-(S)-(1-(R)-(3,5-bis(trifluoromethyl)phenyl)ethoxy)-3-(S)-(4-fluoro)phenyl-4-(3-(1-phosphoryl-5-oxo-4H-1,2,4-triazolo)methylmorpholine, bis(N-methyl-D-glucamine) salt as an amorphous solid. Its purity was determined to be >99% by HPLC. $^1$H NMR (CD$_3$OD, 500 MHz, ppm): δ 1.43 (d, J=6.6, 3H), 2.46 (app t, J=11.2, 1H), 2.72 (s, 6H), 2.84 (d, J=13.9, 1H), 2.94 (d, J=10.3, 1H), 3.12–3.30 (m, 4H), 3.42–3.83 (m, 14H), 4.19–4.25 (m, 3H), 4.35 (d, J=2.2, 1H), 7.04 (t, J=8.5, 2H), 7.30 (s, 2H), 7.52 (br s, 2H), 7.70 (s, 1H). $^{13}$C NMR (CD$_3$OD, 125 MHz, ppm): δ 24.7, 34.4, 52.3, 53.1, 53.5, 60.5, 64.7, 69.9, 70.4, 72.0, 72.4, 72.6, 73.6, 97.1, 116.2 (d, J=21.9), 122.3, 124.5 (q, J=271.0), 127.7, 132.3, 132.7 (q, J=33.8), 134.2, 145.9, 147.5, 158.9, 163.9 (d, J=245.3).

EXAMPLE 98

4-Fluoro-α-[(phenylmethyl)amino]benzeneacetic acid

4-Fluorobenzaldehyde (7.0 kg, 56.4 moles) was added to a solution of sodium metabisulfite (5.76 kg, 30.3 moles) in water (50 L) and rinsed in with methanol (5 L). Sodium cyanide (2.83 kg, 57.7 moles) was added and rinsed in with water (3 L). The batch was stirred at 25° C. for 15 minutes before cooling to 8° C. A solution of benzylamine (6.04 kg, 56.4 moles) in methanol (11 L) was added. The batch was warmed to 34° C. and stirred for 2 hours. Water (23 L) was added and the batch was extracted with isopropyl acetate (30 L). The organic layer was washed with water (2×10 L) followed by saturated aqueous sodium chloride (10 L), then evaporated under reduced pressure to give a nitrile compound. The batch was dissolved in dimethylsulfoxide (50 L). Potassium carbonate (3.27 kg, 23.7 moles) was added and rinsed in with dimethylsulfoxide (6 L). Hydrogen peroxide solution in water (30%, 9.43 L, 83.2 moles) was added and the batch was stirred at room temperature overnight. The batch was diluted with water (120 L) and cooled to 13° C. The batch was filtered and the filter cake was washed with water (50 L). The resulting amide compound was dried on the filter, then slurried in industrial methylated spirits (38 L). A solution of sodium hydroxide pellets (3.27 kg, 81.75 moles) in water (11 L) was added to the batch and rinsed in with industrial methylated spirits (6 L).

After heating at reflux (80° C.) for 3.5 hours, the batch was distilled to low volume, removing the industrial methylated spirits. The batch was diluted with water (100 L) and extracted with isopropyl acetate (30 L). The layers were separated and the aqueous layer was acidified to pH 5–6 with concentrated hydrochloric acid. The precipitated solid was filtered and washed with water (2×10 L), then collected and dried under vacuum to give 12.3 kg (84% yield from 4-fluorobenzaldehyde) of 4-fluoro-α-[(phenylmethyl)amino]benzeneacetic acid.

EXAMPLE 99

4-Fluoro-α-[(phenylmethyl)amino]benzeneacetic acid methyl ester hydrochloride

4-Fluoro-α-[(phenylmethyl)amino]benzeneacetic acid (12.2 kg, 47.1 moles) was slurried in methanol (37 L), then hydrogen chloride gas was passed over the mixture. The resulting slurry was stirred at 35°–45° C. for 3 hours, then concentrated to 30–35 L by distillation. Methyl-t-butyl ether (20 L) was added and the batch was seeded with 4-Fluoro-α-[(phenylmethyl)amino]benzeneacetic acid methyl ester hydrochloride. Upon development of the seed-bed, methyl-t-butyl ether (20 L) was added. The slurry was aged for 1 hour, then filtered. The falter cake was washed with methyl-t-butyl ether:methanol (95:5, 8.0 L), then dried under vacuum at 30° C. to give 12.2 kg (84% yield) of 4-fluoro-α-[(phenylmethyl)amino]-benzeneacetic acid methyl ester hydrochloride.

EXAMPLE 100

α-Amino-4-fluorobenzeneacetic acid methyl ester

4-Fluoro-α-[(phenylmethyl)amino]benzeneacetic acid methyl ester hydrochloride (12.2 kg, 39.4 moles) was added to a slurry of 10% palladium-on-carbon (1.2 kg) in isopropanol (50 L). Ammonium formate (5.0 kg, 79.4 moles) was added and the batch was heated to 50° C. Progress of the reaction was monitored by HPLC. The batch was filtered through Hyflo Supercel and the filter cake was washed with isopropanol (25 L). The filtrate was evaporated to low volume and flushed with isopropyl acetate (50 L). The residue was dissolved in isopropyl acetate (30 L) and washed with 5% aqueous potassium phosphate (40 L), followed by saturated aqueous sodium chloride (10 L). The solution was evaporated under vacuum to give 5.79 kg (87% yield) of racemic α-amino-4-fluorobenzeneacetic acid methyl ester.

HPLC Conditions—Column: Zorbax Rx-C8, 25 cm×4.6 mm; Column temperature: 40° C.; Mobile phase: acetonitrile: 0.1% aqueous phosphoric acid (70:30 v/v); Flow rate: 1 mL/min; Detection: UV at 220 nm; Approximate retention times: α-amino-4-fluorobenzeneacetic acid methyl ester: 2.2 minutes; 4-fluoro-α-[(phenylmethyl)amino]benzeneacetic acid methyl ester 2.6 minutes. If unreacted 4-fluoro-α-[(phenylmethyl)amino]-benzeneacetic acid methyl ester (>2%) remains after 1 hour, a second charge of 10% palladium-on-carbon (300 g) slurried in isopropanol (2.0 L) can be made, followed by ammonium formate (1.0 kg). Heating then continues until the reaction is complete.

EXAMPLE 101

(S)-α-Amino-4-fluorobenzeneacetic acid

A solution of racemic α-amino-4-fluorobenzeneacetic acid methyl ester (3.32 kg, 18.2 moles) in 96% ethanol (5 L) was filtered then water (500 mL) was added to it. A solution of di-O-benzoyl-D-tartaric acid (DBT, 1.32 kg, 3.7 moles) in water:ethanol (1:7, 2.86 L) was then added. The crystallization mixture was cooled to 5° C. and aged for 1.5 hours. The product was collected by filtration, washed with water:ethanol (1:7, 1.1 L), air dried, then dried under vacuum at 50° C. to give 1.91 kg of α-amino-4-fluorobenzeneacetic acid methyl ester, DBT salt (95.8% ee).

Solvent (6.6 L) was removed from the liquors by evaporation under reduced pressure. Benzaldehyde (120 mL) was added and the solution was stirred and heated at 50° C. for 4 hours. The solution was filtered and the solids were washed with water:ethanol (1:7, 2×150 mL) (chiral HPLC showed the filtrate to contain racemic α-amino-4-fluorobenzeneacetic acid methyl ester). A solution of di-O-benzoyl-D-tartaric acid (439 g, 1.23 moles) in water:ethanol (1:7, 960 mL) was added to the filtrate, which was then was cooled to 5° C. and aged for 1.5 hours. The product was collected by filtration, washed with water:ethanol (1:7, 2×1.1 L), air dried, then dried under vacuum at 50° C. to give 1.05 kg of α-amino-4-fluorobenzeneacetic acid methyl ester, DBT salt (95.4% ee). The combined yield of α-amino-4-fluorobenzeneacetic acid methyl ester, DBT salt was 2.96 kg (95% ee). The resolved α-amino-4-fluorobenzeneacetic acid methyl ester, DBT salt was partitioned between methyl-t-butyl ether (5 L) and 5.5M hydrochloric acid (6.2 L). The aqueous phase was washed with methyl-t-butyl ether (5 L), then filtered.

The α-amino-4-fluorobenzeneacetic acid methyl ester, DBT salt (2899 g, >95% ee) was partitioned between 5.5M hydrochloric acid (6.2 L) and the second methyl-t-butyl ether extract from above. The aqueous phase was re-extracted with methyl-t-butyl ether (5 L) and filtered. The aqueous filtrates were combined and concentrated by slow distillation of solvent. The batch was cooled and aged at 5° C. for 2 hours. The product was collected by filtration and air dried for 30 minutes to give 4.055 kg of (S)-α-amino-4-fluorobenzeneacetic acid, hydrochloride salt (98.7% ee).
(1) Recrystallization from 5.5M hydrochloric acid (5 L) gave (S)-α-amino-4-fluorobenzeneacetic acid, hydrochloride salt as a wet cake (3.28 kg, 99.8% ee).

This wet cake was heated in a mixture of water (12 L) and concentrated hydrochloric acid (375 mL). Concentrated aqueous ammonia (1.2 L) and water (4 L) were added, then the batch was cooled to 20° C., and aged overnight. The product was collected by filtration, washed with water (6×4 L), air dried, then dried under vacuum at 50° C. for 24 hours to give 1.905 kg of (S)-α-amino-4-fluorobenzeneacetic acid free base (>99.7% ee, 48% yield from racemic α-amino-4-fluorobenzeneacetic acid methyl ester).

Chiral HPLC Conditions: Column: Crownpak CR(+), 15 cm×4.5 mm; Column temperature: 40° C.; Mobile phase: pH 2.0 aqueous perchloric acid:methanol (95:5 v/v); Flow rate: 1 mL/min; Detection: UV at 220 nm; Approximate retention times: (R)-α-Amino-4-fluorobenzeneacetic acid: 2.9 minutes; (S)-α-Amino-4-fluorobenzeneacetic acid: 5.6 minutes; (R) α-Amino-4-fluorobenzeneacetic acid methyl ester: 7.7 minutes; (S) α-Amino-4-fluorobenzeneacetic acid methyl ester: 14.0 minutes.

EXAMPLE 102

(S)-4-Fluoro-α-[(phenylmethyl)amino]benzeneacetate sodium salt

A solution of (S)-α-amino-4-fluorobenzeneacetic acid (1.00 kg, 5.91 moles) in aqueous sodium hydroxide (1M, 5.91 L) was filtered and added to 10% palladium-on-carbon (25 g). A solution of benzaldehyde (941 g, 8.87 moles) was added and the batch was stirred under hydrogen (50 psi) for 4 hours. The batch was filtered and the filtrate was evaporated to residue under vacuum, then flushed with ethanol (2×3 L). The residue was slurried in boiling ethanol (1.5 L), then cooled to 15° C. The slurry was filtered and the filter cake was washed with cold ethanol (2×500 mL), then dried under vacuum at 55° C. to give 1.83 kg (92% yield) of (S)-4-fluoro-α-[(phenylmethyl)-amino]benzeneacetate sodium salt.

EXAMPLE 103

(S)-3-(4-Fluoropheny)-4-(phenylmethyl)-2-morpholinone hydrochloride (S)-4-Fluoro-α-[(phenylmethyl)-amino]benzeneacetate sodium salt (850 g, 3.02 moles) was added to 1,2-dibromoethane (4.85 kg, 25.8 moles) and diisopropylethylamine (419 g, 3.25 moles) in dimethylformamide (14.7 L). The batch was heated at 90° C. for 5 hours, then concentrated by distillation under vacuum to remove dimethylformamide. The residue was partitioned between ethyl acetate (3.2 L) and water (3.2 L). The aqueous layer was extracted with a second portion of ethyl acetate (2.0 L). The solution was dried over sodium sulfate, then filtered through a pad of silica (1.6 kg). The silica pad was rinsed with ethyl acetate (8.0 L) and the filtrate was evaporated under vacuum. The resulting residue was dissolved in a mixture of isopropanol (1.35 L) and ethyl acetate (400 mL), then filtered. A solution of hydrogen chloride gas in ethyl acetate (2.44M, 1.34 L) was added and the slurry was aged in an ice bath for 1 hour. The slurry was filtered and the filter cake was washed with 1:1 isopropanol:ethyl acetate (600 mL), followed by methyl-t-butyl ether (600 mL). The solid was dried under vacuum to give 749 g (77% yield, 98% ee) of (S)-3-(4-fluoropheny)-4-(phenylmethyl)-2-morpholinone hydrochloride.

Chiral HPLC Conditions: Column: Chiral (D)-Dinitrobenzoylphenylglycine (covalent) normal phase, 25 cm×4.6 mm; Column temperature: 35° C.; Mobile phase: hexane:ethanol (99:1 v/v); Flow rate: 1 mL/min; Detection: UV at 220 nm; Approximate retention times: (R)3-(4-Fluoropheny)-4-(phenylmethyl)-2-morpholinone: 16 minutes; (S)-3-(4-Fluoropheny)-4-(phenylmethyl)-2-morpholinone: 17 minutes.

EXAMPLE 104

Racemisation/Resolution of 3-(4-Fluorophenyl)-4-phenylmethyl-2-morpholinone

To a solution of 3-(4-fluorophenyl)-4-phenylmethyl-2-morpholinone (i.e. N-benzyl-4-fluorophenyl-1,4-oxazin-2-one) (10 g) in isopropyl acetate (110 ml) at room temperature was added a solution of (−)-3-bromocamphor-8-sulphonic acid ((−)-3BCS) (12 g) in acetonitrile (24 ml). Crystallisation began after 2–3 min. The slurry was stirred for 1 h at room temperature. Trifluoroacetic acid (7ml) was added and the mixture stirred at 65° C. for 3 days. The mixture was cooled to 0°–5° C., aged for 1 h. and the solid collected, washed with isopropyl acetate and dried in vacuo at 40° C., to give the N-benzyl-3-(S)-(4-fluorophenyl)-1,4-oxazin-2-one (−)-3BCS salt: yield 17.24 g, ee 98.6% (S) isomer. The chiral composition of the remaining liquors was determined as 79% (R), 21% (S). The liquors were stirred at 65° C. for 3 days, then cooled to 0°–5° C. The solid was collected, washed with isopropyl acetate and dried in vacuo to give a further batch of the N-benzyl-3-(S)-(4-fluorophenyl)-1,4-oxazin-2-one (−)-3BCS salt: yield 0.84 g, ee 98.6% (S) isomer. The chiral composition of the remaining liquors was determined as 64% (R), 36% (S). The liquors were stripped in vacuo and the residue was dissolved in isopropyl acetate (20 ml) containing trifluoroacetic acid (1 ml) and stirred at 65° C. for 20 h. The mixture was cooled to 0°–5° C. for 1 h and the solid collected, washed with isopropyl acetate and dried in vacuo to give a further batch of the N-benzyl-3-(S)-(4-fluorophenyl)-1,4-oxazin-2-one (−)-3BCS salt: yield 2.2 g, ee 99.2% (S) isomer. Total weight of (−)-3BCS salt: 20.28 g, 97% yield. A sample (0.5 g) of the (−)-3BCS salt was retained and the remainder converted back to free base. The salt was partitioned between isopropyl acetate (50 ml) and water (100 ml) containing 0.88 ammonia soln. (3 ml). The layers were separated and the aqueous phase extracted with isopropyl acetate (25 ml). The combined organic phases were washed with water (25 ml). The organic phase was concentrated to residue and flushed with isopropyl acetate to give the 3-(S)-(4-fluorophenyl)-4-phenylmethyl-2-morpholinone (i.e. N-benzyl-3-(S)-(4-fluorophenyl)-1,4-oxazin-2-one) as the free base: yield 8.7 g, 93% recovery, ee 98.4% (S) isomer.

A further batch of N-benzyl-3-(S)-(4-fluorophenyl)-1,4-oxazin-2-one (−)-3BCS salt was prepared substantially according to the previous method except that the following quantities and reaction conditions were used: N-benzyl-3-(4-fluorophenyl)-1,4-oxazin-2-one (racemate) (4.96 g); (−)-3BCS in acetonitrile (1.85M; 9.4 ml); trifluoroacetic acid (2.1 ml); and isopropyl acetate (55 ml). The mixture was stirred at 90° C. for 6 days and then cooled to 0°–5° C. and aged for 1 hour. The solid N-benzyl-3-(S)-(4-fluorophenyl)-1,4-oxazin-2-one (−)-3BCS salt was collected and washed with isopropyl acetate (20 ml). Yield 9.40 g (90%); ee 99.6% (S) isomer. The chiral composition of the remaining liquors was determined as 88% (R), 12% (S).

EXAMPLE 105

(2R-cis)-3,5-bis(Trifluoromethyl)benzeneacetic acid 3-(4-fluorophenyl)-4-(phenylmethyl)-2-morpholinyl ester A stirred suspension of (S)-3-(4-fluoropheny)-4-(phenylmethyl)-2-morpholinone hydrochloride (2.30 kg, 7.15 moles) in ethyl acetate (22 L) was treated with 10% aqueous sodium bicarbonate (22 L). The resulting organic solution was sequentially washed with 10% aqueous sodium bicarbonate (11 L) and water (2×11 L), then dried overnight with 4A molecular sieves (1 L). The solution was evaporated, then flushed with tetrahydrofuran (2×3 L) in order to remove traces of ethyl acetate. The resulting free base of (S)-3-(4-fluoropheny)-4-(phenylmethyl)-2-morpholinone was dissolved in tetrahydrofuran (19 L) and chilled to −75° C. L-Selectride (lithium tri-sec-butylborohydride, 6.74 L, 1.06M, 7.15 moles) was added to the batch while maintaining the temperature at less than −70° C. The batch was aged for 15 minutes, then 3,5-bis(trifluoromethyl)benzoyl chloride (2.57 kg, 9.29 moles) was added, maintaining the temperature at less than −70° C. The reaction was monitored by HPLC. The reaction was quenched with acetic acid (205 mL) in tetrahydrofuran (800 mL), and the batch was allowed to warm to ambient temperature overnight. The solution was vacuum concentrated and the resulting oil was diluted with hexanes (36 L). The batch was washed sequentially with water (17 L), 10% aqueous sodium bicarbonate (3×8.5 L), and water (2×8.5 L), then dried overnight using 4A molecular sieves (1 L). The batch was assayed by HPLC to contain 2.44 kg (65% yield) of (2R-cis)-3,5-bis(trifluoromethyl)benzeneacetic acid 3-(4-fluorophenyl)-4-(phenylmethyl)-2-morpholinyl ester. This batch was combined with another batch of (2R-cis)-3,5-bis(trifluoromethyl)benzeneacetic acid 3-(4-fluorophenyl)-4-(phenylmethyl)-2-morpholinyl ester (0.59 kg assay in 7 L hexanes) that was prepared just prior to the current batch. The combined batch solutions were filtered through a 20 µm line filter then diluted with hexanes (9 L). The crude (2R-cis)-3,5-bis(trifluoromethyl)benzeneacetic acid 3-(4-fluorophenyl)-4-(phenylmethyl)-2-morpholinyl ester solution (3.03 kg assay, 5.74 moles) was treated with hydrochloric acid in diethyl ether (9.6 L, 1.0M), giving a white precipitate of (2R-cis)-3,5-bis(trifluoromethyl) benzeneacetic acid 3-(4-fluorophenyl)-4-(phenylmethyl)-2-morpholinyl ester hydrochloride salt (the hydrochloride salt was formed in order to remove tri-sec-butyl borane residue (from the L-Selectride)). The solid was collected by filtration, washed with hexanes (2×8 L), then dried under nitrogen. The hydrochloride salt of the product was broken by slurrying in a mixture of toluene (36 L) and 10% aqueous sodium bicarbonate (13 L). The resulting organic solution was washed with 10% aqueous sodium bicarbonate (13 L) and water (2×18 L). The toluene solution was assayed to contain 3.00 kg of (2R-cis)-3,5-bis(trifluoromethyl)-benzeneacetic acid 3-(4-fluorophenyl)-4-(phenylmethyl)-2-morpholinyl ester (80% by area, corrected for toluene). The batch was stored over 4A molecular sieves (1 L).

HPLC conditions: Column: Zorbax RX-C8, 25 cm×4.6 mm; Mobile phase: acetonitrile: 0.1% aqueous phosphoric acid (75:25, v/v); Flow rate: 1.5 mL/min; Detection: UV at 220 nm Approximate retention times: Reduced (S)-3-(4-fluoropheny)-4-(phenylmethyl)-2-morpholinone: 1.6 minutes; (S)-3-(4-fluoropheny)-4-(phenylmethyl)-2-morpholinone: 3.3 minutes; (2R-cis)-3,5-bis(trifluoromethyl)-benzeneacetic acid 3-(4-fluorophenyl)-4-(phenylmethyl)-2-morpholinyl ester: 9.2 minutes.

EXAMPLE 106

(2R-cis)-2-[[1-[3,5-bis(Trifluoromethyl)phenyl]ethenyl]oxy]-3-(4-fluorophenyl)-4-(phenylmethyl)mopholine A toluene solution of (2R-cis)-3,5-bis(trifluoromethyl)-benzeneacetic acid 3-(4-fluorophenyl)-4-(phenylmethyl)-2-morpholinyl ester (1.60 kg, 3.02 moles) was evaporated, then purged with nitrogen. Tetrahydrofuran (1.6 L) was added, followed by a solution of dimethyl titanocene in toluene (8.35 wt %, 1.73 kg of reagent, 8.31 moles) (prepared as noted below). The batch was sparged with nitrogen for 25 minutes, then heated to 80° C. The batch was aged in the dark for 5 hours at 80° C., then cooled to ambient temperature and aged overnight. The batch was solvent-switched to heptane by vacuum distillation, maintaining the temperature below 20° C. (126 L heptane added with concomitant distillation of 120 L) (the reaction mixture was solvent-switched to heptane and treated with bicarbonate buffered peroxide in order to precipitate the titanium residues). Water (22 L), sodium bicarbonate (2.0 kg), then 30% hydrogen peroxide (3.5 L) were added to the chilled (7° C.) mixture. The batch was stirred at ambient temperature overnight. The phases were partitioned, with much of the titanium residue remaining in the aqueous phase. The aqueous phase was back extracted with heptane (10 L), and the combined organic phases were filtered, washed with water (2×4 L), then concentrated. The crude product was recrystallized by dissolving in hot methanol (17 L), cooling to ambient temperature, then adding water (1.8 L). The material was isolated by filtration at 0° C. The filter cake was washed with 10% aqueous methanol (2 L, 0° C.), then the solid was dried at ambient temperature under nitrogen (1.45 kg of 94 wt % pure (2R-cis)-2-[[1-[3,5-bis(trifluoromethyl)phenyl]-ethenyl]oxy]-3-(4-fluorophenyl)-4-(phenylmethyl)mopholine, 85% yield).

The dimethyl titanocene reagent may be prepared as follows. Methyl lithium (590 g, 26.9 moles) in a solution of diethyl ether (4.38% w/w, 13.5 kg) was added to a chilled (−8° C.), well-stirred slurry of titanocene dichloride (3.35 kg, 13.5 moles) in methyl-t-butyl ether (13.4 L) while maintaining the temperature below 5° C. The resulting slurry was aged at 0°–5° C. for 1 hour. The reaction was quenched by adding water (8 L) while maintaining the temperature between 0° and 8° C. The organic phase was washed with cold water (4×3 L). The organic layer was then solvent-switched to toluene by distillation with concomitant addition of of toluene (24 L) while maintaining the temperature at 25°

C. or less. Weight percent assay by $^1$H NMR showed the solution to contain 1.75 kg of dimethyl titanocene (63% yield, 8.35 wt % solution in toluene). The material was stored under nitrogen at 0° C. The progress of the reaction was followed by $^1$H NMR (250 MHz, CDCl$_3$, 10 second delay between pulses). Cp$_2$TiMe$_2$: ∂ (ppm) 6.05 (s, 10H), –0.05 (s, 6H); Cp$_2$TiClMe: ∂ 6.22 (s, 10H), 0.80 (s, 3H); Cp$_2$TiCl$_2$: ∂ 6.56 (s, 10H).

Alternatively, the dimethyl titanocene reagent may be prepared as follows. To a well stirred slurry of titanocene dichloride (249 g, 1.00 mol) in toluene (2.75 L) chilled to –5° (internal temp) was added MeMgCl (750 mL, 3.0M in THF, 2.25 mol) over 1 h, maintaining the temperature below 8°. The resulting orange slurry is aged at 0°–5° for 1 h, or until the insoluble purple Cp$_2$TiCl$_2$ has dissolved. A NMR was taken to confirm reaction completion (see below), then the reaction was quenched into a solution of 6% aqueous ammonium chloride (700 mL), maintained at 0°–5°. The organic phase was washed with cold water (3×575 mL) and brine (575 mL), then was dried with Na$_2$SO$_4$ (220 g). The filtered organic layer was evaporated to 1.5 Kg (maintaining an internal temperature of 25° or less). Weight % assay by $^1$H NMR showed the solution to contain 187 g product (90%, 12.5 wt % solution in toluene/THF). Typically, the material was greater than 95% pure, with only traces of the starting material and monomethyl intermediate. The solution may be further concentrated to 1.0 Kg, giving a 18 wt % solution in toluene, allowing for an easier assay. However, the presence of a small mount of THF increases the stability of the reagent. The material was stored under nitrogen in a sealed carboy at 0°. $^1$H NMR Cp$_2$TiMe$_2$: δ 6.05 (s, 10H), –0.05 (s, 6H). Cp$_2$TiClMe: δ 6.22 (s, 10H), 0.80 (s, 3H). Cp$_2$TiCl$_2$: δ 6.56 (s, 10H). $^{13}$C NMR Cp$_2$TiMe$_2$: δ 113.20 (Cp$_2$), 45.77 (Me$_2$). Cp$_2$TiClMe: δ 115.86 (Cp$_2$), 50.37 (Me). Cp$_2$TiCl$_2$: δ 120.18.

HPLC conditions: Column: Zorbax RX-C8, 25 cm×4.6 mm; Mobile phase: acetonitrile: 0.1% aqueous phosphoric acid (65:35, v/v); Flow rate: 1.5 mL/min; Detection: UV at 220 nm; Approximate retention times: (2R-cis)-2-[[1-[3.5-bis(Trifluoromethyl)phenyl]-ethenyl]oxy]-3-(4-fluorophenyl)-4-(phenylmethyl)mopholine: 17.2 minutes; (2R-cis)-3,5-bis(trifluoromethyl)-benzeneacetic acid 3-(4-fluorophenyl)-4-(phenylmethyl)-2-morpholinyl ester: 18.9 minutes.

The dimethyl titanocene reagent alternatively may be prepared as follows. To a well stirred slurry of titanocene dichloride (Cp$_2$TiCl$_2$) (6.0 g, 24.1 mmol) in toluene (72 mL) chilled to –5° C. was added dropwise methyl magnesium chloride (CH$_3$MgCl) (19.8 g, 19.2 mL, 3.0M in THF, 57.6 mmol, 2.4 eq) over 10 min, maintaining the temperature below 5° C. A viscous slurry was formed as magnesium chloride precipitated. The resulting slurry was aged at 0°–5° for 50 min, during which time the insoluble red Cp$_2$TiCl$_2$ had dissolved. A NMR assay on a quenched sample was taken to confirm reaction completion. A 0.2 mL sample was quenched into 1 mL of water and 1 ml of CDCl$_3$. The chloroform layer was used directly for NJR analysis. Dimethyl titanocene has resonances at 6.0 ppm (Cp) group and –0.2 ppm (CH$_3$ group). The monomethyl compound has resonances 0.2–0.3 ppm downfield, and the titanocene dichloride has resonance at 6.5 ppm.

The reaction was then quenched by addition of a solution of 10% aqueous ammonium chloride (20 mL) over 10 min, maintaining the temperature below 10° C. The layers were separated and the organic phase was washed with cold water (3×20 mL) and brine (20 mL), then was dried with Na2SO$_4$ (20 g). The filtered organic layer was concentrated under vacuum to approximately half volume. The total weight of the solution was 43 g, and NMR analysis showed 11.2 wt % in dimethyl titanocene (4.8 g, 96% yield). The THF level was 2%, however, the presence of a small amount of THF increases the stability of the reagent. The material was stored under nitrogen at 0° C.

The dimethyl titanocene reagent alternatively may also be prepared as follows. To a well stirred slurry of titanocene dichloride (Cp$_2$TiCl$_2$) (249 g, 1.00 mol) in toluene (2.75 L) chilled to –5° C. (internal temp) was added methyl magnesium chloride (CH$_3$MgCl) (750 mL, 3.0M in THF, 2.25 mol) over 1h, maintaining the temperature below 8° C. The resulting orange slurry is aged at 0°–5° C. for 1 h, or until the insoluble purple Cp$_2$TiCl$_2$ has dissolved. A NMR was taken to confirm reaction completion (see below), then the reaction was quenched into a solution of 6% aqueous ammonium chloride (700 mL), maintained at 0°–5° C. The layers were separated and the organic phase was washed with cold water (3×575 mL) and brine (575 mL), then was dried with Na$_2$SO$_4$ (220 g). The filtered organic layer was evaporated to 1.5 Kg (maintaining an internal temperature of 25° or less). Weight assay by $^1$H NMR showed the solution to contain 187 g product (90%, 12.5 wt % solution in toluene/THF). Typically, the material was greater than 95% pure, with only traces of the starting material and monomethyl intermediate. The solution may be further concentrated to 1.0 Kg, giving a 18 wt % solution in toluene, allowing for an easier assay. However, the presence of a small mount of THF increases the stability of the compound. The material was stored under nitrogen in a sealed carboy at 0° C. $^1$H NMR Cp$_2$Ti(CH$_3$)$_2$: δ 6.05 (s, 10H), –0.05 (s, 6H). Cp$_2$TiCl(CH$_3$): δ 6.22 (s, 10H), 0.80 (s, 3H). Cp$_2$TiCl$_2$: δ 6.56 (s, 10H). $^{13}$C NMR Cp$_2$Ti(CH$_3$)$_2$: δ 113.20 (Cp$_2$), 45.77 ((CH$_3$)$_2$). Cp$_2$TiClCH$_3$: δ 115.86 (Cp$_2$), 50.37 (CH$_3$). Cp$_2$TiCl$_2$: δ 120.18.

EXAMPLE 107

(2R-cis)-2-[[1-[3.5-bis(Trifluoromethyl)phenyl] ethenyl]oxy]-3-(4-fluorophenyl)-4-(phenylmethyl) mopholine A toluene solution of (2R-cis)-3,5-bis(trifluoromethyl) benzeneacetic acid 3-(4-fluorophenyl)-4-(phenylmethyl)-2-morpholinyl ester [i.e. (4-benzyl-2-(R)-(3,5-bis (trifluoromethyl)benzoyloxy)-3-(S)-(4-fluorophenyl)-1,4-oxazine] solution contained 2.99 Kg, 5.67 mol) was evaporated into a 100 L flask. The flask was purged with nitrogen, then tetrahydrofuran (25 L) was added, followed by a solution of dimethyl titanocene in toluene/THF (12.5 wt %, 4.2 Kg contained reagent, 20.2 mol). The orange solution was sparged with nitrogen for 25 minutes, then was heated to 80° C. The reaction was aged in the dark for 4 h at 80° C., the was cooled to ambient temperature. Methanol (11.6 L) and water (1.9 L) was added and the mixture was heated at 40° C. overnight, precipitating the titanium residues as a green solid. After cooling to ambient temperature, the solid was removed by filtration, the filtercake washed with toluene, and the resulting mother liquors were evaporated. The crude product was recrystallized by dissolving in hot methanol (30 L), cooling to ambient temperature, then adding water (3.4 L) over 3 h. The material was isolated via filtration at 0° C., the filtercake was washed with 0° C. 10% aq. methanol (2 L), and the solid was dried at ambient temperature under nitrogen, 2.55 Kg of (2R-cis)-2-[[1-[3.5-bis(Trifluoromethyl)phenyl]ethenyl]oxy]-3-(4-fluorophenyl)-4-(phenylmethyl)mopholine (85%) was isolated.

EXAMPLE 108

[2R-[2a(R*),3a]]-2-[1-[3,5-bis(Trifluoromethyl) phenyl]ethoxy]-3-(4-fluorophenyl)morpholine 4-methylbenzenesulfonate (salt)

A solution of (2R-cis)-2-[[1-[3.5-bis(trifluoromethyl) phenyl]ethenyl]oxy]-3-(4-fluorophenyl)-4-(phenylmethyl) mopholine (1082 g, 94% pure, 1.94 moles) in 1:1 ethyl acetate:ethanol (13 L) was mixed with 10% palladium-on-carbon (165 g). The resulting slurry was treated with hydrogen (40 psi, 20°–25° C.) for 12 hours. The reaction was monitored by hydrogen uptake and HPLC. The vessel was vented, and the catalyst was removed by filtration. After washing the catalyst with 1:1 ethyl acetate:ethanol (6 L) followed by ethyl acetate (2 L), the combined organic phases containing crude [2R-[2a(R*),3a]]-2-[1-[3,5-bis (Trifluoromethyl)phenyl]ethoxy]-3-(4-fluorophenyl) morpholine were vacuum concentrated. A second batch, starting with 1078 g of (2R-cis)-2-[[1-[3.5-bis (trifluoromethyl)phenyl]ethenyl]oxy]-3-(4-fluorophenyl)-4-(phenylmethyl)mopholine (1.93 moles) was prepared. The resulting crude [2R-[2a(R*),3a]]-2-[1-[3,5-bis (trifluoromethyl)phenyl]ethoxy]-3-(4-fluorophenyl) morpholine was vacuum concentrated and combined with the first batch. The combined batches of crude [2R-[2a(R*) ,3a]]-2-[1-[3,5-bis(trifluoromethyl)phenyl]ethoxy]-3-(4-fluorophenyl)morpholine were flushed with methyl-t-butyl ether (2×3 L) in order to remove residual ethyl acetate and ethanol, then were dissolved in methyl-t-butyl ether (3 L). The solution was assayed to contain 1348 g (3.09 moles, 80% yield) of [2R-[2a(R*),3a]]-2-[1-[3,5-bis (trifluoromethyl)phenyl]ethoxy]-3-(4-fluorophenyl) morpholine (as the free base). Alternatively, 60 g of the vinyl ether, 650 mL of methyl t-butyl ether (MTBE), and 18 g of 5% Pd on alumina were stirred under 40 psi hydrogen pressure at 40° for 12 H. Assay yield was 87%, with a 91:9 ratio of diastereomers. At the end of the reaction age, the catalyst was removed by filtration through Solka-Floc, then the filtrate was concentrated to 140 mL.

The first batch was treated with a warm (40° C.) solution of p-toluene sulfonic acid monohydrate (575 g, 3.03 moles) in methyl-t-butyl ether (3.2 L). The p-toluene sulfonic acid salt of [2R-[2a(R*),3a]]-2-[1-[3,5-bis(trifluoromethyl) phenyl]ethoxy]-3-(4-fluorophenyl)morpholine began to crystallize during the addition. The batch was cooled to ambient temperature and hexane (24 L) was added. The batch was aged for 2 hours, then the product was collected by filtration. The solid was washed with 4:1 hexane:methyl-t-butyl ether (2×2.5 L), then dried under nitrogen (1761 g (1655 g corrected for purity) of [2R-[2a(R*),3a]]-2-[1-[3,5-bis(trifluoromethyl)phenyl]ethoxy]-3-(4-fluorophenyl) morpholine 4-methylbenzenesulfonate (salt), 94 wt % pure, 70% yield). Alternatively, to the second solution was added a solution of 16.0 g p-TsOH monohydrate in 64 mL MTBE at 35° over a 20 min period. The tosylate salt crystallized as a thick slurry. Then 520 mL of hexanes was added over 1 h, and the slurry was stirred 2 h at ambient temperature. The slurry was filtered, washed with 2×60 mL 1:4 MTBE:hexanes, and dried by air suction to give 51.9 g of the tosylate salt (75% yield) containing 0.9% of the undesired diastereomer.

HPLC conditions: Column: Zorbax RX-C18, 25 cm×4.6 mm; Mobile phase: acetonitrile:aqueous 0.005M sodium heptane sulfonate, 0.002M potassium dihydrogen phosphate, 0.0005M disodium hydrogen phosphate (75:25, v/v); Flow rate: 1.5 mL/min; Detection: UV at 220 nm; Approximate retention times: [2R-[2a(R*),3a]]-2-[1-[3,5-bis(trifluoromethyl)phenyl]-ethoxy]-3-(4-fluorophenyl) morpholine: 4.5 minutes; N-benzyl [2R-[2a(R*),3a]]-2-[1-[3,5-bis(trifluoromethyl)phenyl]-ethoxy]-3-(4-fluorophenyl)morpholine: 25.0 minutes; (2R-cis)-2-[[1-[3.5-bis(trifluoromethyl)-phenyl]ethenyl]oxy]-3-(4-fluorophenyl)-4-(phenylmethyl)mopholine: 30.0 minutes.

HPLC conditions: Column: Zorbax RX-C18, 25 cm×4.6 mm; Mobile phase: acetonitrile:aqueous 0.005M sodium heptane sulfonate, 0.002M potassium dihydrogen phosphate, 0.0005M disodium hydrogen phosphate (60:40, v/v); Flow rate: 1.5 mL/min; Detection: UV at 220 nm; Approximate retention times: [2R-[2a(R*),3a]]-2-[1-[3,5-bis(trifluoromethyl)phenyl]-ethoxy]-3-(4-fluorophenyl) morpholine: 9.0 minutes; Diastereomer of [2R-[2a(R*),3a] ]-2-[1-[3,5-bis(trifluoromethyl)phenyl]-ethoxy]-3-(4-fluorophenyl)morpholine: 11.0 minutes (epimeric at methyl group)

EXAMPLE 109

[2R-[2a(R*),3a]]-5-[[2-[1-[3,5-bis(trifluoromethyl) phenyl]ethoxy]-3-(4-fluorophenyl)-4-morpholinyl] methyl]-1,2-dihydro-3H-1,2,4-triazol-3-one Powdered potassium carbonate (682 g, 4.93 moles) was added to a solution of [2R-[2a(R*),3a]]-2-[1-[3,5-bis (trifluoromethyl)phenyl]-ethoxy]-3-(4-fluorophenyl) morpholine 4-methylbenzenesulfonate (salt) (1254 g, 2.06 moles), N-methylcarboxy-2-chloroacetamidrazone (375 g, 2.26 moles), and dimethylformamide (10 L). The reaction was maintained between 15° and 25° C. and aged for 2.5 hours. The batch was diluted with 1:1 hexane:methyl-t-butyl ether (10 L) and 10.9% aqueous ammonium chloride (11 L). The phases were partitioned and the aqueous phase was back extracted with 1:1 hexane:methyl-t-butyl ether (2×8 L), followed by 1:2 hexane:methyl-t-butyl ether (8 L). The combined organic phases were washed with water (2×15 L), then vacuum concentrated. The resulting material was dissolved in xylenes (20 L) and heated to reflux (137° C.). The solution was maintained at reflux for 3 hours, then cooled to ambient temperature, whereupon [2R-[2a(R*),3a]]-5-[[2-[1-[3,5-bis(trifluoromethyl)phenyl]ethoxy]-3-(4-fluorophenyl) -4-morpholinyl]methyl]-1,2-dihydro-3H-1,2,4-triazol-3-one crystallized. The batch was aged overnight, then filtered. The filter cake was washed with xylenes (2 L), then hexanes (2×2 L), then dried under vacuum at 30° C. for three days (696 g, 63% yield of [2R-[2a(R*),3a]]-5-[[2-[1-[3,5-bis (trifluoromethhyl)phenyl]ethoxy]-3-(4-fluorophenyl)-4-morpholinyl]methyl]-1,2-dihydro-3H-1,2,4-triazol-3-one).

Alternatively, the title product may be prepared as follows from the amine TsOH salt, (1.90 Kg, 3.12 mol); N-methylcarboxyl-2-chloroacetamidrazone (516.3 g, 3.12 mol); K₂CO₃ (1.08 kg, 2.5 eq.); and DMSO (15.6 L). To a suspension of amine salt and powder K₂CO₃ in DMSO (7.8 L) at 20° C. is added a solution of N-methylcarboxyl-2-chloroacetamidrazone in DMSO (7.8 L). The first half of the solution is added quickly, (with slight cooling with ice water bath) then the remaining half is added over a period of 1 hr. After the addition, the reaction is checked by LC, and the reaction is quenched with cold water (15 L) and methyl-t-butyl ether (MTBE) (30 L) solution. The organic layr is separated, and washed with water, sat. NaHCO₃, brine, and water (20 L/each) respectively. The aqueous layers is back extracted with additional MTBE (15 L). The combined MTBE solution is concentrated to an oil. The resulting crude product is dissolved in xylene (25 L) and diisopropylethylamine (6.25 L) and is heated to reflux (~135° C.) and the reaction is monitored by LC. The reaction takes 4–6 hours to complete, the the reaction solution is cooled down to room temperature overnight and filter to get the title product (expect 1.33 kg, ~80%, typically purity 98.5A %).

The resulting crude product is dissolved in hot methanol (13.3 L), added charcoal 133 g, then filtered and the charcoal is washed with hot methanol (3.3 L). The methanol solution is cooled down to room temperature, then water (7 L) is added dropwise. After being stirred at room temperature for 2 hrs, the suspension is filtered to isolate purified product as a white crystalline compound (expect 1.20 kg, 90% recovery, typical purity, 99.5A %).

HPLC conditions: Column: Zorbax RX-C8, 25 cm×4.6 mm; Mobile phase: (A) acetonitrile, (B) 0.1% aqueous phosphoric acid; Linear gradient: 40:60 A:B to 70:30 A:B in 10 minutes; Flow rate: 1.5 mL/min; Detection: UV at 220 nm; Approximate retention times: Alkylated intermediate: 5.7 minutes; [2R-[2a(R*),3a]]-5-[[2-[1-[3,5-bis(trifluoromethyl)phenyl]ethoxy]-3-(4-fluorophenyl)-4-morpholinyl]methyl]-1,2-dihydro-3H-1,2,4-triazol-3-one: 8.2 minutes.

EXAMPLE 110

[2R-[2a(R*),3a]]-3-[[2-[1-[3,5-bis(trifluoromethyl)phenyl]ethoxy]-3-(4-fluorophenyl)-4-morpholinyl]methyl]-4,5-dihydro-5-oxo-1H-1,2,4-triazol-1-yl]phosphonic acid compound with 1-deoxy-1-(methylamino)-D-glucitol (1:2)

A solution of sodium bis(trimethylsilyl)amide (2.25 L, 1.0M in tetrahydrofuran) was added dropwise to a cold (−0.5° C.) solution of [2R-[2a(R*),3a]]-5-[[2-[1-[3,5-bis(trifluoromethyl)phenyl]ethoxy]-3-(4-fluorophenyl)-4-morpholinyl]methyl]-1,2-dihydro-3H-1,2,4-triazol-3-one (480.6 g, 0.9 moles) and tetrabenzyl pyrophosphate (576 g, 1.08 moles) in tetrahydrofuran (6.75 L) while maintaining the temperature at 0°–5° C. Additional tetrabenzyl pyrophosphate (48.4 g, 90 moles) was added and the resulting solution was stirred for 45 minutes. The reaction was quenched by pouring the solution into a vigorously stirred mixture of methyl-t-butyl ether (18 L) and saturated aqueous sodium bicarbonate (9 L). The organic layer was separated and sequentially washed with saturated aqueous sodium bicarbonate (2×9 L), 10% aqueous sodium hydrogen sulfate (2×9 L), saturated aqueous sodium chloride (2×9 L), and water (9 L). All aqueous layers were combined and back extracted with methyl-t-butyl ether (9 L). The methyl-t-butyl ether layers were combined and concentrated. The resulting material was dissolved in methanol (4 L), then N-methyl-D-glucamine (440 g, 2.25 moles) in pyrogen-free water (800 mL) was added. The resulting solution was subjected to hydrogenation (40 psi) with 5% palladium-on-carbon (45 g) overnight.

The batch was filtered through Solka Floc, then washed with methanol (4 L). The batch was purified by HPLC. For each injection, about 400 mL of the filtrate was diluted with water (200 mL) and methanol (50 mL), then loaded on a Waters Delta-Pak C18 column (48×300 mm) and eluted with acetonitrile:water. The rich cuts were combined and lyophilized (931 g, 87% yield of [2R-[2a(R*),3a]]-3-[[2-[1-[3,5-bis(trifluoromethyl)phenyl]ethoxy]-3-(4-fluorophenyl)-4-morpholinyl]methyl]-4,5-dihydro-5-oxo-1H-1,2,4-triazol-1-yl]phosphonic acid compound with 1-deoxy-1-(methylamino)-D-glucitol (1:2), i.e. 2-(S)-(1-(R)-(3,5-bis(trifluoro-methyl)phenyl)ethoxy)-3-(S)-(4-fluoro)phenyl-4-(3-(1-phosphoryl-5-oxo-4H-1,2,4-triazolo)methylmorpholine, bis(N-methyl-D-glucamine)).

HPLC conditions: Column: Zorbax RX-C8, 25 cm×4.6 mm; Mobile phase: (A) acetonitrile, (B) 0.1% aqueous phosphoric acid; Linear gradient: 40:60 A:B to 70:30 A:B in 10 minutes, hold for 5 minutes; Flow rate: 1.5 mL/min; Detection: UV at 220 nm; Approximate retention times: [2R-[2a(R*),3a]]-3-[[2-[1-[3,5-bis(trifluoromethyl)phenyl]ethoxy]-3-(4-fluorophenyl)-4-morpholinyl]methyl]-4,5-dihydro-5-oxo-1H-1,2,4-triazol-1-yl]phosphonic acid: 4.2 minutes; Dibenzyl intermediate: 14.3 minutes.

Prep. HPLC conditions: Column: Waters Delta-Pak C18, 48×300 mm, 15 mm particle size, 100 Å pore size; Mobile phase: (A) acetonitrile, (B) water; Step gradient: 10:90 A:B for 10 min, 30:70 A:B for 13 min, 35:65 A:B for 10 min, 40:60 A:B for 10 min; Flow rate: 75 mL/min.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula:

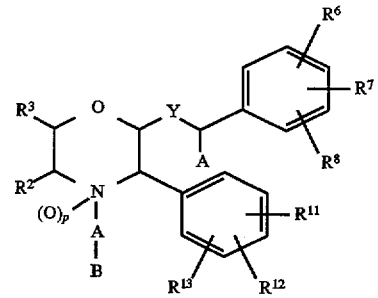

or a pharmaceutically acceptable salt thereof, wherein:

$R^2$ and $R^3$ are independently selected from the group consisting of:
(1) hydrogen,
(2) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —$NR^9R^{10}$, wherein $R^9$ and $R^{10}$ are independently selected from:
(i) hydrogen, (ii) $C_{1-6}$ alkyl,
(iii) hydroxy-$C_{1-6}$ alkyl, and
(iv) phenyl,
  (i) —$NR^9COR^{10}$,
  (j) —$NR^9CO_2R^{10}$,
  (k) —$CONR^9R^{10}$,
  (l) —$COR^9$, and
  (m) —$CO_2R^9$,
(3) $C_{2-6}$ alkenyl, unsubstituted or substituted with one or more of the substituent(s) selected from:
  (a) hydroxy,
  (b) oxo,
  (c) $C_{1-6}$ alkoxy,
  (d) phenyl-$C_{1-3}$ alkoxy,
  (e) phenyl,
  (f) —CN,
  (g) halo,
  (h) —$CONR^9R^{10}$,
  (i) —$COR^9$,
  (j) —$CO_2R^9$;
(4) $C_{2-6}$ alkynyl;
(5) phenyl, unsubstituted or substituted with one or more of the substituent(s) selected from:
  (a) hydroxy,
  (b) $C_{1-6}$ alkoxy,
  (c) $C_{1-6}$ alkyl,
  (d) $C_{2-5}$ alkenyl,
  (e) halo,
  (f) —CN,
  (g) —$NO_2$,
  (h) —$CF_3$,
  (i) —$(CH_2)_m$—$NR^9R^{10}$, wherein m is 0, 1 or 2,
  (j) —$NR^9COR^{10}$,
  (k) —$NR^9CO_2R^{10}$,
  (l) —$CONR^9R^{10}$,
  (m) —$CO_2NR^9R^{10}$,
  (n) —$COR^9$, and
  (o) —$CO_2R^9$;
or the groups $R^2$ and $R^3$ are joined together to form a carbocyclic ring selected from the group consisting of:
  (a) cyclopentyl,
  (b) cyclohexyl,
  (c) phenyl,
and wherein the carbocyclic ring is unsubstituted or substituted with one or more substituents selected from:
  (i) $C_{1-6}$alkyl,
  (ii) $C_{1-6}$alkoxy,
  (iii) —$NR^9R^{10}$,
  (iv) halo, and
  v) trifluoromethyl;
or the groups $R^2$ and $R^3$ are joined together to form a heterocyclic ring selected from the group consisting of:
  (a) pyrrolidinyl,
  (b) piperidinyl,
  (c) pyrrolyl,
  (d) pyridinyl,
  (e) imidazolyl,
  (f) furanyl,
  (g) oxazolyl,
  (h) thienyl, and
  (i) thiazolyl,
and wherein the heterocyclic ring is unsubstituted or substituted with one or more substituent(s) selected from:
  (i) $C_{1-6}$alkyl,
  (ii) oxo,
  (iii) $C_{1-6}$alkoxy,
  (iv) —$NR^9R^{10}$,
  (v) halo, and
  (vi) trifluoromethyl;
$R^6$, $R^7$ and $R^8$ are independently selected from the group consisting of:
(1) hydrogen;
(2) $C_{1-6}$ alkyl, unsubstituted or substituted with one or more of the substituents selected from:
  (a) hydroxy,
  (b) oxo,
  (c) $C_{1-6}$ alkoxy,
  (d) phenyl-$C_{1-3}$ alkoxy,
  (e) phenyl,
  (f) —CN,
  (g) halo,
  (h) —$NR^9R^{10}$,
  (i) —$NR^9COR^{10}$,
  (j) —$NR^9CO_2R^{10}$,
  (k) —$CONR^9R^{10}$,
  (l) —$COR^9$, and
  (m) —$CO_2R^9$;
(3) $C_{2-6}$ alkenyl, unsubstituted or substituted with one or more of the substituent(s) selected from:
  (a) hydroxy,
  (b) oxo,
  (c) $C_{1-6}$ alkoxy,
  (d) phenyl-$C_{1-3}$ alkoxy,
  (e) phenyl,
  (f) —CN,
  (g) halo,
  (h) —$CONR^9R^{10}$,
  (i) —$COR^9$, and
  (j) —$CO_2R^9$;
(4) $C_{2-6}$ alkynyl;
(5) phenyl, unsubstituted or substituted with one or more of the substituent(s) selected from:
  (a) hydroxy,
  (b) $C_{1-6}$ alkoxy,
  (c) $C_{1-6}$ alkyl,
  (d) $C_{2-5}$ alkenyl,
  (e) halo,
  (f) —CN,
  (g) —$NO_2$,
  (h) —$CF_3$,
  (i) —$(CH_2)_m$—$NR^9R^{10}$,
  (j) —$NR^9COR^{10}$,
  (k) —$NR^9CO_2R^{10}$,
  (l) —$CONR^9R^{10}$,
  (m) —$CO_2NR^9R^{10}$,
  (n) —$COR^9$, and
  (o) —$CO_2R^9$;
(6) halo,
(7) —CN,
(8) —$CF_3$,
(9) —$NO_2$,
(10) —$SR^{14}$, wherein $R^{14}$ is hydrogen or $C_{1-5}$alkyl,
(11) —$SOR^{14}$,
(12) —$SO_2R^{14}$,
(13) $NR^9COR^{10}$,
(14) $CONR^9COR^{10}$,
(15) $NR^9R^{10}$,
(16) $NR^9CO_2R^{10}$,
(17) hydroxy,
(18) $C_{1-6}$alkoxy,
(19) $COR^9$,
(20) $CO_2R^9$,
(21) 2-pyridyl,
(22) 3-pyridyl,

(23) 4-pyridyl,
(24) 5-tetrazolyl,
(25) 2-oxazolyl, and
(26) 2-thiazolyl;

$R^{11}$, $R^{12}$ and $R^{13}$ are independently selected from the definitions of $R^6$, $R^7$ and $R^8$, or —OX;

A is selected from the group consisting of:
(1) $C_{1-6}$ alkyl, unsubstituted or substituted with one or more of the substituents selected from:
  (a) hydroxy,
  (b) oxo,
  (c) $C_{1-6}$ alkoxy,
  (d) phenyl-$C_{1-3}$ alkoxy,
  (e) phenyl,
  (f) —CN,
  (g) halo, wherein halo is fluoro, chloro, bromo or iodo,
  (h) —$NR^9R^{10}$,
  (i) —$NR^9COR^{10}$,
  (j) —$NR^9CO_2R^{10}$,
  (k) —$CONR^9R^{10}$,
  (l) —$COR^9$, and
  (m) —$CO_2R^9$;
(2) $C_{2-6}$ alkenyl, unsubstituted or substituted with one or more of the substituent(s) selected from:
  (a) hydroxy,
  (b) oxo,
  (c) $C_{1-6}$ alkoxy,
  (d) phenyl-$C_{1-3}$ alkoxy,
  (e) phenyl,
  (f) —CN,
  (g) halo,
  (h) —$CONR^9R^{10}$,
  (i) —$COR^9$, and
  (j) —$CO_2R^9$; and
(3) $C_{2-6}$ alkynyl;

B is a heterocycle, wherein the heterocycle is selected from the group consisting of:

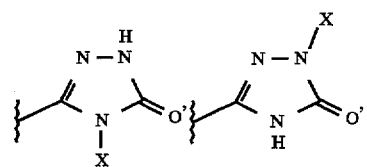

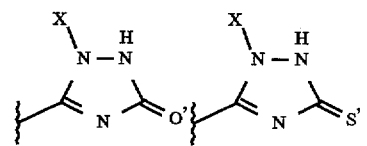

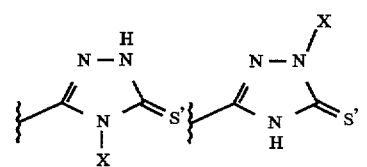

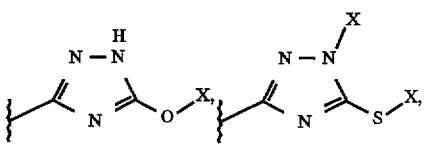

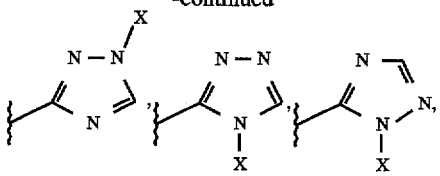

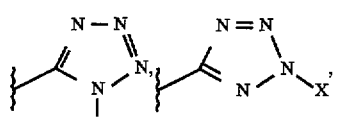

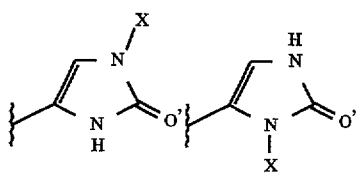

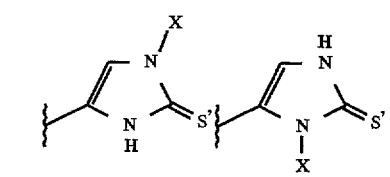

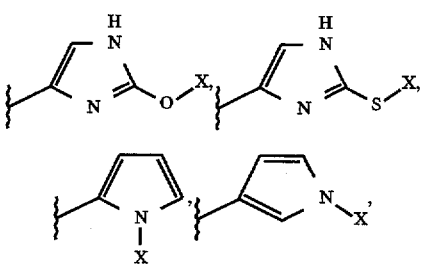

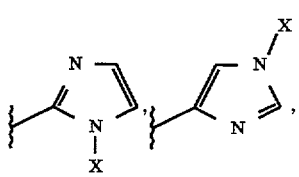

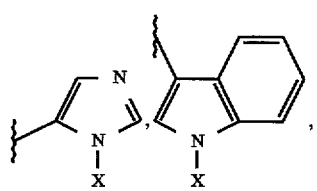

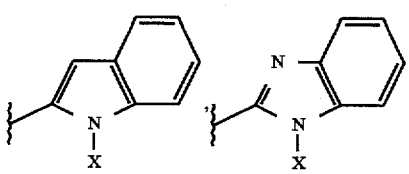

and wherein the heterocycle is substituted in addition to —X with one or more substituent(s) selected from:
  (i) hydrogen;
  (ii) $C_{1-6}$ alkyl, unsubstituted or substituted with halo, —$CF_3$, —$OCH_3$, or phenyl,
  (iii) $C_{1-6}$ alkoxy,
  (iv) oxo,
  (v) hydroxy, (vi) thioxo,
(vii) —$SR^9$,
(viii) halo,
(ix) cyano,
(x) phenyl,
(xi) trifluoromethyl,
(xii) —$(CH_2)_m$—$NR^9R^{10}$,
(xiii) —$NR^9COR^{10}$,
(xiv) —$CONR^9R^{10}$,
(xv) —$CO_2R^9$, and
(xvi) —$(CH_2)_m$—$OR^9$;

p is 0 or 1;

X is selected from:
(a) —$PO(OH)O^-\cdot M^+$, wherein $M^+$ is a pharmaceutically acceptable monovalent counterion,
(b) —$PO(O^-)_2\cdot 2M^+$,
(c) —$PO(O^-)_2\cdot D^{2+}$, wherein $D^{2+}$ is a pharmaceutically acceptable divalent counterion,
(d) —$CH(R^4)$—$PO(OH)O^-\cdot M^+$, wherein $R^4$ is hydrogen or $C_{1-3}$ alkyl,
(e) —$CH(R^4)$—$PO(O^-)_2\cdot 2M^+$,
(f) —$CH(R^4)$—$PO(O^-)_2\cdot D^{2+}$,
(g) —$SO_3^-\cdot M+$,
(h) —$CH(R^4)$—$SO_3^-\cdot M^+$,
(i) —$CO$—$CH_2CH_2$—$CO_2^-\cdot M^+$,
(j) —$CH(CH_3)$—$O$—$CO$—$R^5$, wherein $R^5$ is selected from the group consisting of:

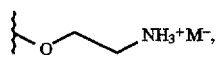 (i)

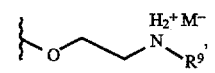 (ii)

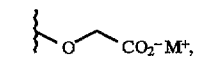 (iii)

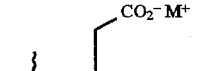 (iv)

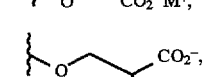 (v)

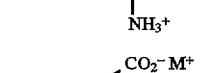 (vi)

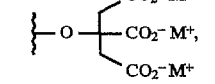 (vii)

; and (k) hydrogen, with the proviso that if p is 0 and none of $R^{11}$, $R^{12}$ or $R^{13}$ are —OX, then X is other than hydrogen;

Y is selected from the group consisting of:
(1) a single bond,
(2) —O—,
(3) —S—,
(4) —CO—,
(5) —$CH_2$—,
(6) —$CHR^{15}$—, and
(7) —$CR^{15}R^{16}$—, wherein $R^{15}$ and $R^{16}$ are independently selected from the group consisting of:

(a) $C_{1-6}$ alkyl, unsubstituted or substituted with one or more of the substituents selected from:
(i) hydroxy,
(ii) oxo,
(iii) $C_{1-6}$ alkoxy,
(iv) phenyl-$C_{1-3}$ alkoxy,
(v) phenyl,
(vi) —CN,
(vii) halo,
(viii) —$NR^9R^{10}$,
(ix) —$NR^9COR^{10}$,
(x) —$NR^9CO_2R^{10}$,
(xi) —$CONR^9R^{10}$,
(xii) —$COR^9$, and
(xiii) —$CO_2R^9$;

(b) phenyl, unsubstituted or substituted with one or more of the substituent(s) selected from:
(i) hydroxy,
(ii) $C_{1-6}$ alkoxy,
(iii) $C_{1-6}$ alkyl,
(iv) $C_{2-5}$ alkenyl,
(v) halo,
(vi) —CN,
(vii) —$NO_2$,
(viii) —$CF_3$,
(ix) —$(CH_2)_m$—$NR^9R^{10}$,
(x) —$NR^9COR^{10}$,
(xi) —$NR^9CO_2R^{10}$,
(xii) —$CONR^9R^{10}$,
(xiii) —$CO_2NR^9R^{10}$,
(xiv) —$COR^9$, and
(xv) —$CO_2R^9$;

Z is selected from:
(1) hydrogen,
(2) $C_{1-6}$ alkyl, and
(3) hydroxy, with the proviso that if Y is —O—, then Z is other than hydroxy, and with the further proviso that if Y is —$CHR^{15}$—, then Z and $R^{15}$ may be joined together to form a double bond between the two carbon atoms.

2. The compound of claim 1 wherein:

$R^2$ and $R^3$ are independently selected from the group consisting of:
(1) hydrogen,
(2) $C_{1-6}$ alkyl,
(3) $C_{2-6}$ alkenyl, and
(4) phenyl;

$R^6$, $R^7$ and $R^8$ are independently selected from the group consisting of:
(1) hydrogen,
(2) $C_{1-6}$ alkyl,
(3) fluoro,
(4) chloro,
(5) bromo,
(6) iodo, and
(7) —$CF_3$;

$R^{11}$, $R^{12}$ and $R^{13}$ are independently selected from the group consisting of:
(1) fluoro,
(2) chloro,
(3) bromo, and
(4) iodo;

A is unsubstituted $C_{1-6}$ alkyl;

B is selected from the group consisting of:

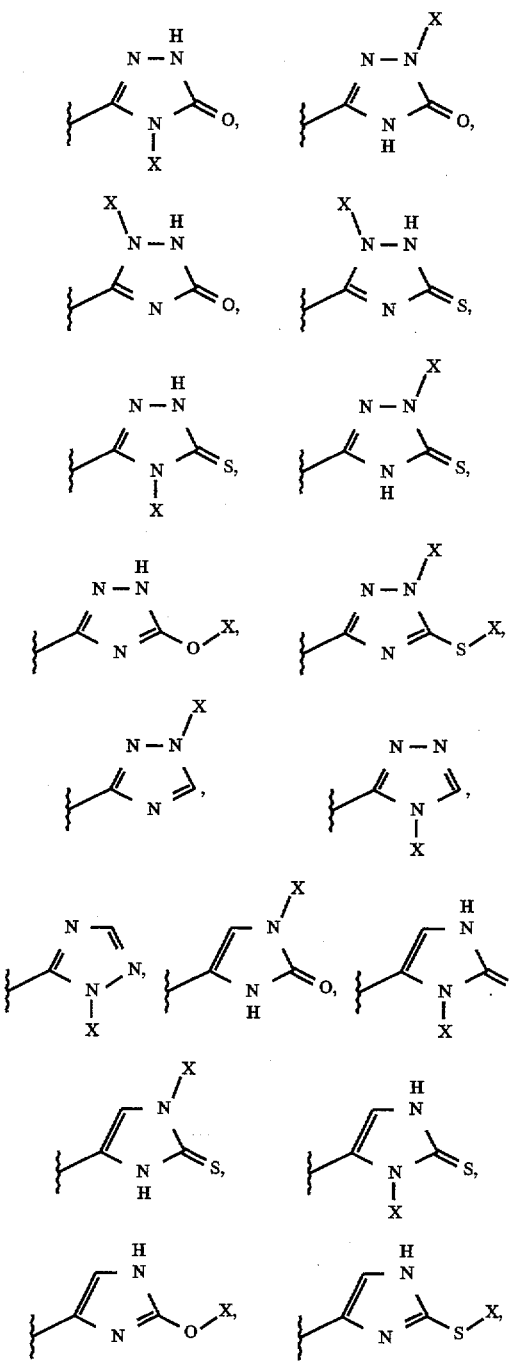

p is 0;
X is selected from:
(a) —PO(OH)O⁻•M⁺, wherein M⁺ is a pharmaceutically acceptable monovalent counterion,
(b) —PO(O⁻)$_2$•2M⁺,
(c) —PO(O⁻)$_2$•D²⁺, wherein D²⁺ is a pharmaceutically acceptable divalent counterion,
(d) —CH(R⁴)—PO(OH)O⁻•M⁺, wherein R⁴ is hydrogen or methyl,
(e) —CH(R⁴)—PO(O⁻)$_2$•2M⁺,
(f) —CH(R⁴)—PO(O⁻)$_2$•D²⁺,
(g) —CO—CH$_2$CH$_2$—CO$_2$⁻•M⁺, (h) —CH(CH$_3$)—O—CO—R⁵, wherein R⁵ is selected from the group consisting of:

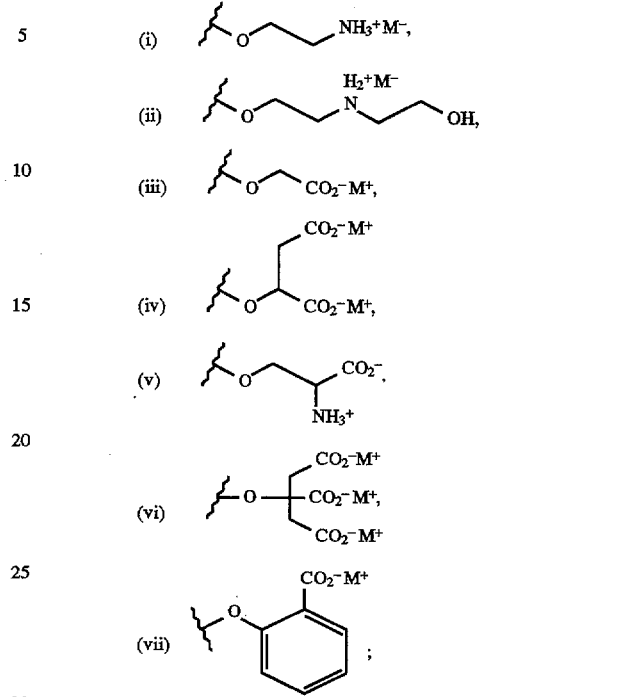

and

Y is —O—;

Z is hydrogen or C$_{1-4}$ alkyl.

3. The compound of claim 1 wherein Z is C$_{1-4}$ alkyl.
4. the compound of claim 1 wherein Z is —CH$_3$.
5. The compound of claim 1 wherein A is —CH$_2$— or —CH(CH$_3$)—.
6. The compound of claim 1 wherein —B is selected from the group consisting of:

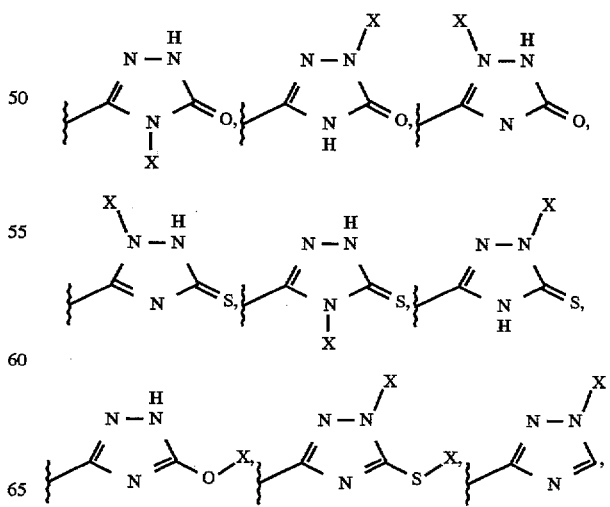

-continued

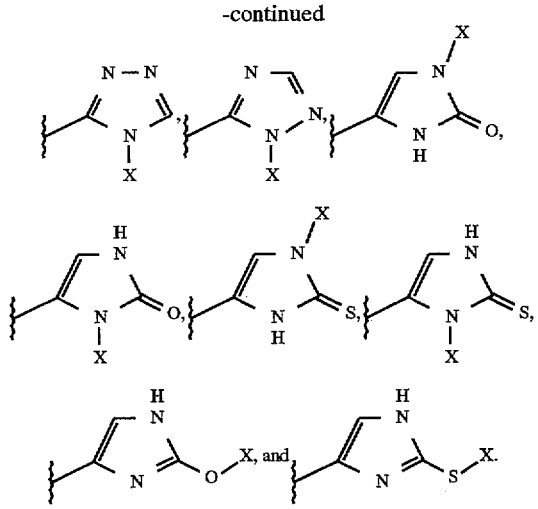

7. The compound of claim 1 wherein —A—B is selected from the group consisting of:

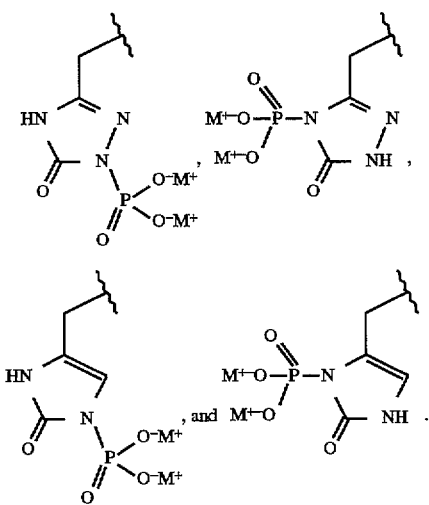

8. The compound of claim 1 wherein X is selected from the group consisting of:

(a) —PO(O⁻)₂·2M⁺, wherein M⁺ is a pharmaceutically acceptable monovalent counterion, and (b) —PO(O⁻)₂·D²⁺, wherein D²⁺ is a pharmaceutically acceptable divalent counterion.

9. The compound of claim 1 of the structural formula II:

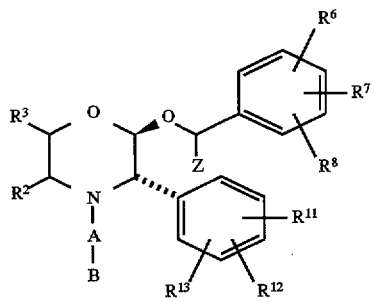

or a pharmaceutically acceptable salt thereof.

10. The compound of claim 1 of the structural formula III:

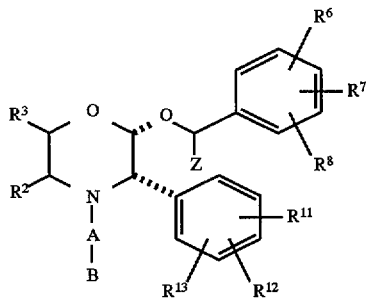

or a pharmaceutically acceptable salt thereof.

11. A compound which is selected from the group consisting of:

(1) 2-(S)-(3,5-bis(trifluoromethyl)benzyloxy)-3-(S)-phenyl-4-(3-(5-oxo-1H,4H-1,2,4-triazolo)methyl)morpholine N-oxide;

(2) 2-(R)-(1-(R)-(3,5-bis(trifluoromethyl)phenyl)ethoxy)-3-(S)-(4-fluoro)-phenyl-4-(3-(4-monophosphoryl-5-oxo-1H-1,2,4-triazolo)methyl)morpholine;

(3) 2-(R)-(1-(R)-(3,5-bis(trifluoromethyl)phenyl)ethoxy)-3-(S)-(4-fluoro)-phenyl-4-(3-(1-monophosphoryl-5-oxo-1H-1,2,4-triazolo)methyl)morpholine;

(4) 2-(R)-1(R)-(3,5-bis(trifluoromethyl)phenyl)ethoxy)-3-(S)-(4-fluoro)-phenyl-4-(3-(2-monophosphoryl-5-oxo-1H-1,2,4-triazolo)methyl)morpholine;

(5) 2-(R)-(1-(R)-(3,5-bis(trifluoromethyl)phenyl)ethoxy)-3-(S)-4-fluoro)-phenyl-4-(3-(5-oxyphosphoryl-1H-1,2,4-triazolo)methyl)morpholine;

(6) 2-(S)-(1-(R)-(3,5-bis(trifluoromethyl)phenyl)ethoxy)-3-(S)-(4-fluoro)-phenyl-4-(3-(1-phosphoryl-5-oxo-4H-1,2,4-triazolo)methyl)morpholine;

or a pharmaceutically acceptable salt thereof.

12. The compound of claim 11 wherein the pharmaceutically acceptable salt is the bis(N-methyl-D-glucamine) salt.

13. A compound which is selected from the group consisting of:

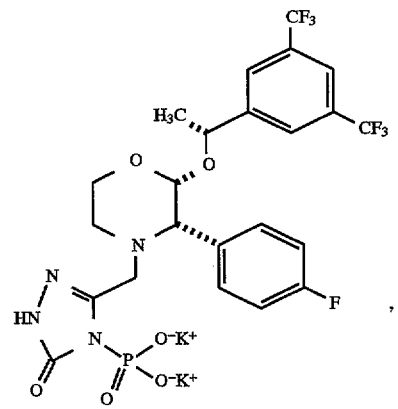

157
-continued

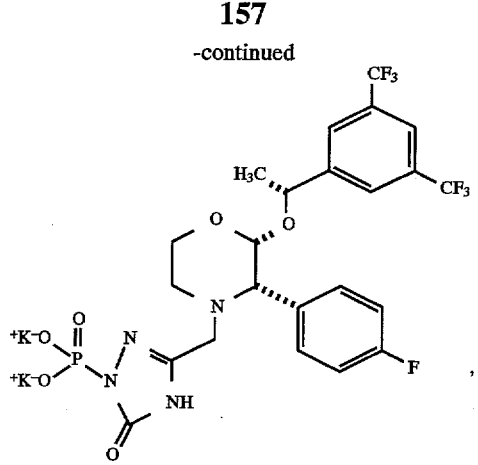

,

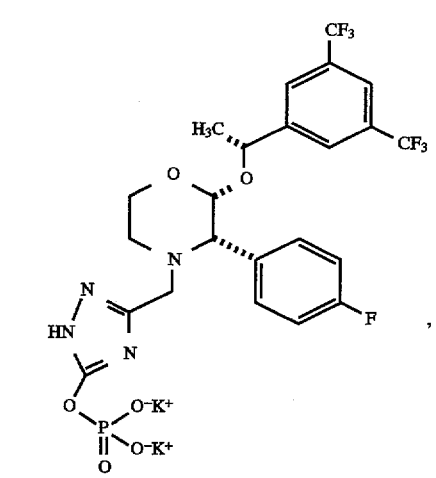

,

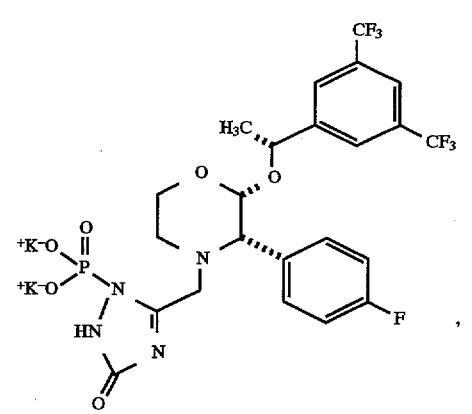

,

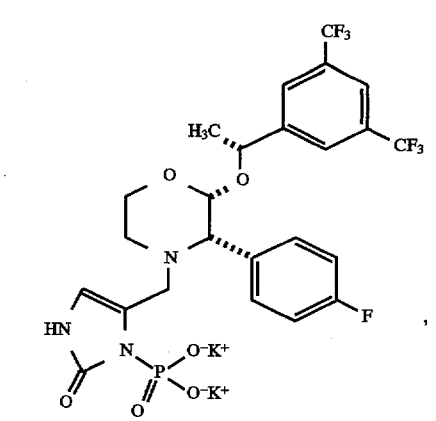

,

158
-continued

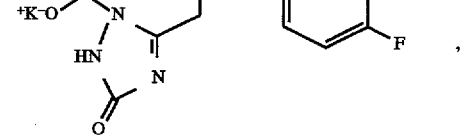

,

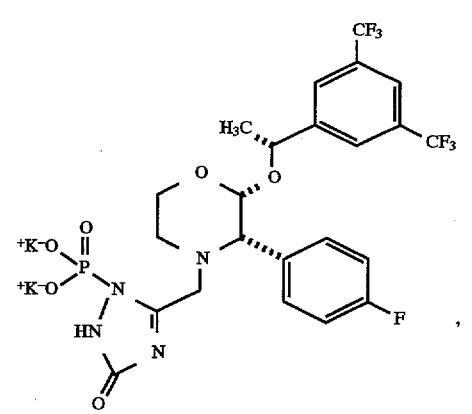

, wherein K⁺ is a pharmaceutically acceptable counterion.

14. A compound which is:

2-(R)-(1-(R)-(3,5-bis(trifluoromethyl)phenyl)ethoxy)-3-(S)-(4-fluoro)phenyl-4-(3-(1-phosphoryl-5-oxo-4H-1,2,4-triazolo)methylmorpholine;

or a pharmaceutically acceptable salt thereof.

15. The compound of claim 14 wherein the pharmaceutically acceptable salt is the bis(N-methyl-D-glucamine) salt.

16. A compound which is 2-(R)-(1-(R)-(3,5-bis(trifluoromethyl)phenyl)ethoxy)-3-(S)-(4-fluoro)phenyl-4-(3-(1-phosphoryl-5-oxo-4H-1,2,4-triazolo)methylmorpholine, bis(N-methyl-D-glucamine).

17. A compound which is:

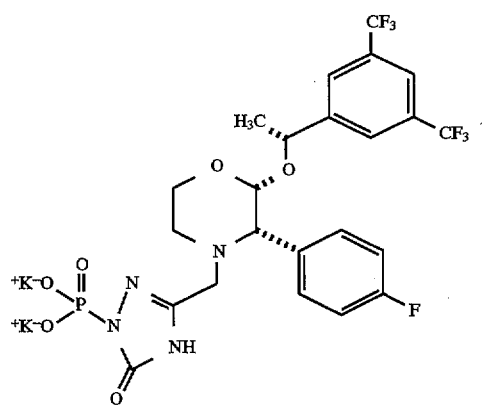

wherein K⁺ is a pharmaceutically acceptable counterion.

18. The compound of claim 17 wherein K⁺ is N-methyl-D-glucamine.

19. A compound which is:

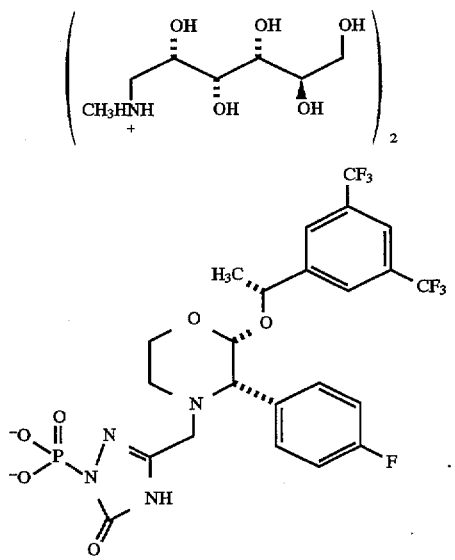

20. A pharmaceutical composition comprising a pharmaceutically acceptable carrier and an effective amount of the compound of claim 1.

21. The pharmaceutical composition of claim 20 wherein the pharmaceutically acceptable carrier comprises water.

22. The pharmaceutical composition of claim 20 wherein the pharmaceutically acceptable carrier comprises a physiologically acceptable saline solution.

23. A pharmaceutical composition comprising a pharmaceutically acceptable carrier and an effective amount of a compound which is:

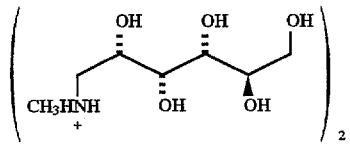

24. A method for antagonizing the effect of substance P at its receptor site or for the blockade of neurokinin-1 receptors in a mammal which comprises the administration to the mammal of the compound of claim 1 in an amount that is effective for antagonizing the effect of substance P at its receptor site or for the blockade of neurokinin-1 receptors in the mammal.

25. A method of treating or preventing pain or nociception which comprises the administration to the mammal of an effective amount of the compound of claim 1.

* * * * *

UNITED STATES PATENT AND TRADEMARK OFFICE
CERTIFICATE OF CORRECTION

| | | |
|---|---|---|
| PATENT NO. | : 5,691,336 | Page 1 of 1 |
| APPLICATION NO. | : 08/525870 | |
| DATED | : November 25, 1997 | |
| INVENTOR(S) | : Conrad P. Dorn et al. | |

It is certified that error appears in the above-identified patent and that said Letters Patent is hereby corrected as shown below:

On Title Page
Abstract

Item [57], ABSTRACT, replace the structure with the following structure:

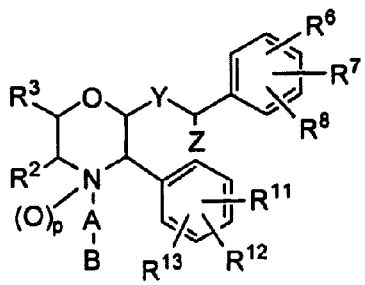

Claims

Column 146, lines 38-51, replace the structure with the following structure:

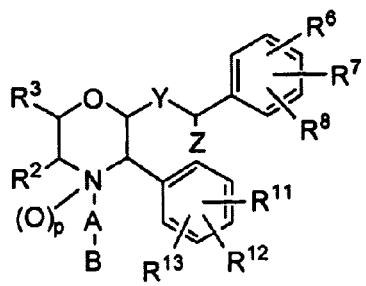

Signed and Sealed this

Twenty-fourth Day of June, 2008

JON W. DUDAS
*Director of the United States Patent and Trademark Office*